US012747290B2

(12) United States Patent
Orecchia et al.

(10) Patent No.: US 12,747,290 B2
(45) Date of Patent: Sep. 29, 2026

(54) IL-33 BINDING ANTIBODIES

(71) Applicant: GlaxoSmithKline Intellectual Property Development Limited, Stevenage (GB)

(72) Inventors: Martin Orecchia, Stevenage (GB); Matthew Edwards, Stevenage (GB); Andrew Beaton, Stevenage (GB); Laura Hook, Stevenage (GB)

(73) Assignee: GlaxoSmithKline Intellectual Property Development Limited, Stevenage (GB)

( * ) Notice: Subject to any disclaimer, the term of this patent is extended or adjusted under 35 U.S.C. 154(b) by 0 days.

(21) Appl. No.: 19/361,756

(22) Filed: Oct. 17, 2025

(65) Prior Publication Data

US 2026/0167710 A1 Jun. 18, 2026

Related U.S. Application Data

(63) Continuation of application No. PCT/IB2024/061799, filed on Nov. 25, 2024.

(60) Provisional application No. 63/602,704, filed on Nov. 27, 2023.

(51) Int. Cl.

| | |
|---|---|
| ***A61K 39/395*** | (2006.01) |
| ***C07K 16/24*** | (2006.01) |
| *A61K 39/00* | (2006.01) |

(52) U.S. Cl.

CPC ...... *C07K 16/244* (2013.01); *A61K 2039/505* (2013.01); *C07K 2317/34* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 9,758,578 | B2 | 9/2017 | Fujino et al. |
| 10,059,764 | B2 | 8/2018 | Horlick et al. |
| 10,544,212 | B2 | 1/2020 | Bloom et al. |
| 11,738,081 | B2 | 8/2023 | Cohen et al. |
| 2016/0168242 | A1 | 6/2016 | Hass et al. |
| 2018/0118821 | A1 | 5/2018 | Benschop et al. |

OTHER PUBLICATIONS

England et al. Tozorakimab (MEDI3506: an anti-IL-33 antibody that inhibits IL-33 signalling via ST2 and RAGE/EGFR to reduce inflammation and epithelial dysfunction. Sci Rep. 13, 9825 (2023).*
Elizabeth E., et al., "Tozorakimab (MEDI3506): An Anti-IL-33 Antibody That Inhibits IL-33 Signalling via ST2 and RAGE/EGFR to Reduce Infammation and Epithelial Dysfunction," Scientific Reports, 2023, vol. 13(9825), pp. 1-15.
International Search Report and Written Opinion for International Application No. PCT/IB2024/061799, Mar. 24, 2025, 19 Pages.

* cited by examiner

*Primary Examiner* — Christine J Saoud
(74) *Attorney, Agent, or Firm* — Kelly A. Gauger

(57) ABSTRACT

The present disclosure relates to the treatment of interleukin 33 (IL-33) mediated diseases, including lung diseases. In particular, the present disclosure relates to IL-33 binding proteins, including anti-IL-33 antibodies, and their uses in the treatment of IL-33 mediated diseases.

22 Claims, 12 Drawing Sheets

Specification includes a Sequence Listing.

concentration effect of 22A06-458 on IL-33 stimulated eosinophil superoxide generation concentration effect of 22A06-458 on IL-33 stimulated $CD4^+$ T cell IFN-γ secretion concentration effect of 22A06-458 on IL-33 stimulated HUVEC IL-8 secretion concentration effect of 22A06-458 on IL-33 stimulated HUVEC IL-6 secretion RCSB:4KC3
ST2 complex with IL33

Overlay of 22A06-458 and
ST2 complexes with IL33

22A06-458 complex with IL33

RCSB:5VI4
mIL33 –mST2- mIL-1RAcP

Overlay of IL33 binding to
22A06-458 and mIL-1RAcP

22A06-458 complex with IL33

SEQUENCE LISTING

Sequence total quantity: 88
SEQ ID NO: 1 moltype = AA length = 5
FEATURE Location/Qualifiers
source 1..5
mol_type = protein
organism = synthetic construct
SEQUENCE: 1
SYGMH 5

SEQ ID NO: 2 moltype = AA length = 17
FEATURE Location/Qualifiers
source 1..17
mol_type = protein
organism = synthetic construct
VARIANT 16
note = K or Q
SEQUENCE: 2
EINPHGGSTS YAQKFXG 17

SEQ ID NO: 3 moltype = AA length = 17
FEATURE Location/Qualifiers
source 1..17

```
                        mol_type = protein
                        organism = synthetic construct
SEQUENCE: 3
EINPHGGSTS YAQKFQG                                                       17

SEQ ID NO: 4            moltype = AA  length = 17
FEATURE                 Location/Qualifiers
source                  1..17
                        mol_type = protein
                        organism = synthetic construct
SEQUENCE: 4
EINPHGGSTS YAQKFKG                                                       17

SEQ ID NO: 5            moltype = AA  length = 13
FEATURE                 Location/Qualifiers
source                  1..13
                        mol_type = protein
                        organism = synthetic construct
VARIANT                 13
                        note = I, L, or M
SEQUENCE: 5
PSAAYSHYLG JDX                                                           13

SEQ ID NO: 6            moltype = AA  length = 13
FEATURE                 Location/Qualifiers
source                  1..13
                        mol_type = protein
                        organism = synthetic construct
SEQUENCE: 6
PSAAYSHYLG IDM                                                           13

SEQ ID NO: 7            moltype = AA  length = 13
FEATURE                 Location/Qualifiers
source                  1..13
                        mol_type = protein
                        organism = synthetic construct
SEQUENCE: 7
PSAAYSHYLG IDL                                                           13

SEQ ID NO: 8            moltype = AA  length = 13
FEATURE                 Location/Qualifiers
source                  1..13
                        mol_type = protein
                        organism = synthetic construct
SEQUENCE: 8
PSAAYSHYLG LDI                                                           13

SEQ ID NO: 9            moltype = AA  length = 11
FEATURE                 Location/Qualifiers
source                  1..11
                        mol_type = protein
                        organism = synthetic construct
VARIANT                 2
                        note = A or T
VARIANT                 8
                        note = P or S
VARIANT                 11
                        note = A or S
SEQUENCE: 9
RXSQGISXWL X                                                             11

SEQ ID NO: 10           moltype = AA  length = 11
FEATURE                 Location/Qualifiers
source                  1..11
                        mol_type = protein
                        organism = synthetic construct
SEQUENCE: 10
RASQGISSWL A                                                             11

SEQ ID NO: 11           moltype = AA  length = 11
FEATURE                 Location/Qualifiers
source                  1..11
                        mol_type = protein
                        organism = synthetic construct
SEQUENCE: 11
RASQGISPWL A                                                             11

SEQ ID NO: 12           moltype = AA  length = 11
FEATURE                 Location/Qualifiers
```

```
source                  1..11
                        mol_type = protein
                        organism = synthetic construct
SEQUENCE: 12
RTSQGISSWL S                                                 11

SEQ ID NO: 13           moltype = AA  length = 7
FEATURE                 Location/Qualifiers
source                  1..7
                        mol_type = protein
                        organism = synthetic construct
VARIANT                 2
                        note = A or G
VARIANT                 4
                        note = R or S
SEQUENCE: 13
AXSXLQS                                                      7

SEQ ID NO: 14           moltype = AA  length = 7
FEATURE                 Location/Qualifiers
source                  1..7
                        mol_type = protein
                        organism = synthetic construct
SEQUENCE: 14
AASRLQS                                                      7

SEQ ID NO: 15           moltype = AA  length = 7
FEATURE                 Location/Qualifiers
source                  1..7
                        mol_type = protein
                        organism = synthetic construct
SEQUENCE: 15
AGSSLQS                                                      7

SEQ ID NO: 16           moltype = AA  length = 7
FEATURE                 Location/Qualifiers
source                  1..7
                        mol_type = protein
                        organism = synthetic construct
SEQUENCE: 16
AASSLQS                                                      7

SEQ ID NO: 17           moltype = AA  length = 9
FEATURE                 Location/Qualifiers
source                  1..9
                        mol_type = protein
                        organism = synthetic construct
VARIANT                 4
                        note = H or N
VARIANT                 6
                        note = F or L
SEQUENCE: 17
QQAXVXPLT                                                    9

SEQ ID NO: 18           moltype = AA  length = 9
FEATURE                 Location/Qualifiers
source                  1..9
                        mol_type = protein
                        organism = synthetic construct
SEQUENCE: 18
QQANVFPLT                                                    9

SEQ ID NO: 19           moltype = AA  length = 9
FEATURE                 Location/Qualifiers
source                  1..9
                        mol_type = protein
                        organism = synthetic construct
SEQUENCE: 19
QQAHVLPLT                                                    9

SEQ ID NO: 20           moltype = AA  length = 122
FEATURE                 Location/Qualifiers
source                  1..122
                        mol_type = protein
                        organism = synthetic construct
VARIANT                 65
                        note = K or Q
VARIANT                 111
                        note = I, L, or M
```

-continued

```
SEQUENCE: 20
QVQLVQSGAE VKKPGASVKV SCKASGYTFI SYGMHWVRQA PGQGLEWMGE INPHGGSTSY  60
AQKFXGRVTM TRDTSTSTVY MELSSLRSED TAVYYCARPS AAYSHYLGJD XWGRGTLVTV  120
SS                                                                 122

SEQ ID NO: 21           moltype = AA  length = 122
FEATURE                 Location/Qualifiers
source                  1..122
                        mol_type = protein
                        organism = synthetic construct
SEQUENCE: 21
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGID MWGRGTLVTV  120
SS                                                                 122

SEQ ID NO: 22           moltype = AA  length = 122
FEATURE                 Location/Qualifiers
source                  1..122
                        mol_type = protein
                        organism = synthetic construct
SEQUENCE: 22
QVQLVQSGAE VKKPGASVKV SCKASGYTFI SYGMHWVRQA PGQGLEWMGE INPHGGSTSY  60
AQKFKGRVTM TRDTSTSTVY MELSSLRSED TAVYYCARPS AAYSHYLGID LWGRGTLVTV  120
SS                                                                 122

SEQ ID NO: 23           moltype = AA  length = 122
FEATURE                 Location/Qualifiers
source                  1..122
                        mol_type = protein
                        organism = synthetic construct
SEQUENCE: 23
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGLD IWGRGTLVTV  120
SS                                                                 122

SEQ ID NO: 24           moltype = AA  length = 122
FEATURE                 Location/Qualifiers
source                  1..122
                        mol_type = protein
                        organism = synthetic construct
SEQUENCE: 24
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGID LWGRGTLVTV  120
SS                                                                 122

SEQ ID NO: 25           moltype = AA  length = 107
FEATURE                 Location/Qualifiers
source                  1..107
                        mol_type = protein
                        organism = synthetic construct
VARIANT                 25
                        note = A or T
VARIANT                 31
                        note = P or S
VARIANT                 34
                        note = A or S
VARIANT                 51
                        note = A or G
VARIANT                 53
                        note = R or S
VARIANT                 92
                        note = H or N
VARIANT                 94
                        note = F or L
SEQUENCE: 25
DIQMTQSPSS VSASVGDRVT ITCRXSQGIS XWLXWYQQKP GKAPKLLIYA XSXLQSGVPS  60
RFSGSGSGTD FTLTISSLQP EDFATYYCQQ AXVXPLTFGG GTKVEIK                107

SEQ ID NO: 26           moltype = AA  length = 107
FEATURE                 Location/Qualifiers
source                  1..107
                        mol_type = protein
                        organism = synthetic construct
SEQUENCE: 26
DIQMTQSPSS VSASVGDRVT ITCRASQGIS SWLAWYQQKP GKAPKLLIYA ASRLQSGVPS  60
RFSGSGSGTD FTLTISSLQP EDFATYYCQQ ANVFPLTFGG GTKVEIK                107

SEQ ID NO: 27           moltype = AA  length = 107
FEATURE                 Location/Qualifiers
```

```
source                1..107
                      mol_type = protein
                      organism = synthetic construct
SEQUENCE: 27
DIQMTQSPSS VSASVGDRVT ITCRASQGIS PWLAWYQQKP GKAPKLLIYA GSSLQSGVPS  60
RFSGSGSGTD FTLTISSLQP EDFATYYCQQ ANVFPLTFGG GTKVEIK                107

SEQ ID NO: 28         moltype = AA  length = 107
FEATURE               Location/Qualifiers
source                1..107
                      mol_type = protein
                      organism = synthetic construct
SEQUENCE: 28
DIQMTQSPSS VSASVGDRVT ITCRTSQGIS SWLSWYQQKP GKAPKLLIYA ASSLQSGVPS  60
RFSGSGSGTD FTLTISSLQP EDFATYYCQQ AHVLPLTFGG GTKVEIK                107

SEQ ID NO: 29         moltype = AA  length = 452
FEATURE               Location/Qualifiers
source                1..452
                      mol_type = protein
                      organism = synthetic construct
VARIANT               65
                      note = K or Q
VARIANT               111
                      note = I, L, or M
SEQUENCE: 29
QVQLVQSGAE VKKPGASVKV SCKASGYTFI SYGMHWVRQA PGQGLEWMGE INPHGGSTSY  60
AQKFXGRVTM TRDTSTSTVY MELSSLRSED TAVYYCARPS AAYSHYLGJD XWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 30         moltype = AA  length = 452
FEATURE               Location/Qualifiers
source                1..452
                      mol_type = protein
                      organism = synthetic construct
SEQUENCE: 30
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGID MWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 31         moltype = AA  length = 452
FEATURE               Location/Qualifiers
source                1..452
                      mol_type = protein
                      organism = synthetic construct
SEQUENCE: 31
QVQLVQSGAE VKKPGASVKV SCKASGYTFI SYGMHWVRQA PGQGLEWMGE INPHGGSTSY  60
AQKFKGRVTM TRDTSTSTVY MELSSLRSED TAVYYCARPS AAYSHYLGID LWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 32         moltype = AA  length = 452
FEATURE               Location/Qualifiers
source                1..452
                      mol_type = protein
                      organism = synthetic construct
SEQUENCE: 32
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGLD IWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452
```

```
SEQ ID NO: 33          moltype = AA  length = 452
FEATURE                Location/Qualifiers
source                 1..452
                       mol_type = protein
                       organism = synthetic construct
SEQUENCE: 33
QVQLVQSGAE VKKPGASVKV SCKASGYTFI SYGMHWVRQA PGQGLEWMGE INPHGGSTSY  60
AQKFQGRVTM TRDTSTSTVY MELSSLRSED TAVYYCARPS AAYSHYLGID LWGRGTLVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
GGPSVFLFPP KPKDTLYITR EPEVTCVVVD VSHEDPEVKF NWYVDGVEVH NAKTKPREEQ  300
YNSTYRVVSV LTVLHQDWLN GKEYKCKVSN KALPAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 34          moltype = AA  length = 214
FEATURE                Location/Qualifiers
source                 1..214
                       mol_type = protein
                       organism = synthetic construct
VARIANT                25
                       note = A or T
VARIANT                31
                       note = P or S
VARIANT                34
                       note = A or S
VARIANT                51
                       note = A or G
VARIANT                53
                       note = R or S
VARIANT                92
                       note = H or N
VARIANT                94
                       note = F or L
SEQUENCE: 34
DIQMTQSPSS VSASVGDRVT ITCRXSQGIS XWLXWYQQKP GKAPKLLIYA XSXLQSGVPS  60
RFSGSGSGTD FTLTISSLQP EDFATYYCQQ AXVXPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 35          moltype = AA  length = 214
FEATURE                Location/Qualifiers
source                 1..214
                       mol_type = protein
                       organism = synthetic construct
SEQUENCE: 35
DIQMTQSPSS VSASVGDRVT ITCRASQGIS SWLAWYQQKP GKAPKLLIYA ASRLQSGVPS  60
RFSGSGSGTD FTLTISSLQP EDFATYYCQQ ANVFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 36          moltype = AA  length = 214
FEATURE                Location/Qualifiers
source                 1..214
                       mol_type = protein
                       organism = synthetic construct
SEQUENCE: 36
DIQMTQSPSS VSASVGDRVT ITCRASQGIS PWLAWYQQKP GKAPKLLIYA GSSLQSGVPS  60
RFSGSGSGTD FTLTISSLQP EDFATYYCQQ ANVFPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 37          moltype = AA  length = 214
FEATURE                Location/Qualifiers
source                 1..214
                       mol_type = protein
                       organism = synthetic construct
SEQUENCE: 37
DIQMTQSPSS VSASVGDRVT ITCRTSQGIS SWLSWYQQKP GKAPKLLIYA ASSLQSGVPS  60
RFSGSGSGTD FTLTISSLQP EDFATYYCQQ AHVLPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 38          moltype = DNA  length = 366
FEATURE                Location/Qualifiers
source                 1..366
                       mol_type = other DNA
                       organism = synthetic construct
```

```
SEQUENCE: 38
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcmthgac mtntggggca ggggcaccct ggtgaccgtg  360
agctct                                                             366

SEQ ID NO: 39          moltype = DNA  length = 366
FEATURE                Location/Qualifiers
source                 1..366
                       mol_type = other DNA
                       organism = synthetic construct
SEQUENCE: 39
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcmthgac ttrtggggca ggggcaccct ggtgaccgtg  360
agctct                                                             366

SEQ ID NO: 40          moltype = DNA  length = 366
FEATURE                Location/Qualifiers
source                 1..366
                       mol_type = other DNA
                       organism = synthetic construct
SEQUENCE: 40
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcytggac mtntggggca ggggcaccct ggtgaccgtg  360
agctct                                                             366

SEQ ID NO: 41          moltype = DNA  length = 366
FEATURE                Location/Qualifiers
source                 1..366
                       mol_type = other DNA
                       organism = synthetic construct
SEQUENCE: 41
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcytggac ttrtggggca ggggcaccct ggtgaccgtg  360
agctct                                                             366

SEQ ID NO: 42          moltype = DNA  length = 366
FEATURE                Location/Qualifiers
source                 1..366
                       mol_type = other DNA
                       organism = synthetic construct
SEQUENCE: 42
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcttagac mtntggggca ggggcaccct ggtgaccgtg  360
agctct                                                             366

SEQ ID NO: 43          moltype = DNA  length = 366
FEATURE                Location/Qualifiers
source                 1..366
                       mol_type = other DNA
                       organism = synthetic construct
SEQUENCE: 43
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcttagac ttrtggggca ggggcaccct ggtgaccgtg  360
agctct                                                             366
```

```
SEQ ID NO: 44          moltype = DNA  length = 366
FEATURE                Location/Qualifiers
source                 1..366
                       mol_type = other DNA
                       organism = synthetic construct
SEQUENCE: 44
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tccagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcatcgac atgtggggca ggggcaccct ggtgaccgtg  360
agctct                                                             366

SEQ ID NO: 45          moltype = DNA  length = 366
FEATURE                Location/Qualifiers
source                 1..366
                       mol_type = other DNA
                       organism = synthetic construct
SEQUENCE: 45
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcaagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcatcgac ctgtggggca ggggcaccct ggtgaccgtg  360
agctct                                                             366

SEQ ID NO: 46          moltype = DNA  length = 366
FEATURE                Location/Qualifiers
source                 1..366
                       mol_type = other DNA
                       organism = synthetic construct
SEQUENCE: 46
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tccagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcctggac atctggggca ggggcaccct ggtgaccgtg  360
agctct                                                             366

SEQ ID NO: 47          moltype = DNA  length = 366
FEATURE                Location/Qualifiers
source                 1..366
                       mol_type = other DNA
                       organism = synthetic construct
SEQUENCE: 47
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tccagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcatcgac ctgtggggca ggggcaccct ggtgaccgtg  360
agctct                                                             366

SEQ ID NO: 48          moltype = DNA  length = 321
FEATURE                Location/Qualifiers
source                 1..321
                       mol_type = other DNA
                       organism = synthetic construct
SEQUENCE: 48
gacatccaga tgacccagag ccccagctca gtgagcgcta gcgtgggcga cagggtgacc  60
atcacctgca ggrcnagcca gggcattagc ycntggctgk cntggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tncccctgac cttcggcggc  300
ggcacaaaag tcgagatcaa g                                            321

SEQ ID NO: 49          moltype = DNA  length = 321
FEATURE                Location/Qualifiers
source                 1..321
                       mol_type = other DNA
                       organism = synthetic construct
SEQUENCE: 49
gacatccaga tgacccagag ccccagctca gtgagcgcta gcgtgggcga cagggtgacc  60
atcacctgca ggrcnagcca gggcattagc ycntggctgk cntggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
```

```
gaggacttcg ccacctacta ctgccagcag gccmaygtgy tnccccctgac cttcggcggc  300
ggcacaaaag tcgagatcaa g                                               321

SEQ ID NO: 50           moltype = DNA  length = 321
FEATURE                 Location/Qualifiers
source                  1..321
                        mol_type = other DNA
                        organism = synthetic construct
SEQUENCE: 50
gacatccaga tgacccagag ccccagctca gtgagcgcta gcgtgggcga cagggtgacc  60
atcacctgca ggrcnagcca gggcattagc ycntggctga gytggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa g                                               321

SEQ ID NO: 51           moltype = DNA  length = 321
FEATURE                 Location/Qualifiers
source                  1..321
                        mol_type = other DNA
                        organism = synthetic construct
SEQUENCE: 51
gacatccaga tgacccagag ccccagctca gtgagcgcta gcgtgggcga cagggtgacc  60
atcacctgca ggrcnagcca gggcattagc ycntggctga gytggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa g                                               321

SEQ ID NO: 52           moltype = DNA  length = 321
FEATURE                 Location/Qualifiers
source                  1..321
                        mol_type = other DNA
                        organism = synthetic construct
SEQUENCE: 52
gacatccaga tgacccagag ccccagctca gtgagcgcta gcgtgggcga cagggtgacc  60
atcacctgca ggrcnagcca gggcattagc agytggctgk cntggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa g                                               321

SEQ ID NO: 53           moltype = DNA  length = 321
FEATURE                 Location/Qualifiers
source                  1..321
                        mol_type = other DNA
                        organism = synthetic construct
SEQUENCE: 53
gacatccaga tgacccagag ccccagctca gtgagcgcta gcgtgggcga cagggtgacc  60
atcacctgca ggrcnagcca gggcattagc agytggctgk cntggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa g                                               321

SEQ ID NO: 54           moltype = DNA  length = 321
FEATURE                 Location/Qualifiers
source                  1..321
                        mol_type = other DNA
                        organism = synthetic construct
SEQUENCE: 54
gacatccaga tgacccagag ccccagctca gtgagcgcta gcgtgggcga cagggtgacc  60
atcacctgca ggrcnagcca gggcattagc agytggctga gytggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa g                                               321

SEQ ID NO: 55           moltype = DNA  length = 321
FEATURE                 Location/Qualifiers
source                  1..321
                        mol_type = other DNA
                        organism = synthetic construct
SEQUENCE: 55
gacatccaga tgacccagag ccccagctca gtgagcgcta gcgtgggcga cagggtgacc  60
atcacctgca ggrcnagcca gggcattagc agytggctga gytggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
```

```
ggcacaaaag tcgagatcaa g                                           321

SEQ ID NO: 56          moltype = DNA  length = 321
FEATURE                Location/Qualifiers
source                 1..321
                       mol_type = other DNA
                       organism = synthetic construct
SEQUENCE: 56
gacatccaga tgacccagag ccccagctca gtgagcgcta gcgtgggcga cagggtgacc  60
atcacctgca gggccagcca gggcattagc agctggctgg cctggtacca gcagaagccc  120
ggcaaggccc ccaagctcct gatctacgcc gccagcaggc tgcagagcgg cgtgccctcc  180
aggtttagcg gcagcggaag cggcaccgac ttcaccctga ccatcagcag cctgcagccc  240
gaggacttcg ccacctacta ctgccagcag gccaacgtgt tcccccctgac cttcggcggc  300
ggcacaaaag tcgagatcaa g                                           321

SEQ ID NO: 57          moltype = DNA  length = 321
FEATURE                Location/Qualifiers
source                 1..321
                       mol_type = other DNA
                       organism = synthetic construct
SEQUENCE: 57
gacatccaga tgacccagag ccccagctca gtgagcgcta gcgtgggcga cagggtgacc  60
atcacctgca gggccagcca gggcattagc ccctggctgg cctggtacca gcagaagccc  120
ggcaaggccc ccaagctcct gatctacgcc ggcagcagcc tgcagagcgg cgtgccctcc  180
aggtttagcg gcagcggaag cggcaccgac ttcaccctga ccatcagcag cctgcagccc  240
gaggacttcg ccacctacta ctgccagcag gccaacgtgt tcccccctgac cttcggcggc  300
ggcacaaaag tcgagatcaa g                                           321

SEQ ID NO: 58          moltype = DNA  length = 321
FEATURE                Location/Qualifiers
source                 1..321
                       mol_type = other DNA
                       organism = synthetic construct
SEQUENCE: 58
gacatccaga tgacccagag ccccagctca gtgagcgcta gcgtgggcga cagggtgacc  60
atcacctgca ggaccagcca gggcattagc agctggctga gctggtacca gcagaagccc  120
ggcaaggccc ccaagctcct gatctacgcc gccagcagcc tgcagagcgg cgtgccctcc  180
aggtttagcg gcagcggaag cggcaccgac ttcaccctga ccatcagcag cctgcagccc  240
gaggacttcg ccacctacta ctgccagcag gcccacgtgc tgcccctgac cttcggcggc  300
ggcacaaaag tcgagatcaa g                                           321

SEQ ID NO: 59          moltype = DNA  length = 1356
FEATURE                Location/Qualifiers
source                 1..1356
                       mol_type = other DNA
                       organism = synthetic construct
SEQUENCE: 59
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcmthgac mtntggggca ggggcaccct ggtgaccgtg  360
agctctgcca gcaccaaggg ccccagcgtg ttccccctgg ccccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgccccccct gccctgcccc cgagctgctg  720
ggaggcccca gcgtgttcct gttccccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                           1356

SEQ ID NO: 60          moltype = DNA  length = 1356
FEATURE                Location/Qualifiers
source                 1..1356
                       mol_type = other DNA
                       organism = synthetic construct
SEQUENCE: 60
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
```

```
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcmthgac ttrtggggca ggggcaccct ggtgaccgtg  360
agctctgcca gcaccaaggg ccccagcgtg ttcccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttccccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 61           moltype = DNA  length = 1356
FEATURE                 Location/Qualifiers
source                  1..1356
                        mol_type = other DNA
                        organism = synthetic construct
SEQUENCE: 61
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcytggac mtntggggca ggggcaccct ggtgaccgtg  360
agctctgcca gcaccaaggg ccccagcgtg ttcccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttccccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 62           moltype = DNA  length = 1356
FEATURE                 Location/Qualifiers
source                  1..1356
                        mol_type = other DNA
                        organism = synthetic construct
SEQUENCE: 62
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcmarggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcytggac ttrtggggca ggggcaccct ggtgaccgtg  360
agctctgcca gcaccaaggg ccccagcgtg ttcccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttccccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
```

agatggcagc agggcaacgt gttcagctgc tccgtgatgc acgaggccct gcacaatcac 1320
tacacccaga agagcctgag cctgtcccct ggcaag 1356

SEQ ID NO: 63 moltype = DNA length = 1356
FEATURE Location/Qualifiers
source 1..1356
mol_type = other DNA
organism = synthetic construct
SEQUENCE: 63
caggtgcagc tggtgcagag cggcgccgaa gtgaaaaagc ccggcgccag cgtgaaggtc 60
agctgcaagg cctccgggta caccttcatc agctacggca tgcactgggt gaggcaggcc 120
cccggccagg gcctcgagtg gatgggcgag atcaaccccc acggaggcag caccagctac 180
gcccagaagt tcmarggcag ggtgaccatg acaagggaca ccagcaccag caccgtgtac 240
atggagctga gcagcctgag gagcgaggac accgccgtgt attactgcgc aaggcccagc 300
gccgcctaca gccactacct gggcttagac mtntggggca ggggcaccct ggtgaccgtg 360
agctctgcca gcaccaaggg ccccagcgtg ttccccctgg cccccagcag caagagcacc 420
agcggcggca cagccgccct gggctgcctg gtgaaggact acttccccga gcccgtgacc 480
gtgtcctgga acagcggagc cctgaccagc ggcgtgcaca ccttccccgc cgtgctgcag 540
agcagcggcc tgtacagcct gagcagcgtg gtgaccgtgc ccagcagcag cctgggcacc 600
cagacctaca tctgtaacgt gaaccacaag cccagcaaca ccaaggtgga caagaaggtg 660
gagcccaaga gctgtgacaa gacccacacc tgccccccct gccctgcccc cgagctgctg 720
ggaggcccca gcgtgttcct gttccccccc aagcctaagg acaccctgta catcaccaga 780
gaacccgagg tgacctgtgt ggtggtggat gtgagccacg aggaccctga ggtgaagttc 840
aactggtacg tggacggcgt ggaggtgcac aatgccaaga ccaagcccag ggaggagcag 900
tacaacagca cctaccgggt ggtgtccgtg ctgaccgtgc tgcaccagga ttggctgaac 960
ggcaaggagt acaagtgtaa ggtgtccaac aaggccctgc ctgcccctat cgagaaaacc 1020
atcagcaagg ccaagggcca gcccagagag ccccaggtgt acaccctgcc ccctagcaga 1080
gatgagctga ccaagaacca ggtgtccctg acctgcctgg tgaagggctt ctaccccagc 1140
gacatcgccg tggagtggga gagcaacggc cagcccgaga acaactacaa gaccaccccc 1200
cctgtgctgg acagcgatgg cagcttcttc ctgtacagca agctgaccgt ggacaagagc 1260
agatggcagc agggcaacgt gttcagctgc tccgtgatgc acgaggccct gcacaatcac 1320
tacacccaga agagcctgag cctgtcccct ggcaag 1356

SEQ ID NO: 64 moltype = DNA length = 1356
FEATURE Location/Qualifiers
source 1..1356
mol_type = other DNA
organism = synthetic construct
SEQUENCE: 64
caggtgcagc tggtgcagag cggcgccgaa gtgaaaaagc ccggcgccag cgtgaaggtc 60
agctgcaagg cctccgggta caccttcatc agctacggca tgcactgggt gaggcaggcc 120
cccggccagg gcctcgagtg gatgggcgag atcaaccccc acggaggcag caccagctac 180
gcccagaagt tcmarggcag ggtgaccatg acaagggaca ccagcaccag caccgtgtac 240
atggagctga gcagcctgag gagcgaggac accgccgtgt attactgcgc aaggcccagc 300
gccgcctaca gccactacct gggcttagac ttrtggggca ggggcaccct ggtgaccgtg 360
agctctgcca gcaccaaggg ccccagcgtg ttccccctgg cccccagcag caagagcacc 420
agcggcggca cagccgccct gggctgcctg gtgaaggact acttccccga gcccgtgacc 480
gtgtcctgga acagcggagc cctgaccagc ggcgtgcaca ccttccccgc cgtgctgcag 540
agcagcggcc tgtacagcct gagcagcgtg gtgaccgtgc ccagcagcag cctgggcacc 600
cagacctaca tctgtaacgt gaaccacaag cccagcaaca ccaaggtgga caagaaggtg 660
gagcccaaga gctgtgacaa gacccacacc tgccccccct gccctgcccc cgagctgctg 720
ggaggcccca gcgtgttcct gttccccccc aagcctaagg acaccctgta catcaccaga 780
gaacccgagg tgacctgtgt ggtggtggat gtgagccacg aggaccctga ggtgaagttc 840
aactggtacg tggacggcgt ggaggtgcac aatgccaaga ccaagcccag ggaggagcag 900
tacaacagca cctaccgggt ggtgtccgtg ctgaccgtgc tgcaccagga ttggctgaac 960
ggcaaggagt acaagtgtaa ggtgtccaac aaggccctgc ctgcccctat cgagaaaacc 1020
atcagcaagg ccaagggcca gcccagagag ccccaggtgt acaccctgcc ccctagcaga 1080
gatgagctga ccaagaacca ggtgtccctg acctgcctgg tgaagggctt ctaccccagc 1140
gacatcgccg tggagtggga gagcaacggc cagcccgaga acaactacaa gaccaccccc 1200
cctgtgctgg acagcgatgg cagcttcttc ctgtacagca agctgaccgt ggacaagagc 1260
agatggcagc agggcaacgt gttcagctgc tccgtgatgc acgaggccct gcacaatcac 1320
tacacccaga agagcctgag cctgtcccct ggcaag 1356

SEQ ID NO: 65 moltype = DNA length = 1356
FEATURE Location/Qualifiers
source 1..1356
mol_type = other DNA
organism = synthetic construct
SEQUENCE: 65
caggtgcagc tggtgcagag cggcgccgaa gtgaaaaagc ccggcgccag cgtgaaggtc 60
agctgcaagg cctccgggta caccttcatc agctacggca tgcactgggt gaggcaggcc 120
cccggccagg gcctcgagtg gatgggcgag atcaaccccc acggaggcag caccagctac 180
gcccagaagt tccagggcag ggtgaccatg acaagggaca ccagcaccag caccgtgtac 240
atggagctga gcagcctgag gagcgaggac accgccgtgt attactgcgc aaggcccagc 300
gccgcctaca gccactacct gggcatcgac atgtggggca ggggcaccct ggtgaccgtg 360
agctctgcca gcaccaaggg ccccagcgtg ttccccctgg cccccagcag caagagcacc 420
agcggcggca cagccgccct gggctgcctg gtgaaggact acttccccga gcccgtgacc 480
gtgtcctgga acagcggagc cctgaccagc ggcgtgcaca ccttccccgc cgtgctgcag 540
agcagcggcc tgtacagcct gagcagcgtg gtgaccgtgc ccagcagcag cctgggcacc 600

```
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttcccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 66          moltype = DNA  length = 1356
FEATURE                Location/Qualifiers
source                 1..1356
                       mol_type = other DNA
                       organism = synthetic construct
SEQUENCE: 66
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tcaagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcatcgac ctgtggggca ggggcaccct ggtgaccgtg  360
agctctgcca gcaccaaggg ccccagcgtg ttccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttcccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 67          moltype = DNA  length = 1356
FEATURE                Location/Qualifiers
source                 1..1356
                       mol_type = other DNA
                       organism = synthetic construct
SEQUENCE: 67
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tccagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcctggac atctggggca ggggcaccct ggtgaccgtg  360
agctctgcca gcaccaaggg ccccagcgtg ttccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttcccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 68          moltype = DNA  length = 1356
FEATURE                Location/Qualifiers
source                 1..1356
                       mol_type = other DNA
                       organism = synthetic construct
```

```
SEQUENCE: 68
caggtgcagc tggtgcagag cggcgccgaa gtgaaaaagc ccggcgccag cgtgaaggtc  60
agctgcaagg cctccgggta caccttcatc agctacggca tgcactgggt gaggcaggcc  120
cccggccagg gcctcgagtg gatgggcgag atcaaccccc acggaggcag caccagctac  180
gcccagaagt tccagggcag ggtgaccatg acaagggaca ccagcaccag caccgtgtac  240
atggagctga gcagcctgag gagcgaggac accgccgtgt attactgcgc aaggcccagc  300
gccgcctaca gccactacct gggcatcgac ctgtggggca ggggcaccct ggtgaccgtg  360
agctctgcca gcaccaaggg ccccagcgtg ttccccctgg cccccagcag caagagcacc  420
agcggcggca cagccgccct gggctgcctg gtgaaggact acttccccga gcccgtgacc  480
gtgtcctgga acagcggagc cctgaccagc ggcgtgcaca ccttccccgc cgtgctgcag  540
agcagcggcc tgtacagcct gagcagcgtg gtgaccgtgc ccagcagcag cctgggcacc  600
cagacctaca tctgtaacgt gaaccacaag cccagcaaca ccaaggtgga caagaaggtg  660
gagcccaaga gctgtgacaa gacccacacc tgcccccct gccctgcccc cgagctgctg  720
ggaggcccca gcgtgttcct gttccccccc aagcctaagg acaccctgta catcaccaga  780
gaacccgagg tgacctgtgt ggtggtggat gtgagccacg aggaccctga ggtgaagttc  840
aactggtacg tggacggcgt ggaggtgcac aatgccaaga ccaagcccag ggaggagcag  900
tacaacagca cctaccgggt ggtgtccgtg ctgaccgtgc tgcaccagga ttggctgaac  960
ggcaaggagt acaagtgtaa ggtgtccaac aaggccctgc ctgcccctat cgagaaaacc  1020
atcagcaagg ccaagggcca gcccagagag ccccaggtgt acaccctgcc ccctagcaga  1080
gatgagctga ccaagaacca ggtgtccctg acctgcctgg tgaagggctt ctaccccagc  1140
gacatcgccg tggagtggga gagcaacggc cagcccgaga acaactacaa gaccaccccc  1200
cctgtgctgg acagcgatgg cagcttcttc ctgtacagca agctgaccgt ggacaagagc  1260
agatggcagc agggcaacgt gttcagctgc tccgtgatgc acgaggccct gcacaatcac  1320
tacacccaga agagcctgag cctgtcccct ggcaag                            1356

SEQ ID NO: 69          moltype = DNA  length = 642
FEATURE                Location/Qualifiers
source                 1..642
                       mol_type = other DNA
                       organism = synthetic construct
SEQUENCE: 69
gacatccaga tgacccagag ccccagctca gtgagcgcta gcgtgggcga cagggtgacc  60
atcacctgca ggrcnagcca gggcattagc ycntggctgk cntggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                     642

SEQ ID NO: 70          moltype = DNA  length = 642
FEATURE                Location/Qualifiers
source                 1..642
                       mol_type = other DNA
                       organism = synthetic construct
SEQUENCE: 70
gacatccaga tgacccagag ccccagctca gtgagcgcta gcgtgggcga cagggtgacc  60
atcacctgca ggrcnagcca gggcattagc ycntggctgk cntggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                     642

SEQ ID NO: 71          moltype = DNA  length = 642
FEATURE                Location/Qualifiers
source                 1..642
                       mol_type = other DNA
                       organism = synthetic construct
SEQUENCE: 71
gacatccaga tgacccagag ccccagctca gtgagcgcta gcgtgggcga cagggtgacc  60
atcacctgca ggrcnagcca gggcattagc ycntggctga gytggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                     642
```

```
SEQ ID NO: 72          moltype = DNA  length = 642
FEATURE                Location/Qualifiers
source                 1..642
                       mol_type = other DNA
                       organism = synthetic construct
SEQUENCE: 72
gacatccaga tgacccagag ccccagctca gtgagcgcta gcgtgggcga cagggtgacc  60
atcacctgca ggrcnagcca gggcattagc ycntggctga gytggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 73          moltype = DNA  length = 642
FEATURE                Location/Qualifiers
source                 1..642
                       mol_type = other DNA
                       organism = synthetic construct
SEQUENCE: 73
gacatccaga tgacccagag ccccagctca gtgagcgcta gcgtgggcga cagggtgacc  60
atcacctgca ggrcnagcca gggcattagc agytggctgk cntggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 74          moltype = DNA  length = 642
FEATURE                Location/Qualifiers
source                 1..642
                       mol_type = other DNA
                       organism = synthetic construct
SEQUENCE: 74
gacatccaga tgacccagag ccccagctca gtgagcgcta gcgtgggcga cagggtgacc  60
atcacctgca ggrcnagcca gggcattagc agytggctgk cntggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 75          moltype = DNA  length = 642
FEATURE                Location/Qualifiers
source                 1..642
                       mol_type = other DNA
                       organism = synthetic construct
SEQUENCE: 75
gacatccaga tgacccagag ccccagctca gtgagcgcta gcgtgggcga cagggtgacc  60
atcacctgca ggrcnagcca gggcattagc agytggctga gytggtacca gcagaagccc  120
ggcaaggccc ccaagctcct gatctacgcc gsnagcmgnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 76          moltype = DNA  length = 642
FEATURE                Location/Qualifiers
source                 1..642
                       mol_type = other DNA
                       organism = synthetic construct
SEQUENCE: 76
gacatccaga tgacccagag ccccagctca gtgagcgcta gcgtgggcga cagggtgacc  60
```

```
atcacctgca ggrcnagcca gggcattagc agytggctga gytggtacca gcagaagccc  120
ggcaaggccc ccaagctcct gatctacgcc gsnagctcnc tgcagagcgg cgtgccctcc  180
aggtttagcg gcagcggaag cggcaccgac ttcaccctga ccatcagcag cctgcagccc  240
gaggacttcg ccacctacta ctgccagcag gccmaygtgy tnccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 77          moltype = DNA  length = 642
FEATURE                Location/Qualifiers
source                 1..642
                       mol_type = other DNA
                       organism = synthetic construct
SEQUENCE: 77
gacatccaga tgacccagag ccccagctca gtgagcgcta gcgtgggcga cagggtgacc  60
atcacctgca gggccagcca gggcattagc agctggctgg cctggtacca gcagaagccc  120
ggcaaggccc ccaagctcct gatctacgcc gccagcaggc tgcagagcgg cgtgccctcc  180
aggtttagcg gcagcggaag cggcaccgac ttcaccctga ccatcagcag cctgcagccc  240
gaggacttcg ccacctacta ctgccagcag gccaacgtgt tccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 78          moltype = DNA  length = 642
FEATURE                Location/Qualifiers
source                 1..642
                       mol_type = other DNA
                       organism = synthetic construct
SEQUENCE: 78
gacatccaga tgacccagag ccccagctca gtgagcgcta gcgtgggcga cagggtgacc  60
atcacctgca gggccagcca gggcattagc cccctggctgg cctggtacca gcagaagccc  120
ggcaaggccc ccaagctcct gatctacgcc ggcagcagcc tgcagagcgg cgtgccctcc  180
aggtttagcg gcagcggaag cggcaccgac ttcaccctga ccatcagcag cctgcagccc  240
gaggacttcg ccacctacta ctgccagcag gccaacgtgt tccccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 79          moltype = DNA  length = 642
FEATURE                Location/Qualifiers
source                 1..642
                       mol_type = other DNA
                       organism = synthetic construct
SEQUENCE: 79
gacatccaga tgacccagag ccccagctca gtgagcgcta gcgtgggcga cagggtgacc  60
atcacctgca ggaccagcca gggcattagc agctggctga gctggtacca gcagaagccc  120
ggcaaggccc ccaagctcct gatctacgcc gccagcagcc tgcagagcgg cgtgccctcc  180
aggtttagcg gcagcggaag cggcaccgac ttcaccctga ccatcagcag cctgcagccc  240
gaggacttcg ccacctacta ctgccagcag gcccacgtgc tgcccctgac cttcggcggc  300
ggcacaaaag tcgagatcaa gcgtacggtg gccgccccca gcgtgttcat cttccccccc  360
agcgatgagc agctgaagag cggcaccgcc agcgtggtgt gtctgctgaa caacttctac  420
ccccgggagg ccaaggtgca gtggaaggtg gacaatgccc tgcagagcgg caacagccag  480
gagagcgtga ccgagcagga cagcaaggac tccacctaca gcctgagcag caccctgacc  540
ctgagcaagg ccgactacga gaagcacaag gtgtacgcct gtgaggtgac ccaccagggc  600
ctgtccagcc ccgtgaccaa gagcttcaac cggggcgagt gc                    642

SEQ ID NO: 80          moltype = AA  length = 20
FEATURE                Location/Qualifiers
source                 1..20
                       mol_type = protein
                       organism = synthetic construct
SEQUENCE: 80
YESQHPSNES GDGVDGKMLM                                             20

SEQ ID NO: 81          moltype = AA  length = 10
FEATURE                Location/Qualifiers
source                 1..10
                       mol_type = protein
                       organism = synthetic construct
SEQUENCE: 81
```

-continued

```
FVLHNMHSNC                                                        10

SEQ ID NO: 82          moltype = AA  length = 20
FEATURE                Location/Qualifiers
source                 1..20
                       mol_type = protein
                       organism = synthetic construct
SEQUENCE: 82
YYESQHPSNE SGDGVDGKML                                             20

SEQ ID NO: 83          moltype = AA  length = 10
FEATURE                Location/Qualifiers
source                 1..10
                       mol_type = protein
                       organism = synthetic construct
SEQUENCE: 83
VLHNMHSNCV                                                        10

SEQ ID NO: 84          moltype = AA  length = 6
FEATURE                Location/Qualifiers
source                 1..6
                       mol_type = protein
                       organism = synthetic construct
SEQUENCE: 84
SPITEY                                                            6

SEQ ID NO: 85          moltype = AA  length = 7
FEATURE                Location/Qualifiers
source                 1..7
                       mol_type = protein
                       organism = synthetic construct
SEQUENCE: 85
VDSSENL                                                           7

SEQ ID NO: 86          moltype = AA  length = 19
FEATURE                Location/Qualifiers
source                 1..19
                       mol_type = protein
                       organism = synthetic construct
SEQUENCE: 86
YESQHPSNES GDGVDGKML                                              19

SEQ ID NO: 87          moltype = AA  length = 9
FEATURE                Location/Qualifiers
source                 1..9
                       mol_type = protein
                       organism = synthetic construct
SEQUENCE: 87
VLHNMHSNC                                                         9

SEQ ID NO: 88          moltype = AA  length = 270
FEATURE                Location/Qualifiers
source                 1..270
                       mol_type = protein
                       organism = Homo sapiens
SEQUENCE: 88
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                   270
```

IL-33 BINDING ANTIBODIES

CROSS-REFERENCE TO RELATED APPLICATIONS

This application is a continuation of International Application No. PCT/IB2024/061799, filed Nov. 25, 2024, which claims priority to and benefit of U.S. Provisional Application No. 63/602,704, filed Nov. 27, 2023, both of which are incorporated by reference herein in their entireties.

SEQUENCE LISTING SUBMITTED ELECTRONICALLY

This application contains a sequence listing, which is provided in XML format with a file name "70387US02_3April2026.xml". The XML file has a size of 119,119 bytes and was created on Apr. 3, 2026. The sequence listing submitted electronically is part of the specification and is incorporated herein by reference in its entirety.

FIELD OF THE INVENTION

The present disclosure relates to the treatment of interleukin 33 (IL-33) mediated diseases, including respiratory diseases. In particular, the present disclosure relates to IL-33 binding proteins, including anti-IL-33 antibodies, and their uses in the treatment of IL-33 mediated diseases.

BACKGROUND TO THE INVENTION

IL-33 plays a role in a number of different diseases including, but not limited to, chronic obstructive pulmonary disease (COPD), asthma, bronchitis, bronchiolitis, acute respiratory failure, inflammatory lung diseases, diabetic kidney disease, endometriosis, chronic rhinosinusitis with nasal polyps, food hypersensitivity, peanut allergy, allergic rhinitis, eosinophilic oesophagitis, atopic dermatitis, cystic fibrosis, and chronic urticaria. These serious diseases affect hundreds of millions of people worldwide.

One example of an IL-33 mediated disease is Chronic Obstructive Pulmonary Disease (COPD), which is a lung disease characterized by persistent respiratory symptoms caused by airway or alveoli abnormalities. COPD is one of the top three leading causes of death in the world (Global Initiative for Chronic Obstructive Lung Disease (GOLD): Global Strategy for the Diagnosis, Management, and Prevention of Chronic Obstructive Pulmonary Disease (2024 Report), available at goldcopd.org/wp-content/uploads/2024/02/GOLD-2024 v1.2-11Jan24_WMV.pdf (last accessed Nov. 8, 2024)). It is estimated that globally three million deaths occur annually due to COPD, and it is projected that 5.4 million annual deaths will occur from COPD and related conditions by 2060. COPD is projected to increase globally due to the population aging and continuing exposure to COPD risk factors. Many individuals suffer with COPD or its complications for years prior to death. Thus, COPD is a global health challenge that requires both prevention and treatment.

COPD is a progressive disease that is not fully reversible. COPD results in periodic exacerbations that may result in long term disability or mortality, reducing the quality of life of those who suffer with the disease. This creates a significant economic burden, with projected costs of $40 billion per year in the United States alone (GOLD 2024).

To prevent these periodic acute exacerbations, many patients with COPD use long-term bronchodilator maintenance therapy. However, there is a substantial unmet need in COPD patients who continue to exacerbate despite maximal bronchodilator maintenance therapy. In the IMPACT study, despite optimizing patients with dual or triple therapy, almost half of the patients continued to experience exacerbations (Bardsley et al., Respir Med. 2022 December: 205: 107040). Thus, there is a need for new therapies for the treatment and/or prevention of COPD, as well as the reduction of acute exacerbations of COPD (AECOPD).

SUMMARY OF THE INVENTION

In a first aspect of the invention, the present disclosure provides an IL-33 binding protein comprising:

(i) CDRH1, CDRH2, and CDRH3 from SEQ ID NO:20 and CDRL1, CDRL2, and CDRL3 from SEQ ID NO:25, wherein SEQ ID NO:20 comprises:
QVQLVQSGAEVKKPGASVKVSCKASGYTFI-SYGMHWVRQAP GQGLEWMGEINPHGGSTSYAQKF$X_1$GRV TMTRDTSTSTVYME LSSLRSEDTAVYYCARP-SAAYSHYLG$X_2$ D$X_3$WGRGTLVTVSS;
and
wherein SEQ ID NO:25 comprises:
DIQMTQSPSSVSASVGDRVTITCR$X_4$SQ GIS$X_5$WL$X_6$WYQQKPG KAPKLLIYA$X_7$S$X_8$LQSGVPSRFSGSGSGT DFTLTISSLQPEDFAT YYCQQA$X_9$V$X_{10}$PLTFGGGTKVEIK; and
wherein:
$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L; or (ii) one or more CDR variants of (i), wherein the variant has 1, 2, or 3 amino acid modifications.

In a second aspect of the invention, the present disclosure provides an IL-33 binding protein comprising:

(i) CDRH1, CDRH2, and CDRH3 from any one of SEQ ID NOs: 21-24 and CDRL1, CDRL2, and CDRL3 from any one of SEQ ID NOs: 26-28; or (ii) one or more CDR variants of (i), wherein the variant has 1, 2, or 3 amino acid modifications.

In a third aspect of the invention, the present disclosure provides an IL-33 binding protein comprising a heavy chain (HC) having at least 90% identity to any one of SEQ ID NOs: 29-33 and a light chain (LC) having at least 90% identity to any one of SEQ ID NOs: 34-37, wherein SEQ ID NO:29 comprises:

QVQLVQSGAEVKKPGASVKVSCKASGYTFI-SYGMHWVRQAPGQGLE WMGEINPHGGSTSYAQKF$X_1$GRVTMT RDTSTSTVYMELSSLRSEDTA VYYCARPSAAYSHYLG$X_2$D$X_3$WGRGTLV TVSSASTKGPSVFPLAPSSK STSGGTAAL-GCLVKDYFPEPVTVSWNSGALT-SGVHTFPAVLQSSGLYS LSSVVTVPSSSLGTQTYICNVNHKPSNT KVDKKVEPKSCDKTHTCPPC PAPELLGGPSVFLFPPKPKDTLYITREPE-VTCVVVDVSHEDPEVKFNW YVDGVEVHNAKTKPREEQYN-STYRVVSVLTVLHQDWLNGKEYKCK VSNKAL-PAPIEKTISKAKGQPREPQVYTLPPSRDELT-KNQVSLTCLVKG

FYPSDIAVEWESNGQPEN-NYKTTPPVLDSDGSFFLYSKLTVDKSRWQ QGNVFSCSVMHEALHNHYTQKSLSLSPGK; and wherein SEQ ID NO:34 comprises:

DIQMTQSPSSVSASVGDRVTITCR$X_4$SQG IS$X_5$WL$X_6$WYQQKPGKAPKL LIYA$X_7$S$X_8$LQSGVPSRFSGSGSGTDFTL TISSLQPEDFATYYCQQA$X_9$V $X_{10}$PLTFGGGTKVEIKRTVAAPSVFIFPPS DEQLKSGTASVVCLLNNFYP REAKVQWKVD-NALQSGNSQESVTEQDSKDSTYSLSSTLTL-SKADYEK HKVYACE-VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In a fourth aspect of the invention, the present disclosure provides a pharmaceutical composition comprising the IL-33 binding protein as defined in any one of the above aspects or embodiments of the invention and a pharmaceutically acceptable excipient.

In a fifth aspect of the invention, the present disclosure provides a method of treating or preventing a disease or condition in a human in need thereof comprising administering to the human a therapeutically effective amount of the IL-33 binding protein of any one of the first three aspects of the invention and corresponding embodiments, or the pharmaceutical composition of the fourth aspect of the invention.

In a sixth aspect of the invention, the present disclosure provides an IL-33 binding protein of any one of the first three aspects of the invention and corresponding embodiments, or a pharmaceutical composition of the fourth aspect of the invention, for use in treating or preventing a disease or condition.

In a seventh aspect of the invention, the present disclosure provides use of the IL-33 binding protein of any one of the first three aspects of the invention and corresponding embodiments, or a pharmaceutical composition of the fourth aspect of the invention, in the manufacture of a medicament for treating or preventing a disease or condition.

In an eighth aspect of the invention, the present disclosure provides a nucleic acid sequence or plurality of nucleic acid sequences encoding an IL-33 binding protein according to any one of the first three aspects of the invention and corresponding embodiments.

In a ninth aspect of the invention, the present disclosure provides nucleic acid sequence or plurality of nucleic acid sequences comprising any one of SEQ ID NOs: 59-64 and/or any one of SEQ ID NOs: 69-76.

In a tenth aspect of the invention, the present disclosure provides a nucleic acid sequence or plurality of nucleic acid sequences comprising any one of SEQ ID NOs: 65-68 and/or any one of SEQ ID NOs: 77-79.

In an eleventh aspect of the invention, the present disclosure provides a nucleic acid sequence or plurality of nucleic acid sequences comprising SEQ ID NO:66 and/or SEQ ID NO: 77.

In a twelfth aspect of the invention, the present disclosure provides an expression vector comprising the nucleic acid sequence or plurality of nucleic acid sequences of the eighth, ninth, tenth, or eleventh aspects of the invention.

In a thirteenth aspect of the invention, the present disclosure provides a host cell that comprises the nucleic acid sequence or plurality of nucleic acids of any one of the eighth, ninth, tenth, or eleventh aspects of the invention, or the expression vector of the twelfth aspect of the invention.

In a fourteenth aspect of the invention, the present disclosure provides a method of producing an IL-33 binding protein, comprising culturing the host cell as defined in the thirteenth aspect of the invention under conditions suitable for expression of said nucleic acid sequence, plurality of nucleic acid sequences, or vector, whereby a polypeptide comprising the IL-33 binding protein is produced.

In a fifteenth aspect of the invention, the present disclosure provides the IL-33 binding protein produced by the method of the fourteenth aspect of the invention.

DETAILED DESCRIPTION OF THE INVENTION

Figure 1:
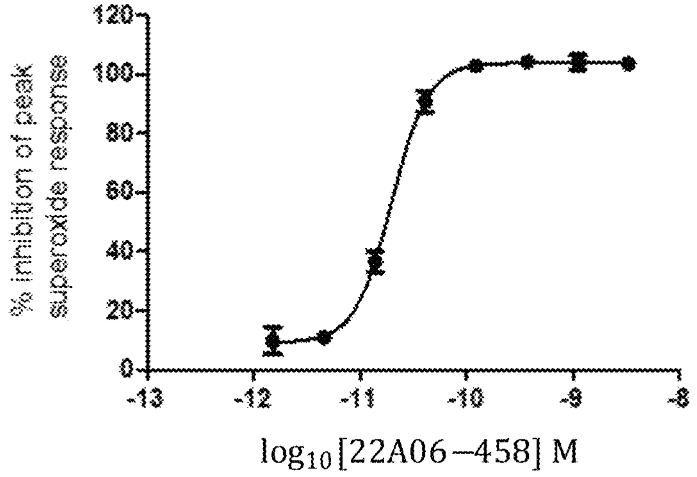
FIG. 1 illustrates eosinophil superoxide production after stimulation with IL-33 pre-complexed with an IL-33 binding protein.

Interleukin 33 (IL-33) is an alarmin and a pleotropic cytokine that is released by epithelium, endothelium, and other cell types following damage or infection (Cayrol and Girard, Cytokine, 2022, 156, 155891). IL-33 promotes inflammation through binding to its receptor (transmembrane ST2) which is present on multiple cells including endothelial cells, type 2 innate lymphoid cells (ILC2s), mast cells, myeloid cells, natural killer (NK) cells, T-cells, NK T-cells, and basophils (Calderon et al., Eur Respir Rev, 2023 32(167), 220144, Erratum in: Eur Respir Rev, 2023, 32 (168)). IL-33 promotes the production of cytokines associated with Type 1 (e.g., interferon gamma, IL-6, IL-8) and Type 2 (e.g., IL-4, IL-5, IL-13) immune responses resulting in further immune cell recruitment to sites of inflammation (Afferni et al., Front Immunol., 2018, 13, 9, 2601; Calderon et al., Eur Respir Rev., 2023, 32(167), 220144, Erratum in: Eur Respir Rev., 2023, 32(168); Yagami et al., J Immunol., 2010, 185(10), 5743-50). Therefore, IL-33 potentially amplifies cytokine/chemokine production, inflammation, and tissue damage. IL-33 has also been implicated as a mediator of eosinophil accumulation, maturation, and release from bone marrow by its effects on ILC2s (Johansson et al., Immunology, 2018, 153(2), 268-278; Johnston et al., J Immunol., 2016, 197(9), 3445-3453; Wu Y H, et al., Allergy, 2020, 75(4), 818-830).

An increasing realization in the field of immunology is the importance of the role played by mucosal epithelial cells. These cells have an important function as a barrier to the environment, but they are also intimately associated with resident dendritic cells (DCs) that initiate adaptive immune responses. IL-33 has been shown to be one of the factors released by epithelial cells very early following airway stress that results in cellular damage. Once released, IL-33 has an important role instructing DCs to induce a Type 2 (T2) immune response and is a driving factor in the emerging concept of tissue-specific control of immunity. As IL-33 is upstream of the subsequent immune responses, it plays a role, as an alarmin, in translating this environmental stress to the subsequent innate and adaptive immune responses, being able to induce the full breadth of the T2 response. Antagonism of this response should therefore dampen the entire T2 response rather than individual elements of this response.

In humans, the IL33 gene is located on chromosome 9p24.1, encoding a full-length protein of 270 amino acids with a calculated molecular weight of 30.759 kDa. Under resting conditions, the full-length protein resides in the nucleus where it associates with histone complexes. IL-33 does not possess a signal peptide; therefore, release of IL-33 is thought to require a cell damage event, where the initial release of full-length IL-33-histone complexes occurs. This complex is rapidly cleaved by proteases such as calpain, neutrophil elastase, chymase, and cathepsin-G producing shorter isoforms of IL-33 which are more biologically active than the full-length version of the protein. IL-33 is released from the airway epithelium by all the key environmental stressors thought to have an impact on lung sensitivity in asthmatics, for example, respiratory (particularly viral) infections, allergens, and various pollutants, including smoke and other inhaled particulates.

In the extra-cellular environment, the IL-33 activity is controlled by a rapid oxidation event of the initial bioactive reduced form (Cohen et al., Nature Comms. 2015; 6:8327). This oxidation results from disulfide bonding in the core of the molecule inducing a significant conformational shift which renders the oxidized IL-33 (oxIL-33) form unable to bind ST2 and induce signaling. This is a relatively fast process in plasma where it is expected that the reduced form only has approximately a 90-minute half-life, while the oxidized IL-33 form is thought to be more stable. Studies using immunoassays specific for each form have shown that the predominant measurable form in asthma is the oxidized form where the reduced form is rarely detected, probably due to its fast transition kinetics (Cohen et al., Nature Comms. 2015; 6:8327). This highlights the complexity of the biology of IL-33 as it is likely that in vivo multiple forms of IL-33 exist, including the reduced form, bioactive fragments, and the oxidized form.

Tissue resident immune cells constitute the major targets of IL-33. IL-33 signaling occurs via a heterodimeric receptor composed of ST2 and ILlRacP. Many immune tissue resident cells express ST2 including mast cells, ILC2 cells, eosinophils, macrophages, DCs NK cells, and T-cell populations including Th2 and T-regs. IL-33 released into a tissue environment acts as an alarmin, amplifying key mechanisms that drive the T2 immune cascade that results in asthma immune pathology. For example, IL-33 primed mast cells increase their sensitivity to IgE driven degranulation, eosinophils are highly sensitive to activation by IL-33 which causes immediate degranulation, macrophages are primed towards an M2 phenotype, allergen specific T2 responses are amplified, and ILC2 cells proliferate and secrete large quantities of IL-5 and IL-13 in response to IL-33 (Chan et al., Frontiers in Immunology, 2019; 10: Article 364). While the influence of IL-33 is strongly linked to T2 inflammation, it is now clear that the action of IL-33 is not limited to the activation of type-2 immune responses. Indeed, recent studies have revealed important roles of IL-33 in the activation of immune cells involved in type-1 immunity, such as Th1 cells (Komai-Koma et al., 2016, Immunobiology 221 (3): 412-417). IL-33 is only capable of stimulating IFN-γ production from human $CD4^+$ T cells when in combination with IL-12, emphasising that the amplification role of IL-33 is dependent on the context of the inflammatory milieu.

In addition to numerous primary human cell-based functional assays, the important impact of the IL-33 pathway on immune responses has been extensively validated in mouse models of lung inflammation using IL-33 over-expression, administration of recombinant IL-33, IL-33/ST2 deficient mice, or anti-ST2/anti-IL-33 blocking antibodies (e.g., Ravanetti et al., J Allergy Clin Immunol. 2019, 143 (4): 1355-1370). In summary, the data from multiple studies are consistent that blocking the IL-33 pathway dampens lung inflammation and pathology.

Definitions

The term "about" as used herein means plus or minus 10%.

"Acceptor antibody" refers to an antibody that is heterologous to a donor antibody, which contributes all (or any portion) of the amino acid sequences encoding its heavy and/or light chain framework regions and/or its heavy and/or light chain constant regions to the first immunoglobulin partner. A human antibody may be an acceptor antibody.

"Affinity", also referred to as "binding affinity", is the strength of binding at a single interaction site, i.e., of one molecule, e.g., an antigen binding protein of the invention, to another molecule, e.g., IL-33, at a single binding site. The binding affinity of an antigen binding protein to its target may be determined by equilibrium methods (e.g., enzyme-linked immunosorbent assay (ELISA), radioimmunoassay (RIA), or solution equilibrium titration (SET)), or kinetics (e.g., BIACORE analysis). For example, MSD-SET methods described in Example 2 may be used to measure binding affinity.

"Antibody" is used herein in the broadest sense to refer to molecules with an immunoglobulin-like domain (for example, IgG, IgM, IgA, IgD, or IgE) and includes monoclonal, recombinant, polyclonal, chimeric, human, humanized, multispecific antibodies, including bispecific antibodies, and heteroconjugate antibodies; a single variable domain (e.g., a domain antibody (DAB)), antigen binding antibody fragments, Fab, F(ab') 2, Fv, disulfide linked Fv, single chain Fv, disulfide-linked scFv, diabodies, TANDABS, etc., and modified versions of any of the foregoing (for a summary of alternative "antibody" formats, see Holliger and Hudson, Nature Biotechnology, 2005, Vol. 23, No. 9, 1126-1136). The terms "full", "whole", or "intact" antibody are used interchangeably herein and refer to a heterotetrameric glycoprotein with an approximate molecular weight of 150,000 Daltons. An intact antibody is composed of two identical heavy chains (HCs) and two identical light chains (LCs) linked by covalent disulfide bonds. This $H_2L_2$ structure folds to form three functional domains comprising two antigen-binding fragments, known as 'Fab' fragments, and a 'Fc' crystallizable fragment. The Fab fragment is composed of the variable domain at the amino-terminus, variable heavy (VH) or variable light (VL), and the constant domain at the carboxyl terminus, CH1 (heavy) and CL (light). The Fc fragment is composed of two domains formed by dimerization of paired CH2 and CH3 regions. The Fc may elicit effector functions by binding to receptors on immune cells or by binding C1q, the first component of the classical complement pathway. The five classes of antibodies IgM, IgA, IgG, IgE, and IgD are defined by distinct heavy chain amino acid sequences, which are called μ, α, γ, ε, and δ, respectively, and each heavy chain can pair with either a K or λ light chain. The majority of antibodies in the serum belong to the IgG class; there are four isotypes of human IgG (IgG1, IgG2, IgG3, and IgG4), the sequences of which differ mainly in their hinge region. An antibody that binds to IL-33 may be referred to herein as an "anti-IL-33 antibody" or an "IL-33 antibody".

"Antigen binding protein" as used herein refers to antibodies, antigen binding fragments thereof, and other protein constructs, such as domains, that are capable of binding to an antigen. The term "IL-33 binding protein" as used herein refers to antibodies and other protein constructs, such as domains, that are capable of binding to IL-33. The terms "IL-33 binding protein" and "antigen binding protein" are used interchangeably herein. This does not include the natural cognate ligand or receptor. An IL-33 binding protein can be capable of binding to one or more of a human IL-33, and an IL-33 protein of another organism (e.g., mouse, rat, cow, dog, cat, pig, monkey, etc.). An IL-33 binding protein can be capable of binding to a fragment of, a variant of, or a mutant of IL-33.

"Antigen binding site" refers to a site on an antigen binding protein that is capable of specifically binding to an antigen. This may be a single variable domain, or it may be paired VH/VL domains as can be found on a standard antibody. Single-chain Fv (ScFv) domains can also provide antigen binding sites.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

"Comprises" or "comprising" as used herein with respect to a SEQ ID NO are understood to include "consists" or "consisting", respectively.

"Domain" as used herein refers to a folded polypeptide structure that can retain its tertiary structure independent of the rest of the polypeptide. Generally, domains are responsible for discrete functional properties of polypeptides and in many cases may be added, removed, or transferred to other polypeptides without loss of function of the remainder of the protein and/or of the domain.

"Donor antibody" as used herein refers to an antibody that contributes the amino acid sequences of one or more of its variable regions, CDRs, or other functional fragments or analogues thereof to a first immunoglobulin partner. A donor, therefore, provides the altered immunoglobulin coding region and resulting expressed altered antibody with the antigenic specificity and neutralizing activity characteristic of a donor antibody.

"Effector Function" as used herein refers to one or more of antibody-mediated effects including antibody-dependent cell-mediated cytotoxicity (ADCC), antibody-mediated complement activation including complement-dependent cytotoxicity (CDC), complement-dependent cell-mediated phagocytosis (CDCP), antibody dependent complement-mediated cell lysis (ADCML), and Fc-mediated phagocytosis or antibody-dependent cellular phagocytosis (ADCP).

"Epitope" as used herein refers to that portion of the antigen (i.e., IL-33) that makes contact with a particular binding domain of the antigen binding protein (i.e., IL-33 binding protein), also known as the paratope. An epitope may be linear, conformational, or discontinuous. A conformational or discontinuous epitope comprises amino acid residues that are separated by other sequences, i.e., not in a continuous sequence in the antigen's primary sequence assembled by tertiary folding of the polypeptide chain. Although the residues may be from different regions of the polypeptide chain, they are in close proximity in the three-dimensional structure of the antigen (i.e., IL-33). In the case of multimeric antigens, a conformational or discontinuous epitope may include residues from different peptide chains. Particular residues comprised within an epitope can be determined through computer modelling programs or via three-dimensional structures obtained through methods known in the art, such as X-ray crystallography. Epitope mapping can be carried out using various techniques known to persons skilled in the art as described in publications such as *Methods in Molecular Biology*, including '*Epitope Mapping Protocols*' by Mike Schutkowski and Ulrich Reineke (volume 524, 2009) and '*An Introduction to Epitope Mapping*' by Johan Rockberg and Johan Nilvebrant (volume 1785, 2018). Exemplary methods include peptide-based approaches such as pepscan, whereby a series of overlapping peptides are screened for binding using techniques such as ELISA or by in vitro display of large libraries of peptides or protein mutants, e.g., on phage. Detailed epitope information can be determined by structural techniques including X-ray crystallography, solution nuclear magnetic resonance (NMR) spectroscopy, and cryogenic-electron microscopy (cryo-EM). Mutagenesis, such as alanine scanning, is an effective approach whereby loss of binding analysis is used for epitope mapping. Another method is hydrogen/deuterium exchange (HDX) combined with proteolysis and liquid-chromatography mass spectrometry (LC-MS) analysis to characterize discontinuous or conformational epitopes.

The term "forced expiratory volume in one second" or "FEV1" refers to the volume of air exhaled during the first second of air forcibly exhaled from the lungs after the point of maximal inspiration. Methods for measuring FEV1 are known in the art, such as spirometry.

The term "forced vital capacity" or "FVC" refers to the volume of air forcibly exhaled after the point of maximal inspiration. Methods for measuring FVC are known in the art, such as spirometry.

"Half-life" (or "$t_{1/2}$") refers to the time required for the serum concentration of an antigen binding protein to reach half of its original value. The serum half-life of proteins can be measured by pharmacokinetic studies according to the method described by Kim et al., 1994, Eur. J. of Immuno. 24:542-548. According to this method, radio-labeled protein is injected intravenously into mice and its plasma concentration is periodically measured as a function of time, for example, at about 3 minutes to about 72 hours after the injection. Other methods for pharmacokinetic analysis and determination of the half-life of a molecule will be familiar to those skilled in the art.

"Humanized antibody" refers to a type of engineered antibody having CDRs derived from a non-human donor immunoglobulin, the remaining immunoglobulin-derived parts of the molecule being derived from one or more human immunoglobulin(s). In addition, framework support residues may be altered to preserve binding affinity. A suitable human acceptor antibody may be one selected from a conventional database (e.g., the KABAT database, Los Alamos database, and Swiss Protein database), or by homology to the nucleotide and/or amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains may originate from the same acceptor antibody or different acceptor antibodies.

The term "IL-33 mediated disease" refers to a disorder or condition that is mediated or modulated by IL-33 mechanisms; therefore, IL-33 mediated diseases are diseases or disorders where inhibition of IL-33 would be beneficial. IL-33 and its role in diseases is described in Cayrol, C, Girard, J-P. Immunol Rev. 2018; 281:154-168; Cayrol C, Girard J-P. Cytokine. 2022 August; 156:155891; Dwyer G K, et al. Annu Rev Immunol. 2022 Apr. 26; 40:15-43; Kotsiou O S, et al. Front Immunol. 2018 Oct. 24; 9:2432; and Yuan C. Int Immunopharmacol. 2022 July; 108:108887. Examples of IL-33 mediated disorders include, but are not limited to, chronic obstructive pulmonary disease (COPD), asthma, bronchitis, bronchiolitis, acute respiratory failure, inflammatory lung diseases, diabetic kidney disease, endometriosis, chronic rhinosinusitis with nasal polyps, food hypersensitivity, food allergy (e.g., peanut allergy), allergic rhinitis, eosinophilic esophagitis, atopic dermatitis, cystic fibrosis, and chronic urticaria.

The term "neutralizes" as used throughout the present specification means that the biological activity of IL-33 is reduced in the presence of an antigen binding protein as described herein in comparison to the activity of IL-33 in the absence of the antigen binding protein, in vitro or in vivo. Neutralization may be due to one or more of blocking IL-33 binding to its receptor, preventing IL-33 from activating its receptor, down regulating IL-33 or its receptor, or affecting effector functionality. For example, the methods described in Example 13 through Example 17 may be used to assess the neutralizing capability of an IL-33 binding protein.

"Percent identity" or "% identity" between a query nucleic acid sequence and a subject nucleic acid sequence is the "Identities" value, expressed as a percentage, that is calculated using a suitable algorithm (e.g., BLASTN, FASTA, Needleman-Wunsch, Smith-Waterman, LALIGN, or GenePAST/KERR) or software (e.g., DNASTAR Lasergene, GenomeQuest, EMBOSS needle, or EMBOSS infoalign), over the entire length of the query sequence after a pair-wise global sequence alignment has been performed using a suitable algorithm (e.g., Needleman-Wunsch or GenePAST/KERR) or software (e.g., DNASTAR Lasergene or GenePAST/KERR). Importantly, a query nucleic acid sequence may be described by a nucleic acid sequence disclosed herein, in particular, in one or more of the claims. "Percent identity" or "% identity" between a query amino acid sequence and a subject amino acid sequence is the "Identities" value, expressed as a percentage, that is calculated using a suitable algorithm (e.g., BLASTP, FASTA, Needleman-Wunsch, Smith-Waterman, LALIGN, or GenePAST/KERR) or software (e.g., DNASTAR Lasergene, GenomeQuest, EMBOSS needle or EMBOSS infoalign), over the entire length of the query sequence after a pair-wise global sequence alignment has been performed using a suitable algorithm (e.g., Needleman-Wunsch or GenePAST/KERR) or software (e.g., DNASTAR Lasergene or GenePAST/KERR). Importantly, a query amino acid sequence may be described by an amino acid sequence disclosed herein, in particular, in one or more of the claims. The query sequence may be 100% identical to the subject sequence, or it may include up to a certain integer number of amino acid or nucleotide alterations as compared to the subject sequence such that the % identity is less than 100%. For example, the query sequence is at least 50%, at least 60%, at least 70%, at least 75%, at least 80%, at least 85%, at least 90%, at least 95%, at least 96%, at least 97%, at least 98%, or at least 99% identical to the subject sequence. In the case of nucleic acid sequences, such alterations include at least one nucleotide residue deletion, substitution, or insertion, wherein said alterations may occur at the 5'- or 3'-terminal positions of the query sequence or anywhere between those terminal positions, interspersed either individually among the nucleotide residues in the query sequence or in one or more contiguous groups within the query sequence. In the case of amino acid sequences, such alterations include at least one amino acid residue deletion, substitution (including conservative and non-conservative substitutions), or insertion, wherein said alterations may occur at the amino- or carboxy-terminal positions of the query sequence or anywhere between those terminal positions, interspersed either individually among the amino acid residues in the query sequence or in one or more contiguous groups within a query sequence. For antibody sequences, the % identity may be determined across the entire length of the query sequence, including the CDRs. Alternatively, the % identity may exclude one or more or all of the CDRs, for example, all of the CDRs are 100% identical to the subject sequence and the % identity variation is in the remaining portion of the query sequence, e.g., the framework sequence, so that the CDR sequences are fixed and intact.

The term "prevention" refers to avoidance of the stated disease in a subject who is not suffering from the stated disease.

"Protein Scaffold" as used herein includes, but is not limited to, an immunoglobulin (Ig) scaffold, for example, an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. A protein scaffold may be an Ig scaffold, for example, an IgG or IgA scaffold. An IgG scaffold may comprise some or all the domains of an antibody (i.e., CH1, CH2, CH3, VH, VL). An antigen binding protein may comprise an IgG scaffold selected from IgG1, IgG2, IgG3, IgG4, or IgG4PE. For example, a scaffold may be IgG1. A scaffold may consist of, or comprise, an Fc region of an antibody or a fragment thereof. A protein scaffold may be a derivative of a scaffold selected from the group consisting of CTLA-4, lipocalin, Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human g-crystallin and human ubiquitin (affilins); PDZ domains; scorpion toxin kunitz type domains of human protease inhibitors; and fibronectin/adnectin which has been subjected to protein engineering in order to obtain binding to an antigen, such as IL-33, other than a natural ligand.

"Recombinant host cell" as used herein refers to a cell that comprises a nucleic acid sequence of interest that was isolated prior to its introduction into the cell.

"Single variable domain" as used herein refers to a folded polypeptide domain comprising sequences characteristic of antibody variable domains. It therefore includes complete antibody variable domains such as VH, VHH, and VL and/or modified antibody variable domains, for example, in which one or more loops have been replaced by sequences that are not characteristic of antibody variable domains, or antibody variable domains that have been truncated or comprise N- or C-terminal extensions, as well as folded fragments of variable domains that retain at least the binding activity and specificity of the full-length domain. A single variable domain herein is capable of binding an antigen or epitope independently of a different variable region or domain. A "domain antibody" or "DAB" can be a human "single variable domain". A single variable domain may be a human single variable domain, but can also be a single variable domains from a non-human species such as rodent (for example, as in WO 00/29004), a nurse shark, or a camelid. Notably, camelid VHHs are immunoglobulin single variable domain polypeptides that are derived from camelid species, such as camel, llama, alpaca, dromedary, and guanaco, which produce heavy chain only antibodies that are naturally devoid of light chains. Such VHH domains may be humanized according to standard techniques available in the art, and such domains can be "single variable domains".

The terms "individual", "subject", and "patient" are used herein interchangeably. The subject may be an animal, in particular a mammal, such as a primate, for example, a marmoset or a monkey. Preferably, the subject is a human.

The term "therapeutically effective amount" refers to the quantity of an IL-33 binding protein or a pharmaceutical composition comprising an IL-33 binding protein which will elicit the desired biological response in a human body. It may vary depending on the IL-33 binding protein or the pharmaceutical composition comprising the IL-33 binding protein, the disease and its severity, and the age and weight of the subject to be treated.

The term "treatment" refers to ameliorating or stabilizing the specified condition, reducing or eliminating the symptoms of the condition, slowing or eliminating the progression of the condition, and preventing or delaying reoccurrence of the condition in a previously afflicted patient or subject.

Embodiments of the Invention

One or more of antigen binding proteins described herein may be an antibody or an antigen binding fragment thereof. An antigen binding protein may be a human antibody or an antigen binding fragment thereof. An antigen binding protein may comprise one of, a plurality of, or all of: a human VH (variable heavy) domain region or a human Heavy Chain (HC) sequence; and/or a human VL (variable light) domain region or a human Light Chain (LC) sequence. An antigen binding protein may be a humanized antibody or an antigen binding fragment thereof. An antigen binding protein may comprise one of, a plurality of, or all of: a humanized VH region or a humanized Heavy Chain (HC) sequence; and/or a humanized VL region or a humanized Light Chain (LC) sequence.

Antibodies provided herein can be fully human antibodies, and can be obtained using a variety of methods, for example, using yeast-based libraries or transgenic animals (e.g., mice) that are capable of producing repertoires of human antibodies. Yeast presenting human antibodies on their surface that bind to an antigen of interest can be selected using FACS (Fluorescence-Activated Cell Sorting)

based methods or by capture on beads using labeled antigens. Transgenic animals that have been modified to express human immunoglobulin genes can be immunized with an antigen of interest and antigen-specific human antibodies isolated using B-cell sorting techniques. Human antibodies produced using these techniques can then be characterized for desired properties such as affinity, developability and selectivity. In an embodiment, the antibodies are human antibodies produced using a yeast-based platform.

An antigen binding fragment may be provided by means of arrangement of one or more CDRs on one or more non-antibody protein scaffolds, such as an affibody, a SpA scaffold, an LDL receptor class A domain, an avimer (see, e.g., U.S. Patent Publication Nos. 2005/0053973, 2005/0089932, 2005/0164301), or an EGF domain.

Throughout this specification, amino acid residues in variable domain sequences and variable domain regions within full-length antigen binding sequences, e.g., within an antibody heavy chain sequence or antibody light chain sequence, are numbered according to the Kabat numbering convention. Similarly, the terms "CDR", "CDRL1", "CDRL2", "CDRL3", "CDRH1", "CDRH2", and "CDRH3" used herein follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full-length antibody sequences. Throughout this specification, amino acid residues in Fc regions, in antibody sequences or full-length antigen binding protein sequences, are numbered according to the EU index numbering convention.

There are also alternative numbering conventions for CDR sequences, for example, those set out in Chothia et al. (1989) Nature 342:877-883. The structure and protein folding of the antigen binding protein may mean that other residues are considered part of the CDR sequence and would be understood to be so by a skilled person.

Other numbering conventions for CDR sequences available to a skilled person include "AbM" (University of Bath) and "contact" (University College London) methods.

Table 1 below represents one definition using each numbering convention for each CDR. The Kabat numbering scheme is used in Table 1 to number the variable domain amino acid sequence. It should be noted that some of the CDR definitions may vary depending on the individual publication used.

TABLE 1

| | CDR Numbering | | | |
|---|---|---|---|---|
| | Kabat CDR | Chothia CDR | AbM CDR | Contact CDR |
| H1 | 31-35/35A/35B | 26-32/33/34 | 26-35/35A/35B | 30-35/35A/35B |
| H2 | 50-65 | 52-56 | 50-58 | 47-58 |
| H3 | 95-102 | 95-102 | 95-102 | 93-101 |
| L1 | 24-34 | 24-34 | 24-34 | 30-36 |
| L2 | 50-56 | 50-56 | 50-56 | 46-55 |
| L3 | 89-97 | 89-97 | 89-97 | 89-96 |

Provided herein are IL-33 binding proteins comprising any one or a combination or all of CDRs selected from CDRH1 of SEQ ID NO:20, CDRH2 of SEQ ID NO:20, CDRH3 of SEQ ID NO: 20, CDRL1 of SEQ ID NO:25, CDRL2 of SEQ ID NO:25, and CDRL3 of SEQ ID NO:25, wherein SEQ ID NO:20 comprises:

QVQLVQSGAEVKKPGASVKVSCKASGYTFI-SYGMHWVRQAPGQGLEWMGEIN PHGGSTSYAQKFX$_1$GRVTMTRDTST STVYMELSSLRSEDTAVYYCARPSAAYSH YLGX$_2$DX$_3$WGRGTLVTVSS; and wherein SEQ ID NO:25 comprises:

DIQMTQSPSSVSASVGDRVTITCRX$_4$SQG ISX$_5$WLX$_6$WYQQKPGKAPKLLIYAX$_7$S X$_8$LQSGVPSRFSGSGSGTDFTLTIS SLQPEDFATYYCQQAX$_9$VX$_{10}$PLTFGGGTKVEI K; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L. In an embodiment, the antigen binding protein comprises all 6 CDRs. In an embodiment, the antigen binding protein is an antibody comprising all 6 CDRs.

Provided herein are IL-33 binding proteins comprising any one or a combination or all of CDRs selected from CDRH1 of SEQ ID NO:21, CDRH2 of SEQ ID NO:21, CDRH3 of SEQ ID NO: 21, CDRL1 of SEQ ID NO:26, CDRL2 of SEQ ID NO:26, and CDRL3 of SEQ ID NO:26. In an embodiment, the antigen binding protein comprises all 6 CDRs. In an embodiment, the antigen binding protein is an antibody comprising all 6 CDRs.

Provided herein are IL-33 binding proteins comprising any one or a combination or all of CDRs selected from CDRH1 of SEQ ID NO:22, CDRH2 of SEQ ID NO:22, CDRH3 of SEQ ID NO: 22, CDRL1 of SEQ ID NO:26, CDRL2 of SEQ ID NO:26, and CDRL3 of SEQ ID NO:26. In an embodiment, the antigen binding protein comprises all 6 CDRs. In an embodiment, the antigen binding protein is an antibody comprising all 6 CDRs.

Provided herein are IL-33 binding proteins comprising any one or a combination or all of CDRs selected from CDRH1 of SEQ ID NO:23, CDRH2 of SEQ ID NO:23, CDRH3 of SEQ ID NO: 23, CDRL1 of SEQ ID NO:27, CDRL2 of SEQ ID NO:27, and CDRL3 of SEQ ID NO:27. In an embodiment, the antigen binding protein comprises all 6 CDRs. In an embodiment, the antigen binding protein is an antibody comprising all 6 CDRs.

Provided herein are IL-33 binding proteins comprising any one or a combination or all of CDRs selected from CDRH1 of SEQ ID NO:24, CDRH2 of SEQ ID NO:24, CDRH3 of SEQ ID NO: 24, CDRL1 of SEQ ID NO:28, CDRL2 of SEQ ID NO:28, and CDRL3 of SEQ ID NO:28. In an embodiment, the antigen binding protein comprises all 6 CDRs. In an embodiment, the antigen binding protein is an antibody comprising all 6 CDRs.

In one embodiment, an IL-33 binding protein described herein comprises any one or a combination or all of CDRs selected from CDRH1 of SEQ ID NO:1, CDRH2 of SEQ ID NO:2, CDRH3 of SEQ ID NO:5, CDRL1 of SEQ ID NO:9, CDRL2 of SEQ ID NO: 13, and CDRL3 of SEQ ID NO:17, wherein SEQ ID NO:2 comprises:

EINPHGGSTSYAQKFX$_1$G;

wherein SEQ ID NO:5 comprises:

PSAAYSHYLGX$_2$DX$_3$;

wherein SEQ ID NO:9 comprises:

RX$_4$SQGISX$_5$WLX$_6$;

wherein SEQ ID NO:13 comprises:

$AX_7SX_8LQS$;

wherein SEQ ID NO:17 comprises:

$QQAX_9VX_{10}PLT$; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In an embodiment, an IL-33 binding protein described herein comprises the following 6 CDRs: CDRH1 of SEQ ID NO:1, CDRH2 of SEQ ID NO:2, CDRH3 of SEQ ID NO:5, CDRL1 of SEQ ID NO: 9, CDRL2 of SEQ ID NO: 13, and CDRL3 of SEQ ID NO: 17. In an embodiment, the antigen binding protein is an antibody.

In one embodiment, an IL-33 binding protein described herein comprises any one or a combination or all of CDRs selected from CDRH1 of SEQ ID NO:1, CDRH2 of SEQ ID NO:4, CDRH3 of SEQ ID NO:7, CDRL1 of SEQ ID NO: 10, CDRL2 of SEQ ID NO: 14, and CDRL3 of SEQ ID NO:18. In an embodiment, an IL-33 binding protein described herein comprises the following 6 CDRs: CDRH1 of SEQ ID NO:1, CDRH2 of SEQ ID NO:4, CDRH3 of SEQ ID NO: 7, CDRL1 of SEQ ID NO: 10, CDRL2 of SEQ ID NO: 14, and CDRL3 of SEQ ID NO:18. In an embodiment, the antigen binding protein is an antibody.

In one embodiment, an IL-33 binding protein described herein comprises any one or a combination or all of CDRs selected from CDRH1 of SEQ ID NO:1, CDRH2 of SEQ ID NO:3, CDRH3 of SEQ ID NO:7, CDRL1 of SEQ ID NO: 12, CDRL2 of SEQ ID NO: 16, and CDRL3 of SEQ ID NO:19. In an embodiment, an IL-33 binding protein described herein comprises the following 6 CDRs: CDRH1 of SEQ ID NO:1, CDRH2 of SEQ ID NO:3, CDRH3 of SEQ ID NO: 7, CDRL1 of SEQ ID NO: 12, CDRL2 of SEQ ID NO: 16, and CDRL3 of SEQ ID NO:19. In an embodiment, the antigen binding protein is an antibody.

In one embodiment, an IL-33 binding protein described herein comprises any one or a combination or all of CDRs selected from CDRH1 of SEQ ID NO:1, CDRH2 of SEQ ID NO:3, CDRH3 of SEQ ID NO:6, CDRL1 of SEQ ID NO: 10, CDRL2 of SEQ ID NO:14, and CDRL3 of SEQ ID NO:18. In an embodiment, an IL-33 binding protein described herein comprises the following 6 CDRs: CDRH1 of SEQ ID NO:1, CDRH2 of SEQ ID NO:3, CDRH3 of SEQ ID NO: 6, CDRL1 of SEQ ID NO:10, CDRL2 of SEQ ID NO: 14, and CDRL3 of SEQ ID NO: 18. In an embodiment, the antigen binding protein is an antibody.

In one embodiment, an IL-33 binding protein described herein comprises any one or a combination or all of CDRs selected from CDRH1 of SEQ ID NO:1, CDRH2 of SEQ ID NO:3, CDRH3 of SEQ ID NO:8, CDRL1 of SEQ ID NO:11, CDRL2 of SEQ ID NO: 15, and CDRL3 of SEQ ID NO:18. In an embodiment, an IL-33 binding protein described herein comprises the following 6 CDRs: CDRH1 of SEQ ID NO:1, CDRH2 of SEQ ID NO:3, CDRH3 of SEQ ID NO: 8, CDRL1 of SEQ ID NO: 11, CDRL2 of SEQ ID NO: 15, and CDRL3 of SEQ ID NO:18. In an embodiment, the antigen binding protein is an antibody.

CDRs of an IL-33 binding protein provided herein can be modified by one or by more than one amino acid substitution, deletion, or addition, wherein the variant IL-33 binding protein substantially retains the biological characteristics of the unmodified protein, such as inhibiting the binding of IL-33 to the ST2 receptor.

It will be appreciated that each of CDRH1, CDRH2, CDRH3, CDRL1, CDRL2, or CDRL3 may be modified alone or in combination with any other CDR, in any permutation or combination. A CDR may be modified by the substitution, deletion, or addition of up to 3 amino acids, for example, 1 or 2 amino acids, for example, 1 amino acid. Each modification of a CDR, VH, VL, or other protein provided herein can be a conservative substitution. A modification can be a conservative substitution, for example, as shown in Table 2A or in Table 2B below.

TABLE 2A

Examples of conservative substitutions by side chain type

| Side chain | Members |
|---|---|
| Hydrophobic | Met, Ala, Val, Leu, Ile |
| Neutral hydrophilic | Cys, Ser, Thr |
| Acidic | Asp, Glu |
| Basic | Asn, Gln, His, Lys, Arg |
| Residues that influence chain orientation | Gly, Pro |
| Aromatic | Trp, Tyr, Phe |

TABLE 2B

Examples of conservative substitutions by amino acid

| Amino Acid | Conservative Substitution |
|---|---|
| A | D, E, G, S, T |
| C | G, R, S, W, Y |
| D | A, E, G, H, N, V, Y |
| E | A, D, G, K, Q, V |
| F | I, L, Y |
| G | A, C, D, E, R |
| H | D, L, N, P, Q, R, Y |
| I | F, L, M, N, V |
| K | E, M, N, Q, R, T |
| L | F, H, I, M, P, Q, R, V, W |
| M | I, K, L, R, T, V |
| N | D, H, I, K, S, T, Y |
| P | H, L, Q, R, S |
| Q | E, H, L, L, P, R |
| R | C, G, H, K, L, M, P, Q, T, W |
| S | A, C, N, P, T, W, Y |
| T | A, K, M, N, R, S |
| V | D, E, I, L, M |
| W | C, L, R, S |
| Y | C, D, F, H, N, S |

For example, in a variant CDR, one or more flanking residues that comprise the CDR as part of alternative definition(s), e.g., Kabat or Chothia, may be substituted with a conservative amino acid residue.

Such antigen binding proteins comprising variant CDRs as described above may be referred to herein as "functional CDR variants".

IL-33 binding proteins described herein may comprise:

a. (i) any one or a combination of CDRs selected from CDRH1, CDRH2, and/or CDRH3 from SEQ ID NO:20 and/or CDRL1, CDRL2, and/or CDRL3 from SEQ ID NO:25, wherein SEQ ID NO:20 comprises:

QVQLVQSGAEVKKPGASVKVSCKASGYTFISYGMHWVRQAP GQGLEWMGEINPHGGSTSYAQ $KFX_1GRVTMTRDTSTSTVYME$ LSSLRSEDTAVYYCARPSAAYS $HYLGX_2DX_3WGRGTLVTVSS$; and wherein SEQ ID NO:25 comprises:

$DIQMTQSPSSVSASVGDRVTITCRX_4SQ$ $GISX_5WLX_6WYQQKPG$ $KAPKLLIYAX_7SX_8LQSGVPSRFSGSG$ SGTDFTLTISSLQPEDFAT $YYCQQAX_9VX_{10}PLTFGGGTKVEIK$; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L; or (ii) a CDR variant of (i), wherein the variant has 1, 2, or 3 amino acid modifications; or b. a VH region comprising a sequence at least 80% identical to the sequence of SEQ ID NO:20 and/or a VL region comprising a sequence at least 80% identical to the sequence of SEQ ID NO:25.

IL-33 binding proteins described herein may comprise:

(i) CDRH1, CDRH2, and/or CDRH3 from any one of SEQ ID NOs: 21-24 and/or CDRL1, CDRL2, and/or CDRL3 from SEQ ID NO:26-28; or (ii) one or more CDR variants of (i), wherein the variant has 1, 2, or 3 amino acid modifications.

IL-33 binding proteins described herein may comprise:

a. (i) any one or a combination of CDRs selected from CDRH1, CDRH2, and/or CDRH3 from SEQ ID NO:21 and/or CDRL1, CDRL2, and/or CDRL3 from SEQ ID NO:26; or (ii) a CDR variant of (i), wherein the variant has 1, 2, or 3 amino acid modifications; or b. a VH region comprising a sequence at least 80% identical to the sequence of SEQ ID NO:21 and/or a VL region comprising a sequence at least 80% identical to the sequence of SEQ ID NO:26.

IL-33 binding proteins described herein may comprise:

a. (i) any one or a combination of CDRs selected from CDRH1, CDRH2, and/or CDRH3 from SEQ ID NO:22 and/or CDRL1, CDRL2, and/or CDRL3 from SEQ ID NO:26; or (ii) a CDR variant of (i), wherein the variant has 1, 2, or 3 amino acid modifications; or b. a VH region comprising a sequence at least 80% identical to the sequence of SEQ ID NO:22 and/or a VL region comprising a sequence at least 80% identical to the sequence of SEQ ID NO:26.

IL-33 binding proteins described herein may comprise:

a. (i) any one or a combination of CDRs selected from CDRH1, CDRH2, and/or CDRH3 from SEQ ID NO:23 and/or CDRL1, CDRL2, and/or CDRL3 from SEQ ID NO:27; or (ii) a CDR variant of (i), wherein the variant has 1, 2, or 3 amino acid modifications; or b. a VH region comprising a sequence at least 80% identical to the sequence of SEQ ID NO:23 and/or a VL region comprising a sequence at least 80% identical to the sequence of SEQ ID NO:27.

IL-33 binding proteins described herein may comprise:

a. (i) any one or a combination of CDRs selected from CDRH1, CDRH2, and/or CDRH3 from SEQ ID NO:24 and/or CDRL1, CDRL2, and/or CDRL3 from SEQ ID NO:28; or (ii) a CDR variant of (i), wherein the variant has 1, 2, or 3 amino acid modifications; or b. a VH region comprising a sequence at least 80% identical to the sequence of SEQ ID NO:24 and/or a VL region comprising a sequence at least 80% identical to the sequence of SEQ ID NO:28.

In one embodiment, IL-33 binding proteins described herein may comprise:

a. any one or a combination of CDRs selected from CDRH1 of SEQ ID NO:1, CDRH2 of SEQ ID NO:2, CDRH3 of SEQ ID NO:5, CDRL1 of SEQ ID NO: 9, CDRL2 of SEQ ID NO: 13, and CDRL3 of SEQ ID NO:17, wherein SEQ ID NO:2 comprises:

EINPHGGSTSYAQKF$X_1$G;

wherein SEQ ID NO:5 comprises:

PSAAYSHYLG$X_2$D$X_3$;

wherein SEQ ID NO:9 comprises:

R$X_4$SQGIS$X_5$WL$X_6$;

wherein SEQ ID NO:13 comprises:

A$X_7$S$X_8$LQS;

wherein SEQ ID NO: 17 comprises:

QQA$X_9$V$X_{10}$PLT; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L; or b. a CDR variant of (a), wherein the variant has 1, 2, or 3 amino acid modifications. In an embodiment, the antigen binding protein is an antibody.

In an embodiment, an IL-33 binding protein described herein comprises the following 6 CDRs or a variant of any one or more thereof: CDRH1 of SEQ ID NO:1, CDRH2 of SEQ ID NO: 2, CDRH3 of SEQ ID NO:5, CDRL1 of SEQ ID NO:9, CDRL2 of SEQ ID NO: 13, and CDRL3 of SEQ ID NO:17, wherein SEQ ID NO:2 comprises:

EINPHGGSTSYAQKF$X_1$G;

wherein SEQ ID NO:5 comprises:

PSAAYSHYLG$X_2$D$X_3$;

wherein SEQ ID NO:9 comprises:

R$X_4$SQGIS$X_5$WL$X_6$;

wherein SEQ ID NO:13 comprises:

A$X_7$S$X_8$LQS;

wherein SEQ ID NO:17 comprises:

QQA$X_9$ V$X_{10}$PLT; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In one embodiment, the variant has 1, 2, or 3 amino acid modifications. In an embodiment, the antigen binding protein is an antibody.

In one embodiment, IL-33 binding proteins described herein may comprise:

a. any one or a combination of CDRs selected from CDRH1 of SEQ ID NO:1, CDRH2 of SEQ ID NO:4, CDRH3 of SEQ ID NO:7, CDRL1 of SEQ ID NO:10, CDRL2 of SEQ ID NO: 14, and CDRL3 of SEQ ID NO:18; or b. a CDR variant of (a), wherein the variant has 1, 2, or 3 amino acid modifications. In an embodiment, the antigen binding protein is an antibody.

In an embodiment, an IL-33 binding protein described herein comprises the following 6 CDRs or a variant of any one or more thereof: CDRH1 of SEQ ID NO:1, CDRH2 of SEQ ID NO: 4, CDRH3 of SEQ ID NO:7, CDRL1 of SEQ ID NO:10, CDRL2 of SEQ ID NO:14, and CDRL3 of SEQ ID NO:18. In one embodiment, the variant has 1, 2, or 3 amino acid modifications. In an embodiment, the antigen binding protein is an antibody.

In one embodiment, IL-33 binding proteins described herein may comprise:

a. any one or a combination of CDRs selected from CDRH1 of SEQ ID NO:1, CDRH2 of SEQ ID NO:3, CDRH3 of SEQ ID NO:7, CDRL1 of SEQ ID NO:12, CDRL2 of SEQ ID NO: 16, and CDRL3 of SEQ ID NO: 19; or b. a CDR variant of (a), wherein the variant has 1, 2, or 3 amino acid modifications. In an embodiment, the antigen binding protein is an antibody.

In an embodiment, an IL-33 binding protein described herein comprises the following 6 CDRs or a variant of any one or more thereof: CDRH1 of SEQ ID NO:1, CDRH2 of SEQ ID NO: 3, CDRH3 of SEQ ID NO:7, CDRL1 of SEQ ID NO: 12, CDRL2 of SEQ ID NO:16, and CDRL3 of SEQ ID NO:19. In one embodiment, the variant has 1, 2, or 3 amino acid modifications. In an embodiment, the antigen binding protein is an antibody.

In one embodiment, IL-33 binding proteins described herein may comprise:

a. any one or a combination of CDRs selected from CDRH1 of SEQ ID NO:1, CDRH2 of SEQ ID NO:3, CDRH3 of SEQ ID NO:6, CDRL1 of SEQ ID NO: 10, CDRL2 of SEQ ID NO: 14, and CDRL3 of SEQ ID NO: 18; or b. a CDR variant of (a), wherein the variant has 1, 2, or 3 amino acid modifications. In an embodiment, the antigen binding protein is an antibody.

In an embodiment, an IL-33 binding protein described herein comprises the following 6 CDRs or a variant of any one or more thereof: CDRH1 of SEQ ID NO:1, CDRH2 of SEQ ID NO: 3, CDRH3 of SEQ ID NO:6, CDRL1 of SEQ ID NO: 10, CDRL2 of SEQ ID NO: 14, and CDRL3 of SEQ ID NO:18. In one embodiment, the variant has 1, 2, or 3 amino acid modifications. In an embodiment, the antigen binding protein is an antibody.

In one embodiment, IL-33 binding proteins described herein may comprise:

a. any one or a combination of CDRs selected from CDRH1 of SEQ ID NO: 1, CDRH2 of SEQ ID NO:3, CDRH3 of SEQ ID NO:8, CDRL1 of SEQ ID NO:11, CDRL2 of SEQ ID NO: 15, and CDRL3 of SEQ ID NO:18; or b. a CDR variant of (a), wherein the variant has 1, 2, or 3 amino acid modifications. In an embodiment, the antigen binding protein is an antibody.

In an embodiment, an IL-33 binding protein described herein comprises the following 6 CDRs or a variant of any one or more thereof: CDRH1 of SEQ ID NO:1, CDRH2 of SEQ ID NO: 3, CDRH3 of SEQ ID NO:8, CDRL1 of SEQ ID NO:11, CDRL2 of SEQ ID NO:15, and CDRL3 of SEQ ID NO:18. In one embodiment, the variant has 1, 2, or 3 amino acid modifications. In an embodiment, the antigen binding protein is an antibody.

In one embodiment, antigen binding proteins of the present disclosure show cross-reactivity between human IL-33 and IL-33 from another species, such as such as cynomolgus IL-33 or rhesus IL-33. An antigen binding protein described herein may specifically bind human IL-33 and cynomolgus IL-33. Such cross-reactivity can be exploited during pre-clinical research, e.g., in one or more non-human primate systems such as rhesus monkey or cynomolgus monkey. Such preclinical research can be performed before the antigen binding protein is tested in humans. Such cross-reactivity can be exploited to make one or more side-by-side comparisons of using an antigen binding protein herein. In one embodiment, cross reactivity between other species used in disease models such as dog or mouse is also envisaged. Optionally, the binding affinity of the antigen binding protein for cynomolgus IL-33 and the binding affinity for human IL-33 differ by no more than a factor of 2, 5, 10, 50, or 100. In one embodiment, the binding affinity of the antigen binding protein for cynomolgus IL-33 and the binding affinity for human IL-33 differ by no more than a factor of 10.

In an embodiment, the equilibrium dissociation constant (KD) of the antigen binding protein-IL-33 interaction is 100 nM or less, 10 nM or less, 2 nM or less, or 1 nM or less. Alternatively, the KD may be between 1 pM and 500 pM or between 500 pM and 1 nM. In one embodiment, the KD is less than or equal to 500 pM, less than or equal to 400 pM, less than or equal to 300 pM, less than or equal to 200 pM, less than or equal to 100 pM, less than or equal to 75 pM, less than or equal to 50 pM, less than or equal to 40 pM, less than or equal to 30 pM, less than or equal to 25 pM, less than or equal to 20 pM, less than or equal to 10 pM, or less than or equal to 5 pM. In one embodiment, the KD is between 1 pM and 10 pM (e.g., between 1.8 pM and 6 pM). In another embodiment, the KD is between 0.01 pM and 100 pM (e.g., between 0.1 pM and 45 pM). In one embodiment, the affinity of the IL-33 binding protein for human IL-33 is less than or equal to 5 pM (e.g., 3.3 pM) at 25° C. In one embodiment, the affinity of the IL-33 binding protein for human IL-33 is less than or equal to 15 pM (e.g., 13.5 pM) at 37° C. In one embodiment, the affinity of the IL-33 binding protein for cynomolgus IL-33 at 25° C. is less than or equal to 30 pM (e.g., 27.5 pM). In one embodiment, the affinity of the IL-33 binding protein for cynomolgus IL-33 at 25° C. is less than or equal to 60 pM at 37° C. (e.g., 56.5 pM). For antigen binding proteins herein, a smaller KD numerical value corresponds with stronger binding to an antigen (e.g., IL-33). The reciprocal of KD (i.e., 1/KD) is the equilibrium association constant (KA) having units $M^{-1}$. For antigen binding proteins herein, a larger KA numerical value corresponds with stronger binding to an antigen (e.g., IL-33).

In one embodiment, the IL-33 binding protein does not bind to human IL-1α and/or human IL-162 . In one embodiment, the IL-33 binding protein does not bind to human IL-1α and human IL-1β.

In one embodiment, the IL-33 binding protein does not bind to human oxidized IL-33 and/or cynomolgus oxidized IL-33. In one embodiment, the IL-33 binding protein does not bind to human oxidized IL-33 and cynomolgus oxidized IL-33.

In one embodiment, the IL-33 binding protein binds to hFcγRI with a KD of less than 25 nM (e.g., 24.3 nM). In one embodiment, the IL-33 binding protein binds to hFcγRIIa (H131) with a KD of less than or equal to 600 nM (e.g., 574.0 nM). In one embodiment, the IL-33 binding protein binds to hFcγRIIa (R131) with a KD of less than or equal to 525 nM (e.g., 502.0 nM). In one embodiment, the IL-33 binding protein binds to hFcγRIIb with a KD of less than or equal to 5250 nM (e.g., 5220.0 nM). In one embodiment, the IL-33 binding protein binds to hFcγRIIIa (V158) with a KD of less than or equal to 225 nM (e.g., 215.0 nM). In one embodiment, the IL-33 binding protein binds to hFcγRIIIa (F158) with a KD of less than or equal to 1000 nM (e.g., 987.0 nM). In one embodiment, the IL-33 binding protein binds to cFcγRIIa with a KD of less than or equal to 2150 nM (e.g., 2110.0 nM). In one embodiment, the IL-33 binding protein binds to cFcγRIIb with a KD of less than or equal to 1125 nM (e.g., 1100.0 nM). In one embodiment, the IL-33 binding protein binds to cFcγRIIIa with a KD of less than or equal to 125 nM (e.g., 119.0 nM).

In one embodiment, the IL-33 binding protein binds to human recombinant neonatal receptor (FcRn) with a KD of less than or equal to 30 nM or less than or equal to 25 nM (e.g., 25.0 nM) at pH 6.0. In one embodiment, the IL-33 binding protein binds to human recombinant neonatal receptor (FcRn) with a KD of less than or equal to 1250 nM (e.g., 1230 nM) at pH 7.4. In one embodiment, the IL-33 binding protein binds to cynomolgus recombinant neonatal receptor (FcRn) with a KD of less than or equal to 30 nM (e.g., 24.7 nM) at pH 6.0. In one embodiment, the IL-33 binding protein binds to cynomolgus recombinant neonatal receptor (FcRn) with a KD of less than or equal to 2600 nM or less than or equal to 2575 nM (e.g., 2560 nM) at pH 7.4.

In one embodiment, the IL-33 binding protein binds to human C1q with a KD of less than or equal to 225 nM (e.g., 213 nM).

The dissociation rate constant (kd) or "off-rate" describes the stability of the antigen binding protein-IL-33 complex, i.e., the fraction of complexes that decay per second. For example, a kd of 0.01 $s^{-1}$ equates to 1% of the complexes decaying per second. In an embodiment, the dissociation rate constant (kd) is $1\times10^{-3}$ $s^{-1}$ or less, $1\times10^{-4}$ $s^{-1}$ or less, $1\times10^{-5}$ $s^{-1}$ or less, or $1\times10^{-6}$ $s^{-1}$ or less. The kd may be between $1\times10^{-5}$ $s^{-1}$ and $1\times10^{-4}$ $s^{-1}$ or between $1\times10^{-4}$ $s^{-1}$ and $1\times10^{-3}$ $s^{-1}$.

The association rate constant (ka) or "on-rate" describes the rate of antigen binding protein-antigen (e.g., IL-33) complex formation. The ka of the antigen binding protein-IL-33 interaction may be about $1.5\times10^{5}$ $M^{-1}$ $s^{-1}$. Alternatively, the ka may be between $1\times10^{6}$ $M^{-1}$ $s^{-1}$ and $1\times10^{5}$ $M^{-1}$ $s^{-1}$. Alternatively, the ka may be between $1\times10^{5}$ $M^{-1}$ $s^{-1}$ and $5\times10^{5}$ $M^{-1}$ $s^{-1}$ or between $1\times10^{5}$ $M^{-1}$ $s^{-1}$ and $8\times10^{5}$ $M^{-1}$ $s^{-1}$.

An IL-33 binding protein described herein can be neutralizing. For example, the methods described in Example 13 through Example 17 may be used to assess the neutralizing capability of an IL-33 binding protein. The reduction or inhibition in biological activity may be partial or total. A neutralizing antigen binding protein may neutralize the activity of IL-33 by at least 20%, at least 30%, at least 40%, at least 50%, at least 55%, at least 60%, at least 65%, at least 70%, at least 75%, at least 80%, at least 82%, at least 84%, at least 86%, at least 88%, at least 90%, at least 92%, at least 94%, at least 95%, at least 96%, at least 97%, at least 98%, at least 99%, or 100% relative to IL-33 activity in the absence of the antigen binding protein. Neutralization may be determined or measured using one or more assays known to the skilled person or as described herein.

In one embodiment, an IL-33 binding protein described herein inhibits IL-33 induced superoxide generation from isolated eosinophils. In one embodiment, the IL-33 binding protein described herein inhibits IL-33 induced superoxide generation from isolated eosinophils with an $IC_{50}$ of less than or equal to 100 pM, less than or equal to 75 pM, less than or equal to 50 pM, less than or equal to 40 pM, less than or equal to 30 pM, less than or equal to 25 pM, or less than or equal to 20 pM (e.g., 19.65 pM). In one embodiment, the IL-33 binding protein described herein inhibits IL-33 induced superoxide generation from isolated eosinophils with a $pIC_{50}$ of less than or equal to 11 or less than or equal to 10.75 (e.g., 10.73).

In one embodiment, an IL-33 binding protein described herein inhibits IL-33 induced IFN-γ secretion from CD4+ T cells. In one embodiment, the IL-33 binding protein described herein inhibits IL-33 induced IFN-γ secretion from CD4+ T cells with an $IC_{50}$ of less than or equal to 1000 pM, less than or equal to 900 pM, less than or equal to 800 pM, or less than or equal to 700 pM (e.g., 675.14). In one embodiment, the IL-33 binding protein described herein inhibits IL-33 induced IFN-γ secretion from CD4+ T cells with a $pIC_{50}$ of less than or equal to 9.5 or less than or equal to 9.25 (e.g., 9.2).

In one embodiment, an IL-33 binding protein described herein inhibits IL-33 induced IL-8 and/or IL-6 secretion from human umbilical vein endothelial cells (HUVECs). In one embodiment, an IL-33 binding protein described herein inhibits IL-33 induced IL-8 and IL-6 secretion from human umbilical vein endothelial cells (HUVECs).

In one embodiment, an IL-33 binding protein described herein inhibits IL-33 induced IL-8 secretion from human umbilical vein endothelial cells (HUVECs). In one embodiment, the IL-33 binding protein described herein inhibits IL-33 induced IL-8 secretion from HUVECs with an $IC_{50}$ of less than or equal to 500 pM, less than or equal to 475 pM, less than or equal to 450 pM, less than or equal to 425 pM, or less than or equal to 400 pM (e.g., 389.90 pM). In one embodiment, the IL-33 binding protein described herein inhibits IL-33 induced IL-8 secretion from HUVECs with a $pIC_{50}$ of less than or equal to 9.75 or less than or equal to 9.5 (e.g., 9.42).

In one embodiment, an IL-33 binding protein described herein inhibits IL-33 induced IL-6 secretion from human umbilical vein endothelial cells (HUVECs). In one embodiment, the IL-33 binding protein described herein inhibits IL-33 induced IL-6 secretion from HUVECs with an $IC_{50}$ of less than or equal to 300 pM, less than or equal to 275 pM, less than or equal to 250 pM, or less than or equal to 225 pM (e.g., 217.30). In one embodiment, the IL-33 binding protein described herein inhibits IL-33 induced IL-6 secretion from HUVECs with a $pIC_{50}$ of less than or equal to 10 or less than or equal to 9.75 (e.g., 9.42).

In one embodiment, an IL-33 binding protein described herein inhibits IL-33 induced β-hexosaminidase release from basophils. In one embodiment, the IL-33 binding protein described herein inhibits IL-33 induced β-hexosaminidase release from basophils with an $IC_{50}$ of less than or equal to 10 nM, less than or equal to 7.75 nM, less than or equal to 5 nM, less than or equal to 4 nM, less than or equal to 3 nM, less than or equal to 2.75 nM, less than or equal to 2.5 nM, or less than or equal to 2.25 nM (e.g., 2.03 nM). In one embodiment, the IL-33 binding protein described herein inhibits IL-33 induced β-hexosaminidase release from basophils with a $pIC_{50}$ of less than or equal to 9.25 or less than or equal to 9 (e.g., 8.78).

In one embodiment, the affinity of IL-33 for the ST2 receptor is not affected when IL-33 is complexed with an IL-33 binding protein described herein.

In one embodiment, an IL-33 binding protein described herein pre-complexed with IL-33 demonstrates concentration dependent inhibition of IL-33/IL-12 stimulated IFN-γ release in whole blood. In one embodiment, the IL-33 binding protein described herein pre-complexed with IL-33 demonstrates concentration dependent inhibition of IL-33/IL-12 stimulated IFN-γ release in whole blood with an IC50 value of less than or equal to 4 nM (e.g., 3.90 nM) for IL-33 concentrations of 100 ng/mL. In one embodiment, the IL-33 binding protein described herein pre-complexed with IL-33 demonstrates concentration dependent inhibition of IL-33/IL-12 stimulated IFN-γ release in whole blood with an IC50 value of less than or equal to 3.50 or less than or equal to 3.25 (e.g., 3.25 nM) for IL-33 concentrations of 30 ng/mL. In one embodiment, the IL-33 binding protein described herein pre-complexed with IL-33 demonstrates concentration dependent inhibition of IL-33/IL-12 stimulated IFN-γ release in whole blood with an IC50 value of less than or equal to 2.5 nM or less than or equal to 2 nM (e.g., 1.95 nM) for IL-33 concentrations of 10 ng/mL. In one embodiment, the IL-33 binding protein described herein pre-complexed with IL-33 demonstrates concentration dependent inhibition of IL-33/IL-12 stimulated IFN-γ release in whole blood with a pIC50 value of less than or equal to 9, less than or equal to 8.75, or less than or equal to 8.5 (e.g., 8.48) for IL-33 concentrations of 100 ng/ml. In one embodiment, the IL-33 binding protein described herein pre-complexed with IL-33 demonstrates concentration dependent inhibition of IL-33/IL-12 stimulated IFN-γ release in whole blood with a pIC50 value of less than or equal to 9 or less than or equal to 8.75 (e.g., 8.53) for IL-33 concentrations of 30 ng/mL. In one embodiment, the IL-33 binding protein described herein pre-complexed with IL-33 demonstrates concentration dependent inhibition of IL-33/IL-12 stimulated IFN-γ release in whole blood with a pIC50 value of less than or equal to 9.25 or less than or equal to 9 (e.g., 8.80) for IL-33 concentrations of 10 ng/ml.

In one embodiment, an IL-33 binding protein described herein that is not pre-complexed with IL-33 also demonstrates concentration dependent inhibition of IL-33/IL-12 stimulated IFN-γ release in whole blood. In one embodiment, the IL-33 binding protein described herein that is not pre-complexed with IL-33 demonstrates concentration dependent inhibition of IL-33/IL-12 stimulated IFN-γ release in whole blood with an IC50 value of less than or equal to 2 nM or less than or equal to 1.75 nM (e.g., 1.57 nM) for IL-33 concentrations of 30 ng/ml. In one embodiment, the IL-33 binding protein described herein that is not pre-complexed with IL-33 demonstrates concentration dependent inhibition of IL-33/IL-12 stimulated IFN-γ release in whole blood with an IC50 value of less than or equal to 1 nM, less than or equal to 0.75 nM, or less than or equal to 0.5 nM (e.g., 0.37 nM) for IL-33 concentrations of 10 ng/ml. In one embodiment, the IL-33 binding protein described herein that is not pre-complexed with IL-33 demonstrates concentration dependent inhibition of IL-33/IL-12 stimulated IFN-γ release in whole blood with a pIC50 value of less than or equal to 9.25 or less than or equal to 9 (e.g., 8.89) for IL-33 concentrations of 30 ng/mL. In one embodiment, the IL-33 binding protein described herein that is not pre-complexed with IL-33 demonstrates concentration dependent inhibition of IL-33/IL-12 stimulated IFN-γ release in whole blood with a pIC50 value of less than or equal to 10 or less than or equal to 9.75 (e.g., 9.51) for IL-33 concentrations of 10 ng/ml.

In one embodiment, an IL-33 binding protein described herein can completely block production of human IL-33 stimulated IL-6, TNF-α, IL-13, and/or IL-18. In one embodiment, an IL-33 binding protein described herein can completely block production of human IL-33 stimulated IL-6, TNF-α, IL-13, and IL-18.

In one embodiment, an IL-33 binding protein described herein can completely block production of human IL-33 stimulated IL-6. In one embodiment, the IL-33 binding protein herein can completely block production of human IL-33 stimulated IL-6 with an IC50 value of less than or equal to 50 pM, less than or equal to 40 pM, or less than or equal to 35 pM (e.g., 31.21 pM) at an IL-33 concentration of 1 ng/mL. In one embodiment, the IL-33 binding protein herein can completely block production of human IL-33 stimulated IL-6 with a pIC50 value of less than or equal to 11 or less than or equal to 10.75 (e.g., 10.51) at an IL-33 concentration of 1 ng/mL. In one embodiment, the IL-33 binding protein herein can completely block production of human IL-33 stimulated IL-6 with an IC50 value of less than or equal to 600 pM or less than or equal to 575 pM (e.g., 566 pM) at an IL-33 concentration of 10 ng/mL. In one embodiment, the IL-33 binding protein herein can completely block production of human IL-33 stimulated IL-6 with a pIC50 value of less than or equal to 9.5 or less than or equal to 9.25 (e.g., 9.25) at an IL-33 concentration of 10 ng/mL.

In one embodiment, an IL-33 binding protein described herein can completely block production of human IL-33 stimulated TNF-α. In one embodiment, the IL-33 binding protein herein can completely block production of human IL-33 stimulated TNF-α with an IC50 value of less than or equal to 50 pM or less than or equal to 40 pM (e.g., 37.35 pM) at an IL-33 concentration of 1 ng/mL. In one embodiment, the IL-33 binding protein herein can completely block production of human IL-33 stimulated TNF-α with a pIC50 value of less than or equal to 11, less than or equal to 10.75, or less than or equal to 10.5 (e.g., 10.43) at an IL-33 concentration of 1 ng/mL. In one embodiment, the IL-33 binding protein herein can completely block production of human IL-33 stimulated TNF-α with an IC50 value of less than or equal to 600 pM or less than or equal to 590 pM (e.g., 581 pM) at an IL-33 concentration of 10 ng/ml. In one embodiment, the IL-33 binding protein herein can completely block production of human IL-33 stimulated TNF-α with a pIC50 value of less than or equal to 9.5 or less than or equal to 9.25 (e.g., 9.24) at an IL-33 concentration of 10 ng/ml.

In one embodiment, an IL-33 binding protein described herein can completely block production of human IL-33 stimulated IL-13. In one embodiment, the IL-33 binding protein herein can completely block production of human IL-33 stimulated IL-13 with an IC50 value of less than or equal to 50 pM, less than or equal to 40 pM, or less than or equal to 30 pM (e.g., 28.01 pM) at an IL-33 concentration of 1 ng/mL. In one embodiment, the IL-33 binding protein herein can completely block production of human IL-33 stimulated IL-13 with a pIC50 value of less than or equal to 1, less than or equal to 0.75, or less than or equal to 0.6 (e.g., 0.55) at an IL-33 concentration of 1 ng/mL. In one embodiment, the IL-33 binding protein herein can completely block production of human IL-33 stimulated IL-13 with an IC50 value of less than or equal to 600 pM or less than or equal to 575 pM (e.g., 567 pM) at an IL-33 concentration of 10 ng/mL. In one embodiment, the IL-33 binding protein herein can completely block production of human IL-33 stimulated IL-13 with a pIC50 value of less than or equal to 9.5 or less than or equal to 9.25 (e.g., 9.25) at an IL-33 concentration of 10 ng/ml.

In one embodiment, an IL-33 binding protein described herein can completely block production of human IL-33 stimulated IL-18. In one embodiment, the IL-33 binding protein herein can completely block production of human IL-33 stimulated IL-18 with an IC50 value of less than or equal to 100 pM, less than or equal to 90 pM, less than or equal to 80 pM, or less than or equal to 70 pM (e.g., 61.26 pM) at an IL-33 concentration of 1 ng/mL. In one embodiment, the IL-33 binding protein herein can completely block production of human IL-33 stimulated IL-18 with a pIC50 value of less than or equal to 11, less than or equal to 10.75, less than or equal to 10.5, or less than or equal to 10.25 (e.g., 10.21) at an IL-33 concentration of 1 ng/mL. In one embodiment, the IL-33 binding protein herein can completely block production of human IL-33 stimulated IL-18 with an IC50 value of less than or equal to 700 pM, less than or equal to 675 pM, or less than or equal to 650 pM (e.g., 631 pM) at an IL-33 concentration of 10 ng/mL. In one embodiment, the IL-33 binding protein herein can completely block production of human IL-33 stimulated IL-18 with a pIC50 value of less than or equal to 9.5 or less than or equal to 9.25 (e.g., 9.20) at an IL-33 concentration of 10 ng/ml.

An IL-33 binding protein described herein may comprise a VH region that is at least 90% identical to SEQ ID NO:20 and/or a VL region that is at least 90% identical to SEQ ID NO:25, wherein SEQ ID NO:20 comprises:

QVQLVQSGAEVKKPGASVKVSCKASGYTFI-
SYGMHWVRQAPGQGLEWMGEIN

PHGGSTSYAQKFX$_1$GRVTMTRDTSTST VYMELSSLRSEDTAVYYCARPSAAYSH YLGX$_2$DX$_3$WGRGTLVTVSS; and wherein SEQ ID NO:25 comprises:

DIQMTQSPSSVSASVGDRVTITCRX$_4$SQ GISX$_5$WLX$_6$WYQQKPGKAPKLLIYAX$_7$S X$_8$LQSGVPSRFSGSGSGTDFTLTISSLQPED FATYYCQQAX$_9$VX$_{10}$PLTFGGGTKVEI K; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L.

An IL-33 binding protein described herein may comprise a VH region that is at least 90% identical to SEQ ID NO:21 and/or a VL region that is at least 90% identical to SEQ ID NO:26. An IL-33 binding protein described herein may comprise a VH region that is at least 90% identical to SEQ ID NO:22 and/or a VL region that is at least 90% identical to SEQ ID NO:26. An IL-33 binding protein described herein may comprise a VH region that is at least 90% identical to SEQ ID NO:23 and/or a VL region that is at least 90% identical to SEQ ID NO:27. An IL-33 binding protein described herein may comprise a VH region that is at least 90% identical to SEQ ID NO:24 and/or a VL region that is at least 90% identical to SEQ ID NO:28.

An IL-33 binding protein described herein may comprise a VH region that is at least 95% identical to SEQ ID NO:20 and/or a VL region that is at least 95% identical to SEQ ID NO:25, wherein SEQ ID NO:20 comprises:

QVQLVQSGAEVKKPGASVKVSCKASGYTFI-SYGMHWVRQAPGQGLEWMGEIN PHGGSTSYAQKFX$_1$GRVTMTRDTSTST VYMELSSLRSEDTAVYYCARPSAAYSH YLGX$_2$DX$_3$WGRGTLVTVSS; and wherein SEQ ID NO:25 comprises:

DIQMTQSPSSVSASVGDRVTITCRX$_4$SQ GISX$_5$WLX$_6$WYQQKPGKAPKLLIYAX$_7$S X$_8$LQSGVPSRFSGSGSGTDFTLTISS LQPEDFATYYCQQAX$_9$VX$_{10}$PLTFGGGTKVEI K; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L.

An IL-33 binding protein described herein may comprise a VH region that is at least 95% identical to SEQ ID NO:21 and/or a VL region that is at least 95% identical to SEQ ID NO:26. An IL-33 binding protein described herein may comprise a VH region that is at least 95% identical to SEQ ID NO:22 and/or a VL region that is at least 95% identical to SEQ ID NO:26. An IL-33 binding protein described herein may comprise a VH region that is at least 95% identical to SEQ ID NO:23 and/or a VL region that is at least 95% identical to SEQ ID NO:27. An IL-33 binding protein described herein may comprise a VH region that is at least 95% identical to SEQ ID NO:24 and/or a VL region that is at least 95% identical to SEQ ID NO:28.

An IL-33 binding protein described herein may comprise a VH region that is 100% identical to SEQ ID NO:20 and/or a VL region that is 100% identical to SEQ ID NO:25, wherein SEQ ID NO:20 comprises:

QVQLVQSGAEVKKPGASVKVSCKASGYTFI-SYGMHWVRQAPGQGLEWMGEIN PHGGSTSYAQKFX$_1$GRVTMTRDTSTSTV YMELSSLRSEDTAVYYCARPSAAYSH YLGX$_2$DX$_3$WGRGTLVTVSS; and wherein SEQ ID NO:25 comprises:

DIQMTQSPSSVSASVGDRVTITCRX$_4$SQ GISX$_5$WLX$_6$WYQQKPGKAPKLLIYAX$_7$S X$_8$LQSGVPSRFSGSGSGTDFTL TISSLQPEDFATYYCQQAX$_9$VX$_{10}$PLTFGGGTKVEI K; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L.

An IL-33 binding protein described herein may comprise a VH region that is 100% identical to SEQ ID NO:21 and/or a VL region that is 100% identical to SEQ ID NO:26. An IL-33 binding protein described herein may comprise a VH region that is 100% identical to SEQ ID NO: 21 and a VL region that is 100% identical to SEQ ID NO:26. An IL-33 binding protein described herein may comprise a VH region that is 100% identical to SEQ ID NO:22 and/or a VL region that is 100% identical to SEQ ID NO:26. An IL-33 binding protein described herein may comprise a VH region that is 100% identical to SEQ ID NO:22 and a VL region that is 100% identical to SEQ ID NO:26. An IL-33 binding protein described herein may comprise a VH region that is 100% identical to SEQ ID NO:23 and/or a VL region that is 100% identical to SEQ ID NO:27. An IL-33 binding protein described herein may comprise a VH region that is 100% identical to SEQ ID NO:23 and a VL region that is 100% identical to SEQ ID NO:27. An IL-33 binding protein described herein may comprise a VH region that is 100% identical to SEQ ID NO: 24 and/or a VL region that is 100% identical to SEQ ID NO:28. An IL-33 binding protein described herein may comprise a VH region that is 100% identical to SEQ ID NO:24 and a VL region that is 100% identical to SEQ ID NO:28.

An IL-33 binding protein described herein may comprise a Heavy Chain (HC) sequence that is at least 90% identical to SEQ ID NO:29 and/or a Light Chain (LC) that is at least 90% identical to SEQ ID NO:34, wherein SEQ ID NO:29 comprises:

QVQLVQSGAEVKKPGASVKVSCKASGYTFI-SYGMHWVRQAPGQGLEWMGEIN PHGGSTSYAQKFX$_1$GRVTMTRDTST STVYMELSSLRSEDTAVYYCARPSAAYSH YLGX$_2$DX$_3$WGRGTLVTVSSASTKGPS VFPLAPSSKSTSGGTAALGCLVKDYFPEP VTVSWNSGALTSGVHTFPAVLQSSGLYS-LSSVVTVPSSSLGTQTYICNVNHKPSN TKVDKKVEPKSCDKTHTCPPCPA-PELLGGPSVFLFPPKPKDTLYITREPEVTCVVV DVSHEDPEVKFNWYVDGVEVHNAKTKPRE-EQYNSTYRVVSVLTVLHQDWLNG KEYKCKVSNKALPA-PIEKTISKAKGQPREPQVYTLPPSRDELT-KNQVSLTCLVKG FYPSDIA VEWESNGQPEN-NYKTTPPVLDSDGSFFLYSKLTVD KSRWQQGNVFSC SVMHEALHNHYTQKSLSL-SPGK; and wherein SEQ ID NO:34 comprises:

DIQMTQSPSSVSASVGDRVTITCRX$_4$SQ GISX$_5$WLX$_6$WYQQKPGKAPKLLIYAX$_7$S X$_8$LQSGVPSRFSGSGSGTDFTLTISSLQPEDF ATYYCQQAX$_9$VX$_{10}$PLTFGGGTKVEI KRTVAAPSVFIFPPSDEQLKSGTASVVCLLNNFY-PREAKVQWKVDNALQSGNSQ ESVTEQDSKDS-TYSLSSTLTLSKADYEKHKVYACE-VTHQGLSSPVTKSFNRGEC;

and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

An IL-33 binding protein described herein may comprise a Heavy Chain (HC) sequence that is at least 90% identical to SEQ ID NO:30 and/or a Light Chain (LC) sequence that is at least 90% identical to SEQ ID NO:35. An IL-33 binding protein described herein may comprise an HC sequence that is at least 90% identical to SEQ ID NO:31 and/or an LC sequence that is at least 90% identical to SEQ ID NO:35. An IL-33 binding protein described herein may comprise an HC sequence that is at least 90% identical to SEQ ID NO:32 and/or an LC sequence that is at least 90% identical to SEQ ID NO:36. An IL-33 binding protein described herein may comprise an HC sequence that is at least 90% identical to SEQ ID NO:33 and/or an LC sequence that is at least 90% identical to SEQ ID NO:37.

An IL-33 binding protein described herein may comprise a Heavy Chain (HC) sequence that is at least 95% identical to SEQ ID NO:29 and/or a Light Chain (LC) that is at least 95% identical to SEQ ID NO:34, wherein SEQ ID NO:29 comprises:

QVQLVQSGAEVKKPGASVKVSCKASGYTFI-SYGMHWVRQAPGQGLEWMGEIN PHGGSTSYAQKF$X_1$GRVTMTRDTSTS TVYMELSSLRSEDTAVYYCARPSAAYSH YLG$X_2$D$X_3$WGRGTLVTVSSASTKGPS VFPLAPSSKSTSGGTAALGCLVKDYFPEP VTVSWNSGALTSGVHTFPAVLQSSGLYS-LSSVVTVPSSSLGTQTYICNVNHKPSN TKVDKKVEPKSCDKTHTCPPCPA-PELLGGPSVFLFPPKPKDTLYITREPEVTCVVV DVSHEDPEVKFNWYVDGVEVHNAKTKPRE-EQYNSTYRVVSVLTVLHQDWLNG KEYKCKVSNKALPA-PIEKTISKAKGQPREPQVYTLPPSRDELT-KNQVSLTCLVKG FYPSDIA VEWESNGQPEN-NYKTTPPVLDSDGSFFLYSKLTVDKSR WQQGNVFSC SVMHEALHNHYTQKSLSLSPGK; and wherein SEQ ID NO:34 comprises:

DIQMTQSPSSVSASVGDRVTITCR$X_4$SQG IS$X_5$WL$X_6$WYQQKPGKAPKLLIYA$X_7$S $X_8$LQSGVPSRFSGSGSGTDFTLTISSLQ PEDFATYYCQQA$X_9$V$X_{10}$PLTFGGGTKVEI KRTVAAPSVFIFPPSDEQLKSGTASVVCLLNNFY-PREAKVQWKVDNALQSGNSQ ESVTEQDSKDS-TYSLSSTLTLSKADYEKHKVYACE-VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

An IL-33 binding protein described herein may comprise a Heavy Chain (HC) sequence that is at least 95% identical to SEQ ID NO:30 and/or a Light Chain (LC) sequence that is at least 95% identical to SEQ ID NO:35. An IL-33 binding protein described herein may comprise an HC sequence that is at least 95% identical to SEQ ID NO:31 and/or an LC sequence that is at least 95% identical to SEQ ID NO:35. An IL-33 binding protein described herein may comprise an HC sequence that is at least 95% identical to SEQ ID NO:32 and/or an LC sequence that is at least 95% identical to SEQ ID NO:36. An IL-33 binding protein described herein may comprise an HC sequence that is at least 95% identical to SEQ ID NO:33 and/or an LC sequence that is at least 95% identical to SEQ ID NO:37.

An IL-33 binding protein described herein may comprise a Heavy Chain (HC) sequence that is 100% identical to SEQ ID NO:29 and/or a Light Chain (LC) that is 100% identical to SEQ ID NO: 34, wherein SEQ ID NO:29 comprises:

QVQLVQSGAEVKKPGASVKVSCKASGYTFI-SYGMHWVRQAPGQGLEWMGEIN PHGGSTSYAQKF$X_1$GRVTMTRDTSTSTV YMELSSLRSEDTAVYYCARPSAAYSH YLG$X_2$D$X_3$WGRGTLVTVSSASTKGPSVFP LAPSSKSTSGGTAALGCLVKDYFPEP VTVSWNSGALTSGVHTFPAVLQSSGLYS-LSSVVTVPSSSLGTQTYICNVNHKPSN TKVDKKVEPKSCDKTHTCPPCPA-PELLGGPSVFLFPPKPKDTLYITREPEVTCVVV DVSHEDPEVKFNWYVDGVEVHNAKTKPRE-EQYNSTYRVVSVLTVLHQDWLNG KEYKCKVSNKALPA-PIEKTISKAKGQPREPQVYTLPPSRDELT-KNQVSLTCLVKG FYPSDIA VEWESNGQPEN-NYKTTPPVLDSDGSFFLYSKLTVDKS RWQQGNVFSC SVMHEALHNHYTQKSLSL-SPGK; and wherein SEQ ID NO:34 comprises:

DIQMTQSPSSVSASVGDRVTITCR$X_4$SQGIS$X_5$ WL$X_6$WYQQKPGKAPKLLIYA$X_7$S $X_8$LQSGVPSRFSGSGSGTDFTLTISSLQPE DFATYYCQQA$X_9$V$X_{10}$PLTFGGGTKVEI KRTVAAPSVFIFPPSDEQLKSGTASVVCLLNNFY-PREAKVQWKVDNALQSGNSQ ESVTEQDSKDS-TYSLSSTLTLSKADYEKHKVYACE-VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

An IL-33 binding protein described herein may comprise a Heavy Chain (HC) sequence that is 100% identical to SEQ ID NO:30 and/or a Light Chain (LC) sequence that is 100% identical to SEQ ID NO:35. An IL-33 binding protein described herein may comprise an HC sequence that is 100% identical to SEQ ID NO:31 and/or an LC sequence that is 100% identical to SEQ ID NO:35. An IL-33 binding protein described herein may comprise an HC sequence that is 100% identical to SEQ ID NO:32 and/or an LC sequence that is 100% identical to SEQ ID NO: 36. An IL-33 binding protein described herein may comprise an HC sequence that is 100% identical to SEQ ID NO:33 and/or an LC sequence that is 100% identical to SEQ ID NO:37.

An IL-33 binding protein provided herein can comprise a sequence that is a variant amino acid sequence. A nucleic acid sequence of an IL-33 binding protein provided herein can comprise a variant nucleic acid sequence. A variant nucleic acid sequence herein can be of an IL-33 binding protein provided herein or of a variant thereof. The variant sequence substantially retains the biological characteristics of the unmodified protein, such as binding affinity for IL-33, cross-reactivity with both human and cynomolgus IL-33, and half-life.

A VH or VL (or HC or LC) sequence may be a variant sequence of a VH or VL (or HC or LC) sequence provided herein with up to 10 amino acid substitutions, additions, or deletions. Such a variant sequence may have 10, 9, 8, 7, 6, 5, 4, 3, 2, or 1 amino acid substitution(s), addition(s), or deletion(s).

An HC sequence may be a variant sequence of an HC sequence provided herein with up to 40 amino acid substitutions, additions, or deletions. An HC variant sequence may have up to 35, up to 30, up to 25, up to 20, up to 15, or up to 10 amino acid substitutions, additions, or deletions. An HC variant sequence may have 10, 9, 8, 7, 6, 5, 4, 3, 2, or 1 amino acid substitutions, additions, or deletions.

An LC sequence may be a variant sequence of an LC sequence provided herein with up to 20 amino acid substitutions, additions, or deletions. An LC variant sequence may have up to 15, up to 10, or up to 5 amino acid substitutions, additions, or deletions. An LC variant sequence may have 10, 9, 8, 7, 6, 5, 4, 3, 2, or 1 amino acid substitutions, additions, or deletions.

A sequence variation may exclude one or more or all of the CDRs. For example, the CDRs portion of the VH or VL (or HC or LC) sequence can be free of a sequence variation, and the variation can be present in a non-CDR portion of a VH or VL (or HC or LC) sequence, i.e., such that the CDR sequences are intact. A variation can be a substitution, such as a conservative substitution, for example, as provided in Table 2A or Table 2B.

An antigen binding protein having a variant sequence can substantially retain the biological characteristics of an unmodified antigen binding protein, such as inhibiting binding of IL-33 to the ST2 receptor. A binding property (e.g., KD, Kd, or Ka) of an IL-33 binding protein having a variant sequence can be substantially identical to an unmodified IL-33 binding protein. A binding property (e.g., KD, Kd, or Ka) of a variant sequence can be at least 75%, at least 80%, at least 85%, at least 90%, at least 95%, at least 96%, at least 97%, at least 98%, or at least 99% identical to that of an unmodified IL-33 binding protein.

An antigen binding protein as described herein, may be encoded by one or more isolated nucleic acid sequences. In an embodiment, the nucleic acid encoding the VH region is selected from the group consisting of SEQ ID NOs: 38-43, wherein:

h=a, c, or t; m=a or c; r=a or g; y=c or t; and n=a, c, g, or t.

In an embodiment, the nucleic acid encoding the VH region is selected from the group consisting of SEQ ID NOs: 44-47.

In an embodiment, the nucleic acid encoding the VL region is selected from the group consisting of SEQ ID NOs: 48-55, wherein:

k=g or t; m=a or c; r=a or g; s=c or g; y=c or t; and n=a, c, g, or t.

In an embodiment, the nucleic acid encoding the VL region is selected from the group consisting of SEQ ID NOs: 56-58.

In an embodiment, the nucleic acid encodes any one of the following combinations of VH region and VL region nucleic acid sequences: SEQ ID NO:38 and SEQ ID NO:48; SEQ ID NO: 38 and SEQ ID NO:49; SEQ ID NO:38 and SEQ ID NO:50; SEQ ID NO:38 and SEQ ID NO: 51; SEQ ID NO:38 and SEQ ID NO:52; SEQ ID NO:38 and SEQ ID NO:53; SEQ ID NO: 38 and SEQ ID NO:54; SEQ ID NO:38 and SEQ ID NO:55; SEQ ID NO:39 and SEQ ID NO: 48; SEQ ID NO:39 and SEQ ID NO:49; SEQ ID NO:39 and SEQ ID NO:50; SEQ ID NO: 39 and SEQ ID NO:51; SEQ ID NO:39 and SEQ ID NO:52; SEQ ID NO:39 and SEQ ID NO: 53; SEQ ID NO:39 and SEQ ID NO:54; SEQ ID NO:39 and SEQ ID NO:55; SEQ ID NO: 43 and SEQ ID NO:48; SEQ ID NO:43 and SEQ ID NO:49; SEQ ID NO:43 and SEQ ID NO: 50; SEQ ID NO:43 and SEQ ID NO:51; SEQ ID NO:43 and SEQ ID NO:52; SEQ ID NO: 43 and SEQ ID NO:53; SEQ ID NO:43 and SEQ ID NO:54; or SEQ ID NO:43 and SEQ ID NO: 55, wherein:

h=a, c, or t; k=g or t; m=a or c; r=a or g; s=c or g; y=c or t; and n=a, c, g, or t.

In an embodiment, the nucleic acid encodes any one of the following combinations of VH region and VL region nucleic acid sequences: SEQ ID NO:44 and SEQ ID NO:56; SEQ ID NO: 45 and SEQ ID NO:56; SEQ ID NO:46 and SEQ ID NO:57; or SEQ ID NO:47 and SEQ ID NO: 58.

In an embodiment, the nucleic acid encoding the heavy chain is selected from the group consisting of SEQ ID NOs: 59-64, wherein:

h=a, c, or t; m=a or c; r=a or g; y=c or t; and n=a, c, g, or t.

In an embodiment, the nucleic acid encoding the heavy chain is selected from the group consisting of SEQ ID NOs: 65-68.

In an embodiment, the nucleic acid encoding the light chain is selected from the group consisting of SEQ ID NOs: 69-76, wherein:

k=g or t; m=a or c; r=a or g; s=c or g; y=c or t; and n=a, c, g, or t.

In an embodiment, the nucleic acid encoding the light chain is selected from the group consisting of SEQ ID NOs: 77-79.

In an embodiment, the nucleic acid encodes any one of the following combinations of heavy chain and light chain nucleic acid sequences: SEQ ID NO:59 and SEQ ID NO:69; SEQ ID NO: 59 and SEQ ID NO: 70; SEQ ID NO:59 and SEQ ID NO:71; SEQ ID NO:59 and SEQ ID NO: 72; SEQ ID NO:59 and SEQ ID NO:73; SEQ ID NO:59 and SEQ ID NO:74; SEQ ID NO: 59 and SEQ ID NO:75; SEQ ID NO: 60 and SEQ ID NO: 69; SEQ ID NO:60 and SEQ ID NO: 70; SEQ ID NO:60 and SEQ ID NO:71; SEQ ID NO:60 and SEQ ID NO:72; SEQ ID NO: 60 and SEQ ID NO:73; SEQ ID NO:60 and SEQ ID NO:74; SEQ ID NO:60 and SEQ ID NO: 75; SEQ ID NO: 64 and SEQ ID NO:69; SEQ ID NO:64 and SEQ ID NO:70; SEQ ID NO: 64 and SEQ ID NO:71; SEQ ID NO:64 and SEQ ID NO:72; SEQ ID NO:64 and SEQ ID NO: 73; SEQ ID NO:64 and SEQ ID NO:74; or SEQ ID NO:64 and SEQ ID NO:75, wherein:

h=a, c, or t; k=g or t; m=a or c; r=a or g; s=c or g; y=c or t; and n=a, c, g, or t.

In an embodiment, the nucleic acid encodes any one of the following combinations of heavy chain and light chain nucleic acid sequences: SEQ ID NO:65 and SEQ ID NO:77; SEQ ID NO: 66 and SEQ ID NO:77; SEQ ID NO: 67 and SEQ ID NO:78; or SEQ ID NO:68 and SEQ ID NO: 79.

Antigen binding proteins may be prepared by any of a number of conventional techniques. For example, antigen binding proteins may be purified from cells that naturally express them (e.g., an antibody can be purified from a hybridoma that produces it) or produced in recombinant Expression systems. Production of an IL-33 binding protein may be achieved in a cell in vitro or in vivo by delivering exogenous isolated nucleic acids encoding the IL-33 binding protein, for example, a heavy chain and a light chain of an antibody.

A number of different expression systems and purification regimes can be used to generate the antigen binding protein of the invention. Generally, host cells are transformed with a recombinant expression vector encoding the desired antigen binding protein. The expression vector may be maintained by the host as a separate genetic element or integrated into the host chromosome depending on the expression system. Expression vectors within the scope of the disclosure may provide necessary elements for eukaryotic or prokaryotic expression and include viral promoter driven vectors, such as CMV promoter driven vectors, e.g., pcDNA3.1, pCEP4, and their derivatives, Baculovirus expression vectors, *Drosophila* expression vectors, and expression vectors that are driven by mammalian gene promoters such as human Ig gene promoters. Other examples include prokaryotic expression vectors, such as T7 promoter driven vectors, e.g., pET41, lactose promoter driven vectors, and arabinose gene promoter driven vectors. Those of ordinary skill in the art will recognise many other suitable expression vectors and expression systems.

Also provided herein are recombinant host cells. The host cell may be an isolated host cell. The host cell is usually not part of a multicellular organism (e.g., plant or animal). For example, a host cell can be a single celled organism, or can be an individual cell of a multicellular organism that is separate from that organism. A host cell can be part of a multicellular organism, for example, a plant or animal. The host cell may be a non-human host cell.

A wide range of host cells can be employed, including Prokaryotes (including Gram-negative or Gram-positive bacteria, for example, *Escherichia coli*, Bacilli sp., *Pseudomonas* sp., *Corynebacterium* sp.), Eukaryotes including yeast (for example, *Saccharomyces cerevisiae, Pichia pastoris*), fungi (for example, *Aspergillus* sp.), or higher Eukaryotes including insect cells and cell lines of mammalian origin (for example, CHO, NS0, PER.C6, HEK293, HeLa, COS-1, COS-7, BHK21, BSC-1, HepG2, 653, SP2/0, myeloma, lymphoma cells, or any derivative thereof). A recombinant cell according to the disclosure may be generated by transfection, cell fusion, immortalisation, or other procedures well known in the art. Appropriate cloning and expression vectors for use with bacterial, fungal, yeast, and mammalian host cells are known in the art.

The cells can be cultured under conditions that promote expression of the antigen binding protein using a variety of equipment, such as shake flasks, spinner flasks, and bioreactors. The polypeptide is recovered by conventional protein purification procedures. Protein purification procedures typically consist of a series of unit operations comprised of various filtration and chromatographic processes developed to selectively concentrate and isolate the antigen binding protein. The purified antigen binding protein may be formulated in a pharmaceutically acceptable composition.

The skilled person will appreciate that, upon production of an antigen binding protein, such as an antibody in a host cell, post-translational modifications may occur. For example, this may include the cleavage of certain leader sequences, the addition of various sugar moieties in various glycosylation patterns, non-enzymatic glycation, deamidation, oxidation, disulfide bond scrambling, and other cysteine variants, such as free sulfhydryls, racemized disulfides, thioethers and trisulfide bonds, isomerization, C-terminal lysine clipping, and N-terminal glutamine cyclisation. The present invention encompasses the use of antigen binding proteins that have been subjected to, or have undergone, one or more post-translational modifications. Thus an "antigen binding protein" or "antibody" of the invention includes an "antigen binding protein" or "antibody", respectively, as defined earlier that has undergone a post-translational modification such as described herein.

Glycation is a post-translational non-enzymatic chemical reaction between a reducing sugar, such as glucose, and a free amine group in the protein, and is typically observed at the epsilon amine of lysine side chains or at the N-Terminus of the protein. Glycation can occur during production and storage only in the presence of reducing sugars.

Deamidation, which can occur during production and storage, is an enzymatic reaction primarily converting asparagine (N) to iso-aspartic acid (iso-aspartate) and aspartic acid (aspartate) (D) at approximately 3:1 ratio. This deamidation reaction is therefore related to isomerization of aspartate (D) to iso-aspartate. The deamidation of asparagine and the isomerization of aspartate both involve the intermediate succinimide. To a much lesser degree, deamidation can occur with glutamine residues in a similar manner. Deamidation can occur in a CDR, in a Fab (non-CDR region), or in the Fc region.

Oxidation can occur during production and storage (i.e., in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR) region, or in the Fc region.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

The formation of a thioether and racemization of a disulfide bond can occur under basic conditions, in production or storage, through a beta elimination of disulfide bridges back to cysteine residues via a dehydroalanine and persulfide intermediate. Subsequent crosslinking of dehydroalanine and cysteine results in the formation of a thioether bond or the free cysteine residues can reform a disulfide bond with a mixture of D- and L-cysteine.

Trisulfides result from insertion of a sulfur atom into a disulfide bond (Cys-S—S—S-Cys) and are formed due to the presence of hydrogen sulfide in production cell culture.

N-terminal glutamine (Q) and glutamate (glutamic acid) (E) in the heavy chain and/or light chain is likely to form pyroglutamate (pGlu) via cyclization. Most pGlu formation happens in the production bioreactor, but it can be formed non-enzymatically, depending on pH and temperature of processing and storage conditions. Cyclization of N-terminal Q or E is commonly observed in natural human antibodies.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Administration to the human subject/patient is likely to result in the removal of any remaining C-terminal lysines.

Fc engineering methods can be applied to modify the functional or pharmacokinetics properties of an antibody. Effector function may be altered by making mutations in the Fc region that increase or decrease binding to C1q or Fcγ receptors and modify complement-dependent cytotoxicity (CDC) or antibody-dependent cell-mediated cytotoxicity (ADCC) activity, respectively. Modifications to the glycosylation pattern of an antibody can also be made to change the effector function. The in vivo half-life of an antibody can be altered by making mutations that affect binding of the Fc to the FcRn (Neonatal Fc Receptor).

Substitutions that increase the binding affinity of IgG to FcRn at pH 6.0 while maintaining the pH dependence of the interaction with target, by engineering the constant region, have been extensively studied (Ghetie et al., Nature Biotech.

15:637-640, 1997; Hinton et al., JBC 279:6213-6216, 2004; Dall'Acqua et al., 10 J Immunol 117:1129-1138, 2006). The in-vivo half-life of antigen binding proteins of the present invention may be altered by modification of a heavy chain constant domain or an FcRn binding domain therein.

In adult mammals, FcRn, also known as the neonatal Fc receptor, plays a key role in maintaining serum antibody levels by acting as a protective receptor that binds and salvages antibodies of the IgG isotype from degradation. IgG molecules are endocytosed by endothelial cells and, if they bind to FcRn, are recycled out of the cells back into circulation. In contrast, IgG molecules that enter the cells and do not bind to FcRn and are targeted to the lysosomal pathway where they are degraded.

FcRn is believed to be involved in both antibody clearance and the transcytosis across tissues (see Junghans R. P. (1997) Immunol. Res., 16. 29-57 and Ghetie et al. (2000) Annu. Rev. Immunol. 18, 739-766). Human IgG1 residues determined to interact directly with human FcRn include Ile253, Ser254, Lys288, Thr307, Gln311, Asn434 and His435. Mutations at any of these positions may enable increased serum half-life and/or altered effector properties of antigen binding proteins of the invention.

Antigen binding proteins of the present invention may have amino acid modifications that increase the affinity of the constant domain or fragment thereof for FcRn. Increasing the half-life (i.e., serum half-life) of therapeutic and diagnostic IgG antibodies and other bioactive molecules has many benefits including reducing the amount and/or frequency of dosing of these molecules. In one embodiment, an antigen binding protein of the invention comprises all or a portion (an FcRn binding portion) of an IgG constant domain having one or more of the following amino acid modifications.

For example, with reference to IgG1, M252Y/S254T/T256E (commonly referred to as "YTE" mutations) and M428L/N434S (commonly referred to as "LS" mutations) increase FcRn binding at pH 6.0 (Wang et al. 2018).

Half-life can also be enhanced by T250Q/M428L, V259I/V308F/M428L, N434A, and T307A/E380A/N434A mutations (with reference to IgG1 and Kabat numbering) (Monnet et al.).

Half-life and FcRn binding can also be extended by introducing H433K and N434F mutations (commonly referred to as "HN" or "NHance" mutations) (with reference to IgG1) (WO2006/130834).

WO00/42072 discloses a polypeptide comprising a variant Fc region with altered FcRn binding affinity, which polypeptide comprises an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 386,388, 400, 413, 415, 424, 433, 434, 435, 436, 439, and 447 of the Fc region (EU index numbering).

WO02/060919 discloses a modified IgG comprising an IgG constant domain comprising one or more amino acid modifications relative to a wild-type IgG constant domain, wherein the modified IgG has an increased half-life compared to the half-life of an IgG having the wild-type IgG constant domain, and wherein the one or more amino acid modifications are at one or more of positions 251, 253, 255, 285-290, 308-314, 385-389, and 428-435.

Shields et al. (2001, J Biol Chem; 276:6591-604) used alanine scanning mutagenesis to alter residues in the Fc region of a human IgG1 antibody and then assessed the binding to human FcRn. Positions that effectively abrogated binding to FcRn when changed to alanine include I253, S254, H435, and Y436. Other positions showed a less pronounced reduction in binding as follows: E233-G236, R255, K288, L309, S415, and H433. Several amino acid positions exhibited an improvement in FcRn binding when changed to alanine; notable among these are P238, T256, E272, V305, T307, Q311, D312, K317, D376, E380, E382, S424, and N434. Many other amino acid positions exhibited a slight improvement (D265, N286, V303, K360, Q362, and A378) or no change (S239, K246, K248, D249, M252, E258, T260, S267, H268, S269, D270, K274, N276, Y278, D280, V282, E283, H285, T289, K290, R292, E293, E294, Q295, Y296, N297, S298, R301, N315, E318, K320, K322, S324, K326, A327, P329, P331, E333, K334, T335, S337, K338, K340, Q342, R344, E345, Q345, Q347, R356, M358, T359, K360, N361, Y373, S375, S383, N384, Q386, E388, N389, N390, K392, L398, S400, D401, K414, R416, Q418, Q419, N421, V422, E430, T437, K439, S440, S442, S444, and K447) in FcRn binding.

The most pronounced effect with respect to improved FcRn binding was found for combination variants. At pH 6.0, the E380A/N434A variant showed over 8-fold better binding to FcRn, relative to native IgG1, compared with 2-fold for E380A and 3.5-fold for N434A. Adding T307A to this resulted in a 12-fold improvement in binding relative to native IgG1. In one embodiment, the antigen binding protein of the invention comprises the E380A/N434A mutations and has increased binding to FcRn.

Dall'Acqua et al. (2002, J Immunol.; 169:5171-80) describes random mutagenesis and screening of human IgG1 hinge-Fc fragment phage display libraries against mouse FcRn. They disclosed random mutagenesis of positions 251, 252, 254-256, 308, 309, 311, 312, 314, 385-387, 389, 428, 433, 434, and 436. The major improvements in IgG1-human FcRn complex stability occur when substituting residues located in a band across the Fc-FcRn interface (M252, S254, T256, H433, N434, and Y436) and to lesser extent substitutions of residues at the periphery, such as V308, L309, Q311, G385, Q386, P387, and N389. The variant with the highest affinity to human FcRn was obtained by combining the M252Y/S254T/T256E ("YTE") and H433K/N434F/Y436H mutations and exhibited a 57-fold increase in affinity relative to the wild-type IgG1. The in vivo behaviour of such a mutated human IgG1 exhibited a nearly 4-fold increase in serum half-life in cynomolgus monkey as compared to wild-type IgG1.

The present invention therefore provides an antigen binding protein with optimized binding to FcRn. In a preferred embodiment, the antigen binding protein comprises at least one amino acid modification in the Fc region of said antigen binding protein, wherein said modification is at an amino acid position selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region.

Additionally, various publications describe methods for obtaining physiologically active molecules with modified half-lives, either by introducing an FcRn-binding polypeptide into the molecules (WO97/43316, U.S. Pat. Nos. 5,869,046, 5,747,035, WO96/32478 and WO91/14438) or by fusing the molecules with antibodies whose FcRn-binding affinities are preserved, but affinities for other Fc receptors have been greatly reduced (WO99/43713), or fusing with FcRn binding domains of antibodies (WO00/09560, U.S. Pat. No. 4,703,039).

Further provided herein are IL-33 binding proteins that bind to an epitope of IL-33.

In one embodiment, the epitope comprises SEQ ID NO:80. In one embodiment, the epitope comprises SEQ ID NO:81. In one embodiment, the epitope comprises SEQ ID NO:80 and SEQ ID NO:81. In one embodiment, the epitope is a linear epitope. In one embodiment, the epitope is determined from deuterium exchange in HDX-MS analysis.

In one embodiment, the epitope comprises SEQ ID NO:82. In one embodiment, the epitope comprises SEQ ID NO:83. In one embodiment, the epitope comprises SEQ ID NO:82 and SEQ ID NO:83. In one embodiment, the epitope comprises SEQ ID NO:82, SEQ ID NO:83, and one or more of the following sequences: SEQ ID NO:84, SEQ ID NO:85, and LSE (residues 267-269). For example, and not limitation, in one embodiment, the epitope comprises SEQ ID NO: 82, SEQ ID NO:83, and SEQ ID NO:84. In another example, and not for limitation, in one embodiment, the epitope comprises SEQ ID NO:82, SEQ ID NO:83, and SEQ ID NO:85. In another example, and not for limitation, in one embodiment, the epitope comprises SEQ ID NO: 82, SEQ ID NO:83, and LSE (residues 267-269). In one embodiment the epitope is a conformational epitope. In one embodiment, the epitope is determined using Cryo-EM.

In one embodiment, the epitope comprises SEQ ID NO:86. In one embodiment, the epitope comprises SEQ ID NO:87. In one embodiment, the epitope comprises SEQ ID NO:86 and SEQ ID NO:87. In one embodiment, the epitope comprises SEQ ID NO:86, SEQ ID NO:87, and one or more of the following sequences: SEQ ID NO:84, SEQ ID NO:85, and LSE (residues 267-269). In one embodiment, the epitope is determined from deuterium exchange in HDX-MS analysis and/or using Cryo-EM.

In one embodiment, the IL-33 binding protein comprises a means for binding to the epitope described herein.

In one embodiment, the epitope comprises any embodiment listed above and the IL-33 binding protein comprises any IL-33 binding protein described herein. In one embodiment, the affinity of IL-33 for the ST2 receptor is not affected when the IL-33 is complexed with the IL-33 binding protein. In one embodiment, the IL-33 is human IL-33. In one embodiment, the IL-33 binding protein further comprises one or more of the following:

(a) the IL-33 binding protein does not bind to human IL-1α;
(b) the IL-33 binding protein does not bind to human IL-1β;
(c) the IL-33 binding protein does not bind to human oxidized IL-33;
(d) the IL-33 binding protein does not bind to cynomolgus oxidized IL-33;
(e) the IL-33 binding protein inhibits IL-33 induced superoxide generation from isolated eosinophils;
(f) the IL-33 binding protein inhibits IL-33 induced IFN-γ secretion from CD4+ T cells;
(g) the IL-33 binding protein inhibits IL-33 induced IL-8 secretion from human umbilical vein endothelial cells (HUVECs);
(h) the IL-33 binding protein inhibits IL-33 induced IL-6 secretion from human umbilical vein endothelial cells (HUVECs);
(i) the IL-33 binding protein inhibits IL-33 induced β-hexosaminidase release from basophils;
(j) the IL-33 binding protein can completely block production of human IL-33 stimulated IL-6;
(k) the IL-33 binding protein can completely block production of human IL-33 stimulated TNF-α;
(l) the IL-33 binding protein can completely block production of human IL-33 stimulated IL-13;
(m) the IL-33 binding protein can completely block production of human IL-33 stimulated IL-18; and
(n) the IL-33 binding protein can completely block production of human IL-33 stimulated IL-6.

Further provided herein are IL-33 binding proteins that bind to IL-33 and compete for binding to the IL-33 with a reference IL-33 binding protein that binds to any epitope described above. In one embodiment, the IL-33 binding protein comprises a means for binding IL-33. In one embodiment, the reference IL-33 binding protein that binds to any epitope described above comprises:

(i) CDRH1, CDRH2, and CDRH3 from SEQ ID NO:20 and CDRL1, CDRL2, and CDRL3 from SEQ ID NO:25, wherein SEQ ID NO:20 comprises:
QVQLVQSGAEVKKPGASVKVSCKASGYTFI-
SYGMHWVRQAPGQGLE
WMGEINPHGGSTSYAQKF$X_1$GRVTMTR
DTSTSTVYMELSSLRSEDTA
VYYCARPSAAYSHYLG$X_2$D$X_3$WGRGTLVTVSS;
and wherein SEQ ID NO:25 comprises:
DIQMTQSPSSVSASVGDRVTITCR$X_4$SQ
GIS$X_5$WL$X_6$WYQQKPGKAPKL
LIYA$X_7$S$X_8$LQSGVPSRFSGSGSGTDF
TLTISSLQPEDFATYYCQQA$X_9$V
$X_{10}$PLTFGGGTKVEIK; and wherein:
$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L; or (ii) CDRH1, CDRH2, and CDRH3 from any one of SEQ ID NOs: 21-24 and CDRL1, CDRL2, and CDRL3 from any one of SEQ ID NOs: 26-28; or
(iii) one or more CDR variants of (i) or (ii), wherein the variant has 1, 2, or 3 amino acid modifications.

In one embodiment, the IL-33 reference binding protein comprises:

(i) CDRH1, CDRH2, and CDRH3 from SEQ ID NO:21 and CDRL1, CDRL2, and CDRL3 from SEQ ID NO:26;
(ii) CDRH1, CDRH2, and CDRH3 from SEQ ID NO:22 and CDRL1, CDRL2, and CDRL3 from SEQ ID NO:26;
(iii) CDRH1, CDRH2, and CDRH3 from SEQ ID NO:23 and CDRL1, CDRL2, and CDRL3 from SEQ ID NO:27;
(iv) CDRH1, CDRH2, and CDRH3 from SEQ ID NO:24 and CDRL1, CDRL2, and CDRL3 from SEQ ID NO:28;
(v) CDRH1 of SEQ ID NO:1, CDRH2 of SEQ ID NO:3, CDRH3 of SEQ ID NO:6, CDRL1 of SEQ ID NO: 10, CDRL2 of SEQ ID NO: 14, and CDRL3 of SEQ ID NO: 18;
(vi) CDRH1 of SEQ ID NO:1, CDRH2 of SEQ ID NO:4, CDRH3 of SEQ ID NO:7, CDRL1 of SEQ ID NO: 10, CDRL2 of SEQ ID NO:14, and CDRL3 of SEQ ID NO: 18;
(vii) CDRH1 of SEQ ID NO:1, CDRH2 of SEQ ID NO:3, CDRH3 of SEQ ID NO:8, CDRL1 of SEQ ID NO:11, CDRL2 of SEQ ID NO: 15, and CDRL3 of SEQ ID NO: 18; or (viii) CDRH1 of SEQ ID NO:1, CDRH2 of SEQ ID NO:3, CDRH3 of SEQ ID NO:7, CDRL1 of SEQ ID NO: 12, CDRL2 of SEQ ID NO: 16, and CDRL3 of SEQ ID NO: 19.

In one embodiment, the IL-33 is human IL-33.

Further provided herein are IL-33 binding proteins that bind to IL-33 and compete for binding to the IL-33 with a reference IL-33 binding protein, wherein the reference IL-33 binding protein comprises:

(i) CDRH1, CDRH2, and CDRH3 from SEQ ID NO:20 and CDRL1, CDRL2, and CDRL3 from SEQ ID NO:25, wherein SEQ ID NO:20 comprises:

QVQLVQSGAEVKKPGASVKVSCKASGYTFI-SYGMHWVRQAPGQGLE WMGEINPHGGSTSYAQKF$X_1$GRVT MTRDTSTSTVYMELSSLRSEDTA VYYCARPSAAYSHYLG$X_2$D$X_3$WGRG TLVTVSS; and wherein SEQ ID NO:25 comprises:

DIQMTQSPSSVSASVGDRVTITCR$X_4$SQ GIS$X_5$WL$X_6$WYQQKPGKAPKL LIYA$X_7$S$X_8$LQSGVPSRFSGSGSGTDFT LTISSLQPEDFATYYCQQA$X_9$V $X_{10}$PLTFGGGTKVEIK; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L; or (ii) CDRH1, CDRH2, and CDRH3 from any one of SEQ ID NOs: 21-24 and CDRL1, CDRL2, and CDRL3 from any one of SEQ ID NOs: 26-28; or (iii) one or more CDR variants of (i) or (ii), wherein the variant has 1, 2, or 3 amino acid modifications.

In one embodiment, the IL-33 reference binding protein comprises:

(i) CDRH1, CDRH2, and CDRH3 from SEQ ID NO:21 and CDRL1, CDRL2, and CDRL3 from SEQ ID NO:26;

(ii) CDRH1, CDRH2, and CDRH3 from SEQ ID NO:22 and CDRL1, CDRL2, and CDRL3 from SEQ ID NO:26;

(iii) CDRH1, CDRH2, and CDRH3 from SEQ ID NO:23 and CDRL1, CDRL2, and CDRL3 from SEQ ID NO:27;

(iv) CDRH1, CDRH2, and CDRH3 from SEQ ID NO:24 and CDRL1, CDRL2, and CDRL3 from SEQ ID NO:28;

(v) CDRH1 of SEQ ID NO:1, CDRH2 of SEQ ID NO:3, CDRH3 of SEQ ID NO:6, CDRL1 of SEQ ID NO: 10, CDRL2 of SEQ ID NO:14, and CDRL3 of SEQ ID NO: 18;

(vi) CDRH1 of SEQ ID NO:1, CDRH2 of SEQ ID NO:4, CDRH3 of SEQ ID NO:7, CDRL1 of SEQ ID NO:10, CDRL2 of SEQ ID NO: 14, and CDRL3 of SEQ ID NO: 18;

(vii) CDRH1 of SEQ ID NO:1, CDRH2 of SEQ ID NO:3, CDRH3 of SEQ ID NO:8, CDRL1 of SEQ ID NO:11, CDRL2 of SEQ ID NO: 15, and CDRL3 of SEQ ID NO: 18; or (viii) CDRH1 of SEQ ID NO:1, CDRH2 of SEQ ID NO:3, CDRH3 of SEQ ID NO:7, CDRL1 of SEQ ID NO: 12, CDRL2 of SEQ ID NO: 16, and CDRL3 of SEQ ID NO: 19.

In one embodiment, the IL-33 is human IL-33.

An antigen binding protein as described herein may be incorporated into pharmaceutical compositions for use in the treatment of the human diseases described herein. In one embodiment, the pharmaceutical composition comprises an antigen binding protein in combination with one or more pharmaceutically acceptable carriers and/or excipients. Such compositions comprise a pharmaceutically acceptable carrier as known and called for by acceptable pharmaceutical practice.

Pharmaceutical compositions may be administered by injection or continuous infusion (examples include, but are not limited to, intravenous, intraperitoneal, intradermal, subcutaneous, intramuscular, intraocular, and intraportal administration). In one embodiment, the composition is suitable for intravenous administration. In one embodiment, the composition is suitable for subcutaneous administration. Pharmaceutical compositions may be suitable for topical administration (which includes, but is not limited to, epicutaneous, inhaled, intranasal, or ocular administration) or enteral administration (which includes, but is not limited to, oral, vaginal, or rectal administration).

A subject in need may be delivered one or more nucleic acids encoding an antigen binding protein provided herein, such as a heavy chain and a light chain of an antibody. The heavy chain and the light chain of the antibody may be delivered by the same or separate nucleic acids. The nucleic acids may be DNA or RNA. The nucleic acids encoding the IL-33 binding protein may be delivered without a delivery vehicle (i.e., "naked") or delivered with a viral or non-viral delivery vehicle (i.e., as a viral vector, adsorbed to or encapsulated in liposomes or polymer-based vehicles, and the like). The nucleic acid may include elements such as a poly A tail, a 5' untranslated region (UTR), and/or a 3' UTR. The nucleic acids may be mRNA. The mRNA may include a cap structure. The mRNA may be self-replicating RNA.

The nucleic acid coding for the IL-33 binding protein may be modified or unmodified. The nucleic acids coding for the IL-33 binding protein may comprise at least one chemical modification. Nucleic acids (e.g., mRNAs) can be modified to enhance stability by including one or more chemical modifications. Such chemical modifications include, but are not limited to, a modified nucleotide, a modified sugar backbone, and the like. Also provided herein is a method of producing an IL-33 binding protein in a cell, tissue, or organism comprising contacting said cell, tissue, or organism with a composition comprising an isolated nucleic acid comprising at least one chemical modification and which encodes the IL-33 binding protein. Also provided herein is a method of producing an IL-33 binding protein in a cell in vitro or in vivo comprising contacting said cell with a composition comprising a nucleic acid comprising at least one chemical modification and which encodes an IL-33 binding protein.

Pharmaceutical compositions provided herein can comprise an effective amount of an antigen binding protein, such as an IL-33 binding protein. A pharmaceutical composition may comprise between 0.5 mg and 10 g of an IL-33 binding protein, and in some cases, can comprise between 5 mg and 1 g of an IL-33 binding protein. In an embodiment, the IL-33 binding protein is an antibody. In one embodiment, the IL-33 binding protein is an IgG1 antibody (e.g., human IgG1 antibody). In one embodiment, the IL-33 binding protein is a human IgG1κ antibody.

A pharmaceutical composition may comprise between 0.5 mg and 10 g or between 5 mg and 1 g of an IL-33 binding protein comprising a VH region that is at least 90% identical to SEQ ID NO: 20 and a VL region that is at least 90% identical to SEQ ID NO:25, wherein SEQ ID NO: 20 comprises:

QVQLVQSGAEVKKPGASVKVSCKASGYTFI-SYGMHWVRQAPGQGLEWMGEIN PHGGSTSYAQKF$X_1$GRVTMTRDTST STVYMELSSLRSEDTAVYYCARPSAAYSH YLG$X_2$D$X_3$WGRGTLVTVSS; and wherein SEQ ID NO:25 comprises:

DIQMTQSPSSVSASVGDRVTITCR$X_4$SQGIS$X_5$ WL$X_6$WYQQKPGKAPKLLIYA$X_7$S $X_8$LQSGVPSRFSGSGSGTDFTL TISSLQPEDFATYYCQQA$X_9$V$X_{10}$PLTFGGGTKVEI K; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L. In one embodiment, the VH region is at least 95% identical to SEQ ID NO:20 and the VL region is at least 95% identical to SEQ ID NO:25. In one embodiment, the VH region is 100% identical to SEQ ID NO:20 and the VL region is 100% identical to SEQ ID NO:25.

A pharmaceutical composition may comprise between 0.5 mg and 10 g or between 5 mg and 1 g of an IL-33 binding protein comprising a VH region that is at least 90% identical to SEQ ID NO: 21 and a VL region that is at least 90% identical to SEQ ID NO:26. In one embodiment, the VH region is at least 95% identical to SEQ ID NO:21 and the VL region is at least 95% identical to SEQ ID NO:26. In one embodiment, the VH region is 100% identical to SEQ ID NO: 21 and the VL region is 100% identical to SEQ ID NO:26.

A pharmaceutical composition may comprise between 0.5 mg and 10 g or between 5 mg and 1 g of an IL-33 binding protein comprising a VH region that is at least 90% identical to SEQ ID NO: 22 and a VL region that is at least 90% identical to SEQ ID NO:26. In one embodiment, the VH region is at least 95% identical to SEQ ID NO:22 and the VL region is at least 95% identical to SEQ ID NO:26. In one embodiment, the VH region is 100% identical to SEQ ID NO: 22 and the VL region is 100% identical to SEQ ID NO:26.

A pharmaceutical composition may comprise between 0.5 mg and 10 g or between 5 mg and 1 g of an IL-33 binding protein comprising a VH region that is at least 90% identical to SEQ ID NO: 23 and a VL region that is at least 90% identical to SEQ ID NO:27. In one embodiment, the VH region is at least 95% identical to SEQ ID NO:23 and the VL region is at least 95% identical to SEQ ID NO:27. In one embodiment, the VH region is 100% identical to SEQ ID NO: 23 and the VL region is 100% identical to SEQ ID NO:27.

A pharmaceutical composition may comprise between 0.5 mg and 10 g or between 5 mg and 1 g of an IL-33 binding protein comprising a VH region that is at least 90% identical to SEQ ID NO: 24 and a VL region that is at least 90% identical to SEQ ID NO:28. In one embodiment, the VH region is at least 95% identical to SEQ ID NO:24 and the VL region is at least 95% identical to SEQ ID NO:28. In one embodiment, the VH region is 100% identical to SEQ ID NO: 24 and the VL region is 100% identical to SEQ ID NO:28.

A pharmaceutical composition may comprise between 0.5 mg and 10 g or between 5 mg and 1 g of an IL-33 binding protein comprising an HC that is at least 90% identical to SEQ ID NO: 29 and an LC that is at least 90% identical to SEQ ID NO:34, wherein SEQ ID NO:29 comprises:

QVQLVQSGAEVKKPGASVKVSCKASGYTFI-SYGMHWVRQAPGQGLEWMGEIN PHGGSTSYAQKF$X_1$GRVTMTRDTST STVYMELSSLRSEDTAVYYCARPSAAYSH YLG$X_2$D$X_3$WGRGTLVTVSSASTKGPS VFPLAPSSKSTSGGTAALGCLVKDYFPEP VTVSWNSGALTSGVHTFPAVLQSSGLYS-LSSVVTVPSSSLGTQTYICNVNHKPSN TKVDKKVEPKSCDKTHTCPPCPA-PELLGGPSVFLFPPKPKDTLYITREPEVTCVVV DVSHEDPEVKFNWYVDGVEVHNAKTKPRE-EQYNSTYRVVSVLTVLHQDWLNG KEYKCKVSNKALPA-PIEKTISKAKGQPREPQVYTLPPSRDELT-KNQVSLTCLVKG FYPSDIA VEWESNGQPEN-NYKTTPPVLDSDGSFFLYSKLTV DKSRWQQGNVFSC SVMHEALHNHYTQKSLSL-SPGK; and wherein SEQ ID NO:34 comprises:

DIQMTQSPSSVSASVGDRVTITCR$X_4$SQ GIS$X_5$WL$X_6$WYQQKPGKAPKLLIYA$X_7$S $X_8$LQSGVPSRFSGSGSGTDFTLTISSLQPE DFATYYCQQA$X_9$V$X_{10}$PLTFGGGTKVEI KRTVAAPSVFIFPPSDEQLKSGTASVVCLLNNFY-PREAKVQWKVDNALQSGNSQ ESVTEQDSKDS-TYSLSSTLTLSKADYEKHKVYACE-VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L. In one embodiment, the HC is at least 95% identical to SEQ ID NO:29 and the LC is at least 95% identical to SEQ ID NO:34. In one embodiment, the HC is 100% identical to SEQ ID NO:29 and the LC is 100% identical to SEQ ID NO:34.

A pharmaceutical composition may comprise between 0.5 mg and 10 g or between 5 mg and 1 g of an IL-33 binding protein comprising an HC that is at least 90% identical to SEQ ID NO:30 and an LC that is at least 90% identical to SEQ ID NO:35. In one embodiment, the HC is at least 95% identical to SEQ ID NO:30 and the LC is at least 95% identical to SEQ ID NO:35. In one embodiment, the HC is 100% identical to SEQ ID NO:30 and the LC is 100% identical to SEQ ID NO:35.

A pharmaceutical composition may comprise between 0.5 mg and 10 g or between 5 mg and 1 g of an IL-33 binding protein comprising an HC that is at least 90% identical to SEQ ID NO:31 and an LC that is at least 90% identical to SEQ ID NO:35. In one embodiment, the HC is at least 95% identical to SEQ ID NO:31 and the LC is at least 95% identical to SEQ ID NO:35. In one embodiment, the HC is 100% identical to SEQ ID NO:31 and the LC is 100% identical to SEQ ID NO:35.

A pharmaceutical composition may comprise between 0.5 mg and 10 g or between 5 mg and 1 g of an IL-33 binding protein comprising an HC that is at least 90% identical to SEQ ID NO:32 and an LC that is at least 90% identical to SEQ ID NO:36. In one embodiment, the HC is at least 95% identical to SEQ ID NO:32 and the LC is at least 95% identical to SEQ ID NO:36. In one embodiment, the HC is 100% identical to SEQ ID NO:32 and the LC is 100% identical to SEQ ID NO:36.

A pharmaceutical composition may comprise between 0.5 mg and 10 g or between 5 mg and 1 g of an IL-33 binding protein comprising an HC that is at least 90% identical to SEQ ID NO:33 and an LC that is at least 90% identical to SEQ ID NO:37. In one embodiment, the HC is at least 95% identical to SEQ ID NO:33 and the LC is at least 95% identical to SEQ ID NO:37. In one embodiment, the HC is 100% identical to SEQ ID NO:33 and the LC is 100% identical to SEQ ID NO:37.

The pharmaceutical composition may be included in a kit containing the antigen binding protein together with other medicaments and/or with instructions for use. For convenience, the kit may comprise the reagents in predetermined amounts with instructions for use. The kit may also include devices used for administration of the pharmaceutical composition.

The antigen binding protein described herein may also be used in methods of treatment (e.g., for IL-33 mediated diseases). It will be appreciated by those skilled in the art that references herein to treatment refer to the treatment of established conditions. However, compounds of the invention may, depending on the condition, also be useful in the prevention of certain diseases. The antigen binding protein described herein is used in an effective amount for therapeutic, prophylactic, or preventative treatment. A therapeutically effective amount of the antigen binding protein described herein is an amount effective to ameliorate or reduce one or more symptoms of, or to prevent or cure, the disease.

Provided herein are methods of treating a disease or condition in a subject in need thereof comprising administering to said subject a therapeutically effective amount of the IL-33 binding protein or pharmaceutical composition as defined herein. The subject may be an animal or a human. In an embodiment, the subject is a human.

The IL-33 binding proteins described herein are provided for use in therapy. In one embodiment, IL-33 binding proteins are provided for use in the treatment of a disease or condition. In one embodiment, the IL-33 binding protein comprises a VH region comprising SEQ ID NO:20 and a VL region comprising SEQ ID NO:25, wherein SEQ ID NO:20 comprises:

QVQLVQSGAEVKKPGASVKVSCKASGYTFI-
SYGMHWVRQAPGQGLEWMGEIN
PHGGSTSYAQKF$X_1$GRVTMTRDTSTS
TVYMELSSLRSEDTAVYYCARPSAAYSH
YLG$X_2$D$X_3$WGRGTLVTVSS; and wherein SEQ ID NO:25 comprises:

DIQMTQSPSSVSASVGDRVTITCR$X_4$SQ
GIS$X_5$WL$X_6$WYQQKPGKAPKLLIYA$X_7$S
$X_8$LQSGVPSRFSGSGSGTDFTLTISSLQPE
DFATYYCQQA$X_9$V$X_{10}$PLTFGGGTKVEI K; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In one embodiment, an IL-33 binding protein is provided for use in the treatment of a disease or condition, wherein the IL-33 binding protein comprises a VH region comprising SEQ ID NO: 21 and a VL region comprising SEQ ID NO:26. In one embodiment, an IL-33 binding protein is provided for use in the treatment of a disease or condition, wherein the IL-33 binding protein comprises a VH region comprising SEQ ID NO:22 and a VL region comprising SEQ ID NO: 26. In one embodiment, an IL-33 binding protein is provided for use in the treatment of a disease or condition, wherein the IL-33 binding protein comprises a VH region comprising SEQ ID NO: 23 and a VL region comprising SEQ ID NO:27. In one embodiment, an IL-33 binding protein is provided for use in the treatment of a disease or condition, wherein the IL-33 binding protein comprises a VH region comprising SEQ ID NO:24 and a VL region comprising SEQ ID NO: 28.

In one embodiment, an IL-33 binding protein is provided for use in the treatment of a disease or condition, wherein the IL-33 binding protein comprises an HC sequence comprising SEQ ID NO:29 and an LC sequence comprising SEQ ID NO:34, wherein SEQ ID NO:29 comprises:

QVQLVQSGAEVKKPGASVKVSCKASGYTFI-
SYGMHWVRQAPGQGLEWMGEIN
PHGGSTSYAQKF$X_1$GRVTMTRDTSTS
TVYMELSSLRSEDTAVYYCARPSAAYSH
YLG$X_2$D$X_3$WGRGTLVTVSSASTKGPS
VFPLAPSSKSTSGGTAALGCLVKDYFPEP
VTVSWNSGALTSGVHTFPAVLQSSGLYS-
LSSVVTVPSSSLGTQTYICNVNHKPSN
TKVDKKVEPKSCDKTHTCPPCPA-
PELLGGPSVFLFPPKPKDTLYITREPEVTCVVV
DVSHEDPEVKFNWYVDGVEVHNAKTKPRE-
EQYNSTYRVVSVLTVLHQDWLNG
KEYKCKVSNKALPA-
PIEKTISKAKGQPREPQVYTLPPSRDELT-
KNQVSLTCLVKG FYPSDIA VEWESNGQPEN-
NYKTTPPVLDSDGSFFLYSKLTVDKSR
WQQGNVFSC SVMHEALHNHYTQKSLSLSPGK; and wherein SEQ ID NO:34 comprises:

DIQMTQSPSSVSASVGDRVTITCR$X_4$SQ
GIS$X_5$WL$X_6$WYQQKPGKAPKLLIYA$X_7$S
$X_8$LQSGVPSRFSGSGSGTDFTL
TISSLQPEDFATYYCQQA$X_9$V$X_{10}$PLTFGGGTKVEI
KRTVAAPSVFIFPPSDEQLKSGTASVVCLLNNFY-
PREAKVQWKVDNALQSGNSQ ESVTEQDSKDS-
TYSLSSTLTLSKADYEKHKVYACE-
VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In one embodiment, an IL-33 binding protein is provided for use in the treatment of a disease or condition, wherein the IL-33 binding protein comprises an HC sequence comprising SEQ ID NO:30 and an LC sequence comprising SEQ ID NO:35. In one embodiment, an IL-33 binding protein is provided for use in the treatment of a disease or condition, wherein the IL-33 binding protein comprises an HC sequence comprising SEQ ID NO:31 and an LC sequence comprising SEQ ID NO:35. In one embodiment, an IL-33 binding protein is provided for use in the treatment of a disease or condition, wherein the IL-33 binding protein comprises an HC sequence comprising SEQ ID NO:32 and an LC sequence comprising SEQ ID NO:36. In one embodiment, an IL-33 binding protein is provided for use in the treatment of a disease or condition, wherein the IL-33 binding protein comprises an HC sequence comprising SEQ ID NO: 33 and an LC sequence comprising SEQ ID NO:37.

Also provided is a method for treatment of a disease or condition in a subject in need thereof comprising administering to said subject a therapeutically effective amount of an IL-33 binding protein or a pharmaceutical composition described herein. Also provided is a method for treatment of a disease or condition in a subject in need thereof comprising administering to said subject a therapeutically effective amount of an IL-33 binding protein, wherein the IL-33 binding protein comprises a VH region comprising SEQ ID NO:20 and a VL region comprising SEQ ID NO: 25, wherein SEQ ID NO:20 comprises:

QVQLVQSGAEVKKPGASVKVSCKASGYTFI-
SYGMHWVRQAPGQGLEWMGEIN
PHGGSTSYAQKF$X_1$GRVTMTRDTSTS

TVYMELSSLRSEDTAVYYCARPSAAYSH YLGX$_2$DX$_3$WGRGTLVTVSS; and wherein SEQ ID NO:25 comprises:

DIQMTQSPSSVSASVGDRVTITCRX$_4$SQGISX$_5$ WLX$_6$WYQQKPGKAPKLLIYAX$_7$S X$_8$LQSGVPSRFSGSGSGTDFTLTISSLQP EDFATYYCQQAX$_9$VX$_{10}$PLTFGGGTKVEI K; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L.

Also provided is a method for treatment of a disease or condition in a subject in need thereof comprising administering to said subject a therapeutically effective amount of an IL-33 binding protein, wherein the IL-33 binding protein comprises a VH region comprising SEQ ID NO: 21 and a VL region comprising SEQ ID NO:26. Also provided is a method for treatment of a disease or condition in a subject in need thereof comprising administering to said subject a therapeutically effective amount of an IL-33 binding protein, wherein the IL-33 binding protein comprises a VH region comprising SEQ ID NO:22 and a VL region comprising SEQ ID NO:26. Also provided is a method for treatment of a disease or condition in a subject in need thereof comprising administering to said subject a therapeutically effective amount of an IL-33 binding protein, wherein the IL-33 binding protein comprises a VH region comprising SEQ ID NO:23 and a VL region comprising SEQ ID NO:27. Also provided is a method for treatment of a disease or condition in a subject in need thereof comprising administering to said subject a therapeutically effective amount of an IL-33 binding protein, wherein the IL-33 binding protein comprises a VH region comprising SEQ ID NO:24 and a VL region comprising SEQ ID NO:28.

In an embodiment, a method for treatment of a disease or condition in a subject in need thereof is provided comprising administering to said subject a therapeutically effective amount of an IL-33 binding protein, wherein the IL-33 binding protein comprises an HC sequence comprising SEQ ID NO:29 and an LC sequence comprising SEQ ID NO:34, wherein SEQ ID NO: 29 comprises:

QVQLVQSGAEVKKPGASVKVSCKASGYTFI-SYGMHWVRQAPGQGLEWMGEIN PHGGSTSYAQKFX$_1$GRVTMTRDTST STVYMELSSLRSEDTAVYYCARPSAAYSH YLGX$_2$DX$_3$WGRGTLVTVSSASTKGPSVFP LAPSSKSTSGGTAALGCLVKDYFPEP VTVSWNSGALTSGVHTFPAVLQSSGLYS-LSSVVTVPSSSLGTQTYICNVNHKPSN TKVDKKVEPKSCDKTHTCPPCPA-PELLGGPSVFLFPPKPKDTLYITREPEVTCVVV DVSHEDPEVKFNWYVDGVEVHNAKTKPRE-EQYNSTYRVVSVLTVLHQDWLNG KEYKCKVSNKALPA-PIEKTISKAKGQPREPQVYTLPPSRDELT-KNQVSLTCLVKG FYPSDIA VEWESNGQPEN-NYKTTPPVLDSDGSFFLYSKLTVDKSR WQQGNVFSC SVMHEALHNHYTQKSLSLSPGK; and wherein SEQ ID NO:34 comprises:

DIQMTQSPSSVSASVGDRVTITCRX$_4$SQGISX$_5$ WLX$_6$WYQQKPGKAPKLLIYAX$_7$S X$_8$LQSGVPSRFSGSGSGTDFTLTISSLQPE DFATYYCQQAX$_9$VX$_{10}$PLTFGGGTKVEI KRTVAAPSVFIFPPSDEQLKSGTASVVCLLNNFY-PREAKVQWKVDNALQSGNSQ ESVTEQDSKDS-TYSLSSTLTLSKADYEKHKVYACE-VTHQGLSSPVTKSFNRGEC; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L.

In an embodiment, a method for treatment of a disease or condition in a subject in need thereof is provided comprising administering to said subject a therapeutically effective amount of an IL-33 binding protein, wherein the IL-33 binding protein comprises an HC sequence comprising SEQ ID NO:30 and an LC sequence comprising SEQ ID NO:35. In an embodiment, a method for treatment of a disease or condition in a subject in need thereof is provided comprising administering to said subject a therapeutically effective amount of an IL-33 binding protein, wherein the IL-33 binding protein comprises an HC sequence comprising SEQ ID NO: 31 and an LC sequence comprising SEQ ID NO:35. In an embodiment, a method for treatment of a disease or condition in a subject in need thereof is provided comprising administering to said subject a therapeutically effective amount of an IL-33 binding protein, wherein the IL-33 binding protein comprises an HC sequence comprising SEQ ID NO:32 and an LC sequence comprising SEQ ID NO:36. In an embodiment, a method for treatment of a disease or condition in a subject in need thereof is provided comprising administering to said subject a therapeutically effective amount of an IL-33 binding protein, wherein the IL-33 binding protein comprises an HC sequence comprising SEQ ID NO:33 and an LC sequence comprising SEQ ID NO: 37.

As previously described, in one embodiment, the IL-33 binding protein is provided for use in the treatment of a disease or condition. In one embodiment, the IL-33 binding protein is provided for use in the treatment of an IL-33 mediated disorder. In some embodiments, the IL-33 mediated disorder is a respiratory disorder, an inflammatory condition, an immune disorder, a fibrotic disorder, an eosinophilic disorder, an infection, pain, a central nervous system disorder, a solid tumor, or an ophthalmologic disorder.

Exemplary IL-33 mediated disorders that may be treated with an IL-33 binding protein include, for example, and not limitation, respiratory disorders (e.g., chronic obstructive pulmonary disease (COPD), asthma, bronchitis, bronchiolitis, acute respiratory failure, inflammatory lung disorders), inflammatory conditions (e.g., chronic obstructive pulmonary disease (COPD), asthma, bronchitis, bronchiolitis, acute respiratory failure, inflammatory lung diseases, diabetic kidney disease, endometriosis, chronic urticaria, atopic dermatitis, allergic rhinitis, rheumatoid arthritis, sepsis, septic shock), immune disorders (e.g., asthma, allergy, anaphylaxis, anaphylactic shock, allergic rhinitis, rheumatoid arthritis, psoriasis, inflammatory bowel disease (IBD), Crohn's disease, diabetes, liver disease), fibrotic disorders (e.g., pulmonary fibrosis (e.g., idiopathic pulmonary fibrosis)), eosinophilic disorders (e.g., eosinophil-associated gastrointestinal disorders (EGIDs) (e.g., eosinophilic esophagitis)), infections (e.g., viral infections, helminth infections, protozoan infections), pain (e.g., inflammatory pain), central nervous system disorders (e.g., Alzheimer's disease), solid tumors (e.g., lung, breast, colon, prostate, kidney, liver, pancreas, stomach, intestinal, brain, bone, or skin tumors), and ophthalmologic disorders (e.g., age-related macular degeneration (AMD), retinopathy). It will be understood by one of ordinary skill in the art that a particular disease may fall into more than of the above-listed categories. For example, asthma is a respiratory disorder and may also be classified as an inflammatory condition and an immune disorder.

For example, and not limitation, in some embodiments, the IL-33 mediated disorder is chronic obstructive pulmonary disease (COPD), asthma, bronchitis, bronchiolitis, acute respiratory failure, inflammatory lung diseases, diabetic kidney disease, endometriosis, chronic rhinosinusitis with nasal polyps, food hypersensitivity, food allergy (e.g., peanut allergy), allergic rhinitis, eosinophilic esophagitis, atopic dermatitis, cystic fibrosis, or chronic urticaria.

For example, and not limitation, in other embodiments, the IL-33 mediated disorder is chronic obstructive pulmonary disease (COPD), asthma, COPD overlap syndrome (ACOS), chronic bronchitis, emphysema, chronic rhinosinusitis with or without nasal polyps, allergic rhinitis, sepsis, septic shock, atopic dermatitis, diabetic kidney disease, rheumatoid arthritis, vasculitis, graft-versus-host disease (GvHD), uveitis, chronic idiopathic urticaria, sinusitis, or pancreatitis.

In one embodiment, the IL-33 binding protein is used to treat a respiratory disorder. Examples of respiratory disorders include, but are not limited to, chronic obstructive pulmonary disease (COPD), asthma, asthma and COPD overlap syndrome (ACOS), bronchitis, bronchiolitis, acute respiratory failure, inflammatory lung diseases, bronchiectasis, and emphysema.

Examples of inflammatory lung diseases include, but are not limited to, chronic obstructive pulmonary disease (COPD), asthma (e.g., allergic asthma), emphysema, sarcoidosis, acute respiratory distress syndrome (ARDS), eosinophilic pulmonary inflammation, pulmonary inflammation (e.g., cytokine storm syndrome (CSS), cytokine release syndrome (CRS)), infection-induced pulmonary conditions (e.g., related to viral infection (e.g., influenza, parainfluenza, respiratory syncytial virus (RSV), rotavirus, human metapneumovirus), bacterial infection, fungal infection (e.g., *Aspergillus*), parasitic infection, or prion infection), pulmonary conditions related to gastric aspiration, pulmonary conditions related to environmental or occupational exposure (e.g., asbestosis, silicosis, berylliosis), immune dysregulation, pulmonary conditions related to physical trauma (e.g., ventilator injury), pneumonia (e.g., community-acquired pneumonia, hospital-acquired pneumonia, bacterial pneumonia, viral pneumonia, fungal pneumonia, aspiration pneumonia, chemical pneumonia), pneumonitis (e.g., checkpoint inhibitor pneumonitis), acute lung injury, chronic lung disease, eosinophilic bronchitis, bronchopulmonary dysplasia, airway exacerbations, allergen-induced pulmonary conditions, histiocytosis, unified airway disease, and lymphangiomyomatosis. Examples of viral infections include, but are not limited to, respiratory tract viral infections related to an influenza virus (e.g., Influenza virus A, Influenza virus B), respiratory syncytial virus (RSV), parainfluenza virus (e.g., hPIV-1, hPIV-2, hPIV-3, hPIV-4), rhinovirus, adenovirus, coxsackie virus, coronaviruses (e.g., SARS-CoV-1, SARS-CoV-2, MERS-CoV), adenovirus, metapneumovirus, cytomegalovirus, echo virus, herpes simplex virus, or smallpox. Examples of bacterial infections include, but are not limited to, *Chlamydia pneumoniae* or *Mycoplasma pneumoniae*.

In one embodiment, the IL-33 binding protein is used to reduce or prevent a respiratory infection in the lung, airways, or small airways.

For example, and not limitation, in one embodiment, the respiratory disorder is chronic obstructive pulmonary disease (COPD), asthma, asthma and COPD overlap syndrome (ACOS), bronchitis, bronchiolitis, acute respiratory failure, or an inflammatory lung disease.

Chronic Obstructive Pulmonary Disease (COPD) is a lung disease characterized by persistent respiratory symptoms caused by airway or alveoli abnormalities. See, e.g., Global Initiative for Chronic Obstructive Lung Disease (GOLD): Global Strategy for the Diagnosis, Management, and Prevention of Chronic Obstructive Pulmonary Disease (2024 Report), available at goldcopd.org/wp-content/uploads/2024/02/GOLD-2024_v1.2-11Jan24_WMV.pdf (last accessed Nov. 8, 2024), which is incorporated herein by reference in its entirety. COPD symptoms include dyspnea, cough, sputum production, and/or activity limitation, and the disease often progresses in stages. Diagnostic criteria include a ratio of a forced expiratory volume in 1 second (FEV1) to the forced vital capacity (FVC) being below a threshold (e.g., FEV1/FVC<0.7) as measured by spirometry. In one embodiment, the subject has COPD and an elevated level of eosinophils. Alternatively, the subject has COPD and does not have an elevated level of eosinophils.

Asthma is an inflammatory disease of the airways characterized by reversible airflow obstruction and bronchospasm. Common symptoms include wheezing, coughing, chest tightness, and shortness of breath. Examples of asthma include, but are not limited to, allergic asthma, severe asthma, moderate to severe asthma, mild asthma, chronic asthma, asthma due to smoking, exercise-induced asthma, drug-induced asthma (e.g., aspirin-induced asthma, nonsteroidal anti-inflammatory drug (NSAID)-induced asthma), atopic asthma, non-atopic asthma, and occupational asthma. In one embodiment, the asthma is eosinophilic asthma. Alternatively, the asthma is non-eosinophilic asthma. In one embodiment, the asthma is allergic asthma. Alternatively, the asthma is non-allergic asthma. In one embodiment, the asthma is not controlled with treatment or resistant to treatment (e.g., with corticosteroids). In one embodiment, the asthma is steroid resistant asthma. In one embodiment, the asthma is steroid sensitive asthma. In one embodiment, the asthma is steroid refractory asthma. In one embodiment, the asthma is severe refractory asthma. In one embodiment, the asthma is an asthma exacerbation. In one embodiment, the asthma is due to smoking.

In one embodiment, the IL-33 binding protein is used to treat an inflammatory condition. Examples of inflammatory conditions include, but are not limited to, chronic obstructive pulmonary disease (COPD), asthma, asthma and COPD overlap syndrome (ACOS), bronchitis, bronchiolitis, acute respiratory failure, inflammatory lung diseases, endometriosis, diabetic kidney disease, chronic rhinosinusitis with nasal polyps, allergic rhinitis, eosinophilic esophagitis, atopic dermatitis, cystic fibrosis, chronic urticaria, allergy, anaphylaxis (e.g., due to peanuts or bee stings), anaphylactic shock, eosinophilic inflammation, rhinosinusitis, nasal polyps, arthritis (e.g., rheumatoid arthritis, osteoarthritis, psoriatic arthritis, enteropathic arthritis), ankylosing spondylitis, osteoporosis, bone erosion, airway inflammation, airway hyperreactivity, airway hyperresponsiveness, pneumonitis, vasculitis, arteritis, angiogenesis, cardiovascular disease (e.g., heart failure), dermatitis, psoriasis, scleroderma, fibrosis, multiple sclerosis, lupus, dermatomyositis, myolitis, polymyolitis, dermatomyolitis, gastrointestinal inflammatory disorders, hepatitis, sepsis, septic shock, Behcet's disease, Sjögren's syndrome, giant cell arteritis, Churg-Strauss syndrome, Henoch-Schönlein purpura, Reiter's syndrome (reactive arthritis), Still's disease, graft versus host disease (GVHD), allograft rejection, seronegative enthesopathy and arthropathy (SEA) syndrome, interstitial cystitis, polymyalgia rheumatica, bullous pemphigoid (BP), polyarteritis nodosa (PAN), granulomatosis with polyangiitis (GPA), cartilage inflammation, inflammatory pain, or mast cell-mediated inflammatory diseases.

Examples of inflammatory lung diseases include, but are not limited to, chronic obstructive pulmonary disease (COPD), asthma (e.g., allergic asthma), emphysema, sarcoidosis, acute respiratory distress syndrome (ARDS), eosinophilic pulmonary inflammation, infection-induced pulmonary conditions (e.g., related to viral infection (e.g., influenza, parainfluenza, respiratory syncytial virus (RSV), rotavirus, human metapneumovirus), bacterial infection, fungal infection (e.g., *Aspergillus*), parasitic infection, or prion infection), pulmonary conditions related to gastric aspiration, pulmonary conditions related to environmental or occupational exposure (e.g., asbestosis, silicosis, berylliosis), immune dysregulation, pulmonary conditions related to physical trauma (e.g., ventilator injury), pneumonia (e.g., community-acquired pneumonia, hospital-acquired pneumonia, bacterial pneumonia, viral pneumonia, fungal pneumonia, aspiration pneumonia, chemical pneumonia), acute lung injury, chronic lung disease, bronchopulmonary dysplasia, airway exacerbations, allergen-induced pulmonary conditions, histiocytosis, unified airway disease, and lymphangiomyomatosis.

Examples of gastrointestinal inflammatory conditions include, but are not limited to, inflammatory bowel disease (IBD), ulcerative colitis (UC), Crohn's disease (CD), or colitis (e.g., related to environmental exposure (e.g., chemotherapy, radiation therapy), infectious colitis, ischemic colitis, necrotizing enterocolitis, collagenous or lymphocytic colitis, colitis related to conditions (e.g., chronic granulomatous disease, celiac disease), food allergy, food hypersensitivity, gastritis, infectious gastritis or enterocolitis (e.g., *Helicobacter pylori*-infected chronic active gastritis, and gastrointestinal inflammation related to infection.

In some embodiments, the inflammatory condition is a type 2 inflammatory disease. Examples of type 2 inflammatory diseases include, but are not limited to, asthma, viral exacerbations of allergic asthma, allergic rhinitis, chronic rhinosinusitis with nasal polyps, atopic dermatitis, chronic spontaneous urticaria, allergic bronchopulmonary aspergillosis, eosinophilic esophagitis, eosinophilic gastritis, eosinophilic gastroenteritis, eosinophilic colitis, allergic conjunctivitis, eosinophilia, fibrosis, allergy, anaphylaxis, anaphylactic shock, and food allergies.

For example, and not limitation, in some embodiments, the inflammatory condition is chronic obstructive pulmonary disease (COPD), asthma, bronchitis, airway inflammation, allergic rhinitis, atopic dermatitis, endometriosis, rheumatoid arthritis, sepsis, or septic shock.

In one embodiment, the IL-33 binding protein is used to treat an immune disorder. Examples of immune disorders include, but are not limited to, asthma (e.g., allergic asthma), atopic dermatitis, allergic rhinitis, allergic fungal rhinosinusitis, allergy, anaphylaxis, anaphylactic shock, allergic bronchopulmonary aspergillosis, allergic conjunctivitis, arthritis (e.g., rheumatoid arthritis, psoriatic arthritis, juvenile rheumatoid arthritis), psoriasis, plaque psoriasis, guttate psoriasis, inverse psoriasis, pustular psoriasis, erythrodermic psoriasis, inflammatory bowel disease (IBD), Crohn's disease, ulcerative colitis, celiac disease, Sjögren's syndrome, Guillain-Barré syndrome, Raynaud's syndrome, Addison's disease, myasthenia gravis, thyroiditis (e.g., Graves' disease), bullous pemphigoid, paraneoplastic syndrome, infection with human immunodeficiency viruses (HIV), autoimmune hepatitis, pancreatitis, diabetes (e.g., type I diabetes), a compromised immune system (e.g., due to infection (e.g., HIV) or chemotherapy), and liver diseases (e.g., fatty liver disease (e.g., metabolic dysfunction-associated steatotic liver disease), primary biliary cirrhosis, primary sclerosing cholangitis, non-alcoholic steatohepatitis (NASH)). In one embodiment, the immune disorder is mediated at least in part by mast cells.

For example, and not limitation, in some embodiments, the immune disorder is asthma, allergy, anaphylaxis, anaphylactic shock, allergic rhinitis, atopic dermatitis, psoriasis, inflammatory bowel disease (IBD), Crohn's disease, rheumatoid arthritis, psoriatic arthritis, diabetes, or liver disease.

In one embodiment, the IL-33 binding protein is used to treat fibrosis. As used herein, "fibrotic disorder" or "fibrosis" refer to conditions characterized by formation of excess of fibrous connective tissue in an organ or tissue. Fibrotic disorders include, but are not limited to, fibrosis due to pathological conditions or diseases, fibrosis due to physical trauma, fibrosis due to radiation damage, and fibrosis due to exposure to chemotherapeutics.

Examples of fibrotic disorders include, but are not limited to, pulmonary fibrosis (e.g., idiopathic pulmonary fibrosis, drug-induced pulmonary fibrosis (e.g., bleomycin-induced pulmonary fibrosis), asbestosis-related pulmonary fibrosis, bronchiolitis obliterans syndrome); fibrosis related to acute lung injury or acute respiratory distress (e.g., bacterial pneumonia induced fibrosis, trauma induced fibrosis, viral pneumonia induced fibrosis, ventilator induced fibrosis, non-pulmonary sepsis induced fibrosis, aspiration induced fibrosis); hepatic fibrosis (e.g., fibrosis related to cirrhosis (e.g., alcohol-induced cirrhosis, viral-induced cirrhosis, post-hepatitis C cirrhosis, primary biliary cirrhosis), alcohol-induced liver fibrosis, non-alcoholic steatohepatitis (NASH), biliary duct injury, schistosomiasis, cholangitis (e.g., sclerosing cholangitis), infection-induced liver fibrosis, viral-induced liver fibrosis, and autoimmune-induced hepatitis); renal fibrosis (e.g., tubulointerstitial fibrosis, scleroderma, diabetic nephritis, glomerular nephritis); dermal fibrosis (e.g., scleroderma, hypertrophic or keloid scarring, nephrogenic fibrosing dermatopathy, burns); myelofibrosis; neurofibromatosis; fibroma; fibrotic adhesions resulting from surgical procedures; cardiac fibrosis (e.g., fibrosis related to myocardial infarction); vascular fibrosis (e.g., fibrosis related to postangioplasty arterial restenosis, stent restenosis, atherosclerosis); ocular fibrosis (e.g., fibrosis related to post cataract surgery, proliferative vitreoretinopathy, retro-orbital fibrosis); bone marrow fibrosis (e.g., idiopathic myelofibrosis, drug-induced myelofibrosis); gastrointestinal fibrosis; colon fibrosis; intestinal fibrosis; pancreatic fibrosis; silicosis; radiation-induced fibrosis; scleroderma; sclerosis; cystic fibrosis; stent restenosis; and atherosclerosis.

In one embodiment, the fibrotic disorder is pulmonary fibrosis related to idiopathic pulmonary fibrosis (IDF), non-specific interstitial pneumonia (NSIP) (e.g., cellular, fibrotic), cryptogenic organizing pneumonia (COP), sarcoidosis, adult respiratory distress syndrome, respiratory bronchiolitis, bronchiolitis obliterans, fibrosis with collagen vascular disease, Hermansky-Pudlak syndrome, or histiocytosis X. In one embodiment, the pulmonary fibrosis is idiopathic pulmonary fibrosis.

The fibrotic disorder may be organ-specific or systemic. The fibrotic disorder may be a result of a chronic disease, immune dysregulation, an infection, a toxin, medical intervention, and/or physical trauma. For example, and not limitation, the fibrotic disorder may be a result of interstitial lung disease; inhalation of environmental or occupational debris, dusts, fibers, fumes, smoke, or vapors; inhalation of chemicals or molds; alcohol abuse; cigarette smoking; hypertension; inflammation (e.g., glomerulonephritis, pancreatsitis); viral infection (e.g., viral hepatitis); autoimmune disease (e.g., metabolic disorders (e.g., diabetes), Crohn's disease, inflammatory bowel disease (IBD), scleroderma); allergy; sepsis; adverse reaction to medications; aspirin overdose; hypersensitivity' to environmental antigens; exposure to chlorine or fluorocarbons; exposure to herbicides; exposure to radiation; chemotherapy; treatment with an immune checkpoint inhibitor; immune dysregulation; or cancer.

In one embodiment, the IL-33 binding protein is used to treat an eosinophilic disorder. As used herein, "eosinophilic disorders" refer to conditions characterized by excess eosinophil levels either locally or systemically.

Examples of eosinophilic disorders include, but are not limited to, asthma (e.g., atopic asthma, severe asthma, drug-induced asthma (e.g., aspirin-induced asthma), COPD, atopic dermatitis, allergic rhinitis, fibrosis (e.g., pulmonary fibrosis (e.g., IPF, pulmonary fibrosis related to sclerosis, hepatic fibrosis), eosinophilic esophagitis, eosinophilic inflammation, non-allergic rhinitis, nasal polyps, allergic bronchopulmonary aspergillosis, chronic eosinophilic pneumonia, eosinophilic bronchitis, celiac disease, Churg-Strauss syndrome, eosinophilic-myalgia syndrome, hypereosinophilic syndrome, eosinophilic gastritis, eosinophilic gastroenteritis, eosinophilic enteritis, eosinophilic colitis, Crohn's disease, inflammatory bowel disease (IBD), scleroderma, endomyocardial fibrosis, aspirin intolerance, obstructive sleep apnea, cancer (e.g., glioblastoma (e.g., glioblastoma multiforme), non-Hodgkin's lymphoma), edema (e.g., angioedema), infection (e.g., helminth infection), or onchocercal dermatitis.

In one embodiment, the eosinophilic disorder is an eosinophil-associated gastrointestinal disorder (EGID), for example, and not limitation, eosinophilic esophagitis, eosinophilic gastritis, eosinophilic gastroenteritis, eosinophilic enteritis, or eosinophilic colitis.

In one embodiment, the IL-33 binding protein is used to treat an infection. The infection may be due to a cause including, but not limited to, a viral infection (e.g., influenza, respiratory syncytial virus (RSV)), a helminth infection (e.g., nematodiasis (e.g., trichuriasis)), or a protozoan infection (e.g., *Leishmania major* infection).

In one embodiment, the IL-33 binding protein is used to treat pain. The pain may be related to inflammatory pain, hyperalgesia (e.g., mechanical hyperalgesia), allodynia, or hypernociception (e.g., cutaneous hypernociception, articular hypernociception). The hypernociception may or may not be induced by an antigen.

In one embodiment, the IL-33 binding protein is used to treat a central nervous system disorder. Examples of central nervous system disorders include, but are not limited to, Alzheimer's disease, subarachnoid hemorrhage, infection of the central nervous system (e.g., viral infection), bipolar disorder, and neurodegenerative diseases. Examples of neurodegenerative diseases include, but are not limited to Alzheimer's disease, multiple sclerosis, Parkinson's disease, Huntington's disease, and experimental autoimmune encephalomyelitis.

In one embodiment, the IL-33 binding protein is used to treat a cancer or tumorigenic disorder. Examples of cancer or tumorigenic disorders include lung cancer, ovarian cancer, breast cancer, prostate cancer, endometrial cancer, renal cancer, esophageal cancer, pancreatic cancer, squamous cell carcinoma, uveal melanoma, cervical cancer, colorectal cancer, bladder cancer, brain cancer, pancreatic cancer, head and neck cancer, liver cancer, leukemia, lymphoma, Hodgkin's disease, multiple myeloma, melanoma, gastric cancer, astrocytoma, stomach cancer, and pulmonary adenocarcinoma.

In one embodiment, the IL-33 binding protein is used to treat a solid tumor. Examples of solid tumors include, but are not limited to, tumors of the lung, breast, ovary, uterus, prostate, male genital organ, kidney, liver, pancreas, brain, head and neck, oral cavity, stomach, duodenum, small intestine, large intestine, gastrointestinal tract, colon, anus, gall bladder, labium, nasopharynx, urinary organs, bladder, skin, connective tissue (e.g., sarcoma), or bone.

For example, and not limitation, in one embodiment, the solid tumor is a breast tumor, a colon tumor, a prostate tumor, a lung tumor, a kidney tumor, a liver tumor, a pancreas tumor, a stomach tumor, an intestinal tumor, a brain tumor, a bone tumor, or a skin tumor.

In one embodiment, the IL-33 binding protein is used to inhibit tumor growth, progression, and/or metastasis.

In one embodiment, the IL-33 binding protein is used to treat an ophthalmological disorder. In one embodiment, the ophthalmological disorder is related to angiogenesis and/or atrophy. Examples of ophthalmological disorders include, but are not limited to, age-related macular degeneration (AMD) (e.g., wet AMD, dry AMD, intermediate AMD, advanced AMD, geographic atrophy (GA)), macular degeneration, macular edema, diabetic macular edema (DME) (e.g., non-center involved DME, center involved DME), retinopathy (e.g., high-altitude retinopathy), diabetic retinopathy (DR) (e.g., proliferative DR (PDR), non-proliferative DR (NPDR), high-altitude DR), hypertensive retinopathy, ischemia-related retinopathies, retinopathy of prematurity (ROP), conjunctivitis (e.g., infectious conjunctivitis, non-infectious conjunctivitis (e.g., allergic conjunctivitis)), choroidal neovascularization (CNV) (e.g., myopic CNV), corneal neovascularization, diseases related to corneal neovascularization, retinal neovascularization, diseases related to retinal/choroidal neovascularization, intraocular neovascularization, iris neovascularization, central serous retinopathy (CSR), pathologic myopia, von Hippel-Lindau disease, histoplasmosis of the eye, uveitis (e.g., infectious uveitis, non-infectious uveitis), vasculitis, retinitis (e.g., CMV retinitis), blepharitis, dry eye, traumatic eye injury, Sjögren's syndrome, Norrie disease, Stargardt disease, Leber congenital amaurosis, familial exudative vitreoretinopathy (FEVR), retinal abnormalities related to osteoporosis-pseudoglioma syndrome (OPPG), subconjunctival hemorrhage, rubeosis, ocular neovascular disease, neovascular glaucoma, retinitis pigmentosa (RP), retinal angiomatous proliferation, macular telangiectasia, retinal degeneration, cystoid macular edema (CME), papilledema, ocular melanoma, retinal blastoma, retinoschisis, rubeosis (e.g., rubeosis iridis), fibrotic disorders of the eye (e.g., proliferative vitreoretinopathy), choroiditis (e.g., multifocal choroiditis), ocular histoplasmosis, and ophthalmological disorders related to ocular neovascularization, vascular leakage, retinal edema, and/or retinal atrophy.

Corneal neovascular may be related to a plurality of diseases and disorders including, but not limited to, Sjögren's syndrome, Terrien marginal degeneration, infections (e.g., Herpes simplex infections, Herpes zoster infections, Mycobacteria infections, protozoan infections), systemic lupus erythematosus (SLE), rheumatoid arthritis, ulcers (e.g., Mooren's ulcer, bacterial ulcers, fungal ulcers), vitamin A deficiency, syphilis, traumatic eye injury, chemical burns, polyarteritis nodosa, Stevens-Johnson syndrome, granulomatous diseases (e.g., sarcoidosis, Wegener's granulomatosis), acne, rosacea, epidemic keratoconjunctivitis, atopic keratoconjunctivitis, superior limbic keratoconjunctivitis, keratoconjunctivitis sicca, phlyctenular keratoconjunctivitis, marginal keratolysis, surgical procedures (e.g., radial keratotomy), scleritis, Kaposi's sarcoma, lipid degeneration (e.g., primary lipid keratopathy), corneal graph rejection, and contact lens overuse.

Choroidal neovascularization and retinal vascular defects may be related to a plurality of diseases and disorders including, but not limited to, diabetic retinopathy, macular degeneration, systemic lupus erythematosus, retinopathy of prematurity, retina edema (e.g., macular edema), traumatic eye injury, surgical procedures (e.g., laser eye surgery), sickle cell anemia, sarcoidosis, syphilis, Lyme disease, Behcet's disease, Eales disease, Paget's disease, presumed ocular histoplasmosis syndrome, Best disease (Best vitelliform macular dystrophy (BVMD)), myopia, vein occlusion, artery occlusion, carotid obstructive disease, pseudoxanthoma elasticum, retinal detachment, toxoplasmosis, mycobacterial infections, infections resulting in retinitis or choroiditis (e.g., multifocal choroiditis), uveitis, vitritis, pars planitis, optic disc pits, and hyperviscosity syndrome.

Retinal atrophy may be related to a plurality of diseases and disorders including, but not limited to, age-related macular degeneration (AMD), macular atrophy, diabetic retinopathy, Stargardt disease, Sorsby's fundus dystrophy (SFD), retinoschisis, and retinitis pigmentosa. In one embodiment, the AMD is geographic atrophy or advanced AMD (e.g., advanced dry AMD). In one embodiment, the AMD is dry AMD. In one embodiment, the macular atrophy is related to neovascularization and/or geographic atrophy.

In one embodiment, the ophthalmological disorder is an intraocular neovascular disease. Examples of intraocular neovascular diseases include, but are not limited to, age-related macular degeneration (AMD), diabetic retinopathy, ischemia-related retinopathies, proliferative retinopathies, diabetic macular edema, pathological myopia, von Hippel-Lindau disease, presumed ocular histoplasmosis syndrome, retinal vein occlusion (RVO) (e.g., CRVO, BRVO), choroidal neovascularization (CNV), corneal neovascularization, retinal neovascularization, and retinopathy of prematurity (ROP).

For example, and not limitation, in one embodiment, the ophthalmological disorder is age-related macular degeneration (AMD), retinopathy of the eye, polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber congenital amaurosis, Stargardt disease, traumatic eye injury, or conjunctivitis (e.g., infectious conjunctivitis, non-infectious conjunctivitis, allergic conjunctivitis). In one embodiment, the AMD is geographic atrophy (GA), wet AMD, or dry AMD. In one embodiment, the GA. In one embodiment, the retinopathy of the eye is diabetic retinopathy (DR) or retinopathy of prematurity (ROP). In one embodiment, the retinopathy of the eye is high-altitude retinopathy. In one embodiment, the conjunctivitis is infection conjunctivitis or non-infections conjunctivitis. In one embodiment, the conjunctivitis is allergic conjunctivitis.

In one embodiment, the IL-33 binding protein or the pharmaceutical composition described herein is administered with other medicaments. For example, and not limitation, the IL-33 binding protein or the pharmaceutical composition described herein may be administered with a beta2-agonist (e.g., a short-acting beta2-agonist (SABA) or a long-acting beta2-agonist (LABA),) an anticholinergic (e.g., a short-acting anticholinergic (SAMA) or a long-acting anticholinergic (LAMA)), a methylxanthine, a corticosteroid (e.g., an inhaled corticosteroid (ICS), an oral corticosteroid (OCS), an intravenous corticosteroid, a topical corticosteroid) or steroid, a phosphodiesterase-4 inhibitor (e.g., roflumilast), a leukotriene receptor antagonist (LTA) (e.g., montelukast, zafirlukast), a mucolytic agent (e.g., erdosteine, carbocysteine, N-acetylcysteine), an analgesic, an antiviral, an antibiotic, an antifungal agent, aspirin, a nonsteroidal anti-inflammatory drug (e.g., naproxen sodium, ibuprofen), insulin, an antihypertensive agent (e.g., calcium channel blocker, thiazide diuretic, beta-blocker, alpha-blocker, angiotensin-converting enzyme (ACE) inhibitor, angiotensin II receptor antagonist), a mast cell stabilizer (e.g., nedocromil sodium, cromolyn sodium), an antioxidant, oxygen, or a combination thereof. In one embodiment, one or more of the other medicaments is included in a kit with the IL-33 binding protein or the pharmaceutical composition described herein.

Examples of SABAs include, but are not limited to, fenoterol, levalbuterol, salbutamol (albuterol), pirbuterol, metaproterenol, and terbutaline. Examples of LABAs include, but are not limited to, arformoterol, formoterol, indacaterol, olodaterol, and salmetrol. Examples of SAMAs include, but are not limited to, ipratropium bromide and oxitropium bromide. Examples of LAMAs include, but are not limited to, aclidinium bromide, glycopyrronium bromide, tiotropium, umeclidinium, glycopyrrolate, and revefenacin. Examples of corticosteroids include, but are not limited to, prednisone, prednisolone (e.g., methylprednisolone), dexamethasone, dexamethasone triamcinolone, hydrocortisone, betamethasone. beclomethasone, budesonide, mometasone, flunisolide, dexamethasone acetate/phenobarbital/theophylline, fluticasone propionate, and fluticasone furonate. Examples of methylxanthines include, but are not limited to, aminophylline and theophylline.

In one embodiment, the IL-33 binding protein or the pharmaceutical composition described herein may be administered with a combination treatment including, but not limited to, a SABA and a SAMA in one device (e.g., fenoterol and ipratropium, salbutamol and ipratropium); a LABA and a LAMA in one device (e.g., formoterol and aclidinium, formoterol and glycopyrronium, indacaterol and glycopyrronium, vilanterol and umeclidinium, olodaterol and tiotropium); a LABA and an ICS in one device (e.g., salmeterol and fluticasone propionate, formoterol and beclometasone, formoterol and budesonide, formoterol and mometasone, vilanterol and fluticasone furoate); or a LABA, LAMA, and ICS in one device (e.g., fluticasone, umeclidinium, and vilanterol; beclometasone, formoterol, and glycopyrronium; budesonide, formoterol, and glycopyrrolate).

For example, and not limitation, a subject with COPD or asthma is provided with the IL-33 binding protein or the pharmaceutical composition described herein administered with an additional treatment including a SABA, a SAMA, a LABA, a LAMA, and/or a corticosteroid or steroid (e.g., an ICS). In one embodiment, a subject with COPD is provided with the "standard of care", which refers to treatments commonly used to treat COPD (e.g., maintenance therapy), including an ICS and a LABA, a LAMA and a LABA, or an ICS, a LAMA, and a LABA.

In a first aspect of the invention, the present disclosure provides an IL-33 binding protein comprising:

(i) CDRH1, CDRH2, and CDRH3 from SEQ ID NO:20 and CDRL1, CDRL2, and CDRL3 from SEQ ID NO:25, wherein SEQ ID NO:20 comprises:

QVQLVQSGAEVKKPGASVKVSCKASGYTFI-SYGMHWVRQAPGQGLEW MGEINPHGGSTSYAQKFX$_1$GRVTMTR DTSTSTVYMELSSLRSEDTAVYYC ARPSAAYSHYLGX$_2$DX$_3$WGRGTLVTVSS; and wherein SEQ ID NO:25 comprises:

DIQMTQSPSSVSASVGDRVTITCRX$_4$SQ GISX$_5$WLX$_6$WYQQKPGKAPKLLIY AX$_7$SX$_8$LQSGVPSRFSGSGSGTDFTLTI SSLQPEDFATYYCQQAX$_9$VX$_{10}$PLTF GGGTKVEIK; and wherein:

X$_1$=K or Q; X$_2$=I or L; X$_3$=I, L, or M; X$_4$=A or T; X$_5$=P or S; X$_6$=A or S; X$_7$=A or G; X$_8$=R or S; X$_9$=H or N; and X$_{10}$=F or L; or (ii) one or more CDR variants of (i), wherein the variant has 1, 2, or 3 amino acid modifications.

In a second aspect of the invention, the present disclosure provides an IL-33 binding protein, wherein the IL-33 binding protein comprises:

(i) CDRH1, CDRH2, and CDRH3 from any one of SEQ ID NOs: 21-24 and CDRL1, CDRL2, and CDRL3 from any one of SEQ ID NOs: 26-28; or (ii) one or more CDR variants of (i), wherein the variant has 1, 2, or 3 amino acid modifications.

In an embodiment of the first aspect or the second aspect of the invention, the IL-33 binding protein comprises CDRH1, CDRH2, and CDRH3 from SEQ ID NO:21 and CDRL1, CDRL2, and CDRL3 from SEQ ID NO:26.

In an embodiment of the first aspect or the second aspect of the invention, the IL-33 binding protein comprises CDRH1, CDRH2, and CDRH3 from SEQ ID NO:22 and CDRL1, CDRL2, and CDRL3 from SEQ ID NO:26.

In an embodiment of the first aspect or the second aspect of the invention, the IL-33 binding protein comprises CDRH1, CDRH2, and CDRH3 from SEQ ID NO:23 and CDRL1, CDRL2, and CDRL3 from SEQ ID NO:27.

In an embodiment of the first aspect or the second aspect of the invention, the IL-33 binding protein comprises CDRH1, CDRH2, and CDRH3 from SEQ ID NO:24 and CDRL1, CDRL2, and CDRL3 from SEQ ID NO:28.

In an embodiment of the first aspect or the second aspect of the invention, the IL-33 binding protein comprises CDRH1 of SEQ ID NO:1, CDRH2 of SEQ ID NO:3, CDRH3 of SEQ ID NO: 6, CDRL1 of SEQ ID NO: 10, CDRL2 of SEQ ID NO: 14, and CDRL3 of SEQ ID NO:18.

In an embodiment of the first aspect or the second aspect of the invention, the IL-33 binding protein comprises CDRH1 of SEQ ID NO:1, CDRH2 of SEQ ID NO:4, CDRH3 of SEQ ID NO: 7, CDRL1 of SEQ ID NO:10, CDRL2 of SEQ ID NO:14, and CDRL3 of SEQ ID NO:18.

In an embodiment of the first aspect or the second aspect of the invention, the IL-33 binding protein comprises CDRH1 of SEQ ID NO:1, CDRH2 of SEQ ID NO:3, CDRH3 of SEQ ID NO: 8, CDRL1 of SEQ ID NO:11, CDRL2 of SEQ ID NO: 15, and CDRL3 of SEQ ID NO:18.

In an embodiment of the first aspect or the second aspect of the invention, the IL-33 binding protein comprises CDRH1 of SEQ ID NO:1, CDRH2 of SEQ ID NO:3, CDRH3 of SEQ ID NO: 7, CDRL1 of SEQ ID NO: 12, CDRL2 of SEQ ID NO: 16, and CDRL3 of SEQ ID NO: 19.

In an embodiment of any one of the preceding aspects or corresponding embodiments, the IL-33 binding protein comprises a heavy chain variable (VH) domain having at least 90% identity to any one of SEQ ID NOs: 20-24 and a light chain variable (VL) domain having at least 90% identity to any one of SEQ ID NOs: 25-28.

In an embodiment of any one of the preceding aspects or corresponding embodiments, the IL-33 binding protein comprises a VH domain having at least 90% identity to SEQ ID NO:22 and a VL domain having at least 90% identity SEQ ID NO:26.

In an embodiment of any one of the preceding aspects or corresponding embodiments, the IL-33 binding protein is an antibody or binding fragment thereof.

In an embodiment of any one of the preceding aspects or corresponding embodiments, the IL-33 binding protein is a monoclonal antibody or binding fragment thereof.

In an embodiment of any one of the preceding aspects or corresponding embodiments, the antibody or binding fragment thereof is a human IgG antibody or binding fragment thereof.

In an embodiment of any one of the preceding aspects or corresponding embodiments, the human IgG antibody or binding fragment thereof is a human IgG1 antibody or binding fragment thereof.

In an embodiment of the first aspect or the second aspect of the invention, the human IgG1 antibody or binding fragment thereof is a human IgG1κ antibody or binding fragment thereof.

In an embodiment of the first aspect or the second aspect of the invention, the antibody comprises a modified Fc region.

In an embodiment of the first aspect or the second aspect of the invention, the modified Fc region comprises Fc mutations to extend half-life. In one embodiment, the modified Fc region comprises Fc mutations to extend half-life as compared to an IL-33 antibody without any Fc mutations to extend half-life. In one embodiment, the modified Fc region comprises Fc mutations to extend half-life as compared to an IL-33 antibody without said Fc mutations to extend half-life.

In an embodiment of the first aspect or the second aspect of the invention, the Fc mutation is YTE.

In a third aspect of the invention, the present disclosure provides an IL-33 binding protein comprising a heavy chain (HC) having at least 90% identity to any one of SEQ ID NOs: 29-33 and a light chain (LC) having at least 90% identity to any one of SEQ ID NOs: 34-37, wherein SEQ ID NO:29 comprises:

QVQLVQSGAEVKKPGASVKVSCKASGYTFI-SYGMHWVRQAPGQGLE WMGEINPHGGSTSYAQKFX$_1$GRVTMTR DTSTSTVYMELSSLRSEDTA VYYCARPSAAYSHYLGX$_2$DX$_3$WGRGTL VTVSSASTKGPSVFPLAPSSK STSGGTAAL-GCLVKDYFPEPVTVSWNSGALT-SGVHTFPAVLQSSGLYS LSSVVTVPSSSLGTQTYICNVNH KPSNTKVDKKVEPKSCDKTHTCPPC PAPELLGGPSVFLFPPKPKDTLYITREPE-VTCVVVDVSHEDPEVKFNW YVDGVEVHNAKTKPREEQYN-STYRVVSVLTVLHQDWLNGKEYKCK VSNKAL-PAPIEKTISKAKGQPREPQVYTLPPSRDELT-KNQVSLTCLVKG FYPSDIA VEWESNGQPENNYKTTPPVLDSDGSFFLYSK-LTVDKSRWQ QGNVFSCSVMHEALHN-HYTQKSLSLSPGK; and wherein SEQ ID NO:34 comprises:

DIQMTQSPSSVSASVGDRVTITCRX$_4$SQ GISX$_5$WLX$_6$WYQQKPGKAPKL LIYAX$_7$SX$_8$LQSGVPSRFSGSGSGTDFTLT ISSLQPEDFATYYCQQAX$_9$V X$_{10}$PLTFGGGTKVEIKRTVAAPSVFIFP

PSDEQLKSGTASVVCLLNNFYP REAKVQWKVD-NALQSGNSQESVTEQDSKDSTYSLSSTLTL-SKADYEK HKVYACE-VTHQGLSSPVTKSFNRGEC; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L.

In an embodiment of the third aspect of the invention, the IL-33 binding protein is an antibody comprising an HC having at least 90% identity to SEQ ID NO:31 and an LC having at least 90% identity to SEQ ID NO:35.

In an embodiment of the third aspect of the invention, the IL-33 binding protein is an antibody comprising an HC of SEQ ID NO:31 and an LC of SEQ ID NO:35.

In a fourth aspect of the invention, the present disclosure provides a pharmaceutical composition comprising the IL-33 binding protein as defined in any one of the above aspects or embodiments of the invention and a pharmaceutically acceptable excipient.

In a fifth aspect of the invention, the present disclosure provides a method of treating or preventing a disease or condition in a human in need thereof comprising administering to the human a therapeutically effective amount of the IL-33 binding protein of any one of the first three aspects of the invention and corresponding embodiments, or the pharmaceutical composition of the fourth aspect of the invention.

In a sixth aspect of the invention, the present disclosure provides an IL-33 binding protein of any one of the first three aspects of the invention and corresponding embodiments, or a pharmaceutical composition of the fourth aspect of the invention, for use in treating or preventing a disease or condition.

In a seventh aspect of the invention, the present disclosure provides use of the IL-33 binding protein of any one of the first three aspects of the invention and corresponding embodiments, or the pharmaceutical composition of the fourth aspect of the invention, in the manufacture of a medicament for treating or preventing a disease or condition.

In an embodiment of the method of the fifth aspect of the invention, the IL-33 binding protein or pharmaceutical composition for use of the sixth aspect of the invention, or the use of the seventh aspect of the invention, the disease or condition is chronic obstructive pulmonary disease (COPD), asthma, bronchitis, bronchiolitis, acute respiratory failure, inflammatory lung diseases, diabetic kidney disease, endometriosis, chronic rhinosinusitis with nasal polyps, food hypersensitivity, food allergy, peanut allergy, allergic rhinitis, eosinophilic oesophagitis, atopic dermatitis, cystic fibrosis, or chronic urticaria.

In an embodiment of the method of the fifth aspect of the invention, the IL-33 binding protein or pharmaceutical composition for use of the sixth aspect of the invention, or the use of the seventh aspect of the invention, the disease or condition is COPD.

In an eighth aspect of the invention, the present disclosure provides a nucleic acid sequence or plurality of nucleic acid sequences encoding an IL-33 binding protein according to any one of the first three aspects of the invention and corresponding embodiments.

In a ninth aspect of the invention, the present disclosure provides a nucleic acid sequence or plurality of nucleic acid sequences comprising any one of SEQ ID NOs: 59-64 and/or any one of SEQ ID NOs: 69-76.

In a tenth aspect of the invention, the present disclosure provides a nucleic acid sequence or plurality of nucleic acid sequences comprising any one of SEQ ID NOs: 65-68 and/or any one of SEQ ID NOs: 77-79.

In an eleventh aspect of the invention, the present disclosure provides a nucleic acid sequence or plurality of nucleic acid sequences comprising SEQ ID NO:66 and/or SEQ ID NO: 77.

In a twelfth aspect of the invention, the present disclosure provides an expression vector comprising the nucleic acid sequence or plurality of nucleic acid sequences of the eighth, ninth, tenth, or eleventh aspects of the invention.

In a thirteenth aspect of the invention, the present disclosure provides a host cell that comprises the nucleic acid sequence or plurality of nucleic acids of any one of the eighth, ninth, tenth, or eleventh aspects of the invention, or the expression vector of the twelfth aspect of the invention.

In a fourteenth aspect of the invention, the present invention provides a method of producing an IL-33 binding protein, comprising culturing the host cell as defined in the thirteenth aspect of the invention under conditions suitable for expression of said nucleic acid sequence, plurality of nucleic acid sequences, or vector, whereby a polypeptide comprising the IL-33 binding protein is produced.

In a fifteenth aspect of the invention, the present disclosure provides an IL-33 binding protein produced by the method of the fourteenth aspect of the invention.

In a sixteenth aspect of the invention, the present disclosure provides an IL-33 binding protein that binds to human IL-33 at amino acid residues 219-227 (SEQ ID NO:87).

In one embodiment of the sixteenth aspect, the IL-33 binding protein also binds to human IL-33 at amino acid residues 164-182 (SEQ ID NO:86).

In one embodiment, the present disclosure provides the IL-33 binding protein of the sixteenth aspect of the invention and corresponding embodiments, wherein the IL-33 binding protein further binds one or more of the following sequences: SEQ ID NO:84, SEQ ID NO:85, and LSE (residues 267-269).

In one embodiment, the present disclosure provides the IL-33 binding protein of the sixteenth aspect of the invention and corresponding embodiments, wherein the IL-33 binding protein is further defined in any of the first, second, third, and fifteenth aspects of the invention and corresponding embodiments.

In a seventeenth aspect of the invention, the present disclosure provides an IL-33 binding protein that binds to human IL-33 and competes for binding to the human IL-33 with a reference IL-33 binding protein that binds to the IL-33 at amino acid residues 219-227 (SEQ ID NO:87), and optionally at amino acid residues 164-182 (SEQ ID NO:86), wherein the reference IL-33 binding protein comprises:

(i) CDRH1, CDRH2, and CDRH3 from SEQ ID NO:20 and CDRL1, CDRL2, and CDRL3 from SEQ ID NO:25, wherein SEQ ID NO:20 comprises:
QVQLVQSGAEVKKPGASVKVSCKASGYTFI-SYGMHWVRQAPGQGLE WMGEINPHGGSTSYAQKF$X_1$GRVT MTRDTSTSTVYMELSSLRSEDTA VYYCARPSAAYSHYLG$X_2$D$X_3$WGR GTLVTVSS; and wherein SEQ ID NO:25 comprises:
DIQMTQSPSSVSASVGDRVTITCR$X_4$SQ GIS$X_5$WL$X_6$WYQQKPGKAPKL LIYA$X_7$S$X_8$LQSGVPSRFSGSGSG TDFTLTISSLQPEDFATYYCQQA$X_9$V $X_{10}$PLTFGGGTKVEIK; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L;

(ii) CDRH1, CDRH2, and CDRH3 from any one of SEQ ID NOs: 21-24 and CDRL1, CDRL2, and CDRL3 from any one of SEQ ID NOs: 26-28; or (iii) one or more CDR variants of (i) or (ii), wherein the variant has 1, 2, or 3 amino acid modifications.

In one embodiment of the seventeenth aspect, the reference IL-33 binding protein also binds to human IL-33 at amino acid residues 164-182 (SEQ ID NO:86).

In one embodiment, the present disclosure provides the IL-33 binding protein of the seventeenth aspect of the invention and corresponding embodiments, wherein the reference IL-33 binding protein further binds one or more of the following sequences: SEQ ID NO:84, SEQ ID NO: 85, and LSE (residues 267-269).

In an eighteenth aspect, the present invention provides an IL-33 binding protein that binds to human IL-33 and competes for binding to the human IL-33 with a reference IL-33 binding protein, wherein the reference IL-33 binding protein comprises:

(i) CDRH1, CDRH2, and CDRH3 from SEQ ID NO:20 and CDRL1, CDRL2, and CDRL3 from SEQ ID NO:25, wherein SEQ ID NO:20 comprises:

QVQLVQSGAEVKKPGASVKVSCKASGYTFI-SYGMHWVRQAPGQGLE WMGEINPHGGSTSYAQKFX$_1$GRVTMTR DTSTSTVYMELSSLRSEDTA VYYCARPSAAYSHYLGX$_2$DX$_3$WGRGTL VTVSS; and wherein SEQ ID NO:25 comprises:

DIQMTQSPSSVSASVGDRVTITCRX$_4$SQ GISX$_5$WLX$_6$WYQQKPGKAPKL LIYAX$_7$SX$_8$LQSGVPSRFSGSGSGTDF TLTISSLQPEDFATYYCQQAX$_9$V X$_{10}$PLTFGGGTKVEIK; and wherein:

$X_1$=K or Q; $X_2$=I or L; $X_3$=I, L, or M; $X_4$=A or T; $X_5$=P or S; $X_6$=A or S; $X_7$=A or G; $X_8$=R or S; $X_9$=H or N; and $X_{10}$=F or L;

(ii) CDRH1, CDRH2, and CDRH3 from any one of SEQ ID NOs: 21-24 and CDRL1, CDRL2, and CDRL3 from any one of SEQ ID NOs: 26-28; or (iii) one or more CDR variants of (i) or (ii), wherein the variant has 1, 2, or 3 amino acid modifications.

EXAMPLES

Example 1—Generation and Isolation of IL-33 Binding Proteins

Fully human antibodies specific for human IL-33 were generated using a yeast-based platform and isolated using biotinylated recombinant human and cynomolgus IL-33 combined with magnetic cell sorting and FACS-based selection techniques. Antibody 22A06-1 was identified from the naïve yeast libraries as a hit and its heavy and light chain variable regions were sequenced.

22A06-1 underwent two further successive cycles of affinity maturation, yielding four high-performing clones: 22A06-429, 22A06-458, 22A06-481 and 22A06-502. Anti-IL-33 antibody 22A06-458 was reformatted with the 'YTE' Fc mutations for half-life extension.

Example 2—Affinity in Solution of an IL-33 Binding Protein to Human and Cynomolgus IL-33

The affinity of IL-33 binding protein 22A06-458 for human and cynomolgus monkey IL-33 at room temperature (25° C.) and 37° C. was determined using an MSD-SET (MESOSCALE DISCOVERY Solution Equilibrium Titration) assay. Two anti-IL-33 antibodies (in-house) were included in the assay as positive controls and a human IgG1 isotype control (in-house) was included as a negative control for non-specific binding.

A. Methods

Two identical 96 well polypropylene plates were prepared with biotinylated human IL-33 (in-house) at a constant concentration of 30 pM and the antibodies to be tested titrated 1 in 3 from 1 nM to $5\times10^{-5}$ nM across the plate, with a final 1 in 10 dilution to $5\times10^{-6}$ nM. All antibodies were tested in duplicate within the plate. Both plates were incubated for 24 hours, one at room temperature, the other at 37° C.

After 24 hours, the same antibodies (20 nM in PBS) were coated on to two identical standard bind MSD plates (Mesoscale Discovery #L15XA) for 30 minutes at room temperature. Plates were then blocked with starting block blocking buffer for 30 minutes with shaking at 700 rpm, followed by three washes with wash buffer. The incubated solutions were added to the MSD plates (each incubation temperature on its own MSD plate) for 150 seconds with shaking at 700 rpm followed by one wash. Antigen captured on the plate was detected with SULFO-TAG-labeled streptavidin (Mesoscale Discovery #R32AD-1). The plates were washed three times with wash buffer and then read on the MSD Sector Imager instrument using 1× Read Buffer T (Mesoscale Discovery #R92TC-1) with surfactant. The percent free antigen was plotted as a function of titrated antibody concentration in GraphPad Prism and fit to a quadratic equation.

To determine the affinity to cynomolgus monkey IL-33 (in-house), the assay was repeated with cynomolgus IL-33 at a constant concentration of 62.5 pM and the antibodies titrated 1 in 3 from 12 nM to $6\times10^{-4}$ nM with a final 1 in 10 dilution to $6\times10^{-5}$ nM.

B. Results

The affinity of 22A06-458 for human IL-33 is 3.3 pM (range 1.8-6 pM) at 25° C. and 13.5 pM (range 0-42 pM) at 37° C. The affinity of 22A06-458 for cynomolgus IL-33 at 25° C. is 27.5 pM (range 4.6-43 pM) and at 37° C. is 56.5 pM (range 30-98 pM). See Table 3 for results.

The positive control antibodies (mAb1 and mAb2) bound both human and cynomolgus IL-33, while the negative isotype control antibody showed no binding to IL-33. All the assay results met the acceptance criteria of $R^2$>0.96.

All the samples were run in duplicate within the plates and the reported results are therefore an average of n=2. One of the 22A06-458 replicates in the cynomolgus IL-33 25° C. assay failed acceptance criteria due to an automation pipetting error. This plate was repeated and hence the result for this sample is an average of n=3.

TABLE 3

Affinity in solution of IL-33 antibodies to human and cynomolgus IL-33 by MSD-SET

| Antibody | Antigen | Temp (° C.) | Average $K_D$ (pM) | Lower 95% confidence interval (pM) | Upper 95% confidence interval (pM) |
|---|---|---|---|---|---|
| 22A06-458 | human IL-33 | 25 | 3.3 | 1.8 | 6 |
| | | 37 | 13.5 | 0 | 42 |
| | cyno IL-33 | 25 | 27.5* | 4.6 | 43 |
| | | 37 | 56.5 | 30 | 98 |
| Anti IL-33 | human IL-33 | 25 | <3.0 | 0 | 2.6 |
| control | | 37 | 9.65 | 0 | 17 |
| mAb1 | cyno IL-33 | 25 | 125 | 95 | 320 |
| | | 37 | 565 | 130 | 990 |
| Anti IL-33 | human IL-33 | 25 | <3.0 | 0 | 1.6 |
| control | | 37 | <3.0 | 0 | 9 |
| mAb2 | cyno IL-33 | 25 | 61.5 | 20 | 100 |
| | | 37 | 140 | 48 | 240 |

Affinity values are an average of n = 2 replicates, apart from (*) which is n = 3

Affinity values of 0 are not possible, but these lower confidence interval values of zero are due to the limits set in the prism macro used to analyze the results.

Following a similar procedure, affinities were determined for 22A06-429, 22A06-481 and 22A06-502 for human IL-33 to be between 1 pM and 5 pM at 25° C. Affinities were determined for 22A06-429, 22A06-481 and 22A06-502 for cynomolgus IL-33 to be between 10 pM and 70 pM at 25° C.

Example 3—Specificity of IL-33 Binding Protein for IL-33 Over IL-1α and IL-1β

The specificity of IL-33 binding protein 22A06-458 for IL-33 over the most closely related proteins, IL-1α and IL-1β, was determined using a single shot binding assay on a FORTEBIO OCTET RED384 biolayer interferometry (BLI) instrument.

A. Methods

22A06-458 at 20 μg/mL PBSF (PBS+0.1% IgG free BSA, in-house) was captured on protein A dip and read biosensors (Fortebio #18-5013) to a level of 1 nm. The loaded sensors were dipped into either human IL-33 (in-house), IL-1α (R&D Systems #200-LA), or IL-1β (R&D Systems #201-LB) all diluted to 100 nM in PBSF for 300 seconds. The sensors were then dipped back into buffer for the dissociation phase for 600 seconds. Blank sensors were included to check for non-specific binding of the proteins to the sensors. Regeneration of the biosensor tips was carried out using 10 mM glycine pH 1.5 (in-house). The analysis was run at 25° C., with a plate shaker speed of 1000 rpm. Data were aligned to the baseline, but no kinetics model was applied to the data.

B. Results

There was no non-specific binding of the proteins to the protein A sensors and there was visible binding of 22A06-458 to human IL-33, confirming that the assay was working. There was no visible binding of 22A06-458 to human IL-1α or human IL-1β.

Example 4—Competition Between IL-33 Binding Protein and ST2 Receptor for Binding to IL-33

A FORTEBIO OCTET RED384 BLI instrument was used to determine whether HEK expressed IL-33 binding protein 22A06-458 competes with the ST2 receptor for binding to IL-33. An anti-IL-33 positive control antibody (in-house) was included for comparison.

A. Methods

1. Competition with ST2-Fc Receptor for Binding to IL-33

22A06-458 at 20 mg/mL in PBSF (phosphate buffered saline+0.1% IgG free BSA, in-house) was captured on protein A dip and read biosensors (Fortebio #18-5013). The loaded sensors were blocked with a human IgG1 isotype control (in-house) at 100 μg/mL for 15 minutes. The loaded and blocked sensors were dipped into ST2-Fc (R&D Systems #523-ST) at 20 μg/mL (100 nM) to check that blocking was complete and that no binding of the Fc tag to the protein A sensors was observed.

The loaded and blocked sensors were dipped into human IL-33 (in-house) at 256 nM in PBSF for 300 seconds and then into ST2-Fc at 100 nM for 300 seconds. The assay was repeated in the reverse orientation with ST2-Fc loaded onto the protein A sensors, which were then dipped into human IL-33 followed by the antibody.

A self-binning control was included where both the loading step and second binding step were carried out in ST2-Fc to check that the receptor competed with itself for binding to human IL-33 and that the assay format was therefore working.

Regeneration of the biosensor tips was carried out using 10 mM glycine pH 1.5 (in-house). The analysis was run at 25° C., with a plate shaker speed of 1000 rpm. Data were aligned to the baseline, but no kinetics model was applied to the data.

2. Competition with Monomeric ST2 for Binding to IL-33

The method described in this example above was repeated with the secondary binding step being performed in either ST2-Fc (dimeric) or ST2-his (monomeric). The ST2 was at a concentration of 75 nM, and the association and dissociation phases were both 180 seconds long. The assay format was not reversed in this experiment, but all other conditions remain the same as described above.

B. Results

1. Competition with ST2-Fc (Dimeric) Receptor for Binding to IL-33

No significant non-specific binding of IL-33 or ST2 to the protein A sensors was observed; therefore, all binding signals seen are specific. No second binding event was observed in the self-binning control step (ST2 competing against itself); therefore, the assay format was working.

When the 22A06-458: IL-33 complex captured on to the sensor was dipped into ST2-Fc, then a clear second binding event was visible, demonstrating that ST2 can bind to IL-33 that is bound to the antibody.

When the ST2: IL-33 complex was dipped into the solution of antibody, then only a very small binding signal (just above the blank buffer signal) was observed. This signal was smaller than would be expected for the binding of a full-size antibody and was much smaller than the ST2 signal in the reverse orientation.

The competition between 22A06-458 and ST2 appears to be dependent on binding order/orientation. When ST2 is bound to IL-33 first, the antibody is unable to bind properly. When the antibody is bound first, ST2 is still able to bind IL-33. Results are shown in Table 4.

TABLE 4

| Competition with ST2-Fc receptor for binding to IL-33 | | |
|---|---|---|
| Loaded | Second Binding Event | |
| to sensors | 22A06-458 | ST2-Fc |
| 22A06-458 | ND | Non-competitor |
| ST2-Fc | Competitor | Competitor |

ND = not determined

2. Competition with Monomeric ST2-his (Monomeric) Receptor for Binding to IL-33

No significant non-specific binding of IL-33 or ST2 to the protein A sensors or the blocking antibody was observed; therefore, all binding signals seen are specific.

When ST2 was binned against itself (i.e., loaded onto the sensor and as the second binding component in solution) as either the his-tagged monomeric version or the dimeric Fc tagged version, no second binding event was observed. Therefore, ST2 is competing with itself for binding to IL-33 which demonstrates that the assay format was working.

For 22A06-458 and the anti-IL-33 control antibody, a binding signal was observed as the antibody binds to IL-33 and then a second binding signal was observed for ST2 binding to IL-33 in both its his-tagged and Fc tagged forms. The binding signal was larger for the dimeric version because the molecular weight is larger.

Therefore, in this assay format 22A06-458 is non-competitive with the ST2 receptor and both the monomeric and dimeric ST2 receptor can form a ternary complex with the IL-33: antibody complexes. Results are shown in Table 5.

TABLE 5

| Competition with monomeric ST2 receptor for binding to IL-33 | | | |
|---|---|---|---|
| | | Second Binding Step | |
| | | ST2-his | ST2-Fc |
| Loaded | 22A06-458 | Non-competitor | Non-competitor |
| onto | Anti IL-33 control | Non-competitor | Non-competitor |
| Sensors | ST2-Fc | Competitor | Competitor |

Example 5—Affinity of IL-33 Binding Protein:IL-33 Complex to ST2

A FORTEBIO OCTET RED384 was used to determine the difference in the binding affinity of IL-33 for ST2 receptor with or without IL-33 binding protein 22A06-458 present. An anti-IL-33 positive control antibody (in-house) was included for comparison.

A. Methods

Human ST2-his (R&D Systems #523-ST) at 20 μg/mL in PBSF (PBS+0.1% IgG free BSA, in-house) was captured onto anti-his dip and read biosensors (Fortebio #18-5120); blank sensors were also included for referencing. All the sensors were then blocked with an irrelevant his tagged protein (OX40-his, in-house) to prevent the his tag on human IL-33 binding to the sensors.

The loaded and blocked sensors were dipped into human IL-33 (in-house) at 100 nM for 900 seconds and the dissociation step was carried out in PBSF buffer for 600 seconds. The assay was then repeated with the IL-33 pre-mixed with a ten-fold excess of 22A06-458 (1 μM) and the assay repeated with all other steps remaining the same.

Regeneration of the biosensor tips was carried out using 10 mM glycine pH 1.5 (in-house). The analysis was run at 25° C., with a plate shaker speed of 1000 rpm. The data were double referenced (blank reference sensors and 0 nM data subtracted) and aligned to the baseline. A steady state equilibrium model with a global fit was applied to the data using the FORTEBIO data analysis software v8.0.

The experiment was repeated on a separate day with fresh solutions to give n=2 data, which were averaged to give the reported result.

B. Results

No binding of IL-33-his to the blocked anti-his sensors was observed (demonstrating that the blocking was complete). No non-specific binding of 22A06-458 to the sensors was observed, though some was seen for the anti-IL-33 control antibody; however, this was removed in the double referencing process.

The affinity values determined in this experiment are for comparison purposes only, as after a 900 second association phase the binding curves had not reached equilibrium and were therefore not likely to do so within a reasonable time frame.

Binding of IL-33 to ST2 receptor was observed with an affinity of 7.2 nM. Binding of the 22A06-458: IL-33 complex to ST2 was also observed and the binding signal was larger, which would be expected as the combined molecular weight is larger than IL-33 alone. The affinity of the 22A06-458: IL-33 complex for ST2 was 11.5 nM.

The positive control antibody:IL-33 complex bound to ST2 with an affinity of 2.4 nM.

These affinities are within normal assay variation of one another and are therefore comparable. Therefore, the affinity of IL-33 for ST2 receptor is not affected when IL-33 is complexed with 22A06-458. Results are shown in Table 6.

TABLE 6

Affinity of IL-33 binding protein: IL-33 complex to ST2 vs affinity of IL-33 to ST2

| Sample | Average KD (nM) |
|---|---|
| Human IL-33 | 7.2 |
| IL-33 + 22A06-458 | 11.5 |
| IL-33 + anti IL-33 control | 2.4 |

Example 6—Binding of IL-33 Binding Protein to Oxidized Human and Cynomolgus IL-33

A FORTEBIO OCTET RED384 biolayer interferometry (BLI) instrument was used to determine whether 22A06-458 binds to oxidized human and cynomolgus IL-33 (the physiologically inactive form). An anti-oxidized IL-33 positive control antibody (in-house) was included for reference.

A. Methods

Oxidized and reduced human and cynomolgus IL-33 (in-house) were captured via their his-tags to anti-his dip and read biosensors (Fortebio #18-5120); blank sensors were also included for referencing. The sensors were then dipped into 22A06-458 at 1 μM for 300 seconds (the positive control antibody was at 150 nM). The dissociation step was carried out in PBSF buffer (in-house) for 300 seconds.

Regeneration of the biosensor tips was carried out using 10 mM glycine pH 1.5 (in-house). The analysis was run at 25° C., with a plate shaker speed of 1000 rpm. The data were aligned to the baseline, but no kinetics model was applied.

B. Results

No non-specific binding of the antibodies to the anti-his sensors was observed; therefore, the binding signals observed were specific. The positive control antibody had a large, clear binding signal to oxidized human IL-33 and a small but visible binding signal to cynomolgus IL-33, demonstrating the suitability of the oxidized material. The positive control antibody does not bind to the reduced form of IL-33.

22A06-458 had a very large binding signal to reduced human and cynomolgus IL-33, showing that the assay was working as expected. There was no significant binding signal observed for 22A06-458 to either human or cynomolgus oxidized IL-33. For the cynomolgus protein, the signal was completely flat. For human IL-33, the signal was lower than the normal binding threshold cut-offs (0.07 nm vs threshold of 0.1 nm) and much lower than the signal for reduced IL-33 (0.07 nm vs 2.5 nm). At the high concentrations used (1 μM), this would be considered a non-binder.

These results were also replicated using different techniques (BIACORE and MSD-SET), which found the same results.

Example 7—HDX-MS of IL-33 Binding Protein

Hydrogen-deuterium exchange coupled to mass spectrometry (HDX-MS, WATERS SYNAPT G2-SI) data for IL-33 binding protein 22A06-458 demonstrated protection at the peptides: YESQHPSNESGDGVDGKMLM [residues 66-85 for 6H-IL33 (113-270), in-house] (SEQ ID NO: 80) and within the peptide FVLHNMHSNC (residues 120-129) (SEQ ID NO:81). Accordingly, these protected areas are good candidates for the epitope of mAb 22A06-458.

Structural modelling was carried out using publicly available complex structures of human IL-33 and ST2 (4KC3, Liu et al., 2013, PNAS, 110 (37), 14918-14923), and human IL1β, human ILIR1 and human IL1 RAcP (4DEP, Thomas et al., 2012, 19, 455-457) to determine the potential binding mechanism for 22A06-458. The ST2 and ILIR1 protein chains from the two structures were superimposed using CCG (Chemical Computing Group) MOE (Molecular Operating Environment) 2015.1001 to orientate IL1 RAcP in relation to the IL33/ST2 complex. Through this structural modeling, the aforementioned two protected peptides were identified as peptide loops within IL-33. If the 22A06-458 mAb were to interact with these loops, it could potentially inhibit binding of both ST2 and IL-1 RAcP to IL-33. However, residues within the potential epitope of the mAb interact mainly with residues within domain 3 of ST2 and domains 2 & 3 of IL-1RAcP, and the prominent flexible loop within IL-33, especially, is distant to domains 1 & 2 of ST2. Counting the number of ST2 residues located within 4.5 Å of IL-33, 18 are within domain 3 (of which 14 are those interacting with the HDX/MS peptides), 14 within domain 2, and 8 within domain 1. Over half of the contacts between IL-33 and ST2 are thus within domains 1 & 2 (22 residues). The linker between domains 2 and 3 of ST2 is 9 residues in length, and one could thus possibly conceive that domain 3 could potentially swing out of the way of 22A06-458, which may allow the antibody to bind IL-33, while at the same time domains 1 & 2 of ST2 are also free to bind IL-33.

Example 8—Binding of IL-33 Binding Protein to FcγR Receptors

The binding of IL-33 binding protein 22A06-458 to recombinant soluble human and cynomolgus Fc gamma receptors (FcγR) was assessed using a PROTEON XPR36 (BIORAD) surface plasmon resonance (SPR) instrument. Human IgG1 wildtype and human IgG1 Fc disabled isotype antibodies were included in the analysis as an assay control.

A. Methods

A murine anti-poly-histidine IgG was immobilized on a GLM biosensor chip (BioRad #176-5012) by primary amine coupling (GE Healthcare #BR100050). Antibodies to be tested were used as the analyte and passed over at 1024 nM, 256 nM, 64 nM, 16 nM, and 4 nM with an injection of 0 nM (i.e., buffer alone) used to double reference the binding curves. The murine anti-poly-histidine IgG surface was regenerated with 100 mM phosphoric acid between interactions. The run was carried out at 25° C. using HBS-EP as running buffer (Teknova #H8022). Data were fitted to the equilibrium model inherent to the PROTEON XPR36 (BIORAD) analysis software using a global R-max value.

B. Results

The anti-RSV wildtype and Fc disabled control antibodies behaved as expected. The wildtype antibody bound all human and cyno Fc gamma receptors and the Fc disabled control did not.

22A06-458 binds to all the human and cynomolgus monkey Fc gamma receptors tested with affinities which are comparable to the human IgG1 wildtype control antibody (see Table 7 and Table 8).

TABLE 7

Binding of 22A06-458 to recombinant soluble human Fc gamma receptors

| Antibody | $K_D$ (nM) hFcgRI | hFcgRIIa (H131) | hFcgRIIa (R131) | hFcgRIIb | hFcgRIIIa (V158) | hFcgRIIIa (F158) |
|---|---|---|---|---|---|---|
| 22A06-458 | 24.3 | 574.0 | 502.0 | 5220.0 | 215.0 | 987.0 |
| Anti-RSV hIgG1 WT control | 28.3 | 884.0 | 528.0 | Weak* | 232.0 | 735.0 |
| Anti-RSV hIgG1 Fc disabled control | NB | NB | NSB | NSB | NB | NB |

NB = no binding

NSB = non-specific binding

Weak* = Binding observed, but too weak to generate an accurate value

TABLE 8

| Binding to recombinant soluble cynomolgus monkey Fc gamma receptors | | | |
|---|---|---|---|
| Antibody | cFcgRIIa | cFcgRIIb | cFcgRIIIa |
| 22A06-458 | 2110.0 | 1100.0 | 119.0 |
| Anti-RSV hIgG1 WT control | 2210.0 | 1450.0 | 141.0 |
| Anti-RSV hIgG1 Fc disabled control | NB | NB | NB |

NB = no binding

Example 9—Binding of IL-33 Binding Protein to Recombinant Human and Cynomolgus Monkey Neonatal Receptor (FcRn)

Binding of IL-33 binding protein 22A06-458 to human and cynomolgus recombinant neonatal receptor (FcRn) at pH 6.0 and pH 7.4 was assessed using a PROTEON XPR36 (BIORAD) surface plasmon resonance (SPR) instrument. A human IgG1 isotype control was included in the experiment as a control for the assay and a human IgG1 control containing the YTE mutation was included for comparison purposes.

A. Methods

Protein L (Thermo Scientific #21189) was immobilized on a CM5 chip (GE Healthcare #BR-1005-30) by primary amine coupling (GE Healthcare #BR100050). This surface was then used to capture the antibodies via the light chain and human and cynomolgus recombinant soluble FcRn were then passed over as the analyte at 512 nM, 128 nM, 32 nM, 8 nM, and 2 nM. An injection of buffer alone (i.e., 0 nM) was used to double reference the binding curves.

Regeneration of the protein L surface was carried out using 10 mM Glycine-HCl pH 1.5. The assay was run at 25° C. in HBS-EP pH 7.4 buffer (Teknova #H8022) and repeated in HBS-EP pH 6.0 buffer. Data was analyzed using the equilibrium model inherent to the PROTEON's analysis software.

B. Results

The human IgG1 wildtype control performed as expected (i.e., binding was observed at pH 6.0 and no binding was observed at pH 7.4).

22A06-458 has binding affinities to human and cynomolgus FcRn at pH 6.0 comparable to those of the human IgG1 YTE control (Table 9). 22A06-458 shows a 5-to-6-fold improvement in its binding affinities to human and cynomolgus monkey FcRn at pH 6.0 compared to the hIgG1 wildtype control. There is also some weak low-level binding visible at pH 7.4 which is not visible for the wildtype IgG1 molecule. The binding affinities of 22A06-458 for human and cynomolgus monkey FcRn are comparable to the YTE control and improved over those seen for the wildtype control.

TABLE 9

| Binding to recombinant human and cynomolgus monkey neonatal receptor (FcRn) | | | | |
|---|---|---|---|---|
| | $K_D$ (nM) | | | |
| | Human | | Cyno | |
| Antibody | pH 6.0 | pH 7.4 | pH 6.0 | pH 7.4 |
| 22A06-458 | 25.0 | 1230 | 24.7 | 2560 |
| Anti-RSV hIG1 wildtype control | 129 | No binding | 146 | No binding |
| Human IgG1 YTE control | 30.4 | 4330 | 39.3 | 2760 |

Example 10—Binding of IL-33 Binding Protein to Human Complement Component C1q Binding of IL-33 binding protein 22A06-458 to human recombinant soluble complement C1q was assessed using a PROTEON XPR36 (BIORAD) surface plasmon resonance (SPR) instrument. Human IgG1 wildtype and human IgG1 Fc disabled isotype antibodies were included in the analysis as an assay control.

A. Methods

The antibodies to be tested were immobilized on a GLC chip (BioRad #176-5011) by primary amine coupling (GE Healthcare #BR100050). C1q (Sigma #C1740-5 mg) was passed over the immobilized antibodies at 512 nM, 128 nM, 32 nM, 8 nM, 2 nM, and 0 nM (i.e., buffer alone). The blank interspot region of the chip was used to double reference binding curves. The analysis was carried out at 25° C. and the running buffer for was HBS-EP (pH 7.4) with 10 mM $CaCl_2$) (Teknova #H8022). Data were fitted to the equilibrium model, inherent to the PROTEON XPR36 (BIORAD) analysis software using a global R-max value.

B. Results

The anti-RSV wildtype and Fc disabled control antibodies behaved as expected (i.e., the wildtype antibody bound C1q and the Fc disabled control did not.

The binding affinities of 22A06-458 and the human IgG1 wildtype control antibody to human C1q were 213 nM and 680 nM, respectively (see Table 10). The affinity of 22A06-458 in this analysis is stronger than that of the wildtype control but is within the range of normal assay variation and is therefore comparable.

TABLE 10

| Binding of 22A06-458 to human complement component C1q | |
|---|---|
| Antibody | $K_D$ (nM) |
| 22A06-458 | 213 |
| Anti-RSV hIgG1 wildtype control | 680 |
| Anti-RSV hIgG1 Fc disabled control | No binding |

Example 11—Characterization of Human FcγRIIIa Engagement with the Complex of IL-33 Binding Protein and IL-33

Studies were carried out to assess the risk that cells treated with IL-33 binding protein 22A06-458 could become targets for antibody-dependent cellular cytotoxicity (ADCC) via engagement of FcγRIIIa.

A. Methods

To determine a positive control antibody for the target/effector cell engagement assay, anti-her1, anti-her2, anti-CD20, or anti-CD52 antibodies were mixed with $1.25\times10^4$ target HEK-BLUE IL-33 cells (InvivoGen #HKB-HIL-33)

for 45 minutes at 37° C./5% $CO_2$. After the addition of $7.5\times10^4$ Jurkat-NFAT-FcγRIIIa-Luc cells (Promega #G7102) to each test well, all four antibodies were at assay concentrations from $1.7\times10^{-4}$ to 66.7 nM. After a further 6 hours of incubation at 37° C./5% $CO_2$, assay plates were allowed to equilibrate to room temperature for 15 minutes before the addition of ONE-GLO luciferase reagent (Promega #E6120). Luminescence intensity was determined using a Perkin Elmer multilabel VICTOR plate reader.

To determine the engagement of target HEK-BLUE IL-33 and effector Jurkat-NFAT-FcγRIIIa-Luc cells with complexed IL-33/22A06-458, IL-33 (in-house) was initially incubated with 22A06-458 for 30 minutes at room temperature. Separately, IL-33 was pre-incubated with either anti-RSV or anti-CD52 assay control antibodies.

Antibody/IL-33 mixtures were incubated with $1.25\times10^6$ target HEK-BLUE IL-33 cells per well of a 96-well plate (Costar #3197) for 45 minutes at 37° C./5% $CO_2$. After the addition of $7.5\times10^6$ Jurkat-NFAT-FcγRIIIa-Luc cells, IL-33 was at 1 nM while test antibodies were present over a concentration range from $1.7\times10^{-4}$ to 66.7 nM. After a further six hours of incubation at 37° C./5% $CO_2$, assay plates were equilibrated to room temperature for 15 minutes before the addition of ONE-GLO luciferase reagent. Luminescence intensity was determined as above.

Each antibody was screened over an increasing concentration range. Each concentration of antibody was assayed in duplicate. Mean raw luminescence values were calculated and the standard deviations determined.

Raw data values were imported into Microsoft Excel and Target/Effector cell engagement at each antibody concentration was expressed as fold change using Equation 1:

$$\frac{\text{Mean luminescence value at test antibody concentration}}{\text{Mean luminescence value in absence of test antibody}} \qquad \text{Equation 1}$$

Data were plotted in Grafit (Erithacus Software).

B. Results

Four antibodies (anti-her1, anti-her2, anti-CD20, and anti-CD52) were screened in a target HEK-BLUE IL-33, Jurkat NFAT-FcγRIIIa-Luc effector cell engagement assay. There was an absence of enhanced luminescent signal with an anti-her1, anti-her2, or anti-CD20 antibody. However, when compared to the absence of antibody, an anti-CD52 antibody showed enhanced luminescence at concentrations in excess of 2.7 nM. There was a 2.4-fold increase in cell engagement at 66.7 nM. Based on this observation, the anti-CD52 antibody was selected as the assay positive control.

While an enhanced luminescence signal was seen when HEK-BLUE IL-33 and Jurkat-NFAT-FcγRIIIa-Luc cells were assayed with an anti-CD52 antibody (concentrations >2.7 nM) that had been pre-incubated with IL-33, there was no evidence of any change in luminescent signal when these two cell types were pre-incubated with anti-IL-33/anti-RSV, anti-IL-33/mAb1, or anti-IL-33/22A06-458 in two independent experiments.

Example 12—Inhibition of Multiple IL-33 Isoforms by IL-33 Binding Protein

Several isoforms of IL-33 have been reported that could arise in vivo from alternative mRNA splicing or by the action of different proteases present in the lung, dependent on the nature of the airway inflammation. For example, Lefrancais et al. (PNAS, 2012; 109:1673-8) reported that the activity of neutrophil proteases (Cathepsin G and neutrophil elastase) can lead to the generation of a number of mature biologically active forms of IL-33 (IL-$33_{95-270}$, IL-$33_{99-270}$, and IL-$33_{109-270}$). These forms were shown to be produced by activated human neutrophils ex vivo, to be biologically active in vivo, and to have a ~10-fold higher activity than full-length IL-33 in cellular assays. Another novel form of IL-33 was reported as a short splice variant that lacks exon 3 containing a proposed caspase-1 cleavage site (Hong et al., J Biol Chem 2011; 286: 20078-86) termed spIL-33. Mature IL-33 (IL-$33_{113-270}$), the spIL-33, and the cleaved forms of IL-33 were recombinantly expressed and the ability of 22A06-458 to inhibit their activity was assessed in a HEK-BLUE reporter assay. 22A06-458 was able to completely inhibit all isoforms of IL-33 but showed a decrease in activity against IL-33 isoforms compared to mature IL-$33_{113-270}$ (Table 11). spIL-33 showed the smallest variation compared with IL-$33_{113-270}$, with IL-$33_{99-270}$ showing the largest difference. It should be noted that this is not likely to reflect biological activity differences as only a single concentration of each IL-33 isoform was tested and the assay was not optimised to the activity for each individual cytokine.

TABLE 11

Inhibition by 22A06-458 of 25 pM of different isoforms of IL-33 in HEK-Blue reporter assay

| | IC50 (pM) (with 95% confidence intervals included) | | | | |
|---|---|---|---|---|---|
| | 95-270 IL-33 | 99-270 IL-33 | 109-270 IL-33 | spIL-33 | 113-270 IL-33 |
| 22A06-458 | 162.2 (147.8 to 178.3) | 436.2 (298.3 to 676.9) | 254 (230.2 to 280.7) | 90.26 (72.32 to 113.6) | 18.18 (12.79 to 25.25) |

Example 13—Inhibition of Eosinophil Superoxide Generation by IL-33 Binding Protein Studies were carried out to measure the transient generation of superoxide anions in response to IL-33 stimulation of isolated eosinophils.

A. Methods

Whole human blood was collected from high eosinophil donors. Typically, 60 mL was collected by venipuncture per donor into a sterile container with anti-coagulant, sodium heparin solution (10IU/mL).

Within 1 hour of collection, and using a microbiological safety cabinet, 20 mL of anti-coagulated blood samples were transferred into 50 mL falcon tubes and diluted by addition of 10 mL PBS (Thermo Fisher #14190144) and 10 mL 4% w/v dextran (Sigma Aldrich #31392-50G) solution. After gentle inversion to mix the blood, the tubes were allowed to stand on ice for up to 30 min allowing the red blood cells (RBC) to sediment.

The granulocytes were separated from the peripheral blood mononuclear cells (PBMCs) by layering the RBC depleted cell suspension (~30 mL) onto 15 mL FICOLL-PAQUE (Sigma Aldrich #GE17-1440-02) pre-loaded into 50 mL falcon tubes followed by centrifugation in a swing bucket rotor (300×g; 25 min; 18° C., no break).

The plasma and PBMCs were aspirated off leaving the RBC contaminated granulocyte pellets. Each separate cell pellet was re-suspended in 300 μL PBS and pooled into a fresh falcon tube.

Contaminating RBCs were lysed through hypotonic shock by the addition of 20 mL ice cold water (20-30 s) followed by neutralization with the addition of 20 mL 2× concentrated PBS.

The granulocytes were pelleted by centrifugation (300× g/5 min) and re-suspended in 1 mL PBS and counted on a hemocytometer.

Untouched eosinophils were purified using an eosinophil isolation kit (Miltenyi Biotec #130-092-101) as per manufacturer's instructions. Non-eosinophils were indirectly magnetically labeled using a cocktail of biotin-conjugated antibodies as well as anti-Biotin MicroBeads. Highly pure eosinophils were obtained by depletion of the magnetically labeled cells. Isolated eosinophils were diluted to a cell density of $1\times10^6$ per mL in superoxide assay buffer (1× phosphate buffered saline (with $Ca^{2+}/Mg^{2+}$)+0.1% BSA).

22A06-458 antibody was diluted to 8× final top assay concentration of 0.5 μg/mL (3.33 nM). Subsequent 1 in 3 serial dilutions were then carried out in superoxide assay buffer to generate an 8-point concentrations response curve. The diluted antibody was then mixed 1:1 (e.g., 30 μL+30 μL in a V bottom polypropylene 96 well plate) with a single concentration of recombinant human (rhu) IL-33 (also made up to 8× final assay concentration (FAC) of 0.3 ng/ml (15 pM)). These pre-complex mixtures (now at 4×FAC) were incubated for 30 min at 37° C. The final concentration range of the antibody tested was 0.00152 nM-3.3 nM.

For the control no antibody treatment (Positive control), IL-33 was mixed 1:1 with assay buffer and the Negative control consisted of assay buffer alone.

Sterile 384 well, white clear bottom plates (Corning #3707) were pre-coated with 1% BSA/PBS solution (25 μL/well; 1 hr incubation at 37° C.). After aspiration the wells were washed once with 25 μL PBS.

30 μL of eosinophil cell suspension (at $1\times10^6$ cells/mL) was added per well ($30\times10^3$ cells/well) followed by addition of 15 μL of pre-mixed luminol+enhancer solution (each kit component diluted 1:10 into PBS assay buffer) and allowed to pre-incubate with eosinophils for 15 min at 37° C.

Next, 15 μL of pre-complexed 22A06-458+IL-33 was then added to the eosinophils in triplicate per concentration.

Non-complexed IL-33 and buffer alone were included as positive and negative controls, respectively.

The assay plate was then immediately placed into the SPECTRAMAX plate reader set at 37° C. and luminescence read at 5 min intervals for a total time period of 60 min.

The peak/max response achieved during the transient superoxide response over the 60 min time period was calculated by the SPECTRAMAX instrument software (SoftMax Pro-6.4). All data was then calculated as % inhibition of the control response, i.e., relative to the mean of 8 high (positive control) and 8 low (negative control) wells on each plate as described in Equation 2 below:

$$\frac{(Pos\ Ctrl - \text{Test Sample})}{(Pos\ Ctrl - Neg\ Ctrl)} \times 100\% \qquad \text{Equation 2}$$

A non-linear regression four-parameter curve fit was applied using the Graph Prism software. Data was presented as the mean $IC_{50}$ value and $pIC_{50}$ with the standard error of the mean of the mean of n experiments.

B. Results

22A06-458 concentration dependently blocked the production of IL-33 stimulated superoxide in isolated human eosinophils. Inhibition by 22A06-458 was expressed as percentage inhibition of the positive control (15 pM IL-33) and the non-stimulated negative control response as shown in FIG. 1. Inhibition by 22A06-458 was tested in 6 separate donor experiments. The antibody was tested twice in one donor, giving a total of 7 tests. The results have been summarized in Table 12. An $IC_{50}$ value of 19.65±2.18 pM (n=7) was observed. The $pIC_{50}$ was calculated as 10.73±0.05 (n=7).

TABLE 12

Determination of Potency: Inhibition of IL-33 induced superoxide generation from eosinophils by pre-complexed 22A06-458.

| | Donor #33778 | Donor #91933 | Donor #30953 | Donor #91885 | Donor #91945 | Donor #90980 | | | |
|---|---|---|---|---|---|---|---|---|---|
| | N = 1 | N = 2 | N = 3 | N = 4 | N = 5 | N = 6 | N = 7 | Mean | SEM |
| pIC50 | 10.66 | 10.63 | 10.78 | 10.59 | 10.83 | 10.98 | 10.61 | 10.73 | 0.05 |
| $IC_{50}$ (pM) | 21.85 | 23.5 | 16.5 | 25.6 | 14.8 | 10.5 | 24.8 | 19.65 | 2.18 |

Example 14—Inhibition of IFN-γ Production from $CD4^+$ T Cells by IL-33 Binding Protein Studies were carried out to measure IL-33 and IL-12 co-stimulated IFN-γ secretion from isolated $CD4^+$ T cells.

A. Methods

Whole human blood was collected from normal healthy donors. Typically, 80 mL was collected by venipuncture per donor into a sterile container with anti-coagulant, sodium heparin solution (10IU/mL).

Within 1 hour of collection red blood cells were sedimented as described for the eosinophil preparation above. Following centrifugation, the layer of PBMCs at the Ficoll/plasma interface was gently removed from each tube using a sterile pastette and dispensed (~10-15 mL) into a fresh 50 mL falcon tube. The volume was made up to 50 mL with PBS and the tubes centrifuged for 10 mins at 300 g. After removal of the buffer by aspiration the cell pellets were pooled into a volume of 10 mL PBS. Cell number was determined using a hemocytometer cell counter.

$CD4^+$ T cells were isolated using a $CD4^+$ T Cell Isolation kit (Miltenyi Biotec #130-096-533) according to the manufacturer's instructions. Non-$CD4^+$ cells were labeled using a cocktail of biotin-conjugated antibodies. Non-target cells were then magnetically labeled with the $CD4^+$ T Cell MicroBead Cocktail. Isolation of highly pure T cells was achieved by depletion of the magnetically labeled non-$CD4^+$ T cells. Isolated $CD4^+$ T cells were suspended to $1.11\times10^6$/mL in RPMI1640 tissue culture media (Thermo Fisher #31870).

A 20× cytokine mix of IL-33+IL-12+IL-2 was prepared in RPMI1640 T-cell assay media based on the dilutions shown in Table 13. 22A06-458 antibody was diluted to 20× final top assay concentration of 1.5 μg/mL (10 nM).

TABLE 13

Dilutions for 20x cytokine mix of IL-33 + IL-12 + IL-2.

| Cytokine | Stock conc | Final assay concentrations required | Working stock conc (x20 final conc) | Dilution required |
|---|---|---|---|---|
| IL-33 | 2.1 mg/mL | 2.5 ng/mL IL-33 | 50 ng/mL IL33 | 1 in 42,000 |
| IL-2 | 1 mg/mL | 2.5 ng/mL IL-2 | 50 ng/mL IL-2 | 1 in 20,000 |
| IL-12 | 1 mg/mL | 12.5 ng/mL IL-12 | 250 ng/mL IL12 | 1 in 4000 |

Subsequent 1 in 4 serial dilutions were then carried out in culture media to generate a 6-point concentration response curve. The diluted antibody was then mixed 1:1 (e.g., 50 μL+50 μL in a V bottom polypropylene sterile 96 well plate) with the cytokine mix of IL-33/IL-12/IL-2 (made up to 20× final assay concentration of 2.5 ng/mL (125 pM), 12.5 ng/ml and 2.5 ng/ml, respectively). The 1:1 diluted mixtures (now at 10×FAC) were incubated for 30 min at 37° C. to allow the antibody to complex with the IL-33. The final concentration range of the antibody tested was between 0.0098 nM-10 nM.

For the control no antibody treatment (positive control), IL-33+cytokine mix (IL-12+IL-2) was combined 1:1 with assay media and the negative control consisted of assay media containing cytokine mix without IL-33.

Following co-incubation of 22A06-458 with the IL-33 cytokine mix, 20 μL was added to a 96 well tissue culture plate in triplicate wells per concentration. Non antibody complexed IL-33 cytokine mix and media containing IL-12+IL-2 alone were included as positive and negative controls respectively. Next, 180 μL of CD4$^+$ T cell suspension was added to the test wells (2×10$^5$ cells/well) and the plate incubated (5% 02/95% air) for a period of 18 h at 37° C.

After 18 h of incubation, the T-cells were centrifuged (300xg/5 min) and 150 μL of the cell free supernatants transferred to a new 96 well plate. MSD plates pre-coated with anti-IFN-γ capture antibody were first pre-blocked with 1% w/v of Blocker B. Standards and samples were then added to the MSD plates and incubated for 1.5 h at RT while shaking. IFN-γ specific detection antibody labeled with the MSD SULFO-TAG reagent was then added to all the samples and incubated for a further 1.5 h at RT while shaking. After washing plates with PBS+0.05% Tween-20 three times and addition of 2× Read Buffer to all the samples, the plates were read on the Sector Imager plate reader.

Levels of IFN-γ (pg/mL) were back calculated from the standard curve using the MSD analysis software (Discovery Workbench 4). All data was then calculated as % inhibition of the control response, i.e., relative to the mean of 6 high (positive control) and 6 low (negative control) wells on each plate as described in Equation 2. A non-linear regression four-parameter curve fit was applied using the Graph Prism software. Data was presented as the mean $IC_{50}$ value and pIC50 with the standard error of the mean.

B. Results

Figure 2:
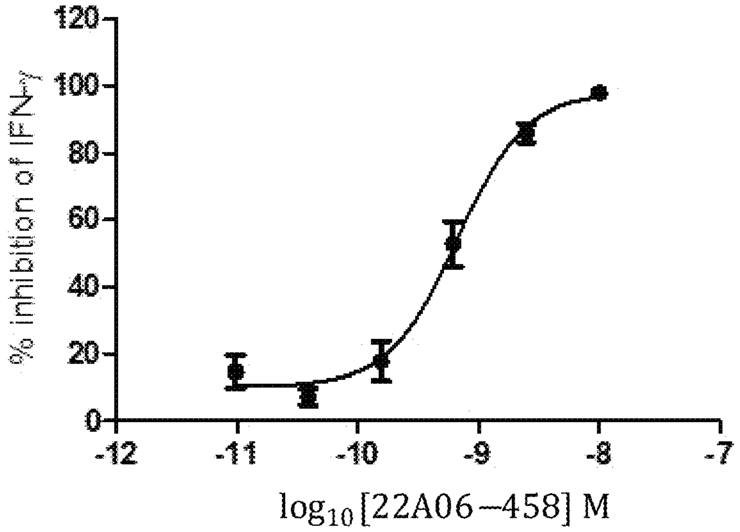
FIG. 2 illustrates $CD4^+$ T cell IFN-γ secretion after co-stimulation with IL-2+IL-12+IL-33 pre-complexed with an IL-33 binding protein.

22A06-458 concentration dependently blocked IL-33+IL-12 stimulated IFN-γ secretion from isolated human CD4$^+$ T cells. Inhibition by 22A06-458 was expressed as percentage inhibition of the positive control (125 pM IL-33) and the non-stimulated negative control response as shown in FIG. 2. Inhibition by 22A06-458 was tested in 6 separate donor experiments. The antibody was tested twice in one donor, giving a total of 7 tests. The results have been summarized in Table 14. An $IC_{50}$ value of 675.14±101.39 pM (n=7) was observed and a $pIC_{50}$ was calculated as 9.2±0.07 (n=7).

TABLE 14

Determination of Potency: Inhibition of IL-33 induced IFN-γ secretion from CD4$^+$ T cells by pre-complexed 22A06-458.

| | Donor # 91738 | Donor # 91806 | Donor # 91936 | Donor # 90290 | Donor # 33778 | Donor # 90980 | | | |
|---|---|---|---|---|---|---|---|---|---|
| | N = 1 | N = 2 | N = 3 | N = 4 | N = 5 | N = 6 | N = 7 | Mean | SEM |
| pIC50 | 8.97 | 9.02 | 9.54 | 9.22 | 9.1 | 9.3 | 9.24 | 9.2 | 0.073 |
| IC50 (pM) | 1056 | 936 | 282 | 591 | 790 | 497 | 574 | 675.14 | 101.39 |

Example 15—Inhibition of Inflammatory Cytokine Production from HUVEC Cells by IL-33 Binding Protein Studies were carried out to measure release of IL-8 and IL-6 in response to direct IL-33 stimulation of human umbilical vein endothelial cells (HUVECs).

A. Methods

HUVECs (pooled donor; Promocell #C12203) were cultured in a T75 cm$^2$ collagen coated tissue culture flask (Greiner bio-one #658950) until approximately 80-90% confluent. After removal of medium and a wash of the cells with PBS (12 mL), the adherent cells were detached by the addition of 2 mL Tryple Express cell detachment solution (5 min; 37° C.) (Thermo Fisher #12604-13). 10 mL fresh endothelial culture media was added to the flask to collect the detached cells then transferred to a 50 mL flacon tube and centrifuged (300xg; 5 min). Pelleted cells were resuspended in 1 mL fresh endothelial media and counted using a haemocytometer.

HUVEC cells (passage 7/8/9) were seeded into 96 well tissue culture plates (collagen coated; Corning Biocoat collagen I #354649) at 1×10$^4$ cells per well (100 L) in endothelial growth media. Plates were incubated for 24 h at 37° C. to allow the cells to settle and adhere.

22A06-458 antibody was diluted to 6× final top assay concentration of 1.5 μg/mL (10 nM). Subsequent 1 in 4 serial dilutions were then carried out in culture media to generate a 6-point concentration response curve. The diluted antibody was then mixed 1:1 (e.g., 100 μL+100 μL in a V bottom polypropylene sterile 96 well plate) with IL-33 (made up to 6× final assay concentration of 10 ng/mL (500 pM). The 1:1 diluted mixtures (now at 3×FAC) were incubated for 30 min at 37° C. to allow the antibody to complex with the IL-33. The final concentration range of the antibody tested was between 0.0098 nM-10 nM.

For the control no antibody treatment (Positive control), IL-33 was combined 1:1 with endothelial culture media and the Negative control consisted of endothelial media alone.

24 h after HUVEC seeding into 96 well plates, the media was aspirated off and the cells washed once with 100 μL fresh media by aspiration and 100 μL was added back to each well. Following co-incubation of 22A06-458 with the IL-33, 50 μL was added to the 96 well HUVEC culture plate in triplicate wells per concentration. Non antibody complexed IL-33 and media alone were included as positive and negative controls, respectively. The plate was then placed into 37° C. incubator (5% $O_2$/95% air) for a period of 18 h. After 18 h of incubation, cell free supernatants were transferred to a new 96 well plate.

Concentrations of IL-8 in the cell supernatants were determined using a human IL-8 ELISA kit (R&D Systems DY208-05) according to the manufacture's protocol. Briefly, samples and standards were added to each well of a microplate, which was pre-coated with anti-human IL-8 monoclonal antibody and incubated for 2 hours. Each well was washed and incubated with the enzyme-linked polyclonal antibody specific for human IL-8 for 2 h. The wells were washed to remove unbound antibody-enzyme reagent and substrate solution was added to each well. After incubation for 20 min at RT, the enzyme reaction was stopped. IL-8 concentrations were determined by comparison of the optical density values with the standard curve.

For determination of IL-6, standards and samples were added to MSD plates already pre-coated with anti-IL-6 capture antibody from a kit (Mesoscale Discovery #K151AKB-4). The MSD plates were incubated for 1.5 h at RT while shaking. IL-6 specific detection antibody labeled with the MSD SULFO-TAG reagent was then added to all the samples and incubated for a further 1.5 h at RT while shaking. Plates were then washed with PBS+0.05% Tween-20 three times and 2× Read Buffer added to all the samples. The plates were read on the Sector Imager plate reader.

Levels of IL-8 and IL-6 (pg/mL) were back calculated from the standard curve using the SPECTRAMAX analysis software (SoftMax Pro-6.4) and the MSD analysis software (Discovery Workbench 4), respectively. All data was then calculated as % inhibition of the control response, i.e., relative to the mean of 6 high (positive control) and 6 low (negative control) wells on each plate as described in Equation 2.

A non-linear regression four-parameter curve fit was applied using the Graph Prism software. Data was presented as the mean $IC_{50}$ value and $pIC_{50}$ with the standard error of the mean of the mean of n experiments.

B. Results

Figure 3A:
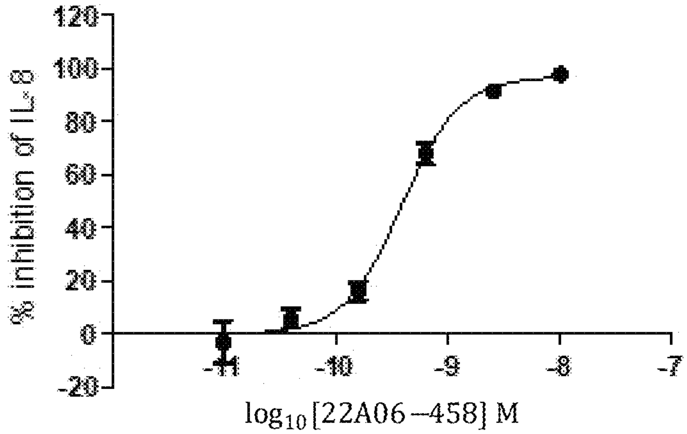
FIG. 3A illustrates inhibition of HUVEC IL-8 secretion by an IL-33 binding protein pre-complexed with IL-33.
Figure 3B:
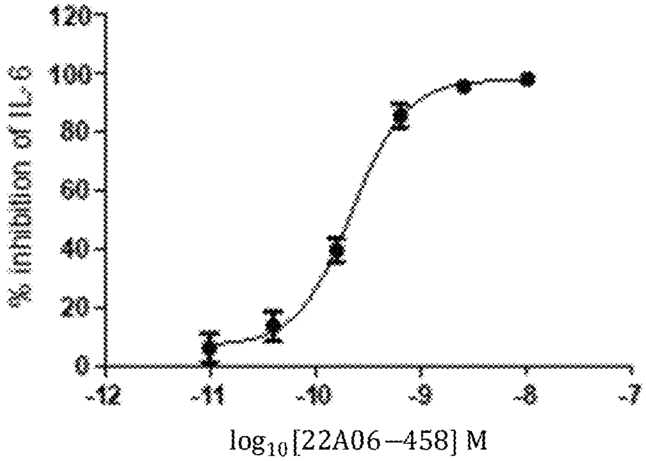
FIG. 3B illustrates inhibition of HUVEC IL-6 secretion by an IL-33 binding protein pre-complexed with IL-33.

22A06-458 concentration dependently blocked IL-33 stimulated IL-8 (FIG. 3A) and IL-6 (FIG. 3B) secretion from HUVECs. Inhibition by 22A06-458 was calculated as percentage inhibition of the positive control (500 pM IL-33) and the non-stimulated negative control response. Inhibition by 22A06-458 was tested in 3 separate HUVEC passage experiments. The results have been summarized in Table 15. $IC_{50}$ values of 389.90±61.22 pM and 217.30±8.61 pM were observed for IL-8 and IL-6 secretion, respectively. The respective $pIC_{50}$ values of 9.42±0.07 and 9.66±0.02 for IL-8 and IL-6 secretion were calculated.

TABLE 15

Determination of Potency: Inhibition of IL-33 induced IL-8 and IL-6 secretion from HUVECs by pre-complexed 22A06-458.

| | HUVEC; P7 | HUVEC; P8 | HUVEC; P9 | Mean | SEM |
|---|---|---|---|---|---|
| Inhibition of IL-8 | | | | | |
| pIC50 | 9.31 | 9.56 | 9.40 | 9.42 | 0.07 |
| IC50 (pM) | 489.00 | 278.30 | 402.50 | 389.90 | 61.22 |
| Inhibition of IL-6 | | | | | |
| pIC50 | 9.67 | 9.69 | 9.63 | 9.66 | 0.02 |
| IC50 (pM) | 213.90 | 204.40 | 233.60 | 217.30 | 8.61 |

Example 16—Inhibition of Basophil Degranulation by IL-33 Binding Protein

Studies were carried out to measure release of the degranulation product, β-hexosaminidase, following co-stimulation with IL-33 and anti-IgE.

A. Methods

Whole human blood was collected from allergic donors. Typically, 60 mL was collected by venipuncture per donor into a sterile container with anti-coagulant, sodium heparin solution (10IU/mL).

Within 1 hour of collection, and using a microbiological safety cabinet, basophils were isolated according to the basophil isolation kit (Stem Cell #19069) instructions. 10 mL of anti-coagulated blood samples were transferred into 15 ml conical tubes and 2 mL HETASEP (Stem Cell #07906) added and mixed with the blood by inversion. The tubes were centrifuged at 110 g (6 min) at room temperature (RT) with the brake off. The samples were then removed and allowed to sit undisturbed for 5-10 minutes until the red blood cell:plasma interface was approximately 40% of the total volume. The plasma fraction containing the nucleated cells was harvested into a 50 mL falcon tubes and 4 parts of cold basophil buffer added to 1 part harvested plasma. Following centrifugation (400 g/10 minutes/RT), the supernatant was discarded, and the cell pellet washed to remove excess platelets by further centrifugation at 120 g (10 min/RT). After aspiration of the supernatants the cells were counted and resuspended at $5\times10^7$/mL in basophil buffer.

Cells at $5\times10^7$ cells/mL were transferred to 5 mL polystyrene round bottom tubes to which 50 μL of enrichment antibody cocktail (kit reagent) was added and allowed to incubate with the cells for 10 min at RT. 100 μL of pre-mixed magnetic particles (kit reagent) were then added and mixed with the cells by pipetting and allowed to incubate for 10 min at RT. The volume in the tube was topped up to 2.5 mL with basophil buffer and then placed inside the EasySep magnet (Stem Cell #18000) for 5 min/RT. The magnet was picked up and in one continuous motion the enriched cell suspension was poured into a new 5 mL tube. The tube inside the magnet was discarded and the tube containing the enriched cell suspension placed into the magnet for a further 5 min. This step was repeated once more and the final contents containing the untouched basophils poured into a 15 ml conical tube.

The enriched basophils were centrifuged (300 g/5 min/RT) and the cell pellet resuspended in RPMI1640 basophil medium (Thermo Fisher #31870) at a cell density of $1\times10^6$/mL.

20 μL of cell suspension ($2\times10^4$ cells/well) was added per well of a 384 well sterile cell culture plate and the cells allowed to rest for 60 min in a 37° C. incubator.

22A06-458 antibody was diluted to 8× final top assay concentration of 10 μg/mL (66 nM). Subsequent 1 in 10 serial dilutions were then carried out in basophil medium to generate a 5-point concentration response curve. The diluted antibody was then mixed 1:1 (e.g., 50 μL+50 μL in a V-bottom polypropylene 96 well plate) with a single concentration of rhu IL-33 (in-house, also made up to 8×FAC) 100 ng/ml (5.0 nM)). These pre-complex mixtures (now at 4×FAC) were incubated for 40 min at RT. The final concentration range of 22A06-458 tested was 6.6 pM-66 nM.

The anti-IgE cross linking antibody was diluted into basophil medium to 4×FAC of 1 μg/mL.

For the control no 22A06-458 treatment, IL-33 was diluted to 4×FAC (100 ng/ml) in basophil media and the negative non-treated control consisted of basophil medium alone.

To duplicate/triplicate wells of basophils in a 384 well plate (Corning #3701), 20 μL of basophil medium only was added to represent the non-treated control. To the IL-33 only stimulated control, 10 μL basophil medium (RPMI1640 (Thermo Fisher #31870) without phenol red+10% FBS+2 mM L-glutamine (Thermo Fisher #25030)) plus 10 μL of IL-33 was added. The anti-IgE negative control had 10 μL basophil medium plus 10 μL anti-IgE stimulus added per well. The positive control consisted of addition of 10 μL IL-33 plus 10 μL anti-IgE. For the test treatments, 10 μL of the pre-complexed IL-33+22A06-458 was added per well followed by addition of 10 μL anti-IgE. Final assay volume per well consisted of 40 μL. The treated plate was incubated for a period of 40 min in a 37° C. incubator.

After the incubation period the cell plate was centrifuged at 300 g/3 min and the cell free supernatants transferred to a new 384 well plate (~30 μL).

10 μL of the cell free supernatant was then transferred into a black opaque 384 well plate (Greiner #781076) into which 10 μL of the β-hexosaminidase substrate (diluted 1 in 100 to 500 μM in citrate buffer (0.2M, pH=4.5) was added. After 60 min incubation at 37° C., 36 μL of Trizma buffer (Sigma Aldrich #T2819) was added to stop the reaction. β-hexosaminidase released from the basophils was quantitated by measuring the fluorescence intensity at Ex:356 nm, Em:450 nm on the SPECTRAMAX iQ plate reader (SoftMax Pro-6.4).

The fluorescence signal data generated by the β-hexosaminidase interacting with its substrate was first normalized by subtracting the background fluorescence signal from substrate+media only treated wells. The % inhibition of the control response was then calculated, i.e., relative to the mean of IL-33+cross linked IgE (positive control) and cross linked IgE alone (negative control) wells as described in Equation 2.

A non-linear regression four-parameter curve fit was applied using the Graph Prism software. Data was presented as the mean $IC_{50}$ value and $pIC_{50}$ with the standard error of the mean of the mean of n experiments.

B. Results

Figure 4:
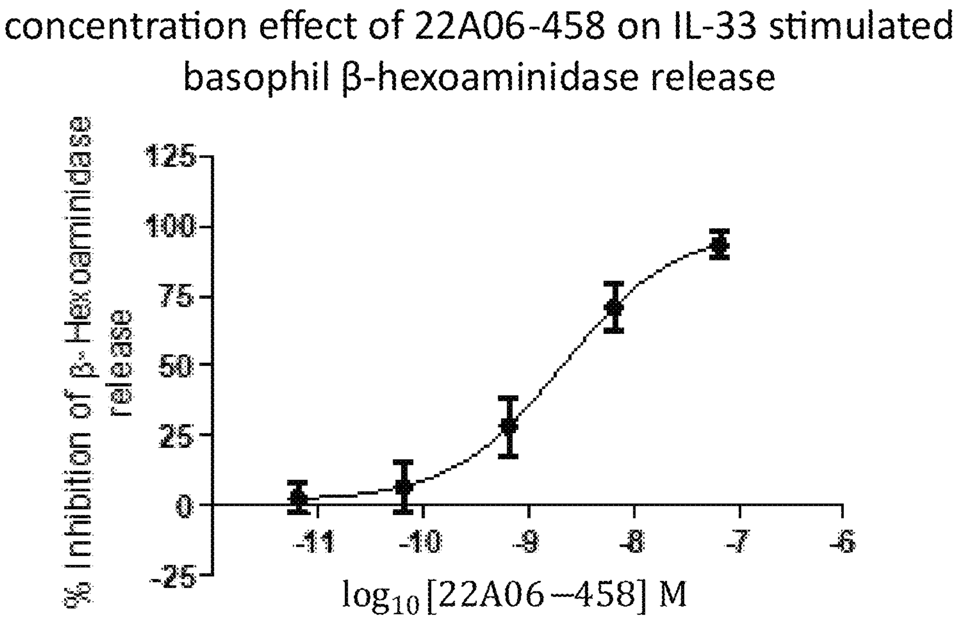
FIG. 4 illustrates inhibition of basophil β-hexosaminidase release after stimulation with IL-33 pre-complexed with an IL-33 binding protein and cross linked IgE (anti-IgE).
Figure 5A:
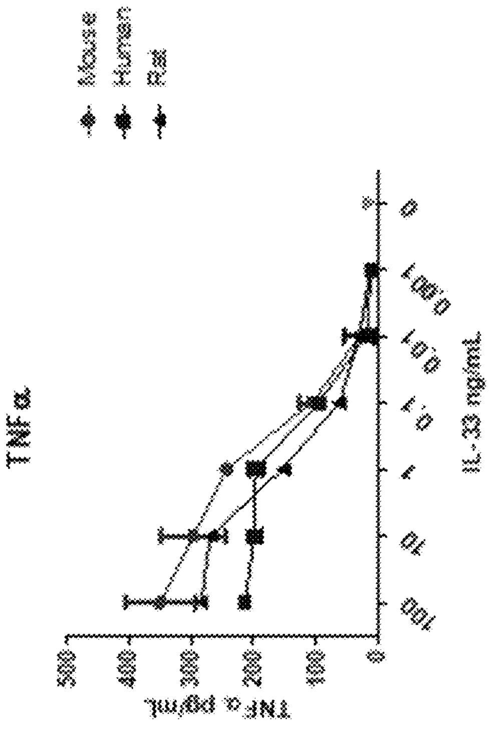
FIG. 5A illustrates mouse, rat, and human IL-33 induced cytokine production from mouse mast cells for TNF-α.
Figure 5B:
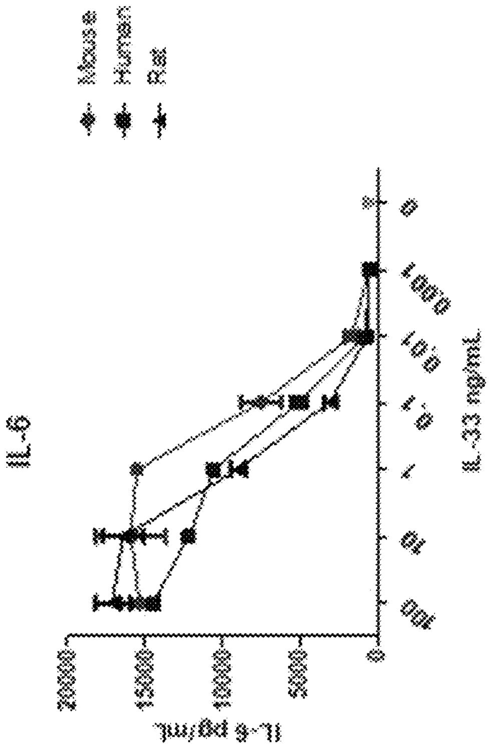
FIG. 5B illustrates mouse, rat, and human IL-33 induced cytokine production from mouse mast cells for IL-6.
Figure 5C:
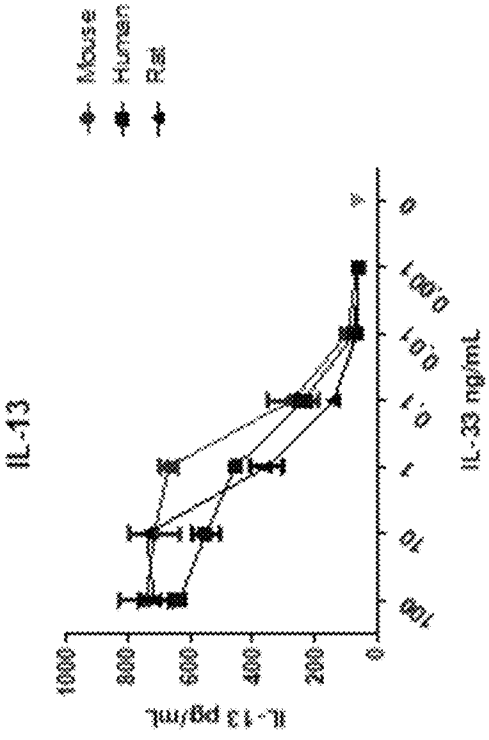
FIG. 5C illustrates mouse, rat, and human IL-33 induced cytokine production from mouse mast cells for IL-13.
Figure 5D:
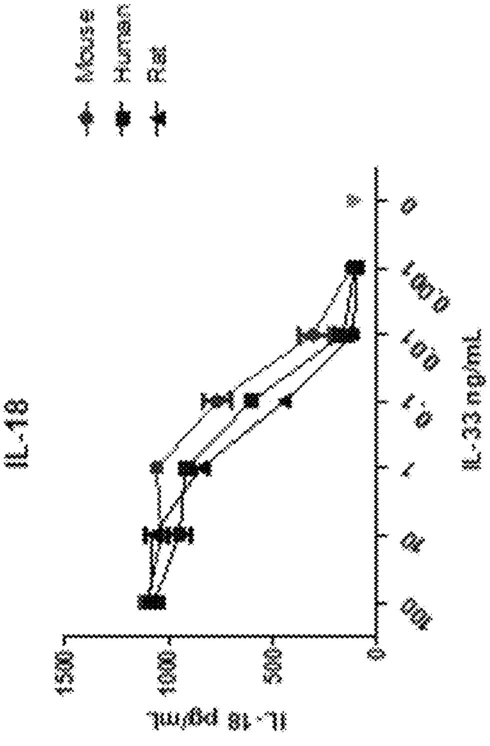
FIG. 5D illustrates mouse, rat, and human IL-33 induced cytokine production from mouse mast cells for IL-18.
Figure 6A:
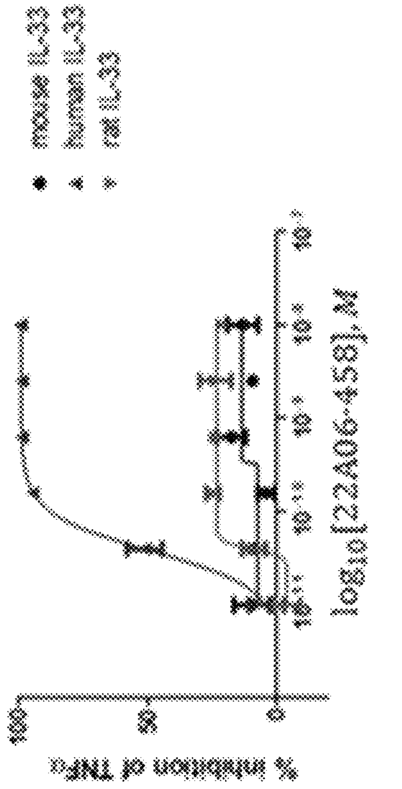
FIG. 6A illustrates inhibition of 1 ng/mL IL-33 induced cytokine production by an IL-33 binding protein for TNF-α.
Figure 6B:
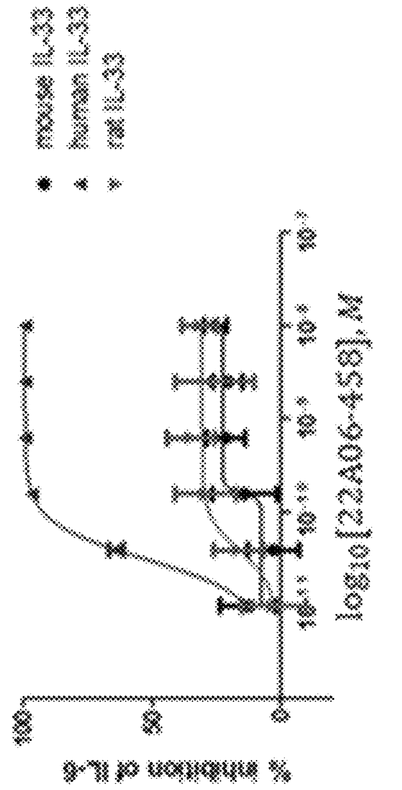
FIG. 6B illustrates inhibition of 1 ng/mL IL-33 induced cytokine production by an IL-33 binding protein for IL-6.
Figure 6C:
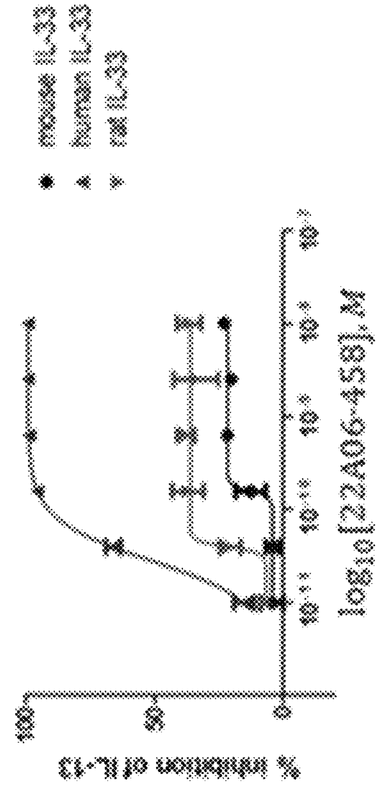
FIG. 6C illustrates inhibition of 1 ng/mL IL-33 induced cytokine production by an IL-33 binding protein for IL-13.
Figure 6D:
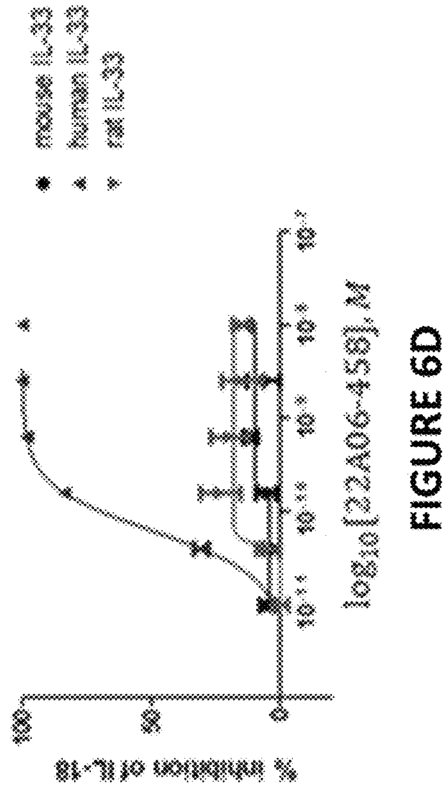
FIG. 6D illustrates inhibition of 1 ng/mL IL-33 induced cytokine production by an IL-33 binding protein for IL-18.
Figure 7A:
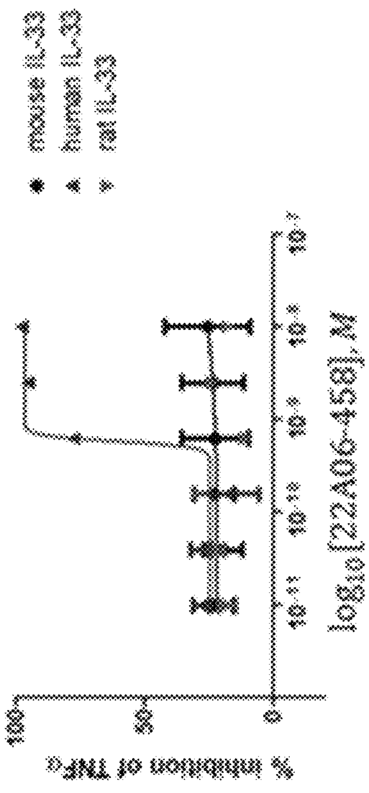
FIG. 7A illustrates inhibition of 10 ng/mL IL-33 induced cytokine production by an IL-33 binding protein for TNF-α.
Figure 7B:
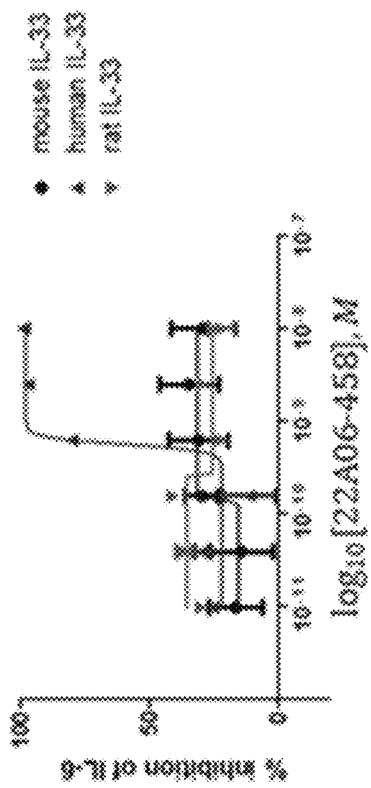
FIG. 7B illustrates inhibition of 10 ng/mL IL-33 induced cytokine production by an IL-33 binding protein for IL-6.
Figure 7C:
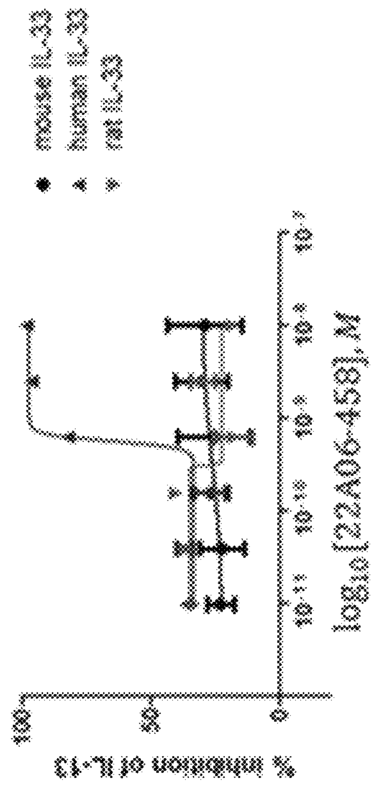
FIG. 7C illustrates inhibition of 10 ng/mL IL-33 induced cytokine production by an IL-33 binding protein for IL-13.
Figure 7D:
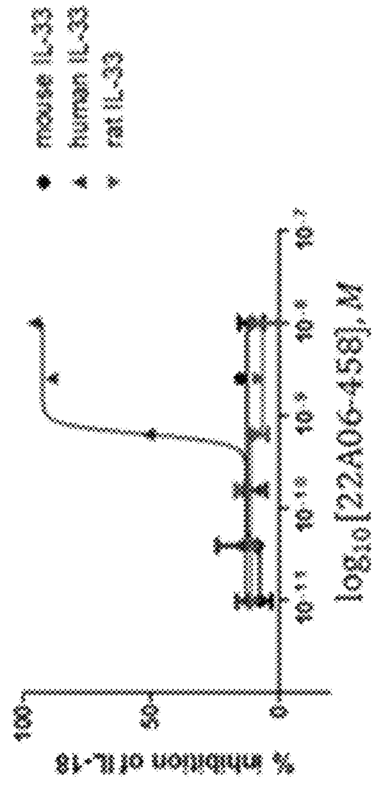
FIG. 7D illustrates inhibition of 10 ng/mL IL-33 induced cytokine production by an IL-33 binding protein for IL-18.
Figure 8A:
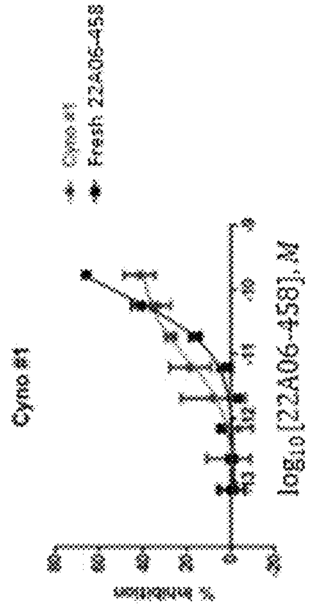
FIG. 8A illustrates inhibition of cyno IL-33 stimulated HEK-BLUE cell activation by cyno PK serum and an IL-33 binding protein for cynomolgus 1.
Figure 8B:
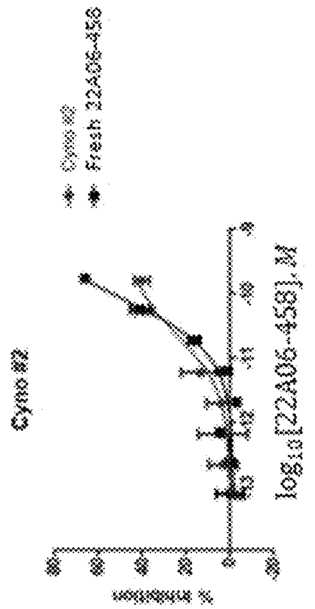
FIG. 8B illustrates inhibition of cyno IL-33 stimulated HEK-BLUE cell activation by cyno PK serum and an IL-33 binding protein for cynomolgus 2.
Figure 8C:
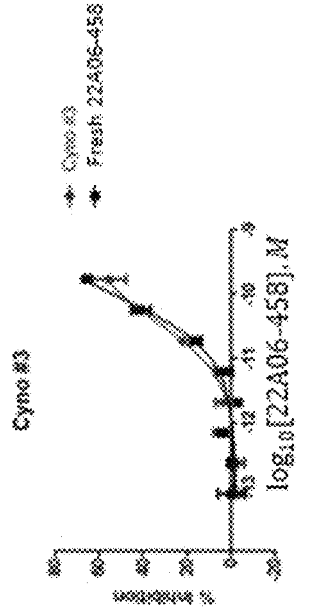
FIG. 8C illustrates inhibition of cyno IL-33 stimulated HEK-BLUE cell activation by cyno PK serum and an IL-33 binding protein for cynomolgus 3.
Figure 8D:
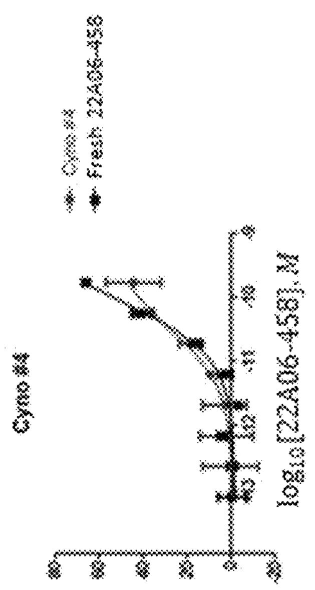
FIG. 8D illustrates inhibition of cyno IL-33 stimulated HEK-BLUE cell activation by cyno PK serum and an IL-33 binding protein for cynomolgus 4.
Figure 8E:
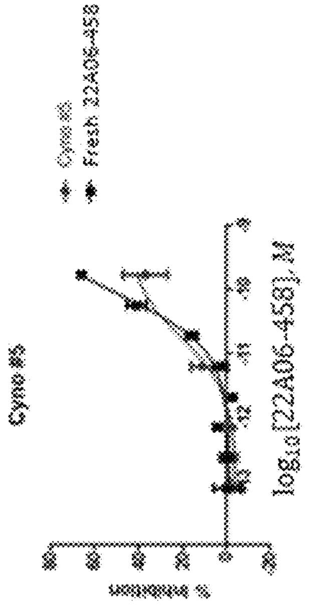
FIG. 8E illustrates inhibition of cyno IL-33 stimulated HEK-BLUE cell activation by cyno PK serum and an IL-33 binding protein for cynomolgus 5.
Figure 8F:
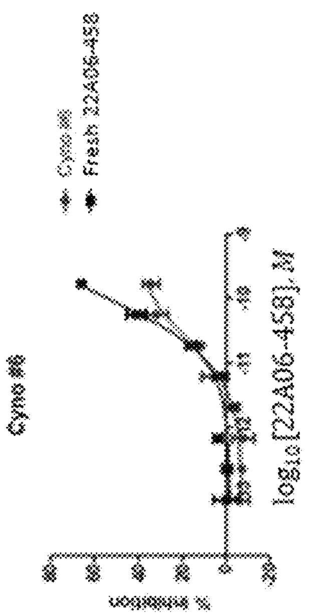
FIG. 8F illustrates inhibition of cyno IL-33 stimulated HEK-BLUE cell activation by cyno PK serum and an IL-33 binding protein for cynomolgus 6.
Figures 9A, 9B, 9C, 9D, 9E:
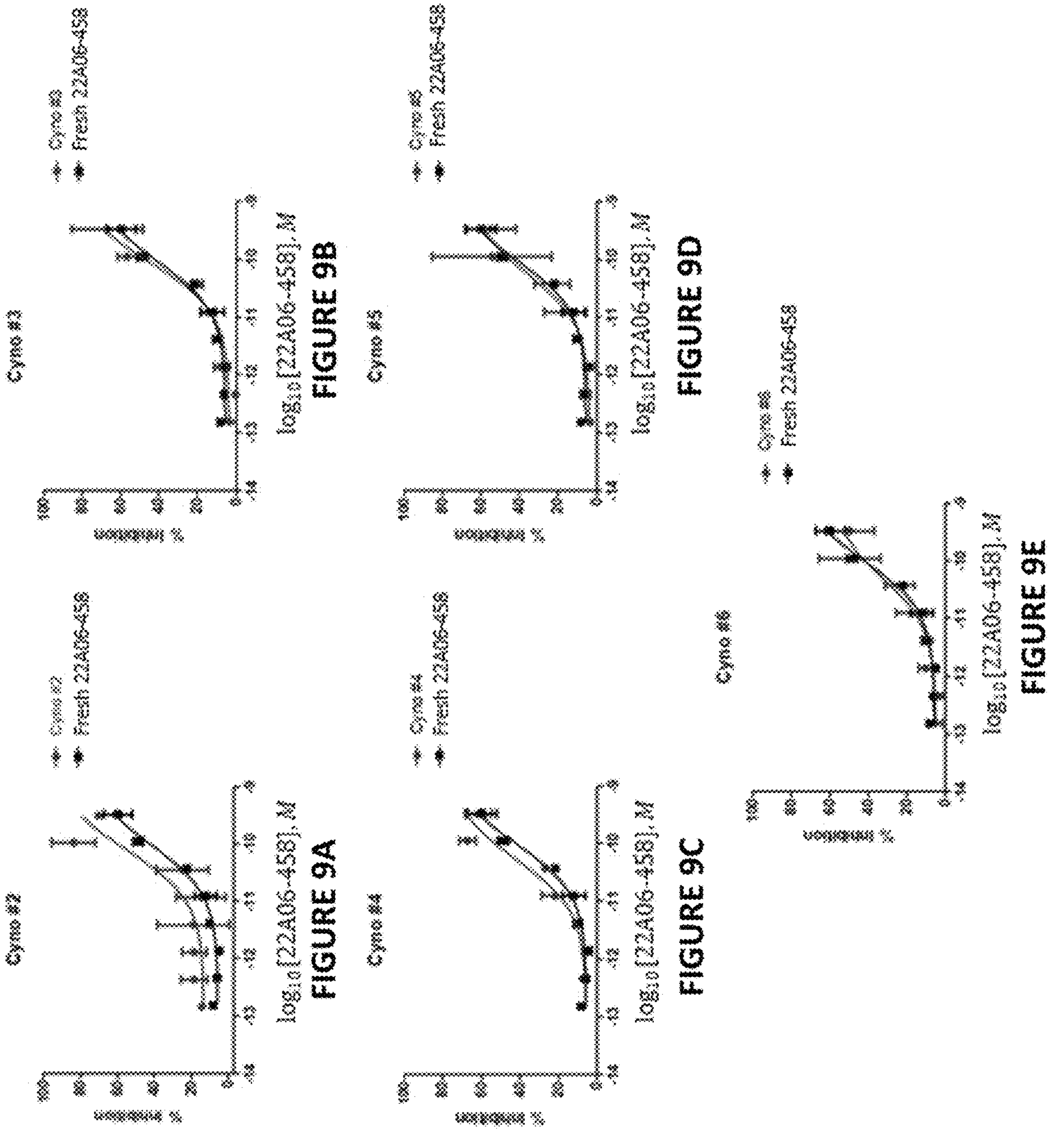
FIG. 9A illustrates inhibition of rhu-IL-33 stimulated HEK-BLUE cell activation by cyno PK serum and an IL-33 binding protein for cynomolgus 2.
FIG. 9B illustrates inhibition of rhu-IL-33 stimulated HEK-BLUE cell activation by cyno PK serum and an IL-33 binding protein for cynomolgus 3.
FIG. 9C illustrates inhibition of rhu-IL-33 stimulated HEK-BLUE cell activation by cyno PK serum and an IL-33 binding protein for cynomolgus 4.
FIG. 9D illustrates inhibition of rhu-IL-33 stimulated HEK-BLUE cell activation by cyno PK serum and an IL-33 binding protein for cynomolgus 5.
FIG. 9E illustrates inhibition of rhu-IL-33 stimulated HEK-BLUE cell activation by cyno PK serum and an IL-33 binding protein for cynomolgus 6.

IL-33 alone failed to induce direct basophil degranulation by way of β-hexosaminidase release. Co-stimulation of basophils with IL-33 and cross linking of cell bound IgE with an anti-IgE antibody caused a synergistic increase in β-hexosaminidase release. 22A06-458 concentration dependently blocked the synergistic effect of IL-33 on cross linked IgE stimulated β-hexosaminidase release. Inhibition by 22A06-458 (FIG. 4) was expressed as percentage inhibition of the IL-33 (5.0 nM)+cross linked IgE response relative to the negative control response (anti-IgE alone). The inhibitory effect of 22A06-458 was tested in 4 separate donor experiments. The results have been summarized in Table 16. An $IC_{50}$ value of 2.03±0.63 nM (n=4) was observed. The $pIC_{50}$ was calculated as 8.78±0.11 (n=4).

TABLE 16

Determination of Potency: Inhibition of IL-33 induced β-hexosaminidase release from basophils by pre-complexed 22A06-458

| | Donor #90356 N = 1 | Donor #90541 N = 2 | Donor #90290 N = 3 | Donor #33235 N = 4 | Mean | SD | SEM |
|---|---|---|---|---|---|---|---|
| pIC50 | 8.91 | 9.01 | 8.34 | 8.86 | 8.78 | 0.30 | 0.11 |
| IC50 (nM) | 1.23 | 0.97 | 4.53 | 1.39 | 2.03 | 1.68 | 0.63 |

Example 17—Inhibition of IL-33/IL-12 Stimulated Blood IFN-γ Release by an IL-33 Binding Protein Inhibition of IL-33/IL-12 induced IFN-γ release from human whole blood with an IL-33 binding protein is described below.

A. Methods

Whole human blood was collected from normal healthy donors. Typically, 20 mL was collected by venipuncture per donor into a sterile container with anti-coagulant, sodium heparin solution (10IU/mL, Leo Laboratories).

A 20× cytokine mix of IL-33 (in-house)+IL-12 (Thermo Fisher #PHC1123) was prepared in PBS assay buffer (Thermo Fisher #14190144) based on the following dilutions:

A volume of rhu IL-12 was made up to 20× Final Assay Concentration (FAC) of 12.5 ng/mL. Stock IL-12 (1 mg/mL) was diluted 1 in 40 followed by a 1 in 100 dilution into PBS (IL-12 at 20×12.5 ng/mL=250 ng/ml). Subsequent dilutions of IL-33 were made into this PBS/IL-12 buffer.

rhu IL-33 was diluted to 3 separate 20×FACs of 100 ng/ml, 30 ng/ml, and 10 ng/mL. First, the highest rhu IL-33 concentration (i.e., 20×100 ng/mL=2000 ng/ml) was prepared by diluting the stock IL-33 (2.1 mg/mL) 1 in 100 into PBS/IL-12 then 1 in 10.5 into PBS/IL-12. To make up the second concentration of IL-33 (i.e., 20×30 ng/ml=600 ng/ml), the 2000 ng/ml stock was diluted 1 in 3.3 into PBS/IL-12. To make the third concentration of IL-33 (i.e., 20×10 ng/mL=200 ng/mL), the 2000 ng/ml preparation stock was diluted 1 in 10 into PBS/IL-12.

22A06-458 anti-IL-33 mAb was produced at a stock concentration of 9.95 mg/mL in 20 mM Histidine, 180 mM Trehalose, 40 mM Arginine, 8 mM Methionine, 0.05 mM EDTA, pH 6. 20 μL aliquots were stored at −80° C. and were thawed and diluted to the appropriate concentration on day of use.

22A06-458 mAb was diluted to 20× final top assay concentration of 10 μg/mL (67 nM) by diluting the stock 1 in 49.5 to 200 μg/mL. Subsequent 1 in 4 serial dilutions were then carried out in PBS in a sterile polypropylene 96 well U-bottom plate to generate a 7-point (0.164 nM-67 nM) and 6-point (0.654 nM-67 nM) concentration response curve for pre-complexed and non-complexed 22A06-458, respectively.

To pre-complex the mAb with IL-33, the diluted antibody was then mixed 1:1 (e.g., 50 μL+50 μL) with each of the prepared concentrations of IL-33/IL-12. The 1:1 diluted mixtures (now at 10×FAC) were incubated for 30 min at room temperature (RT) to allow the antibody to complex with the IL-33.

For the non-complexing of 22A06-458 with IL-33, the diluted mAb was not mixed with the IL-33 and was left at the 20×FAC.

For the no antibody treatment control (positive control), each test IL-33/IL-12 concentration was either diluted 1:1 with PBS buffer to maintain the same concentration as with the pre-complexed preparation or left at the 20×FAC.

The negative control for the assay was represented by PBS/IL-12 (without IL-33). Other assay controls included, consisted of PBS alone and PBS/IL-33 (without IL-12). These controls demonstrate that stimulation of blood with either IL-12 or IL-33 alone induce little or no IFN-γ release.

Following complex formation of 22A06-458 with each of the test concentrations of IL-33/IL-12, 20 μL was added in duplicate wells per sample concentration to a 96 well tissue culture plate containing 180 μL of pre-dispensed blood and mixed by repeated pipetting. Next, 20 μL of the positive controls (IL-33 at 100, 30, and 10 ng/ml) and negative controls (PBS alone, PBS/IL-12 (without IL-33), and PBS/IL-33 (without IL-12)) were also added to the assay plate and mixed. The assay plates were incubated (5% 02/95% air) for a period of 20 h at 37° C.

For the non-complexed 22A06-458, 10 μL (at 20×FAC) was added in duplicate per concentration to 180 μL blood in a 96 well plate and mixed by repeated pipetting. Next, 10 μL of IL-33/IL-12 (at 20×FAC) was added to the blood and mixed. Positive and negative controls were included as above. The assay plates were incubated (5% 02/95% air) for a period of 20 h at 37° C.

After the 20 h incubation period, the blood assay plates were centrifuged (2000 rpm for 10 minutes at RT) and 35 μL of the blood plasma was withdrawn from each well using the 96 well Biomek NXp robot and transferred to a new 96 well polypropylene plate.

Single plex IFN-γ assay kits (Mesoscale Discovery, #K151AEB-4) were used to assay for IFN-γ release in the blood plasma. Standards and plasma samples were added to the MSD plates and incubated for 1.5 h at RT while shaking. IFN-γ specific detection antibody labeled with the MSD SULFO-TAG reagent was then added to all the sample wells and incubated for a further 1.5 h at RT while shaking. After washing plates with PBS+0.05% Tween-20 three times and addition of 2× Read Buffer T, the plates were read on the Sector Imager plate reader.

Levels of IFN-γ (pg/mL) were back calculated from the standard curve using the MSD analysis software (Discovery Workbench 4) and plotted against the log 10 [M] concentration of 22A06-458. A non-linear regression three-parameter curve fit was applied using the Graph Prism software v5.0.4. Data was presented as the mean $IC_{50}$ value and $pIC_{50}$ with the standard error of the mean (SEM) of number (n) of separate experiments.

B. Results

1. Pre-Complexed

22A06-458 pre-complexed with IL-33 concentration dependently blocked IL-33/IL-12 stimulated IFN-γ release in whole blood. Inhibition by 22A06-458 was tested against IL-33 concentrations of 100 ng/ml, 30 ng/mL, and 10 ng/mL. Respective IC50 values of 3.90±0.76 nM (n=8), 3.24±0.63 nM (n=6), and 1.95±0.58 nM (n=5) were observed for IL-33 concentrations of 100 ng/ml (Table 17), 30 ng/ml (Table 18), and 10 ng/ml (Table 19). Respective pIC50 values of 8.48±0.10 (n=8), 8.53±0.09 (n=6), and 8.80±0.14 nM (n=5) were observed for IL-33 concentrations of 100 ng/ml (Table 17), 30 ng/ml (Table 18), and 10 ng/ml (Table 19).

TABLE 17

Determination of Potency: Inhibition of 100 ng/mL IL-33/IL-12 induced IFN-γ secretion from whole blood by pre-complexed 22A06-458 (n = 8 donors)

| Donor # | #91232 | #92187 | #92257 | #91865 | #92186 | #91845 | #92023 | #92258 | Mean | SEM |
|---|---|---|---|---|---|---|---|---|---|---|
| pIC50 | 8.55 | 8.32 | 8.58 | 9.05 | 8.52 | 8.24 | 8.46 | 8.10 | 8.48 | 0.10 |
| $IC_{50}$ (nM) | 2.79 | 4.75 | 2.66 | 0.88 | 3.01 | 5.75 | 3.43 | 7.9 | 3.90 | 0.76 |

TABLE 18

Determination of Potency: Inhibition of 30 ng/mL IL-33/IL-12 induced IFN-γ secretion from whole blood by pre-complexed 22A06-458 (n = 6 donors)

| Donor # | #91232 | #92187 | #92257 | #91845 | #92023 | #92258 | Mean | SEM |
|---|---|---|---|---|---|---|---|---|
| pIC50 | 8.83 | 8.30 | 8.75 | 8.41 | 8.60 | 8.30 | 8.53 | 0.09 |
| $IC_{50}$ (nM) | 1.47 | 4.92 | 1.75 | 3.88 | 2.48 | 4.93 | 3.24 | 0.63 |

TABLE 19

Determination of Potency: Inhibition of 10 ng/mL IL-33/IL-12 induced IFN-γ secretion from whole blood by pre-complexed 22A06-458 (n = 5 donors)

| Donor # | #91232 | #92257 | #91845 | #92023 | #92258 | Mean | SEM |
|---|---|---|---|---|---|---|---|
| pIC50 | 9.19 | 9.08 | 8.56 | 8.72 | 8.42 | 8.80 | 0.14 |
| $IC_{50}$ (nM) | 0.63 | 0.81 | 2.72 | 1.88 | 3.72 | 1.95 | 0.58 |

2. Not Pre-Complexed

22A06-458 that had not been pre-complexed with IL-33 also demonstrated concentration dependent inhibition of IL-33/IL-12 stimulated IFN-γ release in whole blood. Inhibition by 22A06-458 was tested in 6 separate donor experiments against IL-33 concentrations of 30 ng/mL and 10 ng/mL. Respective IC50 values of 1.57±0.43 nM (n=6) and 0.37±0.09 nM (n=6) were observed for IL-33 concentrations of 30 ng/mL (Table 20) and 10 ng/ml (Table 21). Respective pIC50 values of 8.89±0.13 (n=6) and 9.51±0.13 (n=6) were observed for IL-33 concentrations of 30 ng/mL (Table 20) and 10 ng/ml (Table 21).

TABLE 20

Determination of Potency: Inhibition of 30 ng/mL IL-33 induced IFN-γ secretion from whole blood by non-pre-complexed 22A06-458 (n = 6 donors)

| Donor # | #90237 | #91986 | #32871 | #91680 | #92251 | #91955 | Mean | SEM |
|---|---|---|---|---|---|---|---|---|
| pIC50 | 8.58 | 8.51 | 9.01 | 8.79 | 9.13 | 9.31 | 8.89 | 0.13 |
| $IC_{50}$ (nM) | 2.6 | 3.04 | 0.97 | 1.60 | 0.74 | 0.48 | 1.57 | 0.43 |

TABLE 21

Determination of Potency: Inhibition of 10 ng/mL IL-33 induced IFN-γ secretion from whole blood by non-pre-complexed 22A06-458 (n = 6 donors)

| Donor # | #90237 | #91986 | #32871 | #91680 | #92251 | #91955 | Mean | SEM |
|---|---|---|---|---|---|---|---|---|
| pIC50 | 9.13 | 9.44 | 9.67 | 9.37 | 9.37 | 10.06 | 9.51 | 0.13 |
| $IC_{50}$ (nM) | 0.73 | 0.36 | 0.21 | 0.43 | 0.42 | 0.08 | 0.37 | 0.09 |

IL-33 alone did not stimulate IFN-γ release from whole blood, whereas IL-12 alone stimulation did cause some increase in basal IFN-γ release in some donors. However, with co-stimulation, IL-33/IL-12 synergistically caused release of large quantities of this cytokine. The concentrations of IFN-γ secreted was highly variable between donors poststimulation with IL-33/IL-12.

The anti-IL-33 monoclonal antibody (22A06-458) concentration dependently inhibited the synergistic effect of IL-33/IL-12 on whole blood IFN-γ release both when pre-complexed with IL-33 as well as when added directly to blood without pre-complexing.

The assay demonstrated that the potency of inhibition varied depending on the concentration of IL-33 used in the assay. Pre-complexing the anti-IL-33 mAb resulted in little difference in potency compared to non-pre-complexing. These in vitro investigations demonstrate that the anti-IL-33 mAb (22A06-458) can neutralize IL-33 and potently block pro-inflammatory effects, as measured by IFN-γ secretion in human whole blood.

Example 18—IL-33 Binding Protein Inhibition of IL-33-Induced Cytokine Production in Mouse Bone Marrow-Derived Mast Cells A. Methods 22A06-458 was provided at a stock concentration of 9.95 mg/mL in 20 mM Histidine, 180 mM Trehalose, 40 mM Arginine, 8 mM Methionine, 0.05 mM EDTA, pH 6. 20 μL aliquots were stored at −80° C. and were thawed and diluted to the appropriate concentration on day of use. Molar concentrations of the antibody were calculated based on a molecular weight of 150 kDa.

Recombinant human IL-33 (in-house) was provided at a stock concentration of 2.1 mg/mL (Mwt of 19.7 Kda; therefore [M]=106.5 μM) in PBS+0.1% BSA. 20 μL aliquots were stored at −80° C. and were thawed and diluted to the appropriate concentration on day of use.

Recombinant mouse IL-33 (R&D Systems #3626-ML-010) was supplied in lyophilised form from a solution in PBS, EDTA and DTT with a BSA carrier. The protein was reconstituted at 10 μg/mL in sterile PBS containing 0.1% BSA. Aliquots were stored at −80° C. and were thawed and diluted to the appropriate concentration on day of use.

Recombinant rat IL-33 (Biolegend #766404) was supplied at 200 μg/mL in sterile PBS. Aliquots were stored at −80° C. and were thawed and diluted to the appropriate concentration on day of use.

Aqua Zombie dead cell dye (Biolegend #423102) was diluted 1:500 in PBS.

FcR block (Miltenyi #130-092-575) was diluted 1:10 in PBS. The FcER1 (Biolegend #134325), CD117 (Biolegend #105811), and isotype control antibodies (Biolegend #400611) were diluted 1:25 in diluted FcR block.

Mast cells were counted and $1\times10^5$ cells added per U bottom 5 mL tube (Falcon 352235) with 3 mL PBS. The tubes were centrifuged (300 g, 5 mins), the supernatant discarded, and the cell pellet resuspended in 100 μL Aqua Zombie. After incubating for 20 mins at room temperature 100 μL of the diluted antibodies were added. The tubes were incubated in the dark at 4° C. for 20 mins. 3 mL of FACS wash buffer was added per tube and centrifuged (300 g, 5 mins). The supernatant was discarded and 200 μL PBS+0.1% FCS added. The cells were analyzed on an Attune N×T Flow Cytometer.

Mast cells were collected into a 50 mL Falcon tube and centrifuged (1300 rpm, 5 min). The pellet was resuspended in mast cell medium at $1\times10^6$ cells/mL and plated into 96 well U-bottom tissue culture plates (Costar 3799), 100 μL/well. Cells were incubated overnight at 37° C., 5% $CO_2$.

Mouse, rat and human IL-33 were diluted to 200 ng/mL (2 times final assay concentration) in mast cell medium. These were further diluted 1:10 in mast cell medium to generate a 6-point dose response curve.

100 μL mouse, rat, or human IL-33 diluted over the range 0.002-200 ng/ml (2 times final concentration) was added in duplicate to the mouse mast cell culture plate. Cells were incubated for 4 hrs at 37° C., 5% $CO_2$. Plates were centrifuged (350 g, 5 mins) to pellet the cells. The supernatant was collected and frozen at −80° C. for cytokine analysis. The final concentration range of IL-33 tested was 0.001-100 ng/mL.

Mouse, rat and human IL-33 were diluted to 40 ng/ml and 4 ng/mL (4× the final assay concentration) in mast cell medium.

The antibody was diluted to 6 μg/mL (4× the final assay top concentration) in mast cell medium followed by 1 in 4 serial dilutions to generate a 6-point response curve. The diluted antibody was then mixed 1:1 with mouse, rat, or human IL-33 at 40 ng/ml or 4 ng/ml. The pre-complexed mixtures, now at 2× final assay concentration, were incubated at room temperature for 30 mins. The negative control was medium alone. The positive control was mouse, rat, or human IL-33 diluted 1:1 with medium.

A further control was 22A06-458 diluted 1:1 with medium (top concentration only).

100 μL of the 22A06-458-IL-33 complex or controls was added in duplicate to the mast cell tissue culture plate. Cells were incubated for 4 hrs at 37° C., 5% $CO_2$. Plates were centrifuged at 350 g for 5 mins to pellet the cells. The supernatant was collected and frozen at −80° C. for cytokine analysis. The final concentration range of antibody tested was 1.5-1500 ng/ml (0.01-10 nM).

The capture antibody coupled beads were added to the assay plate followed by the standards and samples. Following an incubation at 4° C. overnight the plate was washed with kit assay buffer. The biotinylated detection antibody was added per well and the plate incubated at room temperature for 30 minutes. The plate was washed again, the Streptavidin-PE added per well and incubated at room temperature for 30 minutes. After a final wash the beads were re-suspended in assay read buffer. The plate was read on the Luminex Flexmap 3D using Luminex xPONENT software v4.2.

Mean fluorescent intensity values from Luminex xPONENT were exported into BioPlex Manager v6.1. In this software cytokine levels were back-calculated from the standard curve. Data was calculated as percent inhibition of the control response (10 ng/ml or 1 ng/mL IL-33 stimulation). IC50 values were calculated from a non-linear regression four parameter fit curve drawn in GraphPad Prism v5.1.

B. Results

After 4 weeks in culture 73.6% and 90.2% of the mouse bone marrow cells showed positive expression of FcaR1 and CD117. This positive expression showed that the mouse bone marrow cells had differentiated into mast cells.

Mouse, rat, and human IL-33 all stimulated cytokine release (TNF-α, IL-6, IL-18, and IL-13) from mouse bone marrow derived mast cells showing similar concentration response curves. From these plots, IL-33 concentrations were chosen for the 22A06-458 blocking experiment. Maximal (10 ng/mL) and sub-maximal (1 ng/mL) IL-33 concentrations were selected for all three species (FIGS. 5A-5D).

22A06-458 was able to completely block production of human IL-33 stimulated IL-6, TNF-α, IL-13, and IL-18 at both 1 ng/ml and 10 ng/ml IL-33 concentrations. The antibody did not inhibit cytokines stimulated by 10 ng/mL mouse or rat IL-33 even at the top concentration of 10 nM. At 1 ng/mL mouse or rat IL-33 only minimal activity was observed, with maximal inhibition of only around 20-30% at 10 ng/mL. Inhibition was expressed as the percentage decrease compared to IL-33 at 1 ng/ml (FIGS. 6A-6D) or 10 ng/ml (FIGS. 7A-7D). Each condition was tested in duplicate, and the results are from one experiment.

The IC50 values for 22A06-458 against each cytokine and IL-33 concentration are summarized in Table 22 and Table 23.

TABLE 22

Determination of Potency: Inhibition of 1 ng/mL human IL-33 induced cytokine production complexed with 22A06-458

| | IL-6 | TNF-α | IL-13 | IL-18 |
|---|---|---|---|---|
| IC50 pM | 31.21 | 37.35 | 28.01 | 61.26 |
| pIC50 | 10.51 | 10.43 | 0.55 | 10.21 |

TABLE 23

Determination of Potency: Inhibition of 10 ng/mL human IL-33 induced cytokine production complexed with 22A06-458

| | IL-6 | TNF-α | IL-13 | IL-18 |
|---|---|---|---|---|
| IC50 pM | ~566 | ~581 | ~567 | ~631 |
| pIC50 | ~9.25 | ~9.24 | ~9.25 | ~9.20 |

Example 19—Pharmacokinetics and Pharmacodynamics of IL-33 Binding Protein in Cynomolgus Monkeys A study was carried out to investigate the pharmacokinetics and pharmacodynamics of 22A06-458 in cynomolgus monkeys following single intravenous administration or single subcutaneous administration.

A. Methods

Following either a single intravenous administration or single subcutaneous administration of 22A06-458 at 10 mg/kg, serum samples were taken from each animal at the following nominal times: pre-dose, 0.25, 3, 6, 24, 48, 96, 168, 336, 504, 672, 1008, 1344, 1680, 2016, 2352, and 2688 hours after dosing. All samples were stored at approximately −80° C. until analyzed.

Serum samples were analyzed for 22A06-458 using a validated analytical method based on an antigen capture immunoassay on the GYROLAB platform. The capture method used a biotinylated human IL-33 (in-house) to capture 22A06-458. An Alexa labeled anti-human IgG (Fc specific) (Southern Biotech #9040-1, labeled in-house) was used as the detection antibody. The lower limit of quantification (LLQ) was 0.3 μg/mL and the higher limit of quantification (HLQ) was 100 μg/mL using a 3 μL aliquot of cynomolgus monkey serum diluted 1/50 with REXXIP A buffer (Gyros Protein Technologies #P0004820).

Serum samples with 22A06-458 concentration levels less than 10 μg/mL were analyzed for anti-22A06-458 antibodies using a bridging method with acid dissociation on the Gyrolab platform.

Serum samples were diluted in ADA buffer (Gyros Protein Technologies #P0004820) before being loaded into a 96-well plate and placed into the GYROLAB Workstation. The GYROLAB ADA workflow and Mixing CD (Gyros Protein Technologies #P0020455) uses automated acid pretreatment followed by immunoassay. Briefly, samples were loaded into the CD mixing chamber, before the addition of acid. Following acid treatment, neutralization buffer containing a mix of biotinylated and Alexa labeled 22A06-458 (in-house) was added. Samples were then flowed onto the streptavidin coated capture column before being read.

A positive cut point value was determined by screening the study predose samples. The ADA assay cut point was defined as Mean Response+(1.645*SD). Animals with response values greater than or equal to the ADA assay cut point (0.097 response) in the screening assay were considered potentially positive.

Pharmacokinetic analysis was performed by non-compartmental pharmacokinetic analysis using WINNONLIN (WNL), Version 6.3. All computations utilized the nominal sampling times.

Following either single intravenous or subcutaneous administration, the systemic exposure to 22A06-458 was determined by calculating the area under the serum concentration-time curve (AUC) from the start of dosing to the last quantifiable time point ($AUC_{0-t}$) using the linear log trapezoidal method. The maximum observed peak serum concentration ($C_{max}$) and the time at which it was observed ($T_{max}$) were determined by inspection of the observed data. In addition, the total serum clearance (CL or CL_F); volume of distribution (Vss or Vz_F); terminal half-life ($t_{1/2}$) and mean residence time (MRT) were calculated.

B. Results

The mean and individual derived pharmacokinetic parameters for 22A06-458 in cynomolgus monkeys following either a single intravenous or subcutaneous administration at 10 mg/kg are presented in Table 24.

The individual ADA responses for the samples tested are presented in Table 24. There were no notable responses.

22A06-458 is cleared slowly from systemic circulation and had an estimated terminal half-life of approximately 16.5 days, which is comparable to other YTE modified monoclonal antibodies. The volume of distribution is approximately twice blood volume, suggesting the antibody is mainly confined to the systemic circulation.

Absolute bioavailability, estimated by comparing the mean $AUC_{0-\infty}$ for the subcutaneous administration with the mean $AUC_{0-\infty}$ for the intravenous route, was 74%.

TABLE 24

Mean and individual non-compartmental pharmacokinetic parameters for 22A06-458 in cynomolgus monkeys following single intravenous or subcutaneous administration at a target dose of 10 mg/kg

| Regimen | Animal | AUC (hr*μg/mL) | AUCINf (hr*μg/mL) | Cmax (μg/mL) | Tmax* (hr) | Half-life (hr) | Cl or Cl_F (mL/hr/kg) | Vss or Vz_F (mL/kg) |
|---|---|---|---|---|---|---|---|---|
| IV | 1 | 57800 | 58000 | 194 | 0.25 | 340 | 0.17 | 93 |
| | 2 | 46600 | 47100 | 249 | 0.25 | 400 | 0.21 | 120 |
| | 3 | 51000 | 51700 | 234 | 0.25 | 450 | 0.19 | 130 |
| | Mean | 51800 | 52300 | 226 | 0.25 | 400 | 0.19 | 120 |
| SC | 4 | 41800 | 42400 | 57 | 96 | 430 | 0.24 | 140 |
| | 5 | 37400 | 37700 | 42 | 48 | 360 | 0.27 | 140 |
| | 6 | 36400 | 36700 | 51 | 336 | 370 | 0.27 | 140 |
| | Mean | 38500 | 38900 | 49.9 | 96 | 390 | 0.26 | 140 |

*Median Value reported

A. Methods

HEK BLUE IL-33 cells (InvivoGen #HKB-HIL-33) were cultured in a T75 $cm^2$ tissue culture flask in the presence of 1×HEK-BLUE selection antibiotics until approximately 80-90% confluent. After removal of medium and a wash of the cells with PBS (12 mL), the adherent cells were detached by adding back 10 mL PBS and pipetting several times over the adherent cells followed by tapping the flask. The cell suspension was then transferred to a 15 mL conical tube and centrifuged (350 g/5 min/RT). Pelleted cells were resuspended in 1 mL fresh growth media and counted using a haemocytometer.

HEK-BLUE IL-33 cells (passage <10) were diluted to a cell density of $1.25\times10^6$/mL and 40 μL seeded (50,000 cells/well) into 384 well tissue culture plate (Corning #3701).

Serum concentrations of 22A06-458 in cyno pharmacokinetic samples (2688h) are shown in Table 25.

TABLE 25

Concentration of 22A06-458 in serum from six individual cyno monkeys

| Cyno # | μg/mL of drug | [nM] of drug |
|---|---|---|
| 1 | 0.36 | 2.4 |
| 2 | 0.84 | 5.6 |
| 3 | 1.2 | 8 |
| 4 | 0.94 | 6.3 |
| 5 | 0.67 | 4.5 |
| 6 | 0.62 | 4.2 |

From the serum concentrations of 22A06-458 (Table 25), the highest achievable final assay concentration based on cyno #1 (i.e., the sample having the lowest available drug concentration) was 0.025 μg/mL (167 pM).

Example 20—Inhibition of IL-33 Stimulated HEK-BLUE Cells by an IL-33 Binding Protein in PK Samples and Equivalent to Freshly Prepared IL-33 Binding Protein Studies were conducted to compare whether the inhibitory profile of cyno or human IL-33 by an IL-33 binding protein present in cyno PK samples was equivalent to freshly prepared drug.

All serum samples were diluted with DMEM growth media to 4× final assay concentrations (FAC) of 0.1 μg/mL (0.025 μg/mL×4-0.1 μg/mL) as shown in Table 26 below. This top starting concentration was then subsequently diluted 1 in 3 in DMEM growth media (Thermo Fisher #41965-039) a further 7 times to give a total of 8 concentrations (0.076 pM-167 pM). All dilutions were carried out in a U-bottom sterile polypropylene 96 well plate.

TABLE 26

Cyno serum 22A06-458 concentrations and dilutions conducted to achieve a maximal assay concentration of 167 pM

| Cyno | Concentration in 2688 hour PK samples | | Dilution | [μg/mL] | [nM] | Max FAC |
|---|---|---|---|---|---|---|
| # | μg/mL | [nM] | factor | 4xFAC | 4xFAC | (pM) |
| 1 | 0.36 | 2.4 | 3.6 | 0.1 | 0.67 | 167 |
| *2 | 0.84 | 5.6 | 8.9 | 0.09 | 0.63 | 157 |
| 3 | 1.2 | 8 | 12 | 0.1 | 0.67 | 167 |
| 4 | 0.94 | 6.3 | 9.4 | 0.1 | 0.67 | 167 |
| 5 | 0.67 | 4.5 | 6.7 | 0.1 | 0.67 | 167 |
| 6 | 0.62 | 4.2 | 6.2 | 0.1 | 0.67 | 167 |

*Due to a typographical error in the PK drug concentration, the incorrect dilution was applied to this sample thus the max final assay concentration for serum 22A06-458 was 157 pM.

22A06-458 was produced at a stock concentration of 9.95 mg/mL in 20 mM Histidine, 180 mM Trehalose, 40 mM Arginine, 8 mM Methionine, 0.05 mM EDTA, pH 6. 20 μL aliquots stored at −80° C. were thawed and diluted to the appropriate concentration on day of use. Fresh 22A06-458 was prepared to the same top concentration as the serum drug samples, i.e., fresh drug was diluted to a 4×FAC of 0.1 μg/mL (0.67 nM) into DMEM growth media. Stock concentration of drug, 9.95 mg/mL was diluted 1 in 100 then 1 in 100 again then 1 in 9.5 Subsequent 1 in 3 dilutions were conducted to a total of 8 concentrations (0.076 pM-167 pM).

For this study the same stock cyno serum samples were used. The cyno #1 serum sample had insufficient volume remaining and thus had to be omitted from this study.

Based on the serum concentrations of 22A06-458, the highest assay concentration of the drug based on cyno #6 (i.e., sample having the lowest available drug concentration) was calculated to be 0.05 μg/mL (333 pM).

All serum samples were diluted with DMEM growth media to 4×FAC of 0.2 μg/mL (4×0.05 μg/mL=0.2 μg/mL) as shown in Table 27 below. This top concentration was then subsequently diluted 1 in 3 in DMEM growth media a further 7 times to give a total of 8 concentrations (0.15 pM-333 pM). All dilutions were carried out in a U-bottom sterile polypropylene 96 well plate.

TABLE 27

Cyno serum 22A06-458 concentrations and dilutions conducted to achieve a maximal assay concentration of 333 pM

| Cyno | Concentration in 2688 hour PK samples | | Dilution | [μg/mL] | [nM] | Max FAC |
|---|---|---|---|---|---|---|
| # | μg/mL | [nM] | factor | 4xFAC | 4xFAC | (pM) |
| *1 | 0.36 | 2.4 | 1.8 | 0.2 | 1.3 | 333 |
| **2 | 0.84 | 5.6 | 4.45 | 0.19 | 1.26 | 315 |
| 3 | 1.2 | 8 | 6 | 0.2 | 1.3 | 333 |
| 4 | 0.94 | 6.3 | 4.7 | 0.2 | 1.3 | 333 |
| 5 | 0.67 | 4.5 | 3.35 | 0.2 | 1.3 | 333 |
| 6 | 0.62 | 4.2 | 3.1 | 0.2 | 1.3 | 333 |

*Cyno #1 could not be used due to lack of adequate sample volume

**Due to a typographical error in the PK drug concentration, the incorrect dilution factor was applied to this sample thus the max final assay concentration for serum 22A06-458 was 315 pM 22A06-458 was prepared from a fresh stock sample to the same top concentration as the serum drug samples. i.e., fresh drug was diluted to a 4×FAC of 0.2 μg/mL (1.3 nM) into DMEM growth media.

Stock concentration of drug, 9.95 mg/mL was diluted 1 in 100 then 1 in 100 again then 1 in 4.9. Subsequent 1 in 3 dilutions were conducted to a total of 8 concentrations (0.15 pM-333 pM).

Cyno IL-33 (in-house) was used at a FAC of 75 pg/mL (3.8 pM) (~EC50 concentration for cyno IL-33). Stock [cyno IL-33]=5.9 mg/mL; diluted to 300 pg/mL (4×FAC) in DMEM growth media.

rhu IL-33 (in-house) was used at a FAC of 200 pg/mL (10 pM) (~EC50 concentration for IL-33). Stock [rhu IL-33]=2.1 mg/mL; diluted to 800 pg/mL (4×FAC) in DMEM growth media.

Cyno and rhu IL-33 diluted to 200 pg/mL and 800 pg/mL (4×FAC) respectively were mixed 1:1 (e.g., 50 μL+50 μL) with the prepared 4× concentrated serum 22A06-458 and freshly prepared 22A06-458, then co-incubated for 30 min/RT. This reduced the drug and IL-33 concentrations to 2×FAC's.

The cyno and rhu IL-33 positive assay controls (no 22A06-458) prepared to 4×FAC were also further diluted by mixing 1:1 with DMEM growth media to mimic the pre-complexing treatment with 22A06-458 (as above) and maintain the correct assay concentration (i.e., 2×FAC).

The negative assay control consisted of DMEM growth media alone.

To the 384 well plate containing the 40 μL of HEK BLUE cells, 40 μL of pre-complexed drug-IL-33 including positive and negative controls were added to wells (duplicate wells per test treatment). The plate was then incubated at 37° C. or 24 h.

Following the 24 h incubation period the Quanti Blue substrate reagent (InvivoGen #HB-DET2) was prepared according to manufacturer's instructions, filtered and frozen in aliquots of 10 mL at −20° C. Prior to use, the Quanti Blue substrate reagent was defrosted and warmed to RT. 40 μL Quanti Blue substrate was added to wells of a new 384 well plate and 10 μL of HEK BLUE cell supernatants transferred from treatment plate into the Quanti Blue containing wells. The plate was then incubated at 37° C. for 2 h. The absorbance of the colour formation was read on a spectrophotometer plate reader (665 nm).

Raw absorbance data was transferred to MS Excel, calculated, and expressed as % inhibition of the IL-33 (prepared in Media) control response using Equation 2. This was then plotted relative to the [22A06-458] M and a non-linear regression curve fit (three parameter) was applied using the Graph Prism software v5.0.4.

B. Results

22A06-458 from the individual cyno serum PK samples and freshly prepared sample, concentration-dependently blocked cyno IL-33 mediated stimulation of HEK BLUE cells. To illustrate the concentration dependent inhibition by 22A06-458, graphs of molar concentration of 22A06-458 were plotted against % inhibition of IL-33 (3.8 pM) stimulation for each of the 6 individual cyno monkey serum samples (FIGS. 8A-8F). The inhibition curve for fresh 22A06-458 was included in each graph to illustrate the similarity in activity. Full inhibition curves were not achieved since the maximal concentration of 22A06-458 in the assay was limited to 167 pM (157 pM for cyno #2).

22A06-458 from individual cyno serum PK samples and freshly prepared drug sample, concentration dependently blocked rhu IL-33 mediated stimulation of HEK BLUE cells. To illustrate the concentration dependent inhibition by 22A06-458 of rhu IL-33, graphs of the molar concentration of 22A06-458 were plotted against % inhibition of rhu IL-33 (10 pM) stimulation for each of the 5 individual cyno monkey serum samples (FIGS. 9A-9E). The inhibition curve for fresh 22A06-458 was included in each graph to illustrate the similarity in activity. Full inhibition curves were not achieved since the maximal concentration of 22A06-458 in this assay was limited to 333 pM (315 pM for cyno #2).

Example 21—Cryo-Electron Microscopy Structure of IL-33 Binding Protein

Cryo-electron microscopy (cryo-EM) (200 keV ThermoFisher Glacios transmission electron microscope equipped with an X-FEG source) was used to determine the binding mode of the fAb of IL-33 binding protein 22A06-458 to human IL-33 (SEQ ID NO: 88) and understand the mAb mode of action.

A 4.75 Å Cryo-EM structure of the fAb of anti-IL33 mAb 22A06-458 in complex with reduced IL-33 and a kappa nanobody was determined. This was of sufficient resolution to allow the interaction regions between 22A06-458 fAb (paratope) and reduced IL-33 (epitope) to be identified by Qt-PISA v2.1.0 within the CCP4 program suite (Collaborative Computational Projection Number 4, 1994).

Figure 10A:
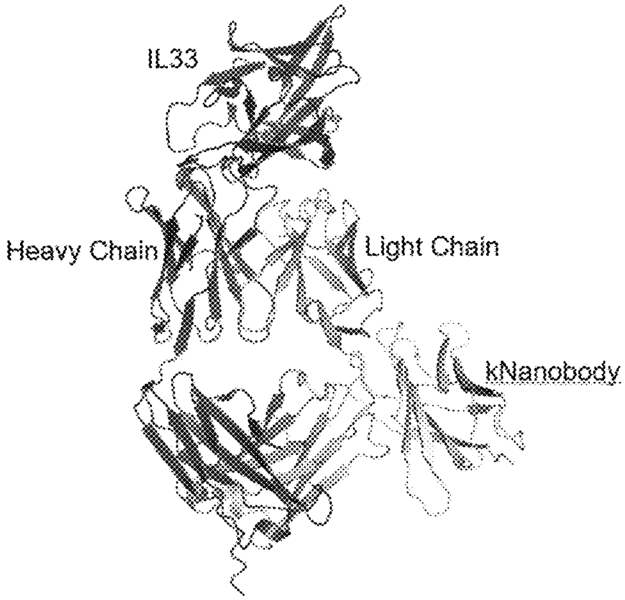
FIG. 10A illustrates a refined structure of a fAb-IL-33-Nanobody complex.
Figure 10B:
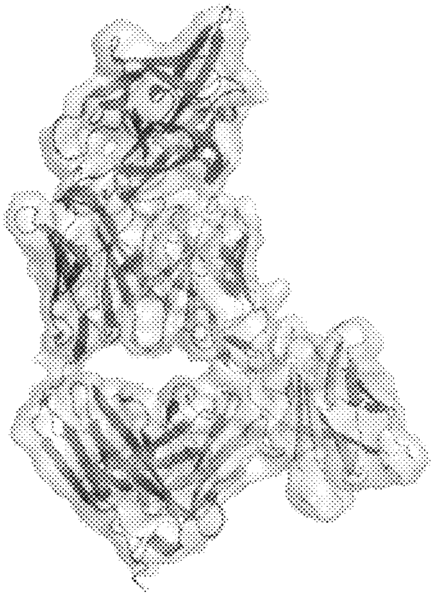
FIG. 10B illustrates a refined structure of a Cryo-EM map superimposed onto the structure in FIG. 10A.

As shown in FIGS. 10A-10B, the epitope is defined by a central region consisting of Y163-L182 (SEQ ID NO: 82) and V219-V228 (SEQ ID NO: 83). This is flanked by epitope regions consisting of S117-Y122 (SEQ ID NO: 84), V252-L258 (SEQ ID NO: 85) and L267-E269 (LSE). The paratope involves residues drawn from all six CDRs of 22A06-458.

Figure 11A:
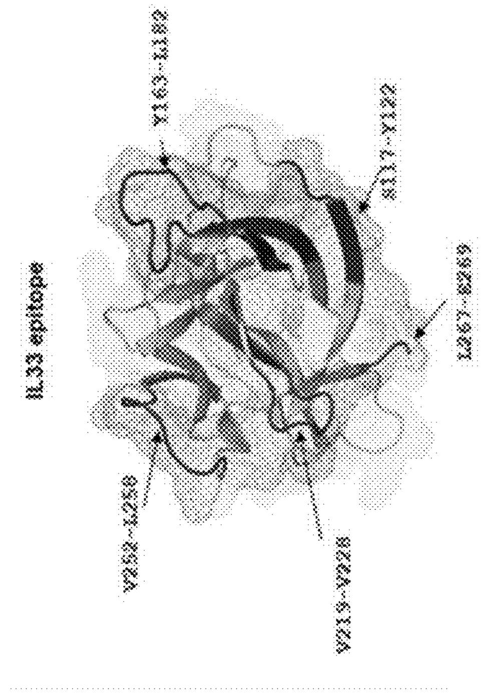
FIG. 11A illustrates a Cryo-EM epitope.
Figure 11B:
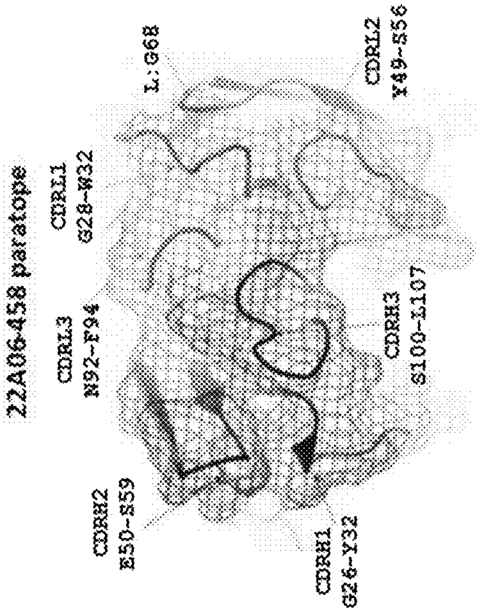
FIG. 11B illustrates the paratope for an IL-33 binding protein.
Figure 11C:
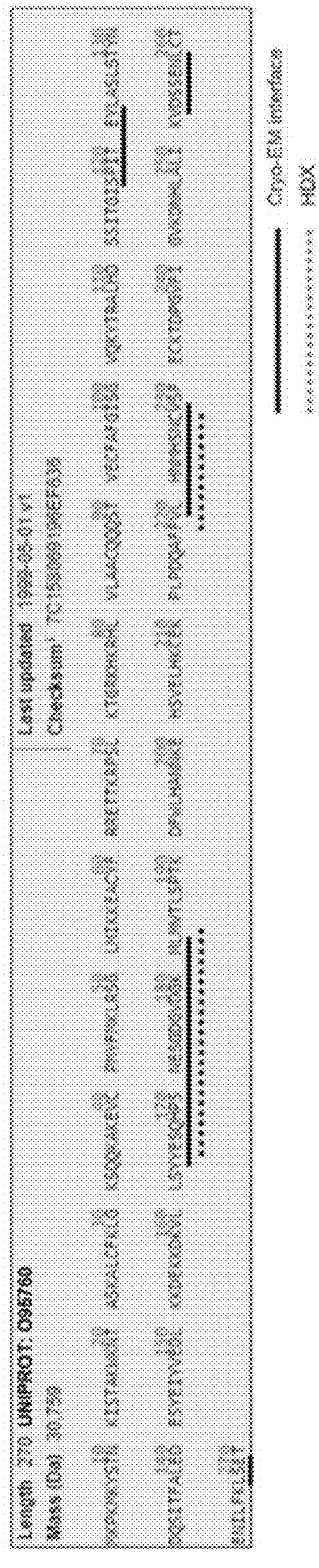
FIG. 11C illustrates a comparison of Cryo-EM data and HDX data to IL-33 (SEQ ID NO: 88).
Figure 12A:
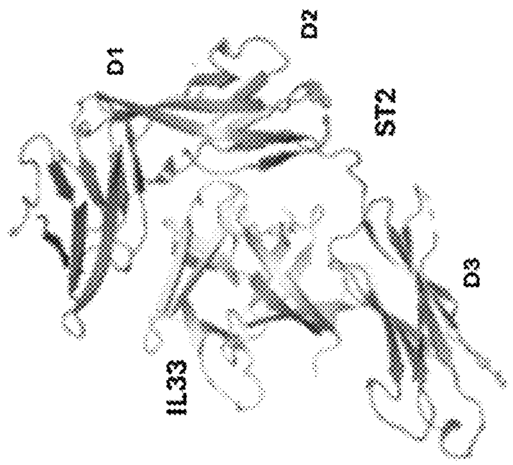
FIG. 12A illustrates crystal structure 4KC3.
Figure 12B:
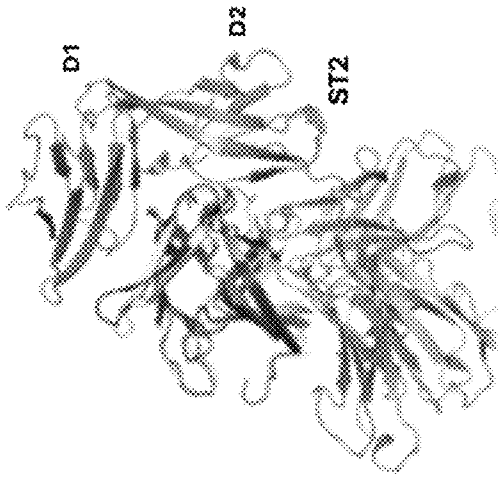
FIG. 12B illustrates an overlay of an IL-33 binding protein and ST2 complexes with IL-33 for crystal structure 4KC3.
Figure 12C:
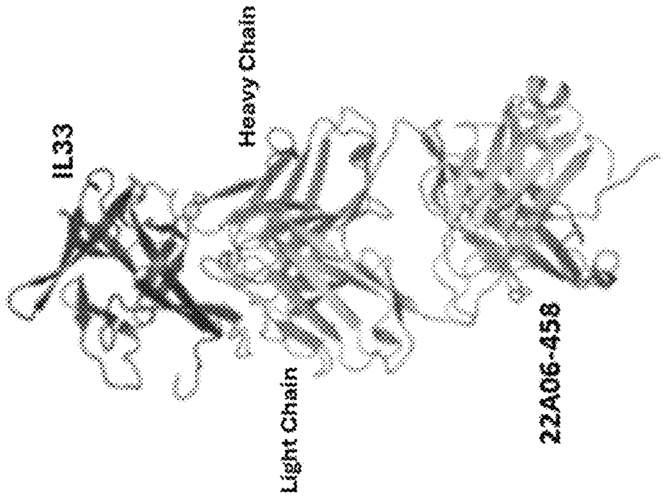
FIG. 12C illustrates an IL-33 binding protein complex with IL-33.
Figure 13A:
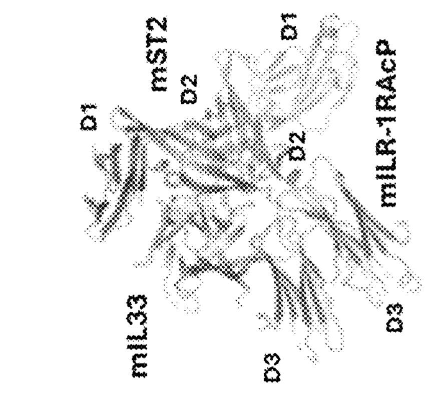
FIG. 13A illustrates crystal structure 5VI4.
Figure 13B:
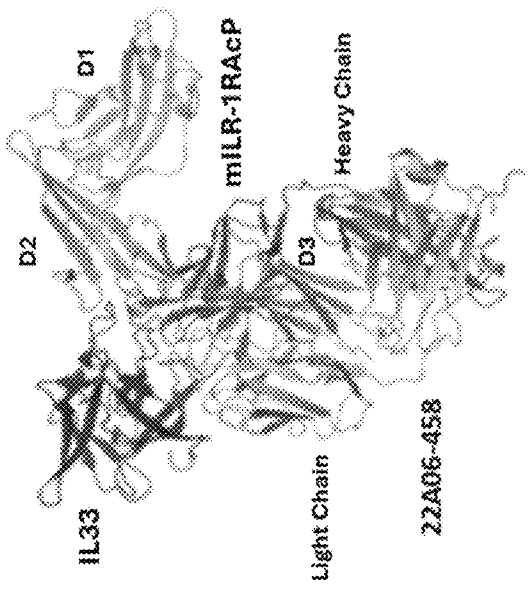
FIG. 13B illustrates an overlay of an IL-33 binding protein and ST2 complexes with IL-33 for crystal structure 5VI4.
Figure 13C:
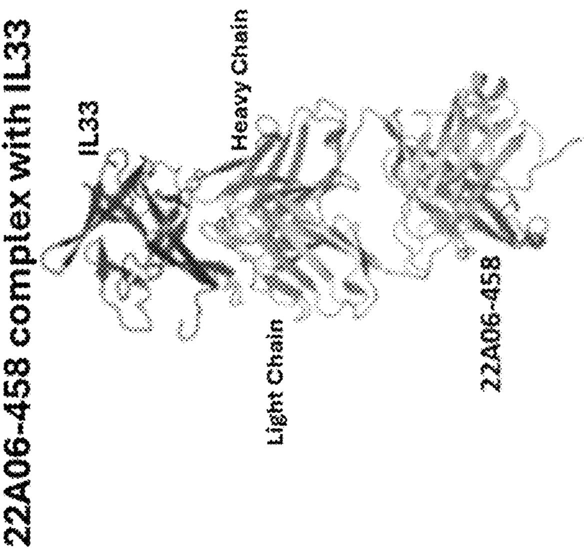
FIG. 13C illustrates an IL-33 binding protein complex with IL-33.

This Cryo-EM fAb epitope shows good agreement with that determined by HDX-MS protection mapping of IL33 binding described in Example 7, namely in the regions Y164-L182 (SEQ ID NO: 86) and V219-C227 (SEQ ID NO: 87) as shown in FIGS. 11A-11C. Enhanced protection of the two central regions of Cryo-EM epitope were observed, consistent with these being the most likely to experience solvent protection on 22A06-458 binding.

As shown in FIGS. 12A-12C and FIGS. 13A-13C, the overlay of the Cryo-EM structure with published crystal structures (PDB: 4KC3 (Liu, 2013) and 5VI4 (Günther, 2017)), respectively, reveals that 22A06-458 blocks both domain 3 (D3) and domain 2 (D2) of the IL-1 Receptor Accessory Protein (IL-1RAcP) from binding to IL-33, effectively obstructing all IL-33 binding sites for this receptor. However, 22A06-458 only hinders D3 of the ST2 receptor, also known as Interleukin 1 receptor type 1 (ILIR1), from interacting with IL-33. This suggests that domain 1 (D1) and D2 of ST2 might still be able to interact with the 22A06-458 fAb-IL33 complex.

This aligns with assay observations showing that the competition between 22A06-458 and ST2 for IL-33 can be influenced by the order of addition. If ST2 is preincubated with IL-33, it prevents 22A06-458 from binding because D1 of ST2 directly blocks 22A06-458 binding. However, if 22A06-458 is preincubated with IL-33, it only prevents D1 of ST2 from binding and ST2 can still interact with IL-33 at the D2 and D3 sites.

Example 22—Developability Analysis

A number of assays, including affinity, developability, and solubility studies, were carried out on 22A06-458, 22A06-429, 22A06-481 and 22A06-502.

22A06-429 had the highest affinity, followed by 22A06-481, 22A06-458, and 22A06-502. Following the developability analysis, it was determined that 22A06-458 and 22A06-502 were the most desirable candidates to progress due to less aggregation and greater stability under stressed conditions.

SEQUENCE LISTINGS

| SEQ ID NO | Sequence Identifier |
|---|---|
| 1 | CDRH1 of 22A06-429, 22A06-458, 22A06-481, and 22A06-502 amino acid sequence |
| 2 | CDRH2 consensus amino acid sequence |
| 3 | CDRH2 of 22A06-429, 22A06-481, and 22A06-502 amino acid sequence |
| 4 | CDRH2 of 22A06-458 amino acid sequence |
| 5 | CDRH3 consensus amino acid sequence |
| 6 | CDRH3 of 22A06-429 amino acid sequence |
| 7 | CDRH3 of 22A06-458 and 22A06-502 amino acid sequence |
| 8 | CDRH3 of 22A06-481 amino acid sequence |
| 9 | CDRL1 consensus amino acid sequence |
| 10 | CDRL1 of 22A06-429 and 22A06-458 amino acid sequence |
| 11 | CDRL1 of 22A06-481 amino acid sequence |
| 12 | CDRL1 of 22A06-502 amino acid sequence |
| 13 | CDRL2 consensus amino acid sequence |
| 14 | CDRL2 of 22A06-429 and 22A06-458 amino acid sequence |
| 15 | CDRL2 of 22A06-481 amino acid sequence |
| 16 | CDRL2 of 22A06-502 amino acid sequence |
| 17 | CDRL3 consensus amino acid sequence |
| 18 | CDRL3 of 22A06-429, 22A06-458 and 22A06-481 amino acid sequence |
| 19 | CDRL3 of 22A06-502 amino acid sequence |
| 20 | VH consensus amino acid sequence |
| 21 | VH of 22A06-429 amino acid sequence |
| 22 | VH of 22A06-458 amino acid sequence |
| 23 | VH of 22A06-481 amino acid sequence |
| 24 | VH of 22A06-502 amino acid sequence |
| 25 | VL consensus amino acid sequence |
| 26 | VL of 22A06-429 and of 22A06-458 amino acid sequence |
| 27 | VL of 22A06-481 amino acid sequence |
| 28 | VL of 22A06-502 amino acid sequence |
| 29 | HC consensus amino acid sequence |
| 30 | HC of 22A06-429 amino acid sequence |
| 31 | HC of 22A06-458 amino acid sequence |
| 32 | HC of 22A06-481 amino acid sequence |
| 33 | HC of 22A06-502 amino acid sequence |
| 34 | LC consensus amino acid sequence |
| 35 | LC of 22A06-429 and of 22A06-458 amino acid sequence |
| 36 | LC of 22A06-481 amino acid sequence |
| 37 | LC of 22A06-502 amino acid sequence |
| 38 | VH consensus nucleic acid sequence 1 |
| 39 | VH consensus nucleic acid sequence 2 |
| 40 | VH consensus nucleic acid sequence 3 |
| 41 | VH consensus nucleic acid sequence 4 |
| 42 | VH consensus nucleic acid sequence 5 |
| 43 | VH consensus nucleic acid sequence 6 |
| 44 | VH of 22A06-429 nucleic acid sequence |
| 45 | VH of 22A06-458 nucleic acid sequence |
| 46 | VH of 22A06-481 nucleic acid sequence |
| 47 | VH of 22A06-502 nucleic acid sequence |
| 48 | VL consensus nucleic acid sequence 1 |
| 49 | VL consensus nucleic acid sequence 2 |
| 50 | VL consensus nucleic acid sequence 3 |
| 51 | VL consensus nucleic acid sequence 4 |
| 52 | VL consensus nucleic acid sequence 5 |
| 53 | VL consensus nucleic acid sequence 6 |
| 54 | VL consensus nucleic acid sequence 7 |
| 55 | VL consensus nucleic acid sequence 8 |
| 56 | VL of 22A06-429 and of 22A06-458 nucleic acid sequence |
| 57 | VL of 22A06-481 nucleic acid sequence |
| 58 | VL of 22A06-502 nucleic acid sequence |
| 59 | HC consensus nucleic acid sequence 1 |
| 60 | HC consensus nucleic acid sequence 2 |
| 61 | HC consensus nucleic acid sequence 3 |
| 62 | HC consensus nucleic acid sequence 4 |
| 63 | HC consensus nucleic acid sequence 5 |
| 64 | HC consensus nucleic acid sequence 6 |
| 65 | HC of 22A06-429 nucleic acid sequence |
| 66 | HC of 22A06-458 nucleic acid sequence |
| 67 | HC of 22A06-481 nucleic acid sequence |
| 68 | HC of 22A06-502 nucleic acid sequence |
| 69 | LC consensus nucleic acid sequence 1 |
| 70 | LC consensus nucleic acid sequence 2 |
| 71 | LC consensus nucleic acid sequence 3 |
| 72 | LC consensus nucleic acid sequence 4 |
| 73 | LC consensus nucleic acid sequence 5 |
| 74 | LC consensus nucleic acid sequence 6 |
| 75 | LC consensus nucleic acid sequence 7 |
| 76 | LC consensus nucleic acid sequence 8 |
| 77 | LC of 22A06-429 and of 22A06-458 nucleic acid sequence |
| 78 | LC of 22A06-481 nucleic acid sequence |
| 79 | LC of 22A06-502 nucleic acid sequence |
| 80 | IL-$33_{113-270}$ residues 66-85 amino acid sequence |
| 81 | IL-$33_{113-270}$ residues 120-129 amino acid sequence |
| 82 | IL-33 residues 163-182 amino acid sequence |
| 83 | IL-33 residues 219-228 amino acid sequence |
| 84 | IL-33 residues 117-122 amino acid sequence |
| 85 | IL-33 residues 252-258 amino acid sequence |
| 86 | IL-33 residues 164-182 amino acid sequence |
| 87 | IL-33 residues 219-227 amino acid sequence |
| 88 | IL-33 amino acid sequence |

SEQ ID NO: 1

SYGMH

SEQ ID NO: 2

EINPHGGSTSYAQKFXG
X Pos 16: K or Q

SEQ ID NO: 3

EINPHGGSTSYAQKFQG

SEQ ID NO: 4

EINPHGGSTSYAQKFKG

SEQ ID NO: 5

PSAAYSHYLGJDX
X Pos 13: I, L, or M

SEQ ID NO: 6

PSAAYSHYLGIDM

-continued

SEQ ID NO: 7

PSAAYSHYLGIDL

SEQ ID NO: 8

PSAAYSHYLGLDI

SEQ ID NO: 9

RXSQGISXWLX
X Pos 2: A or T
X Pos 8: P or S
X Pos 11: A or S

SEQ ID NO: 10

RASQGISSWLA

SEQ ID NO: 11

RASQGISPWLA

SEQ ID NO: 12

RTSQGISSWLS

SEQ ID NO: 13

AXSXLQS
X Pos 2: A or G
X Pos 4: R or S

SEQ ID NO: 14

AASRLQS

SEQ ID NO: 15

AGSSLQS

SEQ ID NO: 16

AASSLQS

SEQ ID NO: 17

QQAXVXPLT
X Pos 4: H or N
X Pos 6: F or L

SEQ ID NO: 18

QQANVFPLT

SEQ ID NO: 19

QQAHVLPLT

SEQ ID NO: 20

QVQLVQSGAEVKKPGASVKVSCKASGYTFISYGMHWVRQAPGQGLEWMGEINPHGGS

TSYAQKFXGRVTMTRDTSTSTVYMELSSLRSEDTAVYYCARPSAAYSHYLGJDXWGRG

TLVTVSS
X Pos 65: K or Q
X Pos 111: I, L, or M

SEQ ID NO: 21

QVQLVQSGAEVKKPGASVKVSCKASGYTFISYGMHWVRQAPGQGLEWMGEINPHGGS

TSYAQKFQGRVTMTRDTSTSTVYMELSSLRSEDTAVYYCARPSAAYSHYLGIDMWGRG

TLVTVSS

SEQ ID NO: 22

QVQLVQSGAEVKKPGASVKVSCKASGYTFISYGMHWVRQAPGQGLEWMGEINPHGGS

TSYAQKFKGRVTMTRDTSTSTVYMELSSLRSEDTAVYYCARPSAAYSHYLGIDLWGRG

TLVTVSS

SEQ ID NO: 23

QVQLVQSGAEVKKPGASVKVSCKASGYTFISYGMHWVRQAPGQGLEWMGEINPHGGS

TSYAQKFQGRVTMTRDTSTSTVYMELSSLRSEDTAVYYCARPSAAYSHYLGLDIWGRG

TLVTVSS

-continued

SEQ ID NO: 24
QVQLVQSGAEVKKPGASVKVSCKASGYTFISYGMHWVRQAPGQGLEWMGEINPHGGS
TSYAQKFQGRVTMTRDTSTSTVYMELSSLRSEDTAVYYCARPSAAYSHYLGIDLWGRG
TLVTVSS

SEQ ID NO: 25
DIQMTQSPSSVSASVGDRVTITCRXSQGISXWLXWYQQKPGKAPKLLIYAXSXLQSGVP
SRFSGSGSGTDFTLTISSLQPEDFATYYCQQAXVXPLTFGGGTKVEIK
X Pos 25: A or T
X Pos 31: P or S
X Pos 34: A or S
X Pos 51: A or G
X Pos 53: R or S
X Pos 92: H or N
X Pos 94: F or L

SEQ ID NO: 26
DIQMTQSPSSVSASVGDRVTITCRASQGISSWLAWYQQKPGKAPKLLIYAASRLQSGVPS
RFSGSGSGTDFTLTISSLQPEDFATYYCQQANVFPLTFGGGTKVEIK

SEQ ID NO: 27
DIQMTQSPSSVSASVGDRVTITCRASQGISPWLAWYQQKPGKAPKLLIYAGSSLQSGVPS
RFSGSGSGTDFTLTISSLQPEDFATYYCQQANVFPLTFGGGTKVEIK

SEQ ID NO: 28
DIQMTQSPSSVSASVGDRVTITCRTSQGISSWLSWYQQKPGKAPKLLIYAASSLQSGVPS
RFSGSGSGTDFTLTISSLQPEDFATYYCQQAHVLPLTFGGGTKVEIK

SEQ ID NO: 29
QVQLVQSGAEVKKPGASVKVSCKASGYTFISYGMHWVRQAPGQGLEWMGEINPHGGS
TSYAQKFXGRVTMTRDTSTSTVYMELSSLRSEDTAVYYCARPSAAYSHYLGJDXWGRG
TLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APELLGGPSVFLFPPKPKDTLYITREPEVTCVVVDVSHEDPEVKFNWYVDGVEVHNAKT
KPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK
X Pos 65: K or Q
X Pos 111: I, L, or M

SEQ ID NO: 30
QVQLVQSGAEVKKPGASVKVSCKASGYTFISYGMHWVRQAPGQGLEWMGEINPHGGS
TSYAQKFQGRVTMTRDTSTSTVYMELSSLRSEDTAVYYCARPSAAYSHYLGIDMWGRG
TLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APELLGGPSVFLFPPKPKDTLYITREPEVTCVVVDVSHEDPEVKFNWYVDGVEVHNAKT
KPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK

SEQ ID NO: 31
QVQLVQSGAEVKKPGASVKVSCKASGYTFISYGMHWVRQAPGQGLEWMGEINPHGGS
TSYAQKFKGRVTMTRDTSTSTVYMELSSLRSEDTAVYYCARPSAAYSHYLGIDLWGRG
TLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCP
APELLGGPSVFLFPPKPKDTLYITREPEVTCVVVDVSHEDPEVKFNWYVDGVEVHNAKT

-continued

KPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 32

QVQLVQSGAEVKKPGASVKVSCKASGYTFISYGMHWVRQAPGQGLEWMGEINPHGGS

TSYAQKFQGRVTMTRDTSTSTVYMELSSLRSEDTAVYYCARPSAAYSHYLGLDIWGRG

TLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLYITREPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 33

QVQLVQSGAEVKKPGASVKVSCKASGYTFISYGMHWVRQAPGQGLEWMGEINPHGGS

TSYAQKFQGRVTMTRDTSTSTVYMELSSLRSEDTAVYYCARPSAAYSHYLGIDLWGRG

TLVTVSSASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCP

APELLGGPSVFLFPPKPKDTLYITREPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPVLDSDGSFFLY

SKLTVDKSRWQQGNVFSCSVMHEALHNHYTQKSLSLSPGK

SEQ ID NO: 34

DIQMTQSPSSVSASVGDRVTITCRXSQGISXWLXWYQQKPGKAPKLLIYAXSXLQSGVP

SRFSGSGSGTDFTLTISSLQPEDFATYYCQQAXVXPLTFGGGTKVEIKRTVAAPSVFIFPPS

DEQLKSGTASVVCLLNNFYPREAKVQWKVDNALQSGNSQESVTEQDSKDSTYSLSSTL

TLSKADYEKHKVYACEVTHQGLSSPVTKSFNRGEC
X Pos 25: A or T
X Pos 31: P or S
X Pos 34: A or S
X Pos 51: A or G
X Pos 53: R or S
X Pos 92: H or N
X Pos 94: F or L

SEQ ID NO: 35

DIQMTQSPSSVSASVGDRVTITCRASQGISSWLAWYQQKPGKAPKLLIYAASRLQSGVPS

RFSGSGSGTDFTLTISSLQPEDFATYYCQQANVFPLTFGGGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

SEQ ID NO: 36

DIQMTQSPSSVSASVGDRVTITCRASQGISPWLAWYQQKPGKAPKLLIYAGSSLQSGVPS

RFSGSGSGTDFTLTISSLQPEDFATYYCQQANVFPLTFGGGTKVEIKRTVAAPSVFIFPPSD

EQLKSGTASVVCLLNNFYPREAKVQWKVDNALQSGNSQESVTEQDSKDSTYSLSSTLTL

SKADYEKHKVYACEVTHQGLSSPVTKSFNRGEC

-continued

SEQ ID NO: 37
DIQMTQSPSSVSASVGDRVTITCRTSQGISSWLSWYQQKPGKAPKLLIYAASSLQSGVPS
RFSGSGSGTDFTLTISSLQPEDFATYYCQQAHVLPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

SEQ ID NO: 38
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcmthgacmtntggggcaggggcacc
ctggtgaccgtgagctct SEQ ID NO: 39
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcmthgacttrtggggcaggggcaccct
ggtgaccgtgagctct SEQ ID NO: 40
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcytggacmtntggggcaggggcaccc
tggtgaccgtgagctct SEQ ID NO: 41
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcytggacttrtggggcaggggcaccctg
gtgaccgtgagctct SEQ ID NO: 42
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcttagacmtntggggcaggggcaccct
ggtgaccgtgagctct SEQ ID NO: 43
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcttagacttrtggggcaggggcaccctg
gtgaccgtgagctct SEQ ID NO: 44
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttccagggcagggtgaccatgacaagggacaccagcaccagcaccgtgtacatggagctgagcagcctgagga -continued gcgaggacaccgccgtgtattactgcgcaaggcccagcgccgcctacagccactacctgggcatcgacatgtggggcaggggcaccct ggtgaccgtgagctct

SEQ ID NO: 45 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttcaagggcagggtgaccatgacaagggacaccagcaccagcaccgtgtacatggagctgagcagcctgagga gcgaggacaccgccgtgtattactgcgcaaggcccagcgccgcctacagccactacctgggcatcgacctgtggggcaggggcaccct ggtgaccgtgagctct

SEQ ID NO: 46 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttccagggcagggtgaccatgacaagggacaccagcaccagcaccgtgtacatggagctgagcagcctgagga gcgaggacaccgccgtgtattactgcgcaaggcccagcgccgcctacagccactacctgggcctggacatctggggcaggggcaccct ggtgaccgtgagctct

SEQ ID NO: 47 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttccagggcagggtgaccatgacaagggacaccagcaccagcaccgtgtacatggagctgagcagcctgagga gcgaggacaccgccgtgtattactgcgcaaggcccagcgccgcctacagccactacctgggcatcgacctgtggggcaggggcaccct ggtgaccgtgagctct

SEQ ID NO: 48 gacatccagatgacccagagccccagctcagtgagcgctagcgtgggcgacagggtgaccatcacctgcaggrcnagccagggcatta gcycntggctgkcntggtaccagcagaagcccggcaaggcccccaagctcctgatctacgccgsnagcmgnctgcagagcggcgtg ccctccaggtttagcggcagcggaagcggcaccgacttcaccctgaccatcagcagcctgcagcccgaggacttcgccacctactactgc cagcaggccmaygtgytnccccctgaccttcggcggcggcacaaaagtcgagatcaag

SEQ ID NO: 49 gacatccagatgacccagagccccagctcagtgagcgctagcgtgggcgacagggtgaccatcacctgcaggrcnagccagggcatta gcycntggctgkcntggtaccagcagaagcccggcaaggcccccaagctcctgatctacgccgsnagctcnctgcagagcggcgtgcc ctccaggtttagcggcagcggaagcggcaccgacttcaccctgaccatcagcagcctgcagcccgaggacttcgccacctactactgcca gcaggccmaygtgytnccccctgaccttcggcggcggcacaaaagtcgagatcaag

SEQ ID NO: 50 gacatccagatgacccagagccccagctcagtgagcgctagcgtgggcgacagggtgaccatcacctgcaggrcnagccagggcatta gcycntggctgagytggtaccagcagaagcccggcaaggcccccaagctcctgatctacgccgsnagcmgnctgcagagcggcgtg ccctccaggtttagcggcagcggaagcggcaccgacttcaccctgaccatcagcagcctgcagcccgaggacttcgccacctactactgc cagcaggccmaygtgytnccccctgaccttcggcggcggcacaaaagtcgagatcaag

SEQ ID NO: 51 gacatccagatgacccagagccccagctcagtgagcgctagcgtgggcgacagggtgaccatcacctgcaggrcnagccagggcatta gcycntggctgagytggtaccagcagaagcccggcaaggcccccaagctcctgatctacgccgsnagctcnctgcagagcggcgtgcc ctccaggtttagcggcagcggaagcggcaccgacttcaccctgaccatcagcagcctgcagcccgaggacttcgccacctactactgcca gcaggccmaygtgytnccccctgaccttcggcggcggcacaaaagtcgagatcaag

SEQ ID NO: 52 gacatccagatgacccagagccccagctcagtgagcgctagcgtgggcgacagggtgaccatcacctgcaggrcnagccagggcatta gcagytggctgkcntggtaccagcagaagcccggcaaggcccccaagctcctgatctacgccgsnagcmgnctgcagagcggcgtg -continued ccctccaggtttagcggcagcggaagcggcaccgacttcaccctgaccatcagcagcctgcagcccgaggacttcgccacctactactgc
cagcaggccmaygtgytnccccctgaccttcggcggcggcacaaaagtcgagatcaag SEQ ID NO: 53
gacatccagatgacccagagccccagctcagtgagcgctagcgtgggcgacagggtgaccatcacctgcaggrcnagccagggcatta
gcagytggctgkcntggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca
gcaggccmaygtgytnccccctgaccttcggcggcggcacaaaagtcgagatcaag SEQ ID NO: 54
gacatccagatgacccagagccccagctcagtgagcgctagcgtgggcgacagggtgaccatcacctgcaggrcnagccagggcatta
gcagytggctgagytggtaccagcagaagcccggcaaggcccccaagctcctgatctacgccgsnagcmgnctgcagagcggcgtg
ccctccaggtttagcggcagcggaagcggcaccgacttcaccctgaccatcagcagcctgcagcccgaggacttcgccacctactactgc
cagcaggccmaygtgytnccccctgaccttcggcggcggcacaaaagtcgagatcaag SEQ ID NO: 55
gacatccagatgacccagagccccagctcagtgagcgctagcgtgggcgacagggtgaccatcacctgcaggrcnagccagggcatta
gcagytggctgagytggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca
gcaggccmaygtgytnccccctgaccttcggcggcggcacaaaagtcgagatcaag SEQ ID NO: 56
gacatccagatgacccagagccccagctcagtgagcgctagcgtgggcgacagggtgaccatcacctgcagggccagccagggcatta
gcagctggctggcctggtaccagcagaagcccggcaaggcccccaagctcctgatctacgccgccagcaggctgcagagcggcgtgc
cctccaggtttagcggcagcggaagcggcaccgacttcaccctgaccatcagcagcctgcagcccgaggacttcgccacctactactgcc
agcaggccaacgtgttcccccctgaccttcggcggcggcacaaaagtcgagatcaag SEQ ID NO: 57
gacatccagatgacccagagccccagctcagtgagcgctagcgtgggcgacagggtgaccatcacctgcagggccagccagggcatta
gcccctggctggcctggtaccagcagaagcccggcaaggcccccaagctcctgatctacgccggcagcagcctgcagagcggcgtgcc
ctccaggtttagcggcagcggaagcggcaccgacttcaccctgaccatcagcagcctgcagcccgaggacttcgccacctactactgcca
gcaggccaacgtgttccccctgaccttcggcggcggcacaaaagtcgagatcaag SEQ ID NO: 58
gacatccagatgacccagagccccagctcagtgagcgctagcgtgggcgacagggtgaccatcacctgcaggaccagccagggcatta
gcagctggctgagctggtaccagcagaagcccggcaaggcccccaagctcctgatctacgccgccagcagcctgcagagcggcgtgcc
ctccaggtttagcggcagcggaagcggcaccgacttcaccctgaccatcagcagcctgcagcccgaggacttcgccacctactactgcca
gcaggcccacgtgctgcccctgaccttcggcggcggcacaaaagtcgagatcaag SEQ ID NO: 59
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcmarggcagggtgaccatgacaagggacaccagcaccagcaccgtgtacatggagctgagcagcctgagga
gcgaggacaccgccgtgtattactgcgcaaggcccagcgccgcctacagccactacctgggcmthgacmtntggggcaggggcacc
ctggtgaccgtgagctctgccagcaccaagggccccagcgtgttcccccctggcccccagcagcaagagcaccagcggcggcacagcc
gccctgggctgcctggtgaaggactacttccccgagcccgtgaccgtgtcctggaacagcggagccctgaccagcggcgtgcacacctt
ccccgccgtgctgcagagcagcggcctgtacagcctgagcagcgtggtgaccgtgcccagcagcagcctgggcacccagacctacatc
tgtaacgtgaaccacaagcccagcaacaccaaggtggacaagaaggtggagcccaagagctgtgacaagacccacacctgcccccccct
gccctgcccccgagctgctgggaggccccagcgtgttcctgttcccccccaagcctaaggacaccctgtacatcaccagagaacccgag
gtgacctgtgtggtggtggatgtgagccacgaggaccctgaggtgaagttcaactggtacgtggacggcgtggaggtgcacaatgccaag
accaagcccagggaggagcagtacaacagcacctaccgggtggtgtccgtgctgaccgtgctgcaccaggattggctgaacggcaagg -continued agtacaagtgtaaggtgtccaacaaggccctgcctgcccctatcgagaaaaccatcagcaaggccaagggccagcccagagagcccca ggtgtacaccctgcccccctagcagagatgagctgaccaagaaccaggtgtccctgacctgcctggtgaagggcttctaccccagcgacat cgccgtggagtgggagagcaacggccagcccgagaacaactacaagaccacccccccctgtgctggacagcgatggcagcttcttcctgt acagcaagctgaccgtggacaagagcagatggcagcagggcaacgtgttcagctgctccgtgatgcacgaggccctgcacaatcactac acccagaagagcctgagcctgtcccctggcaag

SEQ ID NO: 60 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttcmarggcagggtgaccatgacaagggacaccagcaccagcaccgtgtacatggagctgagcagcctgagga gcgaggacaccgccgtgtattactgcgcaaggcccagcgccgcctacagccactacctgggcmthgacttrtggggcaggggcaccct ggtgaccgtgagctctgccagcaccaagggccccagcgtgttccccctggcccccagcagcaagagcaccagcggcggcacagccgc cctgggctgcctggtgaaggactacttccccgagcccgtgaccgtgtcctggaacagcggagccctgaccagcggcgtgcacaccttccc cgccgtgctgcagagcagcggcctgtacagcctgagcagcgtggtgaccgtgcccagcagcagcctgggcacccagacctacatctgta acgtgaaccacaagcccagcaacaccaaggtggacaagaaggtggagcccaagagctgtgacaagacccacacctgccccccctgcc ctgcccccgagctgctgggaggccccagcgtgttcctgttcccccccaagcctaaggacaccctgtacatcaccagagaacccgaggtga cctgtgtggtggtggatgtgagccacgaggaccctgaggtgaagttcaactggtacgtggacggcgtggaggtgcacaatgccaagacc aagcccagggaggagcagtacaacagcacctaccgggtggtgtccgtgctgaccgtgctgcaccaggattggctgaacggcaaggagt acaagtgtaaggtgtccaacaaggccctgcctgcccctatcgagaaaaccatcagcaaggccaagggccagcccagagagccccaggt gtacaccctgcccccctagcagagatgagctgaccaagaaccaggtgtccctgacctgcctggtgaagggcttctaccccagcgacatcgc cgtggagtgggagagcaacggccagcccgagaacaactacaagaccacccccccctgtgctggacagcgatggcagcttcttcctgtaca gcaagctgaccgtggacaagagcagatggcagcagggcaacgtgttcagctgctccgtgatgcacgaggccctgcacaatcactacacc cagaagagcctgagcctgtcccctggcaag

SEQ ID NO: 61 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttcmarggcagggtgaccatgacaagggacaccagcaccagcaccgtgtacatggagctgagcagcctgagga gcgaggacaccgccgtgtattactgcgcaaggcccagcgccgcctacagccactacctgggcytggacmtntggggcaggggcaccc tggtgaccgtgagctctgccagcaccaagggccccagcgtgttccccctggcccccagcagcaagagcaccagcggcggcacagccg ccctgggctgcctggtgaaggactacttccccgagcccgtgaccgtgtcctggaacagcggagccctgaccagcggcgtgcacaccttcc ccgccgtgctgcagagcagcggcctgtacagcctgagcagcgtggtgaccgtgcccagcagcagcctgggcacccagacctacatctgt aacgtgaaccacaagcccagcaacaccaaggtggacaagaaggtggagcccaagagctgtgacaagacccacacctgccccccctgc cctgcccccgagctgctgggaggccccagcgtgttcctgttcccccccaagcctaaggacaccctgtacatcaccagagaacccgaggtg acctgtgtggtggtggatgtgagccacgaggaccctgaggtgaagttcaactggtacgtggacggcgtggaggtgcacaatgccaagac caagcccagggaggagcagtacaacagcacctaccgggtggtgtccgtgctgaccgtgctgcaccaggattggctgaacggcaaggag tacaagtgtaaggtgtccaacaaggccctgcctgcccctatcgagaaaaccatcagcaaggccaagggccagcccagagagccccaggt gtacaccctgcccccctagcagagatgagctgaccaagaaccaggtgtccctgacctgcctggtgaagggcttctaccccagcgacatcgc cgtggagtgggagagcaacggccagcccgagaacaactacaagaccacccccccctgtgctggacagcgatggcagcttcttcctgtaca gcaagctgaccgtggacaagagcagatggcagcagggcaacgtgttcagctgctccgtgatgcacgaggccctgcacaatcactacacc cagaagagcctgagcctgtcccctggcaag

SEQ ID NO: 62 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca -continued gctacgcccagaagttcmarggcagggtgaccatgacaagggacaccagcaccagcaccgtgtacatggagctgagcagcctgagga gcgaggacaccgccgtgtattactgcgcaaggcccagcgccgcctacagccactacctgggcytggacttrtggggcaggggcaccctg gtgaccgtgagctctgccagcaccaagggccccagcgtgttccccctggcccccagcagcaagagcaccagcggcggcacagccgcc ctgggctgcctggtgaaggactacttccccgagcccgtgaccgtgtcctggaacagcggagccctgaccagcggcgtgcacaccttcccc gccgtgctgcagagcagcggcctgtacagcctgagcagcgtggtgaccgtgcccagcagcagcctgggcacccagacctacatctgtaa cgtgaaccacaagcccagcaacaccaaggtggacaagaaggtggagcccaagagctgtgacaagacccacacctgccccccctgccct gcccccgagctgctgggaggccccagcgtgttcctgttccccccaagcctaaggacaccctgtacatcaccagagaacccgaggtgac ctgtgtggtggtggatgtgagccacgaggaccctgaggtgaagttcaactggtacgtggacggcgtggaggtgcacaatgccaagacca agcccagggaggagcagtacaacagcacctaccgggtggtgtccgtgctgaccgtgctgcaccaggattggctgaacggcaaggagta caagtgtaaggtgtccaacaaggccctgcctgcccctatcgagaaaaccatcagcaaggccaagggccagcccagagagccccaggtg tacaccctgcccccctagcagagatgagctgaccaagaaccaggtgtccctgacctgcctggtgaagggcttctaccccagcgacatcgcc gtggagtgggagagcaacggccagcccgagaacaactacaagaccaccccccctgtgctggacagcgatggcagcttcttcctgtacag caagctgaccgtggacaagagcagatggcagcagggcaacgtgttcagctgctccgtgatgcacgaggccctgcacaatcactacaccc agaagagcctgagcctgtcccctggcaag

SEQ ID NO: 63 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttcmarggcagggtgaccatgacaagggacaccagcaccagcaccgtgtacatggagctgagcagcctgagga gcgaggacaccgccgtgtattactgcgcaaggcccagcgccgcctacagccactacctgggcttagacmtntggggcaggggcaccct ggtgaccgtgagctctgccagcaccaagggccccagcgtgttccccctggcccccagcagcaagagcaccagcggcggcacagccgc cctgggctgcctggtgaaggactacttccccgagcccgtgaccgtgtcctggaacagcggagccctgaccagcggcgtgcacaccttccc cgccgtgctgcagagcagcggcctgtacagcctgagcagcgtggtgaccgtgcccagcagcagcctgggcacccagacctacatctgta acgtgaaccacaagcccagcaacaccaaggtggacaagaaggtggagcccaagagctgtgacaagacccacacctgccccccctgcc ctgcccccgagctgctgggaggccccagcgtgttcctgttccccccaagcctaaggacaccctgtacatcaccagagaacccgaggtga cctgtgtggtggtggatgtgagccacgaggaccctgaggtgaagttcaactggtacgtggacggcgtggaggtgcacaatgccaagacc aagcccagggaggagcagtacaacagcacctaccgggtggtgtccgtgctgaccgtgctgcaccaggattggctgaacggcaaggagt acaagtgtaaggtgtccaacaaggccctgcctgcccctatcgagaaaaccatcagcaaggccaagggccagcccagagagccccaggt gtacaccctgcccccctagcagagatgagctgaccaagaaccaggtgtccctgacctgcctggtgaagggcttctaccccagcgacatcgc cgtggagtgggagagcaacggccagcccgagaacaactacaagaccaccccccctgtgctggacagcgatggcagcttcttcctgtaca gcaagctgaccgtggacaagagcagatggcagcagggcaacgtgttcagctgctccgtgatgcacgaggccctgcacaatcactacacc cagaagagcctgagcctgtcccctggcaag

SEQ ID NO: 64 caggtgcagctggtgcagagcggcgccgaagtgaaaaagcccggcgccagcgtgaaggtcagctgcaaggcctccgggtacaccttca tcagctacggcatgcactgggtgaggcaggcccccggccagggcctcgagtggatgggcgagatcaacccccacggaggcagcacca gctacgcccagaagttcmarggcagggtgaccatgacaagggacaccagcaccagcaccgtgtacatggagctgagcagcctgagga gcgaggacaccgccgtgtattactgcgcaaggcccagcgccgcctacagccactacctgggcttagacttrtggggcaggggcaccctg gtgaccgtgagctctgccagcaccaagggccccagcgtgttccccctggcccccagcagcaagagcaccagcggcggcacagccgcc ctgggctgcctggtgaaggactacttccccgagcccgtgaccgtgtcctggaacagcggagccctgaccagcggcgtgcacaccttcccc gccgtgctgcagagcagcggcctgtacagcctgagcagcgtggtgaccgtgcccagcagcagcctgggcacccagacctacatctgtaa cgtgaaccacaagcccagcaacaccaaggtggacaagaaggtggagcccaagagctgtgacaagacccacacctgccccccctgccct gcccccgagctgctgggaggccccagcgtgttcctgttccccccaagcctaaggacaccctgtacatcaccagagaacccgaggtgac ctgtgtggtggtggatgtgagccacgaggaccctgaggtgaagttcaactggtacgtggacggcgtggaggtgcacaatgccaagacca -continued agcccagggaggagcagtacaacagcacctaccgggtggtgtccgtgctgaccgtgctgcaccaggattggctgaacggcaaggagta
caagtgtaaggtgtccaacaaggccctgcctgcccctatcgagaaaaccatcagcaaggccaagggccagcccagagagccccaggtg
tacaccctgccccctagcagagatgagctgaccaagaaccaggtgtccctgacctgcctggtgaagggcttctaccccagcgacatcgcc
gtggagtgggagagcaacggccagcccgagaacaactacaagaccaccccccctgtgctggacagcgatggcagcttcttcctgtacag
caagctgaccgtggacaagagcagatggcagcagggcaacgtgttcagctgctccgtgatgcacgaggccctgcacaatcactacaccc
agaagagcctgagcctgtcccctggcaag SEQ ID NO: 65
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttccagggcagggtgaccatgacaagggacaccagcaccagcaccgtgtacatggagctgagcagcctgagga
gcgaggacaccgccgtgtattactgcgcaaggcccagcgccgcctacagccactacctgggcatcgacatgtggggcaggggcaccct
ggtgaccgtgagctctgccagcaccaagggccccagcgtgttccccctggccccagcagcaagagcaccagcggggcacagccgc
cctgggctgcctggtgaaggactacttccccgagcccgtgaccgtgtcctggaacagcggagccctgaccagcggcgtgcacaccttccc
cgccgtgctgcagagcagcggcctgtacagcctgagcagcgtggtgaccgtgcccagcagcagcctgggcacccagacctacatctgta
acgtgaaccacaagcccagcaacaccaaggtggacaagaaggtggagcccaagagctgtgacaagacccacacctgccccccctgcc
ctgcccccgagctgctgggaggccccagcgtgttcctgttcccccccaagcctaaggacaccctgtacatcaccagagaacccgaggtga
cctgtgtggtggtggatgtgagccacgaggaccctgaggtgaagttcaactggtacgtggacggcgtggaggtgcacaatgccaagacc
aagcccagggaggagcagtacaacagcacctaccgggtggtgtccgtgctgaccgtgctgcaccaggattggctgaacggcaaggagt
acaagtgtaaggtgtccaacaaggccctgcctgcccctatcgagaaaaccatcagcaaggccaagggccagcccagagagccccaggt
gtacaccctgccccctagcagagatgagctgaccaagaaccaggtgtccctgacctgcctggtgaagggcttctaccccagcgacatcgc
cgtggagtgggagagcaacggccagcccgagaacaactacaagaccaccccccctgtgctggacagcgatggcagcttcttcctgtaca
gcaagctgaccgtggacaagagcagatggcagcagggcaacgtgttcagctgctccgtgatgcacgaggccctgcacaatcactacacc
cagaagagcctgagcctgtcccctggcaag SEQ ID NO: 66
caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttcaagggcagggtgaccatgacaagggacaccagcaccagcaccgtgtacatggagctgagcagcctgagga
gcgaggacaccgccgtgtattactgcgcaaggcccagcgccgcctacagccactacctgggcatcgacctgtggggcaggggcaccct
ggtgaccgtgagctctgccagcaccaagggccccagcgtgttccccctggcccccagcagcaagagcaccagcggggcacagccgc
cctgggctgcctggtgaaggactacttccccgagcccgtgaccgtgtcctggaacagcggagccctgaccagcggcgtgcacaccttccc
cgccgtgctgcagagcagcggcctgtacagcctgagcagcgtggtgaccgtgcccagcagcagcctgggcacccagacctacatctgta
acgtgaaccacaagcccagcaacaccaaggtggacaagaaggtggagcccaagagctgtgacaagacccacacctgccccccctgcc
ctgcccccgagctgctgggaggccccagcgtgttcctgttcccccccaagcctaaggacaccctgtacatcaccagagaacccgaggtga
cctgtgtggtggtggatgtgagccacgaggaccctgaggtgaagttcaactggtacgtggacggcgtggaggtgcacaatgccaagacc
aagcccagggaggagcagtacaacagcacctaccgggtggtgtccgtgctgaccgtgctgcaccaggattggctgaacggcaaggagt
acaagtgtaaggtgtccaacaaggccctgcctgcccctatcgagaaaaccatcagcaaggccaagggccagcccagagagccccaggt
gtacaccctgccccctagcagagatgagctgaccaagaaccaggtgtccctgacctgcctggtgaagggcttctaccccagcgacatcgc
cgtggagtgggagagcaacggccagcccgagaacaactacaagaccaccccccctgtgctggacagcgatggcagcttcttcctgtaca
gcaagctgaccgtggacaagagcagatggcagcagggcaacgtgttcagctgctccgtgatgcacgaggccctgcacaatcactacacc
cagaagagcctgagcctgtcccctggcaag

SEQ ID NO: 67 caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttccagggcagggtgaccatgacaagggacaccagcaccagcaccgtgtacatggagctgagcagcctgagga
gcgaggacaccgccgtgtattactgcgcaaggcccagcgccgcctacagccactacctgggcctggacatctggggcaggggcaccct
ggtgaccgtgagctctgccagcaccaagggccccagcgtgttccccctggccccagcagcaagagcaccagggggcacagccgc
cctgggctgcctggtgaaggactacttccccgagcccgtgaccgtgtcctggaacagcggagccctgaccagcggcgtgcacaccttccc
cgccgtgctgcagagcagcggcctgtacagcctgagcagcgtggtgaccgtgcccagcagcagcctgggcacccagacctacatctgta
acgtgaaccacaagcccagcaacaccaaggtggacaagaaggtggagcccaagagctgtgacaagacccacacctgccccccctgcc
ctgcccccgagctgctgggaggccccagcgtgttcctgttccccccaagcctaaggacaccctgtacatcaccagagaacccgaggtga
cctgtgtggtggtggatgtgagccacgaggaccctgaggtgaagttcaactggtacgtggacggcgtggaggtgcacaatgccaagacc
aagcccagggaggagcagtacaacagcacctaccgggtggtgtccgtgctgaccgtgctgcaccaggattggctgaacggcaaggagt
acaagtgtaaggtgtccaacaaggccctgcctgcccctatcgagaaaaccatcagcaaggccaagggccagcccagagagccccaggt
gtacaccctgcccccctagcagagatgagctgaccaagaaccaggtgtccctgacctgcctggtgaagggcttctaccccagcgacatcgc
cgtggagtgggagagcaacggccagcccgagaacaactacaagaccaccccccctgtgctggacagcgatggcagcttcttcctgtaca
gcaagctgaccgtggacaagagcagatggcagcagggcaacgtgttcagctgctccgtgatgcacgaggccctgcacaatcactacacc
cagaagagcctgagcctgtcccctggcaag

SEQ ID NO: 68 caggtgcagctggtgcagagcggcgccgaagtgaaaaagcccggcgccagcgtgaaggtcagctgcaaggcctccgggtacaccttca
tcagctacggcatgcactgggtgaggcaggcccccggccagggcctcgagtggatgggcgagatcaacccccacggaggcagcacca
gctacgcccagaagttccagggcagggtgaccatgacaagggacaccagcaccagcaccgtgtacatggagctgagcagcctgagga
gcgaggacaccgccgtgtattactgcgcaaggcccagcgccgcctacagccactacctgggcatcgacctgtggggcaggggcaccct
ggtgaccgtgagctctgccagcaccaagggccccagcgtgttccccctggccccagcagcaagagcaccagcggcggcacagccgc
cctgggctgcctggtgaaggactacttccccgagcccgtgaccgtgtcctggaacagcggagccctgaccagcggcgtgcacaccttccc
cgccgtgctgcagagcagcggcctgtacagcctgagcagcgtggtgaccgtgcccagcagcagcctgggcacccagacctacatctgta
acgtgaaccacaagcccagcaacaccaaggtggacaagaaggtggagcccaagagctgtgacaagacccacacctgccccccctgcc
ctgcccccgagctgctgggaggccccagcgtgttcctgttccccccaagcctaaggacaccctgtacatcaccagagaacccgaggtga
cctgtgtggtggtggatgtgagccacgaggaccctgaggtgaagttcaactggtacgtggacggcgtggaggtgcacaatgccaagacc
aagcccagggaggagcagtacaacagcacctaccgggtggtgtccgtgctgaccgtgctgcaccaggattggctgaacggcaaggagt
acaagtgtaaggtgtccaacaaggccctgcctgcccctatcgagaaaaccatcagcaaggccaagggccagcccagagagccccaggt
gtacaccctgcccccctagcagagatgagctgaccaagaaccaggtgtccctgacctgcctggtgaagggcttctaccccagcgacatcgc
cgtggagtgggagagcaacggccagcccgagaacaactacaagaccaccccccctgtgctggacagcgatggcagcttcttcctgtaca
gcaagctgaccgtggacaagagcagatggcagcagggcaacgtgttcagctgctccgtgatgcacgaggccctgcacaatcactacacc
cagaagagcctgagcctgtcccctggcaag

SEQ ID NO: 69 gacatccagatgacccagagccccagctcagtgagcgctagcgtgggcgacagggtgaccatcacctgcaggrcnagccagggcatta
gcycntggctgkcntggtaccagcagaagcccggcaaggcccccaagctcctgatctacgccgsnagcmgnctgcagagcggcgtg
ccctccaggtttagcggcagcggaagcggcaccgacttcaccctgaccatcagcagcctgcagcccgaggacttcgccacctactactgc
cagcaggccmaygtgytncccctgaccttcggcggcggcacaaaagtcgagatcaagcgtacggtggccgcccccagcgtgttcatctt
ccccccagcgatgagcagctgaagagcggcaccgccagcgtggtgtgtctgctgaacaacttctacccccgggaggccaaggtgcagt -continued ggaaggtggacaatgccctgcagagcggcaacagccaggagagcgtgaccgagcaggacagcaaggactccacctacagcctgagc
agcaccctgaccctgagcaaggccgactacgagaagcacaaggtgtacgcctgtgaggtgacccaccagggcctgtccagccccgtga
ccaagagcttcaaccggggcgagtgc SEQ ID NO: 70
gacatccagatgacccagagccccagctcagtgagcgctagcgtgggcgacagggtgaccatcacctgcaggrcnagccagggcatta
gcycntggctgkcntggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca
gcaggccmaygtgytncccctgaccttcggcggcggcacaaaagtcgagatcaagcgtacggtggccgcccccagcgtgttcatcttcc
cccccagcgatgagcagctgaagagcggcaccgccagcgtggtgtgtctgctgaacaacttctacccccgggaggccaaggtgcagtg
gaaggtggacaatgccctgcagagcggcaacagccaggagagcgtgaccgagcaggacagcaaggactccacctacagcctgagca
gcaccctgaccctgagcaaggccgactacgagaagcacaaggtgtacgcctgtgaggtgacccaccagggcctgtccagccccgtgac
caagagcttcaaccggggcgagtgc SEQ ID NO: 71
gacatccagatgacccagagccccagctcagtgagcgctagcgtgggcgacagggtgaccatcacctgcaggrcnagccagggcatta
gcycntggctgagytggtaccagcagaagcccggcaaggcccccaagctcctgatctacgccgsnagcmgnctgcagagcggcgtg
ccctccaggtttagcggcagcggaagcggcaccgacttcaccctgaccatcagcagcctgcagcccgaggacttcgccacctactactgc
cagcaggccmaygtgytncccctgaccttcggcggcggcacaaaagtcgagatcaagcgtacggtggccgcccccagcgtgttcatctt
cccccccagcgatgagcagctgaagagcggcaccgccagcgtggtgtgtctgctgaacaacttctacccccgggaggccaaggtgcagt
ggaaggtggacaatgccctgcagagcggcaacagccaggagagcgtgaccgagcaggacagcaaggactccacctacagcctgagc
agcaccctgaccctgagcaaggccgactacgagaagcacaaggtgtacgcctgtgaggtgacccaccagggcctgtccagccccgtga
ccaagagcttcaaccggggcgagtgc SEQ ID NO: 72
gacatccagatgacccagagccccagctcagtgagcgctagcgtgggcgacagggtgaccatcacctgcaggrcnagccagggcatta
gcycntggctgagytggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca
gcaggccmaygtgytncccctgaccttcggcggcggcacaaaagtcgagatcaagcgtacggtggccgcccccagcgtgttcatcttcc
cccccagcgatgagcagctgaagagcggcaccgccagcgtggtgtgtctgctgaacaacttctacccccgggaggccaaggtgcagtg
gaaggtggacaatgccctgcagagcggcaacagccaggagagcgtgaccgagcaggacagcaaggactccacctacagcctgagca
gcaccctgaccctgagcaaggccgactacgagaagcacaaggtgtacgcctgtgaggtgacccaccagggcctgtccagccccgtgac
caagagcttcaaccggggcgagtgc SEQ ID NO: 73
gacatccagatgacccagagccccagctcagtgagcgctagcgtgggcgacagggtgaccatcacctgcaggrcnagccagggcatta
gcagytggctgkcntggtaccagcagaagcccggcaaggcccccaagctcctgatctacgccgsnagcmgnctgcagagcggcgtg
ccctccaggtttagcggcagcggaagcggcaccgacttcaccctgaccatcagcagcctgcagcccgaggacttcgccacctactactgc
cagcaggccmaygtgytncccctgaccttcggcggcggcacaaaagtcgagatcaagcgtacggtggccgcccccagcgtgttcatctt
cccccccagcgatgagcagctgaagagcggcaccgccagcgtggtgtgtctgctgaacaacttctacccccgggaggccaaggtgcagt
ggaaggtggacaatgccctgcagagcggcaacagccaggagagcgtgaccgagcaggacagcaaggactccacctacagcctgagc
agcaccctgaccctgagcaaggccgactacgagaagcacaaggtgtacgcctgtgaggtgacccaccagggcctgtccagccccgtga
ccaagagcttcaaccggggcgagtgc SEQ ID NO: 74
gacatccagatgacccagagccccagctcagtgagcgctagcgtgggcgacagggtgaccatcacctgcaggrcnagccagggcatta
gcagytggctgkcntggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca -continued gcaggccmaygtgytnccccctgaccttcggggcggcacaaaagtcgagatcaagcgtacggtggccgcccccagcgtgttcatcttcc
cccccagcgatgagcagctgaagagcggcaccgccagcgtggtgtgtctgctgaacaacttctacccccgggaggccaaggtgcagtg
gaaggtggacaatgccctgcagagcggcaacagccaggagagcgtgaccgagcaggacagcaaggactccacctacagcctgagca
gcaccctgaccctgagcaaggccgactacgagaagcacaaggtgtacgcctgtgaggtgacccaccagggcctgtccagccccgtgac
caagagcttcaaccggggcgagtgc SEQ ID NO: 75
gacatccagatgacccagagccccagctcagtgagcgctagcgtgggcgacagggtgaccatcacctgcaggrcnagccagggcatta
gcagytggctgagytggtaccagcagaagcccggcaaggcccccaagctcctgatctacgccgsnagcmgnctgcagagcggcgtg
ccctccaggtttagcggcagcggaagcggcaccgacttcaccctgaccatcagcagcctgcagcccgaggacttcgccacctactactgc
cagcaggccmaygtgytnccccctgaccttcggcggcggcacaaaagtcgagatcaagcgtacggtggccgcccccagcgtgttcatctt
cccccccagcgatgagcagctgaagagcggcaccgccagcgtggtgtgtctgctgaacaacttctacccccgggaggccaaggtgcagt
ggaaggtggacaatgccctgcagagcggcaacagccaggagagcgtgaccgagcaggacagcaaggactccacctacagcctgagc
agcaccctgaccctgagcaaggccgactacgagaagcacaaggtgtacgcctgtgaggtgacccaccagggcctgtccagccccgtga
ccaagagcttcaaccggggcgagtgc SEQ ID NO: 76
gacatccagatgacccagagccccagctcagtgagcgctagcgtgggcgacagggtgaccatcacctgcaggrcnagccagggcatta
gcagytggctgagytggtaccagcagaagcccggcaaggcccccaagctcctgatctacgccgsnagctcnctgcagagcggcgtgcc
ctccaggtttagcggcagcggaagcggcaccgacttcaccctgaccatcagcagcctgcagcccgaggacttcgccacctactactgcca
gcaggccmaygtgytnccccctgaccttcggcggcggcacaaaagtcgagatcaagcgtacggtggccgcccccagcgtgttcatcttcc
cccccagcgatgagcagctgaagagcggcaccgccagcgtggtgtgtctgctgaacaacttctacccccgggaggccaaggtgcagtg
gaaggtggacaatgccctgcagagcggcaacagccaggagagcgtgaccgagcaggacagcaaggactccacctacagcctgagca
gcaccctgaccctgagcaaggccgactacgagaagcacaaggtgtacgcctgtgaggtgacccaccagggcctgtccagccccgtgac
caagagcttcaaccggggcgagtgc SEQ ID NO: 77
gacatccagatgacccagagccccagctcagtgagcgctagcgtgggcgacagggtgaccatcacctgcagggccagccagggcatta
gcagctggctggcctggtaccagcagaagcccggcaaggcccccaagctcctgatctacgccgccagcaggctgcagagcggcgtgc
cctccaggtttagcggcagcggaagcggcaccgacttcaccctgaccatcagcagcctgcagcccgaggacttcgccacctactactgcc
agcaggccaacgtgttccccctgaccttcggcggcggcacaaaagtcgagatcaagcgtacggtggccgcccccagcgtgttcatcttcc
cccccagcgatgagcagctgaagagcggcaccgccagcgtggtgtgtctgctgaacaacttctacccccgggaggccaaggtgcagtg
gaaggtggacaatgccctgcagagcggcaacagccaggagagcgtgaccgagcaggacagcaaggactccacctacagcctgagca
gcaccctgaccctgagcaaggccgactacgagaagcacaaggtgtacgcctgtgaggtgacccaccagggcctgtccagccccgtgac
caagagcttcaaccggggcgagtgc SEQ ID NO: 78
gacatccagatgacccagagccccagctcagtgagcgctagcgtgggcgacagggtgaccatcacctgcagggccagccagggcatta
gcccctggctggcctggtaccagcagaagcccggcaaggcccccaagctcctgatctacgccggcagcagcctgcagagcggcgtgcc
ctccaggtttagcggcagcggaagcggcaccgacttcaccctgaccatcagcagcctgcagcccgaggacttcgccacctactactgcca
gcaggccaacgtgttccccctgaccttcggcggcggcacaaaagtcgagatcaagcgtacggtggccgcccccagcgtgttcatcttccc
ccccagcgatgagcagctgaagagcggcaccgccagcgtggtgtgtctgctgaacaacttctacccccgggaggccaaggtgcagtgg
aaggtggacaatgccctgcagagcggcaacagccaggagagcgtgaccgagcaggacagcaaggactccacctacagcctgagcag
caccctgaccctgagcaaggccgactacgagaagcacaaggtgtacgcctgtgaggtgacccaccagggcctgtccagccccgtgacc
aagagcttcaaccggggcgagtgc -continued SEQ ID NO: 79
gacatccagatgacccagagccccagctcagtgagcgctagcgtgggcgacagggtgaccatcacctgcaggaccagccagggcatta gcagctggctgagctggtaccagcagaagcccggcaaggcccccaagctcctgatctacgccgccagcagcctgcagagcggcgtgcc ctccaggtttagcggcagcggaagcggcaccgacttcaccctgaccatcagcagcctgcagcccgaggacttcgccacctactactgcca gcaggcccacgtgctgcccctgaccttcggcggcggcacaaaagtcgagatcaagcgtacggtggccgcccccagcgtgttcatcttccc ccccagcgatgagcagctgaagagcggcaccgccagcgtggtgtgtctgctgaacaacttctacccccgggaggccaaggtgcagtgg aaggtggacaatgccctgcagagcggcaacagccaggagagcgtgaccgagcaggacagcaaggactccacctacagcctgagcag caccctgaccctgagcaaggccgactacgagaagcacaaggtgtacgcctgtgaggtgacccaccagggcctgtccagccccgtgacc aagagcttcaaccggggcgagtgc

SEQ ID NO: 80
YESQHPSNESGDGVDGKMLM

SEQ ID NO: 81
FVLHNMHSNC

SEQ ID NO: 82
YYESQHPSNESGDGVDGKML

SEQ ID NO: 83
VLHNMHSNCV

SEQ ID NO: 84
SPITEY

SEQ ID NO: 85
VDSSENL

SEQ ID NO: 86
YESQHPSNESGDGVDGKML

SEQ ID NO: 87
VLHNMHSNC

SEQ ID NO: 88
MKPKMKYSTNKISTAKWKNTASKALCFKLGKSQQKAKEVCPMYFMKLRSGLMIKKEA

CYFRRETTKRPSLKTGRKHKRHLVLAACQQQSTVECFAFGISGVQKYTRALHDSSITGIS

PITEYLASLSTYNDQSITFALEDESYEIYVEDLKKDEKKDKVLLSYYESQHPSNESGDGV

DGKMLMVTLSPTKDFWLHANNKEHSVELHKCEKPLPDQAFFVLHNMHSNCVSFECKT

DPGVFIGVKDNHLALIKVDSSENLCTENILFKLSET

The invention claimed is:

1. An IL-33 binding protein comprising:

CDRH1 of SEQ ID NO:1, CDRH2 of SEQ ID NO:4, CDRH3 of SEQ ID NO:7, CDRL1 of SEQ ID NO:10, CDRL2 of SEQ ID NO: 14, and CDRL3 of SEQ ID NO: 18, wherein the IL-33 binding protein is an antibody or an antigen binding fragment thereof.

2. The IL-33 binding protein of claim 1, wherein the IL-33 binding protein comprises a heavy chain variable (VH) domain having at least 90% identity to SEQ ID NO:22 and a light chain variable (VL) domain having at least 90% identity to SEQ ID NO:26.

3. The IL-33 binding protein of claim 1, wherein the IL-33 binding protein comprises a heavy chain variable (VH) domain having 100% identity to SEQ ID NO:22 and a light chain variable (VL) domain having 100% identity to SEQ ID NO:26.

4. The IL-33 binding protein of claim 1, wherein the antibody or antigen binding fragment thereof is a human IgG antibody or antigen binding fragment thereof.

5. The IL-33 binding protein of claim 4, wherein the human IgG antibody or antigen binding fragment thereof is a human IgG1 antibody or antigen binding fragment thereof.

6. The IL-33 binding protein of claim 5, wherein the human IgG1 antibody or antigen binding fragment thereof is a human IgG1κ antibody or antigen binding fragment thereof.

7. The IL-33 binding protein of claim 1, wherein the antibody comprises a modified Fc region.

8. The IL-33 binding protein of claim 7, wherein the modified Fc region comprises at least one Fc mutation to extend half-life.

9. The IL-33 binding protein of claim 8, wherein the at least one Fc mutation is M252Y/S254T/T256E according to the EU index numbering system and the antibody is an IgG1 antibody.

10. The IL-33 binding protein of claim 1, wherein the IL-33 binding protein is an antibody comprising a heavy chain (HC) having at least 90% identity to SEQ ID NO:31 and a light chain (LC) having at least 90% identity to SEQ ID NO: 35.

11. The IL-33 binding protein of claim 1, wherein the IL-33 binding protein is an antibody comprising a heavy chain (HC) of SEQ ID NO:31 and a light chain (LC) of SEQ ID NO:35.

12. A pharmaceutical composition comprising the IL-33 binding protein as defined in claim 1 and a pharmaceutically acceptable excipient.

13. The pharmaceutical composition of claim 12, wherein the IL-33 binding protein comprises:

(i) a heavy chain variable (VH) domain having at least 90% identity to SEQ ID NO: 22 and a light chain variable (VL) domain having at least 90% identity to SEQ ID NO:26;

(ii) a heavy chain variable (VH) domain having 100% identity to SEQ ID NO:22 and a light chain variable (VL) domain having 100% identity to SEQ ID NO:26;

(iii) a heavy chain (HC) having at least 90% identity to SEQ ID NO:31 and a light chain (LC) having at least 90% identity to SEQ ID NO:35; or (iv) a heavy chain (HC) of SEQ ID NO:31 and a light chain (LC) of SEQ ID NO:35.

14. A method of reducing or inhibiting IL-33 in a human in need thereof comprising administering to the human a therapeutically effective amount of the IL-33 binding protein of claim 1.

15. The method of claim 14, wherein the IL-33 binding protein comprises:

(i) a heavy chain variable (VH) domain having at least 90% identity to SEQ ID NO: 22 and a light chain variable (VL) domain having at least 90% identity to SEQ ID NO:26;

(ii) a heavy chain variable (VH) domain having 100% identity to SEQ ID NO:22 and a light chain variable (VL) domain having 100% identity to SEQ ID NO:26;

(iii) a heavy chain (HC) having at least 90% identity to SEQ ID NO:31 and a light chain (LC) having at least 90% identity to SEQ ID NO:35; or (iv) a heavy chain (HC) of SEQ ID NO:31 and a light chain (LC) of SEQ ID NO:35.

16. The method of claim 14, wherein the human has a disease or condition, wherein the disease or condition is chronic obstructive pulmonary disease (COPD), asthma, bronchitis, bronchiolitis, bronchiectasis, acute respiratory failure, inflammatory lung diseases, diabetic kidney disease, endometriosis, chronic rhinosinusitis with nasal polyps, chronic rhinosinusitis without nasal polyps, food hypersensitivity, food allergy, peanut allergy, allergic rhinitis, eosinophilic oesophagitis, atopic dermatitis, cystic fibrosis, or chronic urticaria.

17. The method of claim 14, wherein the disease or condition is COPD.

18. The method of claim 14, wherein the disease or condition is bronchiectasis.

19. The method of claim 14, wherein the disease or condition is asthma.

20. The method of claim 14, wherein the disease or condition is chronic rhinosinusitis with nasal polyps.

21. The method of claim 14, wherein the disease or condition is chronic rhinosinusitis without nasal polyps.

22. A kit comprising:

(ii) the IL-33 binding protein of claim 1; and (ii) instructions for use.

* * * * *